US011561228B2

United States Patent
Tamura et al.

(10) Patent No.: US 11,561,228 B2
(45) Date of Patent: Jan. 24, 2023

(54) METHOD FOR DISCRIMINATING A MICROORGANISM

(71) Applicants: SHIMADZU CORPORATION, Kyoto (JP); MEIJO UNIVERSITY, Nagoya (JP)

(72) Inventors: Hiroto Tamura, Nagoya (JP); Naomi Yamamoto, Nagoya (JP); Teruyo Kato, Toyota (JP); Keisuke Shima, Kyoto (JP); Shinji Funatsu, Kyoto (JP)

(73) Assignees: SHIMADZU CORPORATION, Kyoto (JP); MEIJO UNIVERSITY, Nagoya (JP)

( * ) Notice: Subject to any disclaimer, the term of this patent is extended or adjusted under 35 U.S.C. 154(b) by 0 days.

(21) Appl. No.: 16/089,922

(22) PCT Filed: Mar. 31, 2016

(86) PCT No.: PCT/JP2016/060868
§ 371 (c)(1),
(2) Date: Sep. 28, 2018

(87) PCT Pub. No.: WO2017/168743
PCT Pub. Date: Oct. 5, 2017

(65) Prior Publication Data
US 2019/0056407 A1 Feb. 21, 2019

(51) Int. Cl.
*G01N 33/68* (2006.01)
*C12Q 1/04* (2006.01)
*C12N 15/09* (2006.01)

(52) U.S. Cl.
CPC .......... *G01N 33/6848* (2013.01); *C12Q 1/04* (2013.01); *C12N 15/09* (2013.01); *G01N 2333/195* (2013.01); *G01N 2560/00* (2013.01)

(58) Field of Classification Search
None
See application file for complete search history.

(56) References Cited

U.S. PATENT DOCUMENTS

2014/0288852 A1  9/2014  Ojima et al.

FOREIGN PATENT DOCUMENTS

| JP | 2006-191922 A | 7/2006 |
| JP | 2007-316063 A | 12/2007 |

(Continued)

OTHER PUBLICATIONS

Zhu, X., et al. Phenotypic, Proteomic, and Genomic Characterization of a Putative ABC-Transporter Permease Involved in Listeria monocytogenes Biofilm Formation, Foodborne Pathogens and Disease vol. 8, No. 4, 2011 (Year: 2011).*

(Continued)

*Primary Examiner* — Xiaoyun R Xu
(74) *Attorney, Agent, or Firm* — Sughrue Mion, PLLC

(57) ABSTRACT

To provide a method for discriminating a microorganism by selecting and using a marker protein capable of reproducibly and quickly discriminating a bacterial species of the genus *Listeria*. The method for discriminating a microorganism according to the present invention includes: a step of subjecting a sample containing a microorganism to mass spectrometry to obtain a mass spectrum; a reading step of reading a mass-to-charge ratio m/z of a peak derived from a marker protein from the mass spectrum; and a discrimination step of discriminating which bacterial species of *Listeria* bacteria the microorganism contained in the sample contains based on the mass-to-charge ratio m/z, in which at least one of 17 ribosomal proteins L3, L4, L23, L2, L24, L6, L18, S5, L15, S13, S11, L10, L21, L13, S9, L31, S16 is used as the marker (Continued)

protein and particularly at least one of 8 ribosomal proteins L24, L6, L18, L15, S9, L31, S16 among the 17 ribosomal proteins is used.

2 Claims, 18 Drawing Sheets

Specification includes a Sequence Listing.

(56) References Cited

FOREIGN PATENT DOCUMENTS

| JP | 2013-85517 A | 5/2013 |
|---|---|---|
| JP | 2015-184020 A | 10/2015 |

OTHER PUBLICATIONS

Ojima-Kato, T. et al. Discrimination of *Escherichia coli* O157, O26 and O111 from Other Serovars by MALDI-TOF MS Based on the S10-GERMS Method, PLOS One, vol. 9(11), e113458 (Year: 2014).*
Hanna, S.E. et al. Assessment of Environmental Factors on Listeria monocytogenes Scott A inIA Gene Expression by Relative Quantitative Taqman Real-Time Reverse Transcriptase PCR, Journal of Food Protection, vol. 69, No. 11, 2006, pp. 2754-2757 (Year: 2006).*
Promadel, N. et al. Cell Wall Teichoic Acid Glycosylation in Listeria monocytogenes Serotype 4b Requires gtcA, a Novel, Serogroup-Specific Gene, Journal of Bacteriology, 181(2), p. 418-425 (Year: 1999).*
List of prokaryotic names with standing in nomenclature, [searched on Sep. 18, 2015], Internet <URL: http://www.bacterio.net/>, 16 pages total.
Henk C den Bakker et al., "Comparative genomics of the bacterial genus *Listeria*: Genome evolution is characterized by limited gene acquisition and limited gene loss", BMC Genomics 2010, 11, 688, 20 pages total.
Marco Favaro et al., "First case of *Listeria innocua* meningitis in a patient on steroids and eternecept", JMM Case Reports (2014), 5 pages total.
Bala Swaminathan et al., "The epidemiology of human listeriosis", Microbes and Infection 9 (2007) pp. 1236-1243, 8 pages total.
Renato H. Orsi et al., "*Listeria monocytogenes* lineages: Genomics, evolution, ecology, and phenotypic characteristics", International Journal of Medical Microbiology 301 (2011) pp. 79-96, 18 pages total.
Todd J. Ward et al., "Multilocus Genotyping Assays for Single Nucleotide Polymorphism-Based Subtyping of *Listeria monocytogenes* Isolates", Applied and Environmental Microbiology, vol. 74, No. 24, Dec. 2008, pp. 7629-7642, 14 pages total.
Lewis M. Graves et al., "PulseNet standardized protocol for subtyping *Listeria monocytogenes* by macrorestriction and pulsed-field gel electrophoresis", International Journal of Food Microbiology 65 (2001) pp. 55-62, 8 pages total.
C. Salcedo et al., "Development of a Multilocus Sequence Typing Method for Analysis of *Listeria monocytogenes* Clones", Journal of Clinical Microbiology, vol. 41, No. 2, Feb. 2003, pp. 757-762, 6 pages total.
Marie Ragon et al., "A New Perspective on *Listeria monocytogenes* Evolution", PLoS Pathogens, vol. 4, Issue 9, e1000146, Sep. 2008, 14 pages total.
Monica K. Borucki et al., "Discrimination among *Listeria monocytogenes* isolates using a mixed genome DNA microarray", Veterinary Microbiology 92 (2003) pp. 351-362, 12 pages total.
Snehal Jadhav et al., "Rapid identification and source-tracking of *Listeria monocytogenes* using MALDI-TOF mass spectrometry", International Journal of Food Microbiology 202 (2015) pp. 1-9, 9 pages total.

Po-Ren Hsueh et al., "Bruker Biotyper Matrix-Assisted Laser Desorption Ionization—Time of Flight Mass Spectrometry System for Identification of *Nocardia, Rhodococcus, Kocuria, Gordonia, Tsukamurella*, and *Listeria* Species", Journal of Clinical Microbiology, vol. 52, No. 7, Jul. 2014, pp. 2371-2379, 9 pages total.
Michel Doumith et al., "Differentiation of the Major *Listeria monocytogenes* Serovars by Multiplex PCR", Journal of Clinical Microbiology, vol. 42, No. 8, Aug. 2004, pp. 3819-3822, 4 pages total.
Hotta et al., "Classification of Genus *Pseadomonas* by MALDMOF IVIS Based on RibosomaS Protein Codjng in S10—spc—afpha Operon at Strain Level", Journal of Proteome Research, vol. 9, 2010, pp. 6722-6728, 7 pages total.
Hotta et al., Classification of the Genus *Bacillus* Based on MALDI-TOF MS Analysis of Ribosomal Proteins Coded in S10 and spc Operons, Journal of Agricultural and Food Chemistry, vol. 59, 2011, pp. 5222-5230, 9 pages total.
Suarez et al., Ribosomal proteins as biomarkers for bacterial identification by mass spectrometry in the clinical microbiology laboratory, Journal of Microbiological Methods, vol. 94, 2013, pp. 390-396, 7 pages total.
Sukhadeo B. Barbuddhe et al., "Rapid Identification and Typing of *Listeria* Species by Matrix-Assisted Laser Desorption Ionization—Time of Flight Mass Spectrometry", Applied and Environmental Microbiology, vol. 74, No. 17, Sep. 2008, pp. 5402-5407, 6 pages total.
E. Farfour et al., "Evaluation of the Andromas Matrix-Assisted Laser Desorption Ionization—Time of Flight Mass Spectrometry System for Identification of Aerobically Growing Gram-Positive Bacilli", Journal of Clinical Microbiology, vol. 50, No. 8, Aug. 2012, pp. 2702-2707, 6 pages total.
International Search Report dated Jul. 5, 2016 issued by the International Searching Authority in PCT/JP2016/060868.
International Preliminary Report on Patentability with the translation of Written Opinion dated Oct. 2, 2018 issued by the International Bureau in PCT/JP2016/060868.
Office Action dated Dec. 3, 2021 in Chinese Application No. 201680084038.9.
Yang et al., "Two-dimensional electrophoresis map of Listeria monocytogenes proteome and proteomic analysis of stationary growth phase cells", Chinese Journal of Health Laboratory Technology, 2009, vol. 19, No. 3 (12 pages total).
"VITEK® MS Plus", VITEK R MS IVD and VITEK® MS Research Use Only software combination, Website bioMerieux, Sep. 29, 2015 (5 pages total).
"SARAMIS™ Softwareupdate V.4.0 and Mycobacteria Database Update V.4.12.0 for VITEK MS RUO", bioMerieux Germany GmbH, Oct. 8, 2013 (3 pages total).
"SARAMIS™ database update containing *Nocardia* and *Aspergillus* species (V.4.13.0) for the VITEK® MS Plus and the VITEK® MS RUO System", Mar. 2014 (1 page total).
"SARAMIS update KB V.4.13.0, VITEK® MS Plus & VITEK® MS RUO", Apr. 4, 2014 (5 pages total).
"VITEK® MS Plus—SARAMIS KB 4.14 Update", Jul. 18, 2016 (2 pages total).
"Bailiff report on SARAMIS Database V4.13", Apr. 2014 (34 pages total).
Gulsen Hascilek et al., "Identification of Viridans Streptococks Isolated From Clinical Samples with BD Phoenix, Vitek MS, Maldi Biotyper and Comparison with 16S RDNA Gene Sequence", Cover, summary and p. 167 of the Leaflet of a Microbiology congress in Turkish language https://www.klimud.ord/public/uploads/content/files/2015%20ko ngre%20kitab%C4%BI.PDF, Nov. 18-22, 2015 (5 pages total).
Snehal Jadhav, "Detection, subtyping and control of Listeria monocytogenes in food processing environments", A thesis submitted for the degree of Doctor of Philosophy, Department of Chemistry and Biotechnology, Swinburne University of Technology, Nov. 2015 (248 pages total).
Tamura et al., "Novel Accurate Bacterial Discrimination by MALDI-Time-of-Flight MS Based on Ribosomal Proteins coding in S10-spc-alpha Operon at Strain Level S10-GERMS", J. Am. Soc. Mass Spectrom, vol. 24, pp. 1185-1193, 2013 (9 Pages total).

(56) References Cited

OTHER PUBLICATIONS

Sato et al., " Characterization of the *Lactobacillus casei* group based on the profiling of ribosomal proteins coded in S10-spc-alpha operons as observed by MALDI-TOF MS", Systematic and Applied Microbiology, vol. 35, pp. 447-454, 2012 (8 pages total).
Teramoto et al. "Phylogenetic Classification of *Pseudomonas putida* Strains by MALDI-MS using Ribosomal Subunit Proteins as Biomarkers", Analytical Chemistry, vol. 79, No. 22, Nov. 15, 2007, pp. 8712-8719 (8 pages total).
Notice of Opposition dated Feb. 23, 2022 from European Patent Office in European Patent No. 3438276.
Communication dated Apr. 26, 2022 from The State Intellectual Property Office of P.R. of China in Application No. 201680084038.9.

\* cited by examiner

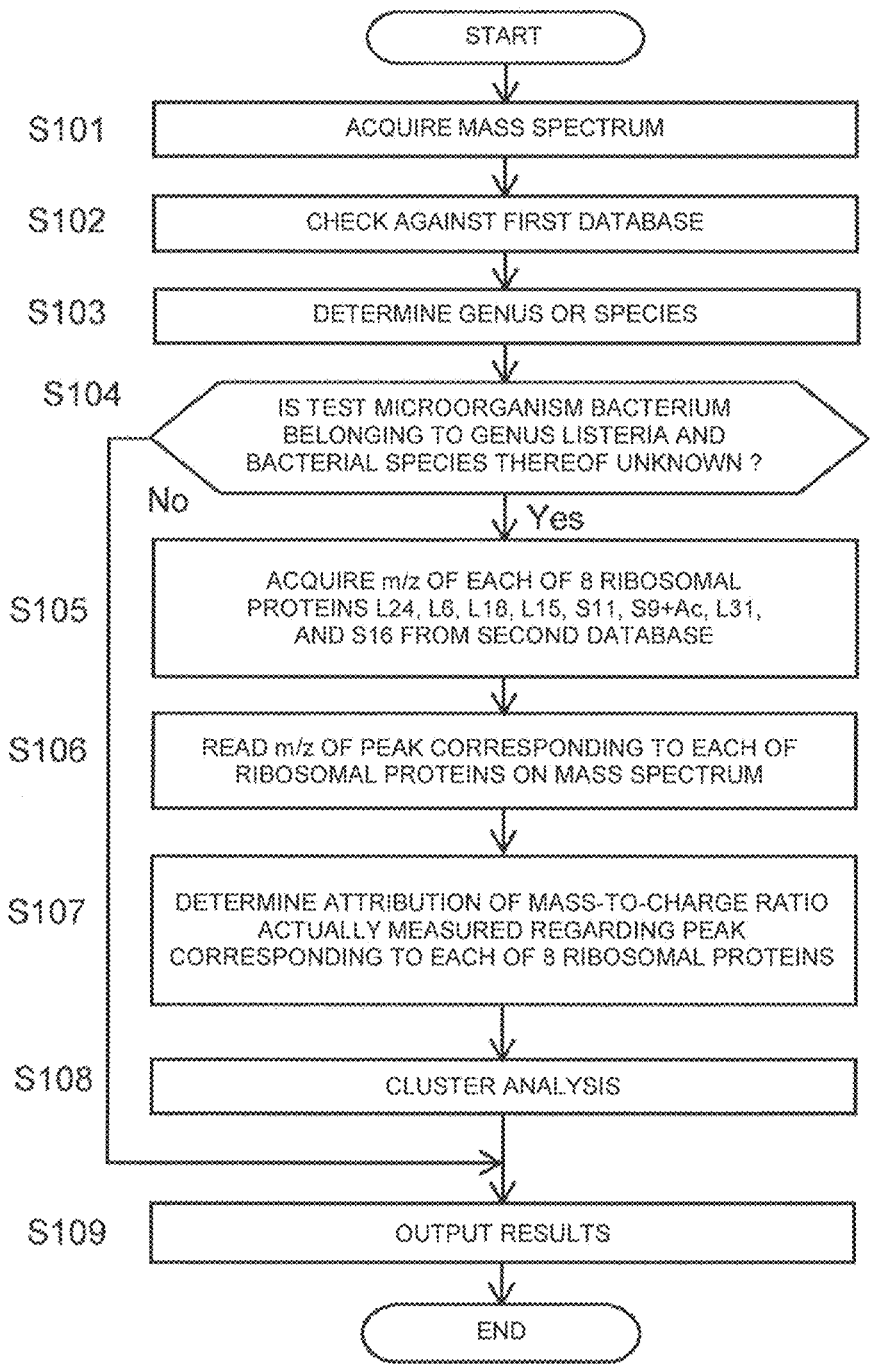

Fig. 3

| No. | Genus | Species | Subspecies | Strain | Serotype | Lineage | Supplier |
|---|---|---|---|---|---|---|---|
| 1 | *Listeria* | *monocytogenes* | | ATCC15313$^T$ | 1/2a(※) | II | ATCC |
| 2 | *Listeria* | *monocytogenes* | | JCM2873 | 4d | I | JCM |
| 3 | *Listeria* | *monocytogenes* | | JCM7671 | 1/2a | II | JCM |
| 4 | *Listeria* | *monocytogenes* | | JCM7672 | 1/2c | II | JCM |
| 5 | *Listeria* | *monocytogenes* | | JCM7673 | 3a | II | JCM |
| 6 | *Listeria* | *monocytogenes* | | JCM7674 | 4a | III | JCM |
| 7 | *Listeria* | *monocytogenes* | | JCM7675 | 4b | I | JCM |
| 8 | *Listeria* | *monocytogenes* | | JCM7676 | 1/2b | I | JCM |
| 9 | *Listeria* | *monocytogenes* | | JCM7677 | 3b | I | JCM |
| 10 | *Listeria* | *monocytogenes* | | JCM7678 | 3c | II | JCM |
| 11 | *Listeria* | *seeligeri* | | JCM7679 | 4c | | JCM |
| 12 | *Listeria* | *monocytogenes* | | JCM7680 | 4d | I | JCM |
| 13 | *Listeria* | *seeligeri* | | JCM7682 | 4c | | JCM |
| 14 | *Listeria* | *monocytogenes* | | JCM7683 | 3b | I | JCM |
| 15 | *Listeria* | *monocytogenes* | | ATCC51772 | 1/2a | II | ATCC |
| 16 | *Listeria* | *monocytogenes* | | ATCC19115 | 4b | I | ATCC |
| 17 | *Listeria* | *innocua* | | ATCC33090$^T$ | 6a | | ATCC |
| 18 | *Listeria* | *innocua* | | GTC02960 | | | NBRP |
| 19 | *Listeria* | *ivanovii* | *ivanovii* | JCM7681 | | | JCM |
| 20 | *Listeria* | *ivanovii* | *londoniens* | ATCC49954 | | | ATCC |
| 21 | *Listeria* | *seeligeri* | | ATCC35967$^T$ | | | ATCC |
| 22 | *Listeria* | *welshimeri* | | GTC02963 | 6b | | NBRP |
| 23 | *Listeria* | *grayi* | | ATCC19120$^T$ | | | ATCC |
| 24 | *Listeria* | *rocourtiae* | | GTC16429$^T$ | | | NBRP |

Weak agglutination of H antigen in agglutination test
Listeria of Nos. 11 and 13 was supplied from supplier as L. monocytogenes, but was identified as L. seeligeri by biochemistry test and sequence analysis of 16S RNA

Fig. 4

| Name | Sequence (5'-3') | Application |
|---|---|---|
| Lm-S10-1 | CATGGCGGATGTTCAGGTAA | Amplification and sequence analysis of S10 region |
| Lm-S10-R | CTCCTTCCAGAATAACGGGT | Amplification and sequence analysis of S10 region |
| Lm-S10-2 | AGCAGCACAAAACGTGGTAC | Sequence analysis of S10 region |
| Lm-S10-3 | AAGGAGGACTAACGAATGCC | Sequence analysis of S10 region |
| Lm-S10-4 | TGCACGCAACTTACAAGGCA | Sequence analysis of S10 region |
| Lm-S10-5 | CGGACGCAATAACCAAGGTA | Sequence analysis of S10 region |
| Lm-S10-6 | AATGAACCCGAACGATCACC | Sequence analysis of S10 region |
| Lm-S10-7 | TACAAGCGCAAAAGCCGTTG | Sequence analysis of S10 region |
| Lm-S10-8 | GTGCAGCTAACCGTGTGAAT | Sequence analysis of S10 region |
| Lm-S10-9 | AGGCGGAACTGAAGTTGCAT | Sequence analysis of S10 region |
| Lm-spc-1 | ACCCGTTATTCTGGAAGGAG | Amplification and sequence analysis of spc region |
| Lm-spc-R | AAGGCATTACACCCATGGCA | Amplification and sequence analysis of spc region |
| Lm-spc-F | CTCGTCCATTGTCTGCAACT | Sequence analysis of spc region |
| Lm-spc-2 | CAAACGTAATGCTAMTTGACCG | Sequence analysis of spc region |
| Lm-spc-3 | CGTGGTAACTATACGTTGGGT | Sequence analysis of spc region |
| Lm-spc-4 | GACTGGCGAACGTGTAATCA | Sequence analysis of spc region |
| Lm-spc-5 | TCCTGCAAACACWCAAGTGATT | Sequence analysis of spc region |
| Lm-spc-6 | GGAGGGACATATTACATGCCTG | Sequence analysis of spc region |
| Lm-spc-7 | TTAATCGGACGCCGTCAA | Sequence analysis of spc region |
| Lm-alpha-F | CTCTACCAAACGCGATGTTC | Amplification and sequence analysis of alpha region |
| Lm-alpha-R | GGAAACACAGAGCTAGACAAGG | Amplification and sequence analysis of alpha region |
| Lm-alpha-1 | CCTGACACGCGGAAGAATTA | Sequence analysis of alpha region |
| Lm-alpha-2 | AAGGCCCGTCCAAAACAGTA | Sequence analysis of alpha region |
| Lm-alpha-3 | CAGCGATGATGCCAAGTATG | Sequence analysis of alpha region |
| Lm-alpha-4 | GAAGCAGTTTCACTTGGAGC | Sequence analysis of alpha region |
| Lm-alpha-5 | AACTGGCTGACCTTGGCTTA | Sequence analysis of alpha region |
| Lm-L21-F | CCCGTGTGATGGCGAGTGTT | Amplification and sequence analysis of L21 gene |
| Lm-L21-R | TCTTCTGGCATAACATCGACTTGAA | Amplification of L21 gene |
| Lm-S21-F | TGAAGGATTTAAGTGAGTGCATGT | Amplification and sequence analysis of S21 gene |
| Lm-S21-R | CGCATCGCTTGTTTCATATCT | Amplification of S21 gene |
| Lm-S9-F | TTCGGGAGCTAATTTGTTTCAA | Amplification and sequence analysis of S9 gene and L13 gene |
| Lm-S9-R | AACGTTTTCAGAACTCAGGTGC | Amplification and sequence analysis of S9 gene and L13 gene |
| Lm-S9-F2 | CACATATCGACACTGGAGACTTTG | Sequence analysis of S9 gene and L13 gene |
| Lm-L10-F | CTGGAATCAAAGTCGACCCA | Amplification and sequence analysis of L10 gene |
| Lm-L10-R | GCAGCAGTTACGCCAAATTCTT | Amplification of L10 gene |
| Listeria_sp-L31-F | TGTTATAATATYTATACTGTGTGTAAAAGC | Amplification and sequence analysis of L31 gene |
| Listeria_sp-L31-R | TGAGACCGTAYTTTTTGTTGAAGC | Amplification and sequence analysis of L31 gene |

| Amino acid | Mass |
| --- | --- |
| A | 71.079 |
| R | 156.188 |
| N | 114.103 |
| D | 115.088 |
| C | 103.145 |
| Q | 128.13 |
| E | 129.114 |
| G | 57.052 |
| H | 137.141 |
| I | 113.159 |
| L | 113.159 |
| K | 128.174 |
| M | 131.198 |
| F | 147.176 |
| P | 97.116 |
| S | 87.078 |
| T | 101.104 |
| W | 186.213 |
| Y | 163.175 |
| V | 99.132 |

| Biomarker | Attribution No. | | |
|---|---|---|---|
| | 1 | 2 | |
| L24 | 11180.22 | 11194.25 | 11254.35 |
| L6 | 19270.08 | 19256.01 | |
| L18 | 13098.86 | 13110.89 | |
| L15 | 15782.02 | 15797.08 | |
| S11 | 13655.65 | 13674.66 | |
| S9+Ac | 14283.40 | 14359.50 | |

Fig. 8

| Biomarker | A<br>L. monocytogenes | B | C | D | E<br>L. innocua | F<br>L. ivanovii | G<br>L. ivanovii<br>ivanovii | H<br>L. ivanovii<br>londoniensis | I<br>L. seeligeri | J<br>L. seeligeri | K<br>L. welshimeri | L<br>L. rocourtiae | M<br>L. grayi |
|---|---|---|---|---|---|---|---|---|---|---|---|---|---|
| strain | | | | | ATCC 33090T | GTC02960 | JCM7681 | ATCC49954 | JCM7678<br>JCM7682 | ATCC 35967T | GTC02983 | GTC16439T | ATCC19120T |
| serotype | 1/2a, 1/2c, | 1/2b,3b,4b | 4d | 4e | | | | | | | | | |
| Lineage | 3a,3c | 4d, 4e | | | 6a | | | | | | | | |
| L24 | 11180.22 | 11194.25 | | | 11180.22 | 11194.25 | 11194.25 | 11194.25 | 11194.25 | 11194.25 | 11194.25 | 11194.25 | |
| L6 | 19270.04 | 19255.01 | 19255.01 | 19270.04 | 19270.04 | 19270.04 | 19270.04 | 19270.04 | 19270.04 | 19270.04 | 19270.04 | 19270.04 | |
| L18 | 13096.86 | 13096.86 | 13096.86 | 13096.86 | 13096.86 | 13096.86 | 13096.86 | 13096.86 | 13110.83 | 13110.83 | | | |
| L13 | 15782.02 | 15782.02 | 15782.02 | 15782.02 | | | | | 15797.98 | 15797.98 | 15797.98 | | |
| S11 | 13655.65 | 13655.65 | 13655.65 | 13655.65 | 13655.65 | 13655.65 | 13655.65 | 13655.65 | 13674.66 | 13674.66 | | | |
| S9-Ac | 14283.40 | 14359.50 | 14359.50 | 14359.50 | 14359.50 | 14359.50 | 14359.50 | 14359.50 | 14283.40 | 14283.40 | | | 15831.77 |
| L31 type B | 9253.36 | 9259.36 | 9259.36 | 9259.36 | 9259.36 | 9259.36 | 9259.36 | 9259.36 | 9290.37 | 9290.37 | 9290.37 | | |
| S16 | 10234.94 | 10234.94 | 10234.94 | 10234.94 | 10234.94 | 10234.94 | 10234.94 | 10234.94 | 10234.94 | 10234.94 | 10234.94 | | |

The mass value of S11 of L. grayi was calculated assuming that the mass of Methyl group was added to the theoretical mass value.
The mass value of S11 of L. rocourtiae was calculated assuming that 17 was added to the theoretical mass value.

Fig. 10

| sample | % | family | genus | species |
|---|---|---|---|---|
| L. innocua-ATCC33090T | 91.8 | Family IV Listeriaceae | Listeria | sp. |
| L. innocua-GTC02960 | 99.9 | Family IV Listeriaceae | Listeria | sp. |
| L. ivanovii-GTC02961 | 84.4 | Family IV Listeriaceae | Listeria | monocytogenes |
| L. ivanovii-ATCC49954T | 99.9 | Family IV Listeriaceae | Listeria | sp. |
| L. seeligeri-ATCC35967 | 91.8 | Family IV Listeriaceae | Listeria | sp. |
| L. welshimeri-GTC02963T | 97.2 | Family IV Listeriaceae | Listeria | sp. |
| L. rocouritiae-GTC16429T | 0 | | | |
| L. grayi-ATCC19120 | 99.9 | Family IV Listeriaceae | Listeria | grayi |
| L. seeligeri-JCM7679 | 81.1 | Family IV Listeriaceae | Listeria | monocytogenes |
| L. seeligeri-JCM7682 | 81.1 | Family IV Listeriaceae | Listeria | monocytogenes |

Figures 12A, 12B:
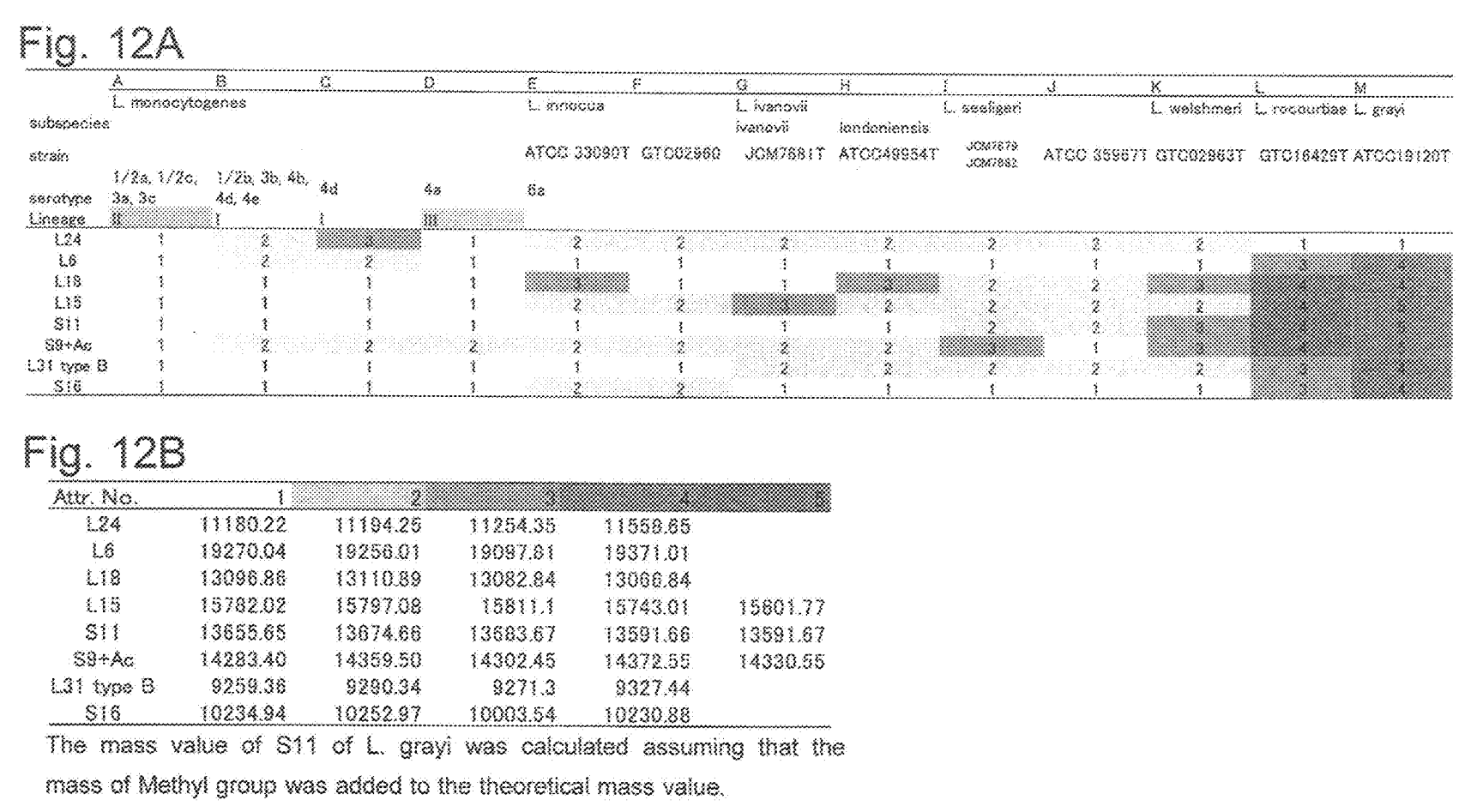

The mass value of S11 of L. grayi was calculated assuming that the mass of Methyl group was added to the theoretical mass value.

METHOD FOR DISCRIMINATING A MICROORGANISM

CROSS REFERENCE TO RELATED APPLICATIONS

This application is a National Stage of International Application No. PCT/JP2016/060868 filed Mar 31, 2016.

TECHNICAL FIELD

The present invention relates to a method for discriminating a microorganism using mass spectrometry.

BACKGROUND ART

Homology analysis based on DNA base sequences has been known as one of methods for discriminating types of microorganisms and has been widely used for classification, identification or the like of microorganisms (see, for example, Patent Literature 1). In this method, DNA is first extracted from a test microorganism, and the DNA base sequence of a region, such as rRNA genes, existing in high conservation in all organisms is determined. Next, using the DNA base sequence, a database involving a large number of DNA base sequence data of known microorganisms is searched and a base sequence showing high similarity to the DNA base sequence of the test microorganism is selected. Then, the species from which the base sequence is derived is determined to be of the same species or closely related species to the test microorganism.

However, with such a method utilizing the DNA base sequence, it takes a relatively long time to extract DNA from a test microorganism and to determine a DNA base sequence, so that there is a problem that it is difficult to quickly identify the microorganisms.

Therefore, in recent years, a method of identifying a microorganism based on a mass spectrum pattern obtained by mass spectrometry of a test microorganism has been increasingly used. According to the mass spectrometry, analytical results can be obtained in a short time using a trace amount of a microorganism sample, and continuous analysis of multiple specimens is easily carried out, so that simple and quick microorganism identification is possible. In this method, a solution containing proteins extracted from a test microorganism, a suspension of a test microorganism or the like is analyzed by a mass spectrometer using a soft ionization method such as MALDI-MS (matrix assisted laser desorption ionization mass spectrometry). Note that the "soft" ionization method is an ionization method that hardly causes decomposition of a high-molecular weight compound. Then, the test microorganism is identified by comparing the obtained mass spectrum pattern with mass spectrum patterns of known microorganisms that have been involved in advance in a database in large numbers. Such a method is called a fingerprint method because a mass spectrum pattern is used as information (that is, a fingerprint) specific to each microorganism.

However, in the identification of microorganisms by the fingerprint method using mass spectrometry, it is possible to identify at the genus level or a relatively distant species level, but discrimination between closely related species and identification at the level of subspecies, pathogenic types, strains or the like as a classification level lower than the species are normally considered to be difficult. Further, in the fingerprint method, it is not determined from which protein each peak appearing on the mass spectra originates, leaving a problem of the theoretical basis of identification and reliability. Therefore, in order to solve the problem, utilizing the fact that about half of peaks obtained by mass spectrometry of microbial cells is derived from ribosomal proteins, a method of attributing the type of protein from which a peak is derived by associating a mass-to-charge ratio of the peak obtained by mass spectrometry with a calculated mass estimated from the amino acid sequence obtained by translating base sequence information of ribosomal protein genes have been developed (see Patent Literatures 2 and 3). According to this method, it is possible to perform microorganism identification with high reliability based on the theoretical basis by using mass spectrometry.

However, since peaks with different mass-to-charge ratios differ depending on the classification level of microorganisms (family, genus, species, subspecies, pathogenic type, serotype, strain, etc.), for example, in order to perform discrimination reproducibly at the pathogenic type or strain level, it is necessary to select marker peaks that can be used for discrimination at the pathogenic type or strain level to be identified. For example, as marker proteins for identifying and discriminating *Pseudomonas putida* and its analogous cells, 23 ribosomal subunit proteins (L5, L13, L14, L15, L18, L19, L20, L22, L23, L24, L28, L30, L35, L36, S7, S8, S10, S13, S14, S17, S19, S20, and S21) are available (Patent Literature 2).

CITATION LIST

Patent Literature

Patent Literature 1: JP 2006-191922 A
Patent Literature 2: JP 2007-316063 A
Patent Literature 3: JP 2013-085517 A

Non Patent Literature

Non Patent Literature 1: List of prokaryotic names with standing in nomenclature, [searched on Sep. 18, 2015], Internet <URL: http://www.bacterio.net/>
Non Patent Literature 2: BMC Genomics 2010, 11, 688
Non Patent Literature 3: JMM Case Reports, 2014, DOI 10.1099/jmmcr.0.003103
Non Patent Literature 4: Microbes Infect 2007, 9, 1236-1243
Non Patent Literature 5: Int J med Microbiol, 2011, 301, 79-96
Non Patent Literature 6: Appl Environ Microbiol, 2008, 74, 7629-7642
Non Patent Literature 7: Int J Food Microbiol 2001, 65:55-62
Non Patent Literature 8: J Clin Microbiol 2003, 41:757-762
Non Patent Literature 9: PLoS Pathog 2008, 4: e1000146
Non Patent Literature 10: Vet Microbiol, 2003, 92, 351-362.
Non Patent Literature 11: Appl Environ Micribiol, 2008, 74, 5402-5407
Non Patent Literature 12: J Clin Microbiol. 2012, 50, 2702-2707
Non Patent Literature 13: Int J Food Microbiol. 2015, 202, 1-9
Non Patent Literature 14: J Clin Microbiol. 2014, 52, 2371-2379
Non Patent Literature 15: J Clin Microbiol. 2004, 42, 3819-3822

SUMMARY OF INVENTION

Technical Problem

Incidentally, *Listeria monocytogenes* (hereinafter, "*Listeria*" is abbreviated as "*L.*") is known as one causative bacterium for food poisoning. *Listeria monocytogenes* is a bacterium belonging to the genus *Listeria* of gram-positive bacteria and has characteristics such as growth ability at low temperature (4° C.) and salt tolerance.

In the genus *Listeria*, 18 bacterial species have been discovered so far (Non Patent Literature 1) and numerous findings particularly about 8 species discovered in the 1960's and 1980's (*Listeria monocytogenes* (*L. monocytogenes*), *Listeria innocua* (*L. innocua*), *Listeria welshimeri* (*L. welshimeri*), *Listeria seeligeri* (*L. seeligeri*), *Listeria ivanovii* (*L. ivanovii*), *Listeria grayi* (*L. grayi*), *Listeria marthii* (*L. marthii*), and *Listeria rocourtiae* (*L. rocourtiae*)) have been reported as conventional species (Non Patent Literatures 2 and 3). According to such findings, *Listeria monocytogenes* and *Listeria ivanovii* have pathogenicity to animals and, in particular, *Listeria monocytogenes* has been reported to infect humans frequently via familiar uncooked ready-to-eat foods such as meat, dairy products, vegetables, etc., causing outbreaks of food poisoning. In addition, when pregnant women, newborns, elderly persons, and immunity deficient persons such as patients suffering from AIDS or cancer, and organ transplant patients are infected with *Listeria monocytogenes*, severe symptomatic listeriosis such as sepsis or meningitis is caused, which may lead to death. Further, in recent years, examples have also been reported in which *Listeria innocua* infected patients develop listeriosis (Non Patent Literature 3).

*Listeria monocytogenes* is known to have 13 serotypes (1/2a, 1/2b, 1/2c, 3a, 3b, 3c, 4a, 4ab, 4b, 4c, 4d, 4e, and 7), serotype 4b is the most common in epidemic outbreak cases, and serotype 1/2b and serotype 1/2a have been reported to be included (Non Patent Literature 4). In addition, *Listeria monocytogenes* can be genetically classified into four evolutionary lineages (lineages I, II, III, and IV) (Non Patent Literature 5). Serotypes frequently isolated from infected individuals belong to lineages I and II, and more specifically, serotypes 1/2b, 3b, 4b, 4d, and 4e belong to the lineage I and serotypes 1/2a, 1/2c, 3a, and 3c belong to the lineage II. On the other hand, serotypes 4a and 4c belong to the lineage III. The lineage IV is a recently proposed classification, and it has been reported that serotypes 4a, 4b, and 4c may belong to IV (Non Patent Literature 6). The lineages III and IV are less isolated from humans and are mainly detected from ruminants.

For this reason, among *Listeria* bacteria, *Listeria monocytogenes* need to be managed in the food field and the medical field as food poisoning bacteria harming humans, and development of a rapid detection method and an identification and discrimination technology has been desired.

Heretofore, as a method for discriminating serotypes of the genus *Listeria* and *Listeria monocytogenes*, pulse field gel electrophoresis (Non Patent Literature 7), multi-locus sequence typing method (Non Patent Literatures 8 and 9), microarray method (Non Patent Literature 10) and the like have been reported. However, each of these methods poses a problem that complicated operations are needed and a time is required.

Meanwhile, in the clinical field and the food field, a microorganism identification technology using matrix-assisted laser desorption/ionization time-of-flight mass spectrometry (MALDI-TOF MS) has been rapidly spreading in recent years. This is a method of identifying a microorganism based on a mass spectrum pattern obtained using a trace amount of a microorganism sample, and an analysis result can be obtained in a short time. In addition, continuous analysis of multiple specimens is easily carried out, so that simple and quick microorganism identification is possible.

For this reason, it has been attempted to discriminate *Listeria* bacteria using MALDI-TOF MS by a plurality of research groups (Non Patent Literatures 11 to 14). For example, Non Patent Literature 10 reports that *Listeria monocytogenes, Listeria innocua, Listeria welshimeri, Listeria ivanovii,* and *Listeria seeligeri* have been discriminated by pattern matching of all detected mass peaks with existing databases and calculating their scores. In addition, serotype 4a and serotype 4c of *Listeria monocytogenes* are distinguished by the fact that specific mass peaks (mass-to-charge ratios [m/z] 5590 and 11179) are detected as indexes (biomarkers).

On the other hand, according to Non Patent Literature 12, it is possible to identify species of *Listeria grayi* only, with 6 bacterial species of the genus *Listeria* being discriminated at the genus level. In Non Patent Literature 14, it has been reported that *Listeria monocytogenes* is classified into groups of serotype 1/2a, serotype 1/2b, and serotype 4b by using peaks of five detection masses (m/z 5594.85, 6184.39, 11871.31, 5601.21, 11199.33) as biomarkers.

As described above, although there are a plurality of reports on discrimination of bacterial species of *Listeria* bacteria and the serotype of *Listeria monocytogenes* by MALDI-TOF MS, from which protein each peak appearing on the mass spectra or each biomarker peak originates is not determined, lacking in the theoretical basis of identification and discrimination as well as reliability. In addition, the results of identification and discrimination are different from research group to research group, and unified views have not yet been obtained. In other words, a highly reliable marker protein that can be suitably used for discrimination of bacterial species and serotype of *Listeria* bacteria has not yet been established.

The present invention has been made in view of the above points, and an object of the present invention is to select a marker protein capable of reproducibly and quickly discriminating a bacterial species of the genus *Listeria* and to provide a method for discriminating a microorganism using the marker protein.

Solution to Problem

As a result of diligent discussion, the present inventors have found that *Listeria* bacteria can be discriminated by using at least one of 17 ribosomal proteins L3, L4, L23, L2, L24, L6, L18, S5, L15, S13, S11, L10, L21, L13, S9, L31, S16 as a marker protein for discriminating *Listeria* bacteria contained in a sample by mass spectrometry, and that *Listeria* bacteria can be discriminated reproducibly and quickly in particular by using at least one of 8 ribosomal proteins L24, L6, L18, L15, S11, S9, L31, S16 among these 17 ribosomal proteins.

That is, a method for discriminating a microorganism according to the present invention, which has been made to solve the above problem, includes:

a) a step of subjecting a sample containing a microorganism to mass spectrometry to obtain a mass spectrum;

b) a reading step of reading a mass-to-charge ratio m/z of a peak derived from a marker protein from the mass spectrum; and c) a discrimination step of discriminating which bacterial species of *Listeria* bacteria the microorganism contained in the sample contains based on the mass-to-charge ratio m/z, wherein at least one of 17 ribosomal proteins L3, L4, L23, L2, L24, L6, L18, S5, L15, S13, S11, L10, L21, L13, S9, L31, S16 is used as the marker protein.

Particularly in the method for discriminating a microorganism, it is preferable to use at least one of 8 ribosomal proteins L24, L6, L18, L15, S9, L31, S16 among the 17 ribosomal proteins.

The method for discriminating a microorganism is suitable as a method for discriminating one of *Listeria monocytogenes* (*L. monocytogenes*), *Listeria innocua* (*L. innocua*), *Listeria welshimeri* (*L. welshimeri*), *Listeria seeligeri* (*L. seeligeri*), *Listeria ivanovii* (*L. ivanovii*), *Listeria grayi* (*L. grayi*), and *Listeria rocourtiae* (*L. rocourtiae*) as a bacterial species of the *Listeria* bacteria.

Specifically, the discrimination step discriminates whether or not *Listeria monocytogenes* is contained in the microorganism based on at least a mass-to-charge ratio m/z of a peak derived from each of the ribosomal proteins L15, S11, and S9, or a mass-to-charge ratio m/z of a peak derived from each of the ribosomal proteins L24, L6, L18, and S9, or a mass-to-charge ratio m/z of a peak derived from each of the ribosomal proteins S11, S9, L31, and S16, or a mass-to-charge ratio m/z of a peak derived from each of the ribosomal proteins L18, S9, L31, and S16, or a mass-to-charge ratios m/z of a peak derived from each of the ribosomal proteins L18, L15, and S9, or a mass-to-charge ratio m/z of a peak derived from each of the ribosomal proteins L24, L6, S11, and S9.

When the microorganism is discriminated as containing *Listeria monocytogenes*, the discrimination step further discriminates a lineage of *Listeria monocytogenes* based on a mass-to-charge ratio m/z of a peak derived from the ribosomal protein S9 and a mass-to-charge ratio m/z of a peak derived from at least one of the ribosomal proteins L24 and L6.

The discrimination step discriminates whether or not *Listeria innocua* is contained in the microorganism based on at least a mass-to-charge ratio m/z of a peak derived from the ribosomal protein S16 or a mass-to-charge ratio m/z of a peak derived from each of the ribosomal proteins L15 and L31. Then, when the microorganism is discriminated as containing *Listeria innocua*, the discrimination step further determines a strain of *Listeria innocua* based on at least a mass-to-charge ratio m/z of a peak derived from the ribosomal protein L18.

In addition, the discrimination step discriminates whether or not a strain of a group similar to a type strain (reference strain) of *Listeria innocua* in pattern of a mass-to-charge ratio of a ribosomal protein is contained in the microorganism based on at least a mass-to-charge ratio m/z of a peak derived from each of the ribosomal proteins L18 and S16, or a mass-to-charge ratios m/z of a peak derived from each of the ribosomal proteins L18 and L31.

Further, the discrimination step classifies a strain contained in the microorganism into a group similar to a type strain of *Listeria innocua* in pattern of a mass-to-charge ratio of a ribosomal protein or a non-similar group based on at least a mass-to-charge ratio m/z of a peak derived from each of the ribosomal proteins L18 and S16 or a mass-to-charge ratio m/z of a peak derived from each of the ribosomal proteins L18 and L31.

Also, the discrimination step discriminates whether or not *Listeria ivanovii* is contained in the microorganism based on at least a mass-to-charge ratio m/z of a peak derived from the ribosomal proteins S9 and L31.

Further, when the microorganism is discriminated as containing *Listeria ivanovii*, the discrimination step further discriminates a subspecies of *Listeria ivanovii* based on at least one of a mass-to-charge ratio m/z of a peak derived from the ribosomal protein L18 and a mass-to-charge ratio m/z of a peak derived from the ribosomal protein L15.

Then, the discrimination step discriminates whether or not *Listeria ivanovii ivanovii* (*L. ivanovii ivanovii*) as a subspecies of *Listeria ivanovii* is contained in the microorganism based on at least a mass-to-charge ratio m/z of a peak derived from the ribosomal protein L15 or a mass-to-charge ratio m/z of a peak derived from each of the ribosomal proteins L18 and L31, and discriminates whether or not *Listeria ivanovii londiniensis* (*L. ivanovii londiniensis*) as a subspecies of *Listeria ivanovii* is contained in the microorganism based on at least a mass-to-charge ratio m/z of a peak derived from each of the ribosomal proteins L18, S9, and L31, or a mass-to-charge ratio m/z of a peak derived from each of the ribosomal proteins L15, S11, and L31, or a mass-to-charge ratio m/z of a peak derived from each of the ribosomal proteins L15, S9, and L31, or a mass-to-charge ratio m/z of a peak derived from each of the ribosomal proteins L18, S11, and L31.

Further, the discrimination step discriminates whether or not *Listeria seeligeri* is contained in the microorganism based on a mass-to-charge ratio m/z of a peak derived from the ribosomal protein S9 and a mass-to-charge ratio m/z of a peak derived from at least one of the ribosomal proteins L18 and S11.

When the microorganism is discriminated as containing *L. seeligeri*, the discrimination step further determines a strain of *L. seeligeri* based on at least the mass-to-charge ratio m/z of a peak derived from the ribosomal protein S9.

The discrimination step discriminates whether or not a strain of a group similar to a type strain of *Listeria seeligeri* in pattern of a mass-to-charge ratio of a ribosomal protein is contained in the microorganism based on at least a mass-to-charge ratio m/z of a peak derived from the ribosomal protein S9 and a mass-to-charge ratio m/z of a peak derived from at least one of the ribosomal proteins L24, L18, L15, S11, and L31.

The discrimination step classifies a strain contained in the microorganism into a group similar to a type strain of *Listeria seeligeri* in pattern of a mass-to-charge ratio of a ribosomal protein or a non-similar group based on at least a mass-to-charge ratios m/z of a peak derived from each of the ribosomal proteins S9 and L18 or a mass-to-charge ratio m/z of a peak derived from each of the ribosomal proteins S9 and S1.

Further, the discrimination step discriminates whether or not *Listeria welshimeri* is contained in the microorganism based on at least a mass-to-charge ratio m/z of a peak derived from the ribosomal protein S11 or a mass-to-charge ratio m/z of a peak derived from each of the ribosomal proteins L18 and S9.

In addition, the discrimination step discriminates whether the bacterial species of the *Listeria* bacteria contained in the microorganism is *Listeria grayi* or *Listeria rocourtiae* based on a mass-to-charge ratio m/z of a peak derived from at least one of the ribosomal proteins L6, L15, S11, S9, L31, and S16.

Also, in the above method for discriminating a microorganism according to the present invention, the discrimination step may discriminate which bacterial species of *Listeria* bacteria the microorganism contained in the sample contains using a cluster analysis in which at least a mass-to-charge ratio m/z of a peak of each of the ribosomal proteins L24, L18, S9, and L31 and a mass-to-charge ratio m/z of a peak of one of the ribosomal proteins L6, L15, and S11, or a mass-to-charge ratio m/z, of a peak of each of the ribosomal proteins L24, L18, S9, and S16 and a mass-to-charge ratio m/z of a peak of one of the ribosomal proteins L6, L15, and S11 are used as indexes, and in particular, if the cluster analysis in which all of the mass-to-charge ratios m/z of peaks derived from 8 marker proteins (L24, L18, S9, L31, S16, L6, L15, S11) are used as indexes, it is possible to accurately discriminate which bacterial species of *Listeria* bacteria the microorganism contained in the sample is.

In this case, it is preferable to further include a step of creating a dendrogram representing a discrimination result by the cluster analysis.

Advantageous Effects of Invention

In the method for discriminating a microorganism according to the present invention described above, a ribosomal protein having a mutation peculiar to a bacterial species of the genus *Listeria* is used as a marker protein, and therefore, the bacterial species of the genus *Listeria* can be reproducibly and quickly discriminated.

By using a ribosomal protein having a mutation peculiar to a bacterial species of the genus *Listeria* as a marker protein and carrying out cluster analysis using a mass-to-charge ratio m/z of a peak derived from the marker protein on the mass spectra as an index, the bacteria of the genus *Listeria* contained in a plurality of samples can be collectively discriminated.

BRIEF DESCRIPTION OF DRAWINGS

FIG. 3 is a diagram showing a list of bacterial species names and strain names of the genus *Listeria* used in Example.

FIG. 4 is a diagram showing a list of primers used in Example. In particular, FIG. 4 shows catggcggat gttcaggtaa (SEQ ID NO: 305), ctccttccag aataacgggt (SEQ ID NO: 306), agcagcacaa aacgtggtac (SEQ ID NO: 307), aaggaggact aacgaatgcc (SEQ ID NO: 308), tgcacgcaac ttacaaggca (SEQ ID NO: 309), cggacgcaat aaccaaggta (SEQ ID NO: 310), aatgaacccg aacgatcacc (SEQ ID NO: 311), tacaagcgca aaagccgttg (SEQ ID NO: 312), gtgcagctaa ccgtgtgaat (SEQ ID NO: 313), aggcggaact gaagttgcat (SEQ ID NO: 314), acccgttatt ctggaaggag (SEQ ID NO: 315), aaggcattac acc-catggca (SEQ ID NO: 316), ctcgtccatt gtctgcaact (SEQ ID NO: 317), caaacgtaat gctamttgac cc (SEQ ID NO: 318), cgtggtaact atacgttggg t (SEQ ID NO: 319), gactggcgaa cgtgtaatca (SEQ ID NO: 320), tcctgcaaac acwcaagtga tt (SEQ ID NO: 321), ggagggacat attacatgcc tg (SEQ ID NO: 322), ttaatcggac gccctcaa (SEQ ID NO: 323), ctctaccaaa cgcgatgttc (SEQ ID NO: 324), ggaaacacag agctagacaa gg (SEQ ID NO: 325), cctgacacgc ggaagaatta (SEQ ID NO: 326), aaggcccgtc caaaacagta (SEQ ID NO: 327), cagcgatgat gccaagtatg (SEQ ID NO: 328), gaagcagttt cacttggagc (SEQ ID NO: 329), aactggctga ccttggctta (SEQ ID NO: 330), cccctgtgat ggcgagtctt (SEQ ID NO: 331), tcttctcgca taa-catcgac ttgaa (SEQ ID NO: 332), tgaaggattt aagtgagtgc atgt (SEQ ID NO: 333), cgcatcgctt gtttcatatc t (SEQ ID NO: 334), ttcgggagct aatttgtttc aa (SEQ ID NO: 335), aacgttttca gaactgaggt gc (SEQ ID NO: 336), cacatatcga cactggagac tttg (SEQ ID NO: 337), ctggaatcaa agtcgaccca (SEQ ID NO: 338), gcagcagtta cgccaaattc tt (SEQ ID NO: 339), tgtttataata tytatactgt gtgtaaaagc (SEQ ID NO: 340), and tgagaccgta yttttgttg aagc (SEQ ID NO: 341).

FIG. 5 is a diagram showing the mass of each amino acid.

FIG. 6 is a diagram showing a list of theoretical mass values of respective proteins in a *Listeria monocytogenes* strain used in Example.

FIG. 7A is a diagram showing a list of attribution of actual easurement values of respective ribosomal proteins in the strain used in Example.

FIG. 7B is a diagram showing the relationship between the attribution number in FIG. 7A and the theoretical mass value of each ribosomal protein.

FIG. 8 is a diagram showing a list of theoretical mass values of respective proteins in a species of the genus *Listeria* used in Example.

FIG. 10 is an analysis result based on SARAMIS.

FIGS. 11A-1 and 11A-2 show a peak chart obtained by MALDI-TOF MS measurement (part 1).

FIGS. 11B-1 and 11B-2 is a peak chart obtained by MALDI-TOF MS measurement (part 2).

FIG. 12A is an attribution result by actual measurement values of 8 ribosomal proteins.

FIG. 12B is a table showing the relationship between the attribution number shown in FIG. 12A and the theoretical mass value.

DESCRIPTION OF EMBODIMENTS

Hereinafter, a specific embodiment of a method for discriminating a microorganism according to the present invention will be described.

Figure 1:
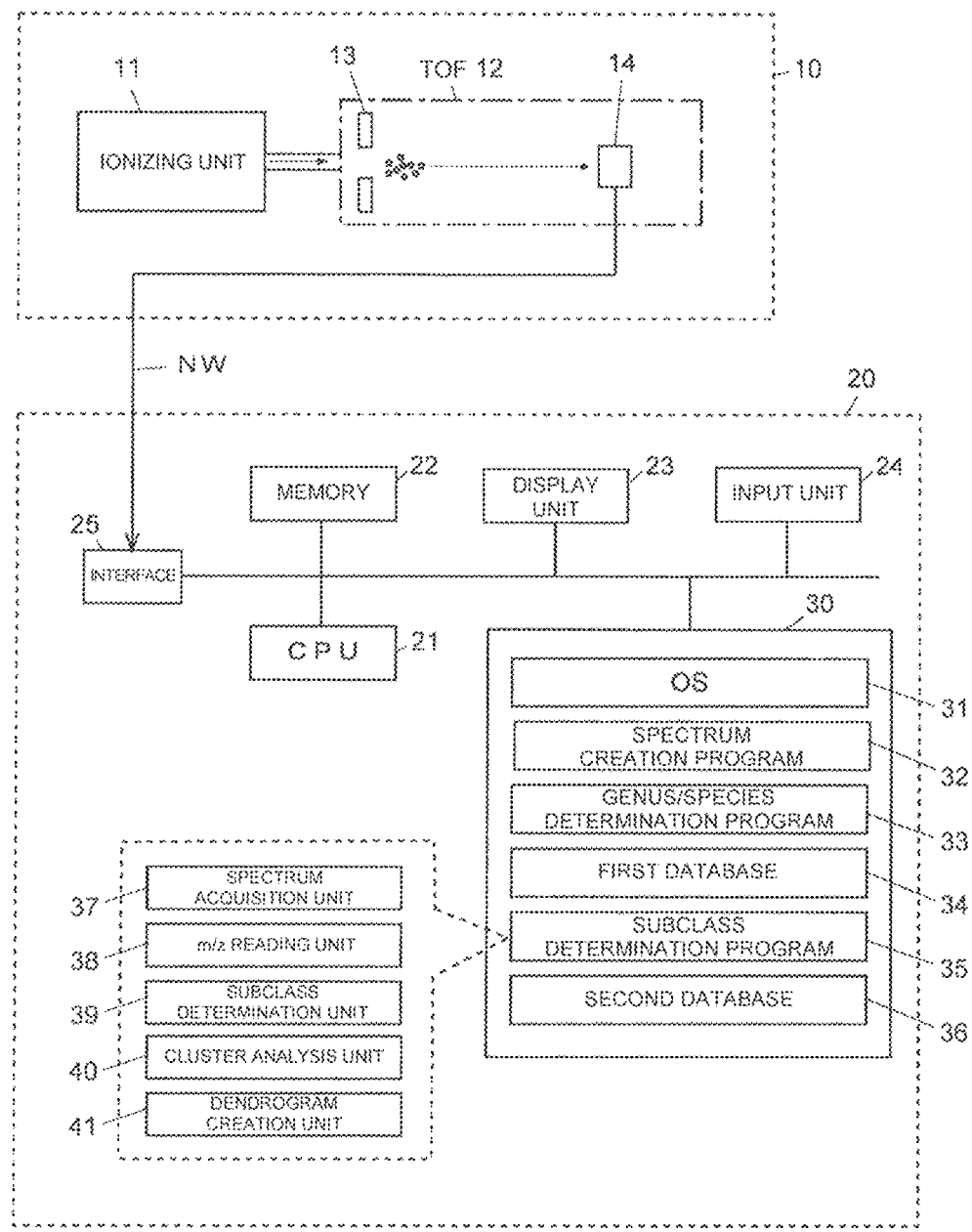
FIG. 1 is a block diagram showing principal units of a microorganism discrimination system used in a method for discriminating a microorganism according to the present invention.

FIG. 1 is an overall view of a microorganism discrimination system used by the method for discriminating a microorganism according to the present invention. The microorganism discrimination system is roughly made up of a mass spectrometry unit 10 and a microorganism determination unit 20. The mass spectrometry unit 10 includes an ionization unit 11 that ionizes molecules and atoms in a sample by a matrix-assisted laser desorption ionization (MALDI) method and a time-of-flight mass separator (TOF) 12 that separates various ions emitted from the ionization unit 11 in accordance with the mass-to-charge ratio.

The TOF 12 includes an extraction electrode 13 that extracts ions from the ionization unit 11 to guide the ions into an ion flight space in the TOF 12 and a detector 14 that detects ions mass-separated in the ion flight space.

The substance of the microorganism determination unit 20 is a computer such as a workstation or a personal computer, and a central processing unit (CPU) 21 as a central processing unit, a memory 22, a display unit 23 including a liquid crystal display (LCD), an input unit 24 including a keyboard, a mouse and the like, and a storage unit 30 including a mass storage device such as a hard disk and a solid state drive (SSD) are connected to each other. An operating system (OS) 31, a spectrum creation program 32, a genus/species determination program 33, and a subclass determination program 35 (program according to the present invention) are stored in the storage unit 30 and also, a first database 34 and a second database 36 are stored. The microorganism determination unit 20 further includes an interface (I/F) 25 to control direct connection with an external device and connection via a network such as a Local Area Network (LAN) with an external device or the like and is connected to the mass spectrometry unit 10 from the interface 25 via a network cable NW (or wireless LAN).

In FIG. 1, a spectrum acquisition unit 37, an m/z reading unit 38, a subclass determination unit 39, a cluster analysis unit 40, and the dendrogram (lineage diagram) creation unit 41 are shown as relating to the subclass determination program 35. Basically, these units are functional means implemented by software by the subclass determination program 35 being executed by the CPU 21. The subclass determination program 35 is not necessarily a single program, but may be a function incorporated into a portion of a program for controlling the genus/species determination program 33 or the mass spectrometry unit 10 and its form is not particularly limited. As the genus/species determination program 33, for example, a program for performing microorganism identification by a conventional fingerprint method or the like can be used.

Also, in FIG. 1, the spectrum creation program 32, the genus/species determination program 33, the subclass determination program 35, the first database 34, and the second database 36 are mounted on the terminal operated by the user, but at least a portion or all of these units may be provided in another device connected to the terminal via a computer network so that processing by a program and/or access to a database provided in the other device is performed according to instructions from the terminal.

A large number of mass lists related to known microorganisms are registered in the first database 34 of the storage unit 30. These mass lists enumerate the mass-to-charge ratios of ions detected upon mass spectrometry of a certain microorganism cell and include, in addition to the information of the mass-to-charge ratios, at least information (classification information) of the classification group to which the microbial cell belongs (family, genus, species, etc.). Such mass lists are desirably created based on data (actual measurement data) obtained by actual mass spectrometry of various microbial cells in advance by the same ionization method and mass separation method as those by the mass spectrometry unit 10.

When creating a mass list from the actual measurement data, a peak appearing in a predetermined mass-to-charge ratio range is first extracted from the mass spectrum acquired as the actual measurement data. At this point, by setting the mass-to-charge ratio range to about 2,000 to 35,000, protein-derived peaks can be mainly extracted. Also, by extracting only peaks whose peak height (relative intensity) is equal to or greater than a predetermined threshold, undesirable peaks (noise) can be excluded. Since the ribosomal protein group is expressed in a large amount in the cell, most of the mass-to-charge ratios listed in the mass list can be derived from the ribosomal proteins by setting the threshold appropriately. Then, the mass-to-charge ratios (m/z) of the peaks extracted in the above manner are listed for each cell and registered in the first database 34 after adding the classification information and the like. In order to suppress variations in gene expression due to culture conditions, it is desirable to standardize culture conditions in advance for each microbial cell used for collecting actual measurement data.

Information about marker proteins to discriminate known microorganisms at a level lower than the classification level discriminable by the genus/species determination program 33 is registered in the second database 36 of the storage unit 30. That is, information about marker proteins to discriminate the classification subordinate to the genus (species, subspecies, pathogenic type, serotype, strain, etc.) when the genus/species determination program 33 can discriminate the genus of a known microorganism and to discriminate the classification subordinate to the species (subspecies, pathogenic type, serotype, strain, etc.) when the species of a known microorganism can be discriminated is registered. Information about the marker protein includes at least information about the mass-to-charge ratio (m/z) of the marker protein in the known microorganism. In the second database 36 according to the present embodiment, as information about marker proteins to discriminate which of 7 species (*Listeria monocytogenes* (*L. monocytogenes*), *Listeria innocua* (*L. innocua*), *Listeria ivanovii* (*L. ivanovii*), *Listeria seeligeri* (*L. seeligeri*), *Listeria welshimeri* (*L. welshimeri*), *Listeria rocourtiae* (*L. rocourtiae*), and *Listeria grayi* (*L. grayi*)) of the genus *Listeria* the test microorganism is, mass-to-charge ratio values of at least 8 ribosomal proteins, the mass-to-charge ratio value of L24 (m/z 11180.22, 11194.25, 11254.35, 11558.65), the mass-to-charge ratio value of L6 (m/z 19270.04, 19256.01, 19097.81, 19371.01), the mass-to-charge ratio value of L18 (m/z 13096.86, 13110.89, 13082.84, 13066.84), the mass-to-charge ratio value of L15 (m/z 15782.02, 15797.08, 15811.1, 15743.01, 15601.77), the mass-to-charge ratio value of S11 (m/z 13655.65, 13674.66, 13683.67, 13591.66, 13591.67), the mass-to-charge ratio value of S9+Ac (m/z 14283.40, 14359.50, 14302.45, 14372.55, 14330.55), the mass-to-charge ratio value of L31 type B (m/z 9259.36, 9290.34, 9271.3, 9327.44), and the mass-to-charge ratio value of S16 (m/z 10234.94, 10252.97, 10003.54, 10230.88) are stored. The subclass determination program 35 uses at least one of these 8 ribosomal proteins to discriminate which of the 7 bacterial species of *Listeria* genus is the test microorganism.

Specifically, based on at least the mass-to-charge ratio m/z of a peak derived from each of the ribosomal proteins L15, S11, and S9, or the mass-to-charge ratio m/z of a peak derived from each of the ribosomal proteins L24, L6, L18, and S9, or the mass-to-charge ratio m/z of a peak derived from each of the ribosomal proteins S11, S9, L31, and S16, or the mass-to-charge ratio m/z of a peak derived from each of the ribosomal proteins L18, S9, L31, and S16, or the mass-to-charge ratio m/z of a peak derived from each of the ribosomal proteins L18, L15, and S9, or the mass-to-charge ratio m/z of a peak derived from each of the ribosomal proteins L24, L6, S11, and S9, whether or not *Listeria monocytogenes* is contained in the test microorganism is discriminated.

Also, based on at least the mass-to-charge ratio m/z of a peak derived from the ribosomal protein S16 or the mass-to-charge ratio m/z of a peak derived from each of the ribosomal proteins L15 and L31, whether or not *Listeria innocua* is contained in the test microorganism is discriminated.

Further, based on the mass-to-charge ratio m/z of a peak derived from the ribosomal proteins S9 and L31, whether or not *Listeria ivanovii* is contained in the test microorganism is discriminated.

Further, based on the mass-to-charge ratio m/z of a peak derived from the ribosomal protein S9 and the mass-to-charge ratio m/z of a peak derived from at least one of the ribosomal proteins L18 and S11, whether or not *Listeria seeligeri*, is contained in the test microorganism is discriminated.

Further, based on at least the mass-to-charge ratio m/z of a peak derived from the ribosomal protein S11 or the mass-to-charge ratios m/z of a peak derived from each of the ribosomal proteins L18 and S9, whether or not *Listeria welshimeri* is contained in the test microorganism is discriminated.

As described above, the above 8 ribosomal proteins can be used as marker proteins to discriminate the bacterial species of the genus *Listeria* alone or as a combination of a plurality of ribosomal proteins and therefore, the value of the mass-to-charge ratio is stored in the second database 36 together with information about the bacterial species.

When discriminated that *Listeria monocytogenes* is contained in the test microorganism, based on the mass-to-charge ratio m/z of a peak derived from the ribosomal protein S9 and the mass-to-charge ratio m/z of a peak derived from at least one of the ribosomal proteins L24 and L6, the lineage of *Listeria monocytogenes* can be discriminated. Thus, the ribosomal proteins S9, L24, and L6 can also be used as marker proteins to discriminate *Listeria monocytogenes* lineage (Lineage), and the ribosomal proteins L24, L18, L15, S11, S9, and L31 can also be used as marker proteins to discriminate the serotype of *Listeria monocytogenes*. Therefore, the values of the mass-to-charge ratio of these ribosomal proteins are also stored in the second database 36 as information about the marker proteins for discriminating the lineage and serotype of *Listeria monocytogenes*.

In addition, when discriminated that *Listeria innocua* is contained in the test microorganism, the strain of the *innocua* can be determined based on at least the mass-to-charge ratio m/z of a peak derived from the ribosomal protein L18.

Further, based on at least the mass-to-charge ratios m/z of a peak derived from each of the ribosomal proteins L18 and S16, or the mass-to-charge ratios m/z of a peak derived from each of the ribosomal proteins L18 and L31, whether or not a strain (for example, *Listeria innocua* ATCC33090T (*L. innocua* ATCC33090T)) as a group similar to the type strain (reference strain) of *Listeria innocua* in pattern of the mass-to-charge ratio of the ribosomal protein is contained in the microorganism can be discriminated.

Further, based on at least the mass-to-charge ratio m/z of a peak derived from each of the ribosomal proteins L18 and S16, or the mass-to-charge ratio m/z of a peak derived from each of the ribosomal proteins L18 and L31, the strains contained in the microorganism can be classified into a group similar to the type strain of *Listeria innocua* in pattern of the mass-to-charge ratio of the ribosomal protein and a non-similar group.

Therefore, the values of the mass-to-charge ratios of these ribosomal proteins L18, S16, and L31 are also stored in the second database 36 as information about the marker proteins for discriminating the strain of *Listeria innocua*.

In addition, when discriminated that *Listeria ivanovii* is contained in the test microorganism, based on at least one of the mass-to-charge ratio m/z of a peak derived from the ribosomal protein L18 and the mass-to-charge ratio m/z of a peak derived from the ribosomal protein L15, the subspecies of *Listeria ivanovii* can be discriminated.

Further, based on at least the mass-to-charge ratio m/z of a peak derived from the ribosomal protein L15 or the mass-to-charge ratio m/z of a peak derived from each of the ribosomal proteins L18 and L31, whether or not *Listeria ivanovii ivanovii* (*L. ivanovii ivanovii*) as a subspecies of *Listeria ivanovii* is contained in the test microorganism can be discriminated.

Further, based on at least the mass-to-charge ratio m/z of a peak derived from each of the ribosomal proteins L18, S9, and L31, or the mass-to-charge ratio m/z of a peak derived from each of the ribosomal proteins L15, S11, and L31, or the mass-to-charge ratio m/z of a peak derived from each of the ribosomal proteins L15, S9, and L31, or the mass-to-charge ratio m/z of a peak derived from each of the ribosomal proteins L18, S11, and L31, whether or not *Listeria ivanovii londiniensis* (*L. ivanovii londiniensis*) as a subspecies of *Listeria ivanovii* is contained in the test microorganism can be discriminated.

Therefore, the values of the mass-to-charge ratios of the ribosomal proteins L18, S9, L31, L15, and S11 are also stored in the second database 36 as information about the marker proteins for discriminating the subspecies of *Listeria ivanovii*.

Also, based on the mass-to-charge ratio m/z of a peak derived from at least one of the ribosomal proteins L6, L15, S11, S9, L31, and S16, whether the bacterial species of *Listeria* bacteria contained in the test microorganism is *Listeria grayi* or *Listeria rocourtiae* can be discriminated.

Therefore, the values of the mass-to-charge ratios of the ribosomal proteins L6, L15, S11, S9, L31, and S16 are stored in the second database 36 as information about the marker proteins for discriminating *Listeria grayi* or *Listeria rocourtiae*.

The fact that the 8 ribosomal proteins described above can be used for discrimination of bacterial species of the genus *Listeria*, discrimination of lineage and serotype of *Listeria monocytogenes*, determination of strains of *Listeria innocua* and grouping of strains, and discrimination of subspecies of *Listeria ivanovii* and the like is derived from the result of determining the mass-to-charge ratios of 8 ribosomal proteins for each bacterial species or each strain of the genus *Listeria* and attributing the mass-to-charge ratios of 8 ribosomal proteins of each bacterial species or each strain. For example, with respect to *Listeria innocua*, ribosomal proteins useful for grouping the strains are selected by comparing the mass-to-charge ratios of 8 ribosomal proteins of *Listeria innocua* ATCC33090T (*L. innocua* ATCC33090T) as the type strain and the mass-to-charge ratios of 8 ribosomal proteins of *Listeria innocua* GTC02960 (*L. innocua* GTC02960), which is not the type strain (for details, refer to Examples to be described below, FIG. 8 showing the theoretical mass values of 8 ribosomal proteins, FIG. 12A showing the attribution results based on actual measurement values of 8 ribosomal proteins, and the like)).

The value of the mass-to-charge ratio of the marker proteins stored in the second database 36 is desirably selected by comparing the calculated mass obtained by translating the base sequence of each marker protein into an amino acid sequence with the mass-to-charge ratio detected by actual measurement. The base sequence of the marker protein may be, in addition to determining by sequencing, acquired from a public database, for example, a database or the like of National Center for Biotechnology Information (NCBI) and used. When calculating the calculated mass from the amino acid sequence, it is desirable to consider cleavage of the N-terminal methionine residue as a post-translational modification. More specifically, when the penultimate amino acid residue is Gly, Ala, Ser, Pro, Val, Thr, or Cys, the theoretical value is calculated assuming that the N-terminal methionine is cleaved. In addition, molecules added with protons are actually observed by MALDI-TOF MS and thus, it is desirable to determine the calculated mass by factoring in protons (that is, the theoretical value of the mass-to-charge ratio of ions obtained when each protein is analyzed by MALDI-TOF MS).

Note that a portion or all of the information about the marker proteins stored in the second database 36 may also be stored in the first database 34.

Figures 1, 11A:
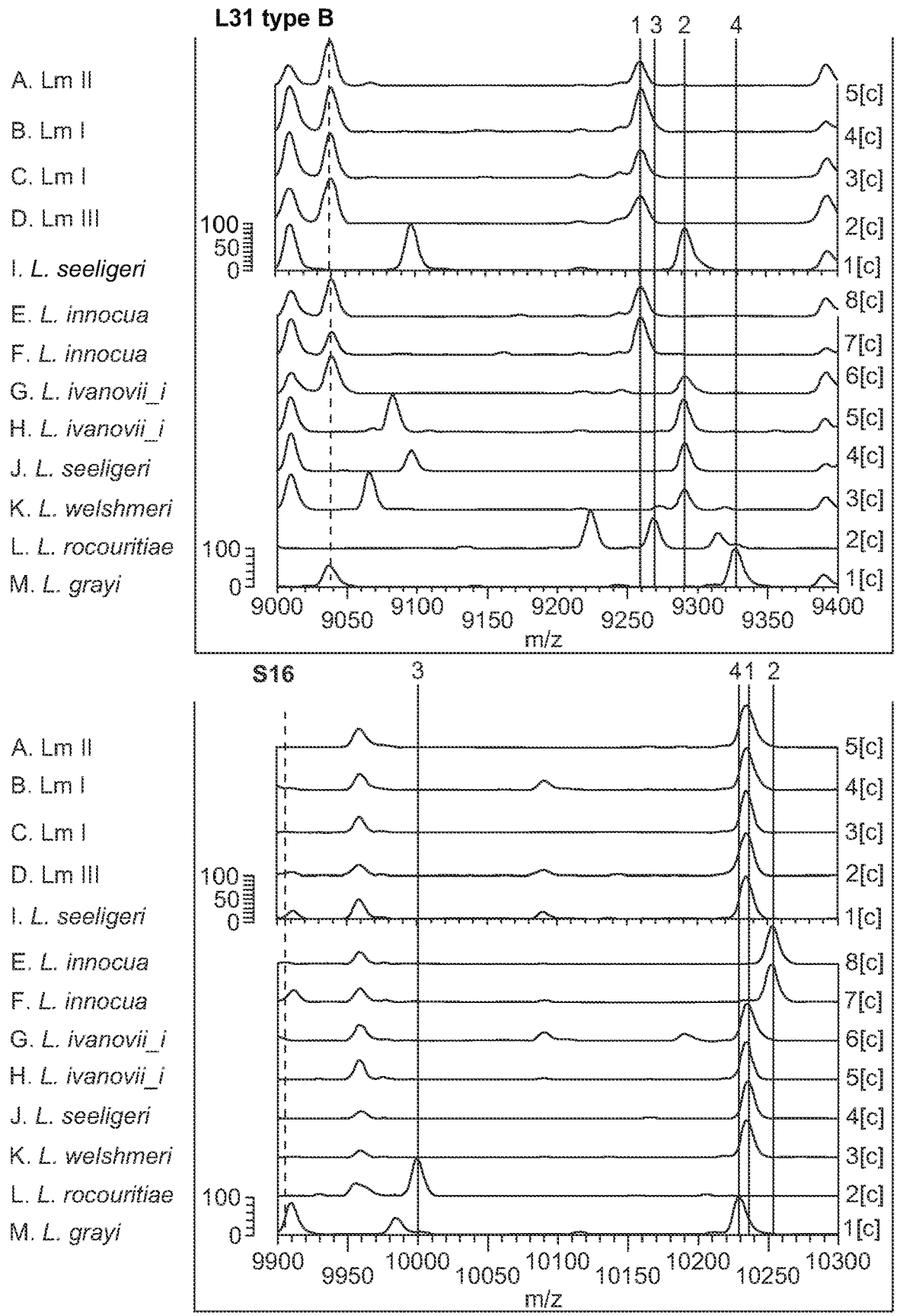
Figures 2, 11A:
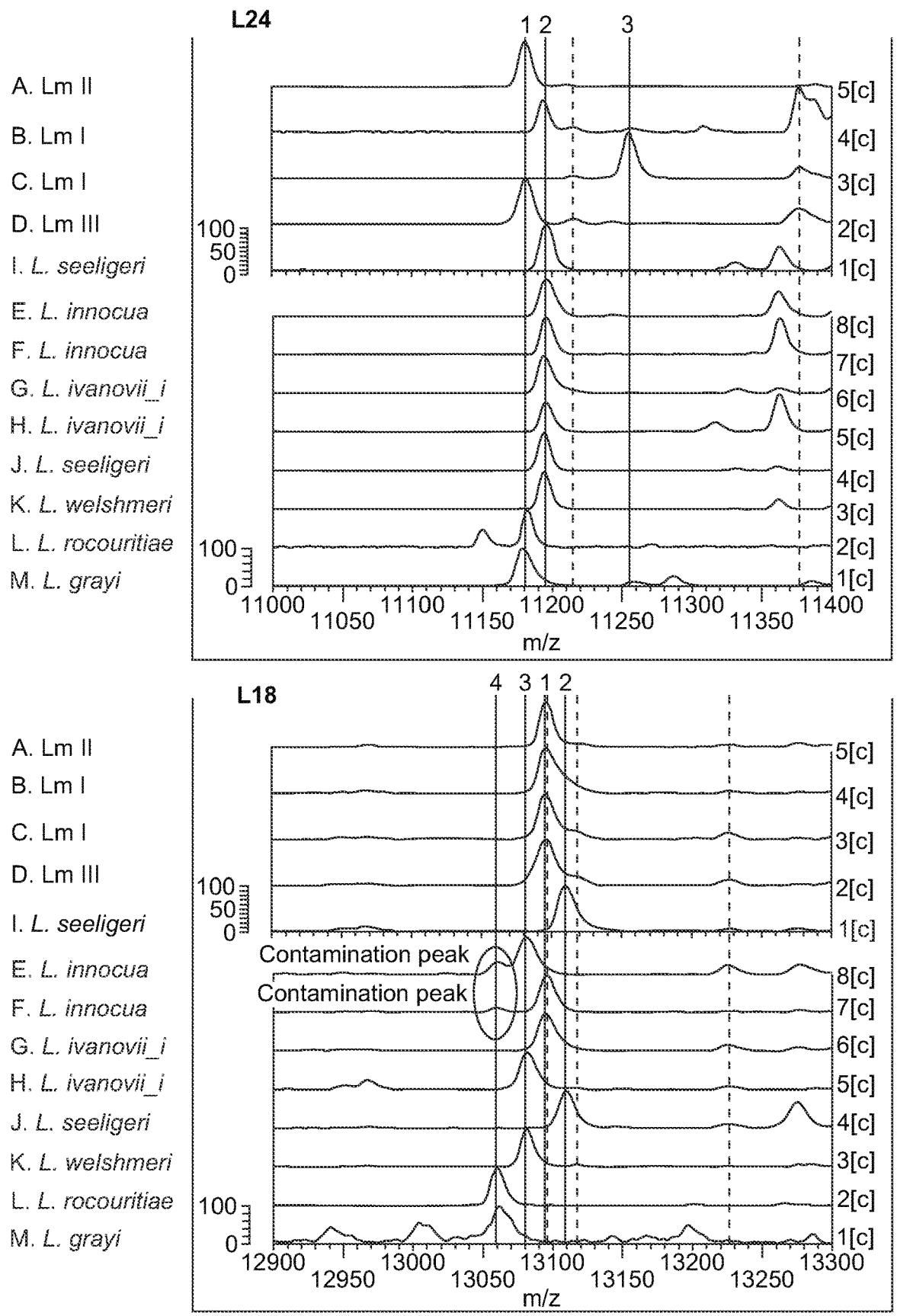
Figure 11B:
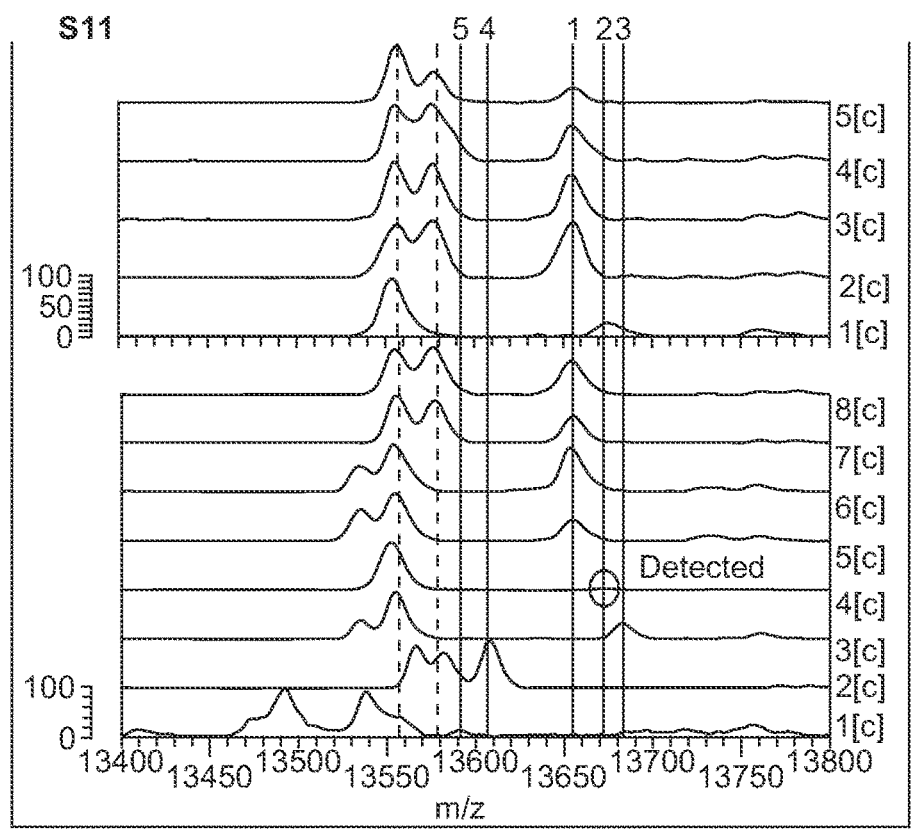
Figure 1:
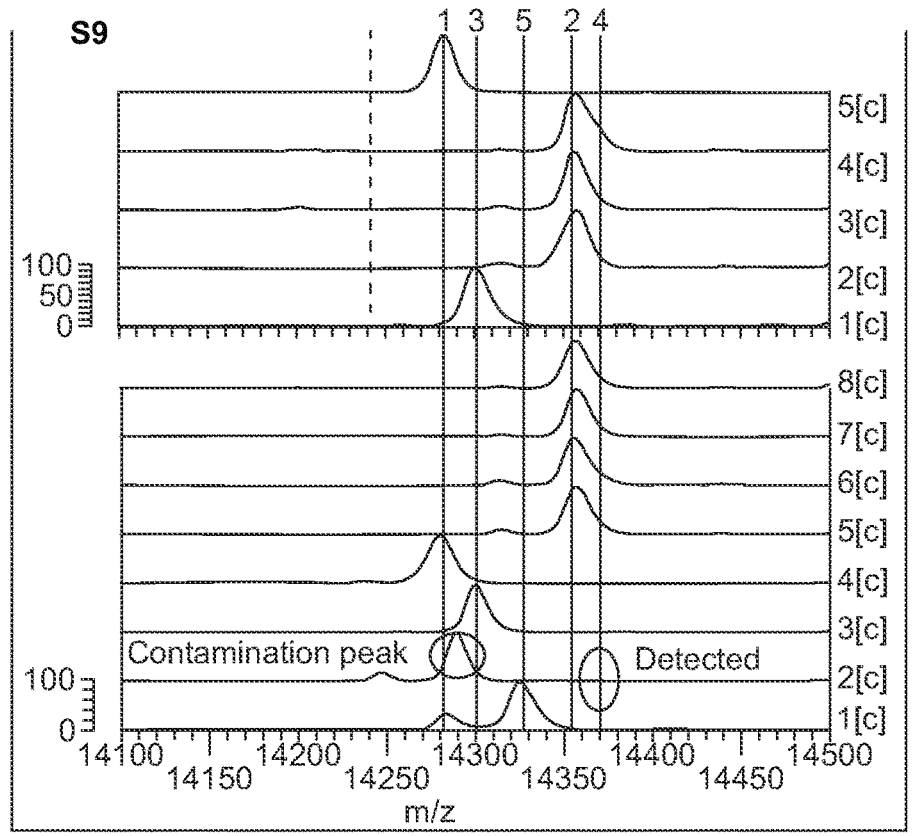
Figure 11B:
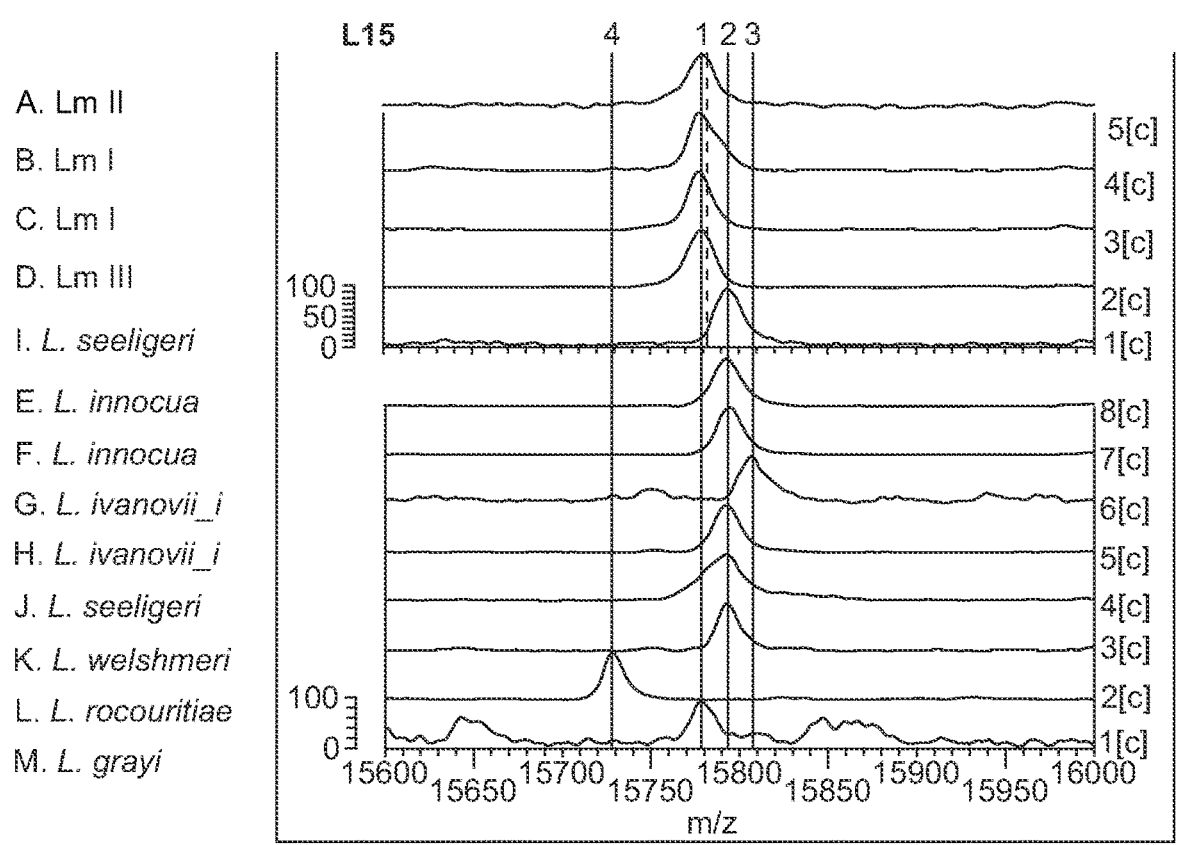
Figure 2:
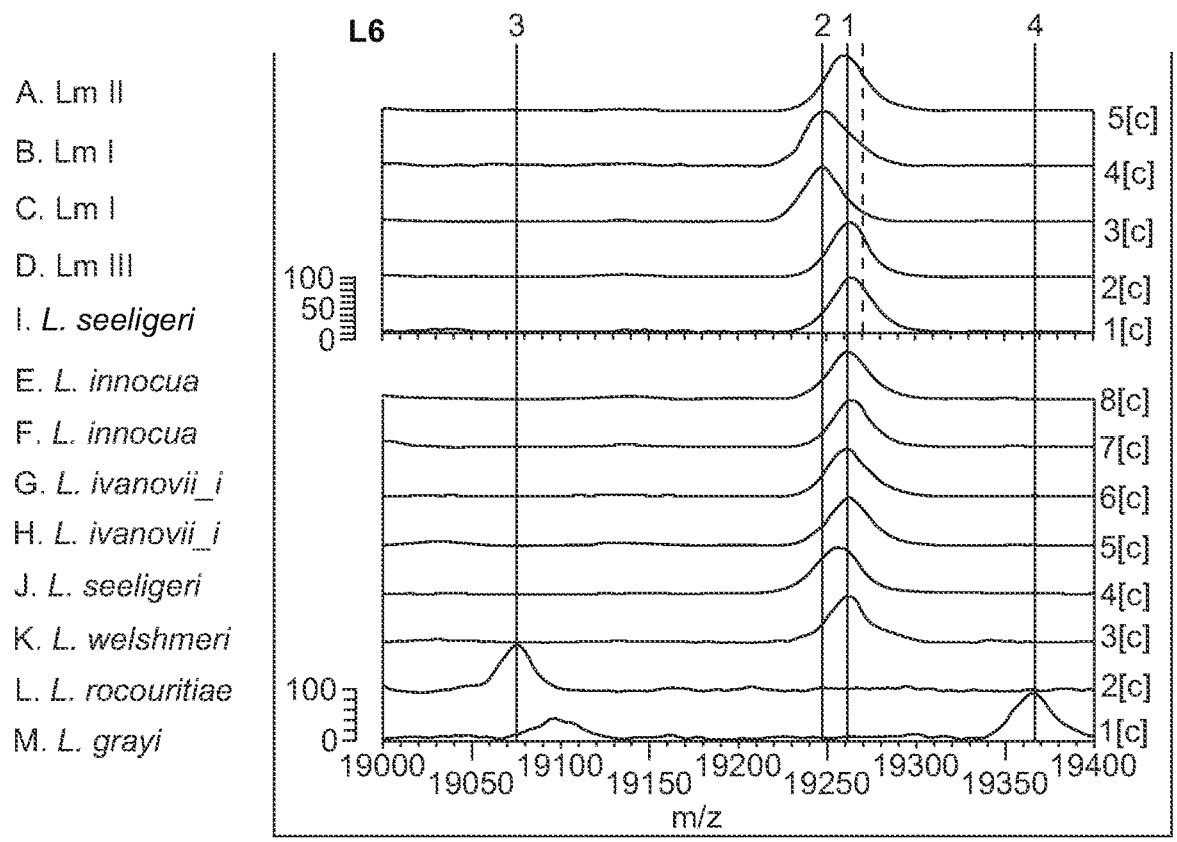
FIG. 2 is a flowchart showing an example of a procedure for the method for discriminating a microorganism according to the present invention.

The discrimination procedure of bacterial species of the genus *Listeria* using a microorganism discrimination system according to the present embodiment will be described with reference to the flowchart shown in FIG. 2.

First, the user prepares a sample containing constituent components of a test microorganism and sets the sample to the mass spectrometry unit 10 to perform mass spectrometry. At this point, in addition to a cell extract or a cellular component such as a ribosomal protein purified from a cell extract, bacterial cells or a cell suspension may be used as it is.

The spectrum creation program 32 acquires a detection signal obtained from the detector 14 of the mass spectrometry unit 10 via the interface 25 and creates a mass spectrum of the test microorganism based on the detection signal (step S101).

Next, the genus/species determination program 33 checks the mass spectrum of the test microorganism against a mass list of known microorganisms recorded in the first database 34 and extracts a mass list of known microorganisms having a mass-to-charge ratio pattern similar to the mass spectrum of the test microorganism, for example, a mass list including peaks that coincide with each peak in the mass spectrum of the test microorganism within a predetermined error range (step S102). Subsequently, the genus/species determination program 33 refers to the classification information stored in the first database 34 in association with the mass list extracted in step S102, thereby determining the classification (genus or species) of the known microorganism corresponding to the mass list (step S103). If the test microorganism is not bacteria belonging to the genus *Listeria*, or the test microorganism is a bacterium belonging to the genus *Listeria* and the bacterial species thereof is determined (No in step S104), the classification is output the display unit 23 as a classification of the test microorganism (step S112) before the discrimination processing is terminated. On the other hand, if the species is a bacterium belonging to the genus *Listeria* and the bacterial species thereof is unknown (Yes in step S104), then the processing proceeds to the discrimination processing by the subclass determination program 35. If it is determined in advance that the sample contains *Listeria* bacteria by other methods, the processing may proceed to the subclass determination program 35 without using the genus/species determination program using a mass spectrum.

In the subclass determination program 35, first the subclass determination unit 39 reads the mass-to-charge ratio values of the 8 ribosomal proteins L24, L6, L18, L15, S11, S9+Ac, L31 type B, and S16 as marker proteins from the second database 36 (step S105). Subsequently, the spectrum acquisition unit 37 acquires the mass spectrum of the test microorganism created in step S101. Then, the m/z reading unit 38 selects peaks appearing in the mass-to-charge ratio range stored in the second database 36 in association with each of the marker proteins on the mass spectrum as peaks corresponding to each of the marker proteins and reads the mass-to-charge ratios thereof (step S106). Then, the cluster analysis is performed using the read mass-to-charge ratio as an index. More specifically, the subclass determination unit 39 compares the mass-to-charge ratio with the value of the mass-to-charge ratio of each marker protein read out from the second database 36 and determines the attribution of the protein with respect to the read mass-to-charge ratio (Step S107). Then, the cluster analysis is performed based on the determined attribution to determine the species of the test microorganism (step S108), and the determined species is output to the display unit 23 as the discrimination result of the test microorganisms (step S109).

In the foregoing, an embodiment to carry out the present invention has been described above with reference to the drawings, but the present invention is not limited to the above embodiment and appropriate modifications are permitted within the scope of the spirit of the present invention.

For example, in the above embodiment, for convenience of description, to which species of the genus *Listeria* the test microorganism belongs is determined and then, the serotype and lineage of *Listeria monocytogenes* are discriminated, but the determination and the discrimination may be performed simultaneously. Also, the discrimination of serotypes and lineage of bacterial species of *Listeria monocytogenes* may be omitted.

EXAMPLE

Hereinafter, an experiment conducted to demonstrate the selection procedure of marker proteins in the present invention and the effect of the present invention will be described.
(1) Strains Used and Culture Medium In order to construct a protein mass database, 14 strains of *Listeria monocytogenes*, two strains of *Listeria innocua*, two strains of *Listeria ivanovii*, three strains of *Listeria seeligeri*, one strain of each of *Listeria welshimeri*, *Listeria grayi* (*L. grayi*, and *Listeria rocourtiae*, and so 24 strains in total were used (FIG. 3). These strains were obtained from National Bioresource Project (NBRP, Pathogenic Bacteria Department, Gifu University, Gifu city, Japan), American Type Culture Collection (ATCC, Rockville, Md., USA), Japan Collection of Microorganisms (JCM, RIKEN BioResource Center, Tsukuba City, Japan), National institute of Technology and Evaluation, Biological Resource Center (NBRC, Kisarazu City, Japan). For the cultivation, a Brain Heart Infusion liquid medium (Nippon Becton Dickinson Company, Ltd., Tokyo, Japan) or an agar medium was used. In addition, the serotype of *Listeria monocytogenes* shown in FIG. 3 was determined by the multiplex polymerase chain reaction (PCR) method (see Non Patent Literature 15) using the *Listeria* type immunity serum "*Listeria* Antisera" (DENKA SEIKEN Co., Ltd., Tokyo, Japan).
(2) Analysis of DNA The DNA sequence of the ribosomal protein encoded into the S10-spc-alpha operon and the ribosomal protein genes of biomarker candidates was sequenced by DNA sequencing with a primer designed based on the consensus sequence upstream and downstream of the target region of a genome sequencing strain. More specifically, the genomes were extracted from various strains of the genus *Listeria* shown in FIG. 3 by a conventional method, and the region of the ribosomal protein gene (up to 5 kbp) and the region of the biomarker proteins were amplified as a template thereof by the polymerase chain reaction (PCR) using KOD plus (Toyobo, Osaka, Japan) as high fidelity DNA polymerase. The obtained PCR product was purified and used as a template for DNA sequencing. DNA sequencing was performed using Big Dye ver. 3.1 Cycle Sequencing Kit (Applied Biosystems, Foster City. Calif.). The primers used for PCR and DNA sequencing are shown in FIG. 4.

Further, a mass-to-charge ratio of the ribosomal protein was calculated from the amino acid sequence obtained by translating the DNA base sequence of the ribosomal protein gene determined as described above and the mass of each amino acid shown in FIG. 5, and the mass-to-charge ratio was defined as the theoretical mass value.

(3) Measurement by MALDI-TOF MS

Bacterial cells were recovered from the Brain Heart Infusion liquid medium or agar medium, and about 3 colonies of bacterial cells were suspended in 0.5 mL of 70% ethanol. The suspension was centrifuged at 10,000 rpm for 2 minutes, and the obtained bacterial cell pellet was dried in a vacuum drier for 5 minutes to evaporate the ethanol. 10 μL of 35% formic acid was added to the dried pellet and stirred, which was obtained as an analysis sample. 1.5 μL of the analysis sample was added to 10 μL of a sinapinic acid matrix agent (solution containing 20 mg/mL sinapinic acid (Wako Pure Chemical Corporation, Osaka, Japan) in a solution of 50 v/v % acetonitrile and 1 v/v % trifluoroacetic acid) and sufficiently mixed. Then, 1.5 μL of the mixed solution was dropped on a sample plate and allowed to air dry. For the MALDI-TOF MS measurement, an AXIMA microorganism identification system (Shimadzu Corporation, Kyoto City, Japan) was used and the sample was measured in the positive linear mode and in the spectral range of 2000 m/z to 35000 m/z. The theoretical mass value calculated by the above method was matched with the measured mass-to-charge ratio with a tolerance of 500 ppm and appropriately corrected. For the calibration of the AXIMA microorganism identification system, the *Escherichia coli* DH5α strain was used.

(4) Construction of a Protein Mass Database for Discrimination of *Listeria monocytogenes*

Figure 6:
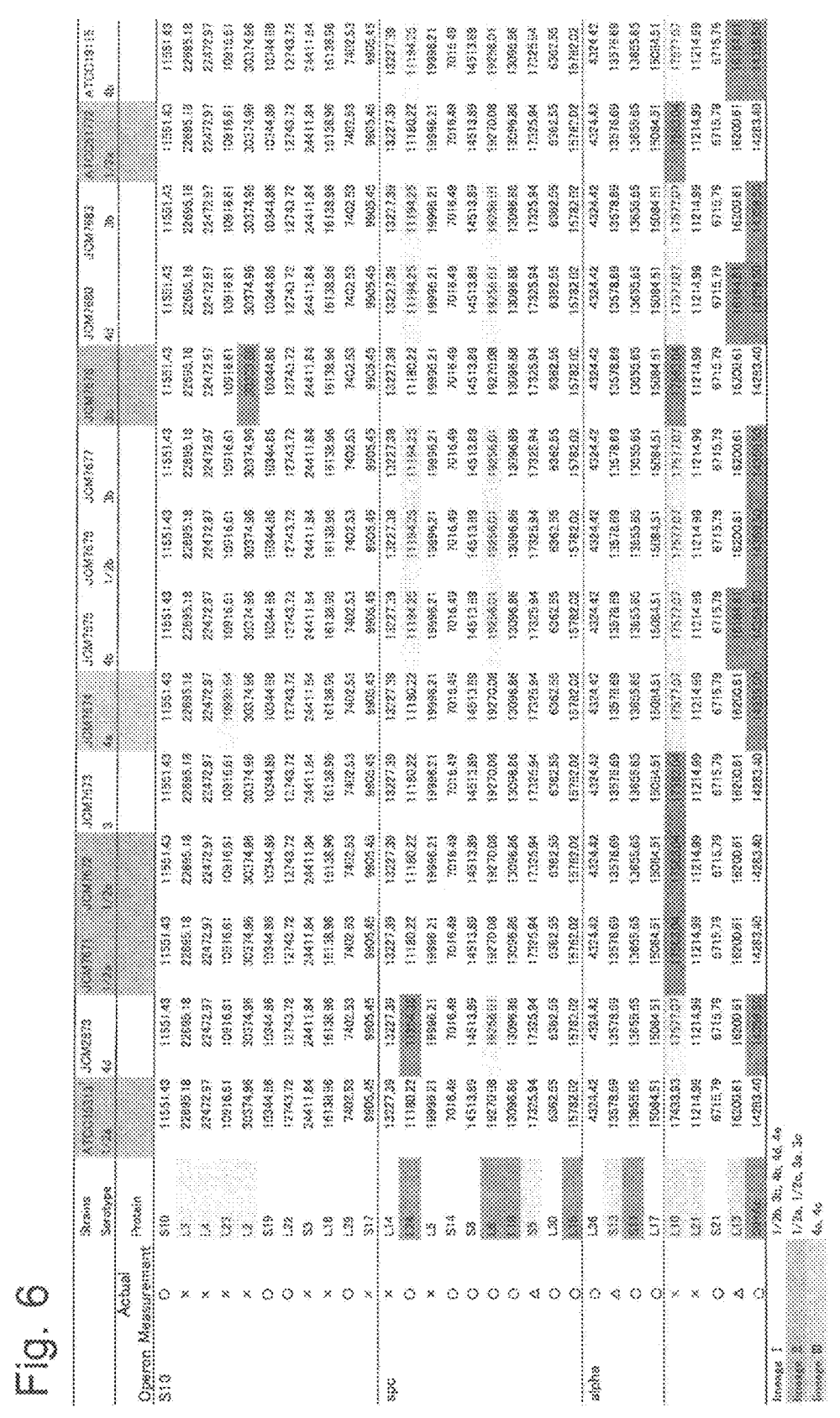

With respect to the above 14 strains of *Listeria monocytogenes*, the theoretical mass value of the ribosomal protein described above was checked against the peak chart obtained by MALDI-TOF MS measurement and regarding the ribosomal proteins that could be actually detected, it was confirmed that there was no difference between the theoretical mass value and the actual measurement value. Next, the ribosomal proteins encoded into the S10-spc-alpha operon and other ribosomal proteins of the biomarker candidates were examined for the relationship between *Listeria monocytogenes* strain or serotype and the mass-to-charge ratio. The result is shown in FIG. 6. Because the acetyl group (COCH$_3$) was found to be modified in the ribosomal protein S9, the mass value of (S9+Ac) to which the acetyl group was added to the mass value calculated from the DNA sequence of the gene was defined as the theoretical mass value.

FIG. 6 shows the theoretical mass values (mass-to-charge ratios (m/z)) of ribosomal proteins encoded into the S10-spc-alpha operon and other ribosomal proteins of the biomarker candidates for 14 strains of *Listeria monocytogenes*. Serotypes 1/2b, 3b, 4b, 4d, and 4e are classified into Lineage I, serotypes 1/2a, 1/2c, 3a, and 3c are classified into Lineage II, and serotype 4a is classified into lineage III. In addition, ○, ×, and Δ shown in FIG. 6 each indicate the results of peak processing under the default processing conditions (threshold offset: 0.015 mV, threshold response: 1.200) of the AXIMA microorganism identification system. That is, ○ indicates that the peak was detected within the tolerance of 500 ppm from the theoretical mass value, and × indicates that the peak was not detected in some cases. Also, Δ indicates that the peak was detected, but the difference from the theoretical mass value of other strains or other serotypes was small or the difference from the peak of other ribosomal proteins was within 500 ppm.

As can be seen from FIG. 6, the ribosomal proteins L3, L4, L23, L2, L24, L6, L18, S5, L15, S13, and S11 encoded into the S10-spc-alpha operon and the ribosomal proteins L10, L21, L13, and S9+Ac other than the operon, a total of 15, were found to have different theoretical mass values from other strains in some strains of *Listeria monocytogenes* used for the measurement. This suggested that these 15 ribosomal proteins are marker proteins that can be used to discriminate strains or serotypes of *Listeria monocytogenes*. The DNA base sequence in each strain of these 15 ribosomal proteins is shown in SEQ ID NO: 1 to 240 in the sequence listing. The outline of the sequence corresponding to each sequence number is as follows.

The DNA base sequences of 14 strains of *Listeria monocytogenes* (ATCC 15313T, JCM 2873, JCM 7671, JCM 7672, JCM 7673, JCM 7674, JCM 7675, JCM 7676, JCM 7677, JCM 7678, JCM 7680, JCM 7683, ATCC 51772, and ATCC 19115) and two strains of *Listeria seeligeri* (JCM 7679 and JCM 7682) are as follows.

SEQ ID NOs: 1 to 16: DNA base sequence of L3 in the above 16 strains.

SEQ ID NOs: 17 to 32: DNA base sequence of L4 in the above 16 strains.

SEQ ID NOs: 33 to 48: DNA base sequence of L23 in the above 16 strains.

SEQ ID NOs: 49 to 64: DNA base sequence of L2 in the above 16 strains.

SEQ ID NOs: 65 to 80: DNA base sequence of L24 in the above 16 strains.

SEQ ID NOs: 81 to 96: DNA sequence of L6 in the above 16 strains.

SEQ ID NOs: 97 to 112: DNA nucleotide sequence of L18 in the above 16 strains.

SEQ ID NOs: 113 to 128: the DNA nucleotide sequence of S5 in the above 16 strains.

SEQ ID NOs: 129 to 144: DNA base sequence of L15 in the above 16 strains.

SEQ ID NOs: 145 to 160: DNA base sequence of S13 in the above 16 strains.

SEQ ID NOs: 161 to 176: DNA base sequence of S11 in the above 16 strains.

SEQ ID NOs: 177 to 192: DNA base sequence of L10 in the above 16 strains.

SEQ ID NOs: 193 to 208: DNA base sequence of L21 in the above 16 strains.

SEQ ID NOs: 209 to 224: DNA nucleotide sequence of L13 in the above 16 strains.

SEQ ID NOs: 225 to 240: DNA sequence of S9 in the above 16 strains.

However, among the above 15 ribosomal proteins, L3, L4, L23, L2, L10, and L21 have one or more strains having a difference in theoretical mass value from other strains of 500 ppm or more and are considered as biomarker candidates to be used for discrimination of the strains, the peak shape was unclear or the peak intensity was insufficient and so it was not possible to detect the peak and therefore, these ribosomal proteins are considered to be inappropriate as stable biomarkers.

In addition, though ribosomal proteins S5 and L13 were able to detect peaks in MALDI-TOF MS measurement, the difference in theoretical mass value from other strains was 500 ppm or less, which makes the ribosomal proteins inappropriate as biomarkers. Further, S13 (m/z 13578.69 or 13552.65) overlaps with the peak of another ribosomal protein L20 (m/z 13552.08) and both peaks cannot be distinguished so S13 is still inappropriate as a biomarker.

On the other hand, 6 ribosomal proteins, L24, L6, L18, L15, S11, and S9+Ac, were detected in a stable manner regardless of the strain and the difference in theoretical mass value from other strains was 500 ppm or more and so were considered to be useful as biomarkers. Therefore, in the present embodiment, these 6 ribosomal proteins were used as biomarkers for discriminating the serotype or strain (or lineage) of *Listeria monocytogenes* in MALDI-TOF MS measurement.

(5) Construction of a Mass Database for Discrimination of the Genus *Listeria*

The 6 biomarkers L24, L6, L18, L15, S11, and S9+Ac, which have been shown to be useful for discriminating serotypes or strains of *Listeria monocytogenes*, were detected in a stable manner in all the strains of *Listeria monocytogenes* in MALDI-TOF MS measurement and thus, it was expected that the peaks of these proteins are likely to be detected in a stable manner in the same way even for samples of different species of the genus *Listeria*.

Thus, with respect to 10 strains of 6 species of *Listeria grayi, Listeria innocua, Listeria ivanovii, Listeria rocourtiae, Listeria seeligeri,* and *Listeria welshimeri* that were available from public distributors of the genus *Listeria*, the theoretical mass values of the 6 marker proteins were calculated by the method described above. As a result of MALDI-TOF MS measurement on these 10 strains, the peaks of the above 6 proteins were detected in a stable manner. In addition to the above 6 biomarkers, it was found that the ribosomal proteins L31 type B and S16 detected as distinct mass peaks showed characteristic peak masses depending on the species of the genus *Listeria*. Therefore, these two ribosomal proteins are also considered to be biomarkers that can be used to discriminate species of the genus *Listeria*, and a table of theoretical mass values for discrimination of species of the genus *Listeria* with respect to 8 ribosomal proteins newly including L31 type B (m/z 9259.36, 9290.34, 9327.44, or 9271.3) and S16 (m/z 10234.94, 10252.97, 10230.88, or 10003.54), in addition to the above 6 ribosomal proteins (L24, L6, L18, L15, S11, and S9), was created (FIG. 8). It is a matter of course that these 8 ribosomal proteins are biomarkers that can be used not only for discriminating species of the genus *Listeria*, but also for discriminating the serotype of *Listeria monocytogenes*.

The 56th amino acid of the ribosomal protein S11 of *Listeria grayi* has been specifically changed to lysine and further, in the result of MALDI-TOF MS measurement, the mass peak was observed at the position where the mass of the methyl group ($CH_3$) was added. From the above, the theoretical mass value was calculated assuming that S11 of *Listeria grayi* was methylated. Also, since S11 of *Listeria rocourtiae* (*L. rocourtiae* was observed to have a peak at a position larger than the theoretical mass value by about 17 in m/z, 17 was added to the theoretical mass value. Further, with respect to S16, theoretical values were calculated from the sequence information of genome-sequenced strains, and it was confirmed that the theoretical values are not different from the measured values of the strains actually measured this time. In addition, two patterns of DNA sequences were registered in S16 of *Listeria monocytogenes*, but the amino acid sequences matched.

The DNA base sequences of the above 8 ribosomal proteins determined in the above manner in 8 strains of 6 species are shown in SEQ ID NOs: 241 to 304 in the sequence listing. The outline of the sequence corresponding to each sequence number is as follows.

SEQ ID NOs: 241 to 248: DNA bae sequence of L24, L6, L18, L15, S11, S9+Ac, L31 type B, and S16 in the strain ATCC 33090T of *Listeria innocua*. The strain ATCC 33090T is the type strain (standard strain) of *Listeria innocua*.

SEQ ID NOs: 249 to 256: DNA base sequence of L24, L6, L18, L15, S11, S9+Ac, L31 type B, and S16 in the strain GTC02960 of *Listeria innocua*.

SEQ ID NOs: 257 to 264: DNA base sequence of L24, L6, L18, L15, S11, S9+Ac, L31 type B, and S16 in the strain JCM7681 of *Listeria ivanovii ivanovii*.

SEQ ID NOs: 265 to 272: DNA base sequence of L24, L6, L18, L15, S11, S9+Ac, L31 type B, and S16 in the strain ATCC44954 of *Listeria ivanovii londiniensis*.

SEQ ID NOs: 273 to 280: DNA base sequence of L24, L6, L18, L15, S11, S9+Ac, L31 type B, and S16 in the strain ATCC35967T of *Listeria seeligeri*.

SEQ ID NOs: 281 to 288: DNA base sequence of L24, L6, L18, L15, S11, S9+Ac, L31 type B, and S16 in the strain GTC02963 of *Listeria welshimeri*.

SEQ ID NOs: 289 to 296: DNA base sequence of L24, L6, L18, L15, S11, S9+Ac, L31 type B, and S16 in the strain GTC16429T of *Listeria rocourtiac*.

SEQ ID NOs: 297 to 304: DNA base sequence of L24, L6, L18, L15, S11, S9+Ac, L31 type B, and S16 in the strain ATCC19120T of *Listeria grayi*.

(6) Identification of Bacterial Species of the Genus *Listeria*

The mass pattern of the protein was analyzed by the fingerprint method using SARAMIS (trademark, Spectral Archive and Microbial Identification System), and it was confirmed that all the strains were bacteria of the genus *Listeria*. Subsequently, profile data was created by evaluating those having the mass-to-charge ratio of the peak on the mass spectrum of each strain matching the mass-to-charge ratio of a biomarker protein without mutation as "1", those that did not match as "2" to "5" (2 to 5 indicate mutually different mass-to-charge ratios), and those in which no peak corresponding to the biomarker protein was present as "0". This data was imported into PAST software (Natural History Museum, University of Oslo, Norway) and cluster-analyzed by the proximity coupling method using the Kimura algorithm. In addition, a phylogenetic tree (FIG. 13A) was created using FigTree ver. 1.4.0 software. As a result, as is clear from FIG. 13A, 7 bacterial species of the genus *Listeria* were correctly classified and further, *Listeria monocytogenes* was correctly classified for each lineage.

(7) Identification of the Strain or Serotype/Lineage of *Listeria monocytogenes*

By associating the mass-to-charge ratio of a peak obtained by MALDI-TOF MS measurement with the theoretical mass values of the above 6 ribosomal proteins, the attribution of the type of protein from which the peak was derived was analyzed to identify the strain of *Listeria monocytogenes*. For the analysis of attribution of protein types, software for discriminating bacteria was developed and used based on S10-GERMS (S10-spc-alpha operon Gene Encoded Ribosomal protein Mass Spectrum) method (see Patent Literature 3).

First, the above software was activated to register the theoretical mass value for each strain of the 6 ribosomal proteins L24, L6, L18, L15, S11, and S9+Ac (the value of the mass-to-charge ratio of the ribosomal protein L24 (m/z 11180.22, 11194.25. 11254.35), the value of the mass-to-charge ratio of the ribosomal protein L6 (m/z 19270.08 (19270.80), 19256.01), the value of the mass-to-charge ratio of the ribosomal protein L18 (m/z 13096.86, 13110.89), the value of the mass-to-charge ratio of the ribosomal protein L15 (m/z 15782.02, 15797.08), the value of the mass-to-charge ratio of the ribosomal protein S11 (m/z 13655.65, 13674.66), and the value of the mass-to-charge ratio of the ribosomal protein S9+Ac (m/z 14283.40, 14359.50, 14302.45)). Two theoretical mass values m/z 19270.08 and 19270.04 of L6 having a mass difference of 500 ppm or less were deemed not to be distinguishable from each other and so were registered as m/z 19270.08.

Next, mass spectrum data obtained by MALDI-TOF MS measurement was analyzed for each strain to examine Whether or not the peak corresponding to a biomarker was correctly attributed to the theoretical mass value of the registered biomarker. As a result, as shown in FIG. 7A, for all strains, peaks corresponding to all biomarkers were attributed to the theoretical mass values of the registered biomarkers. FIG. 7B shows the relationship between the mass-to-charge ratios of the 6 ribosomal proteins and the attribution numbers 1 to 3 shown in FIG. 7A. Attribution patterns were classified into groups A to D and checked against the serotypes of each strain and it turned out that strains of lineage II belong to group A, strains of lineage I belong to groups B, C, and strains of lineage III belong to group D.

From the above, it is verified that L24 (m/z 11180.22, 11194.25, 11254.35), L6 (m/z 19270.08, 19256.01), L18 (m/z 13096.86, 13110.89), L15 (m/z 15782.02, 15797.08, 15668.86), S11 (m/z 13655.65, 13674.66) and S9+Ac (m/z 14283.40, 14359.50, or 14302.45) are useful marker proteins for discrimination of the serotype and lineage of *Listeria monocytogenes* in MALDI-TOF MS measurement. In addition, accurate masses of these marker proteins were calculated from these genetic information and these marker proteins were also checked against actual measurement values and therefore, it became clear that a mass database with high reliability can be constructed.

Figure 9A:
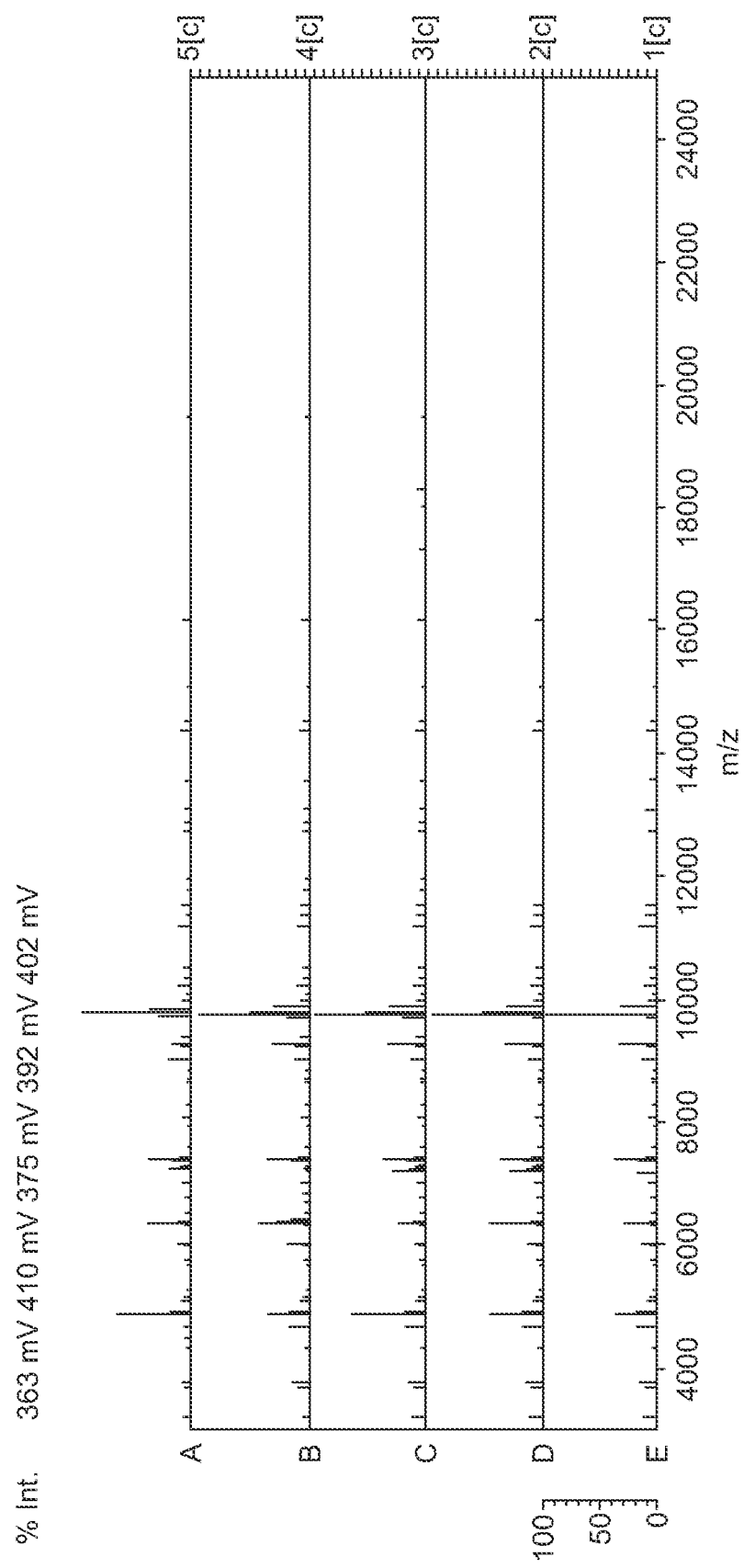
FIG. 9A is a chart obtained by MALDI-TOF MS measurement (part 1).
Figure 9B:
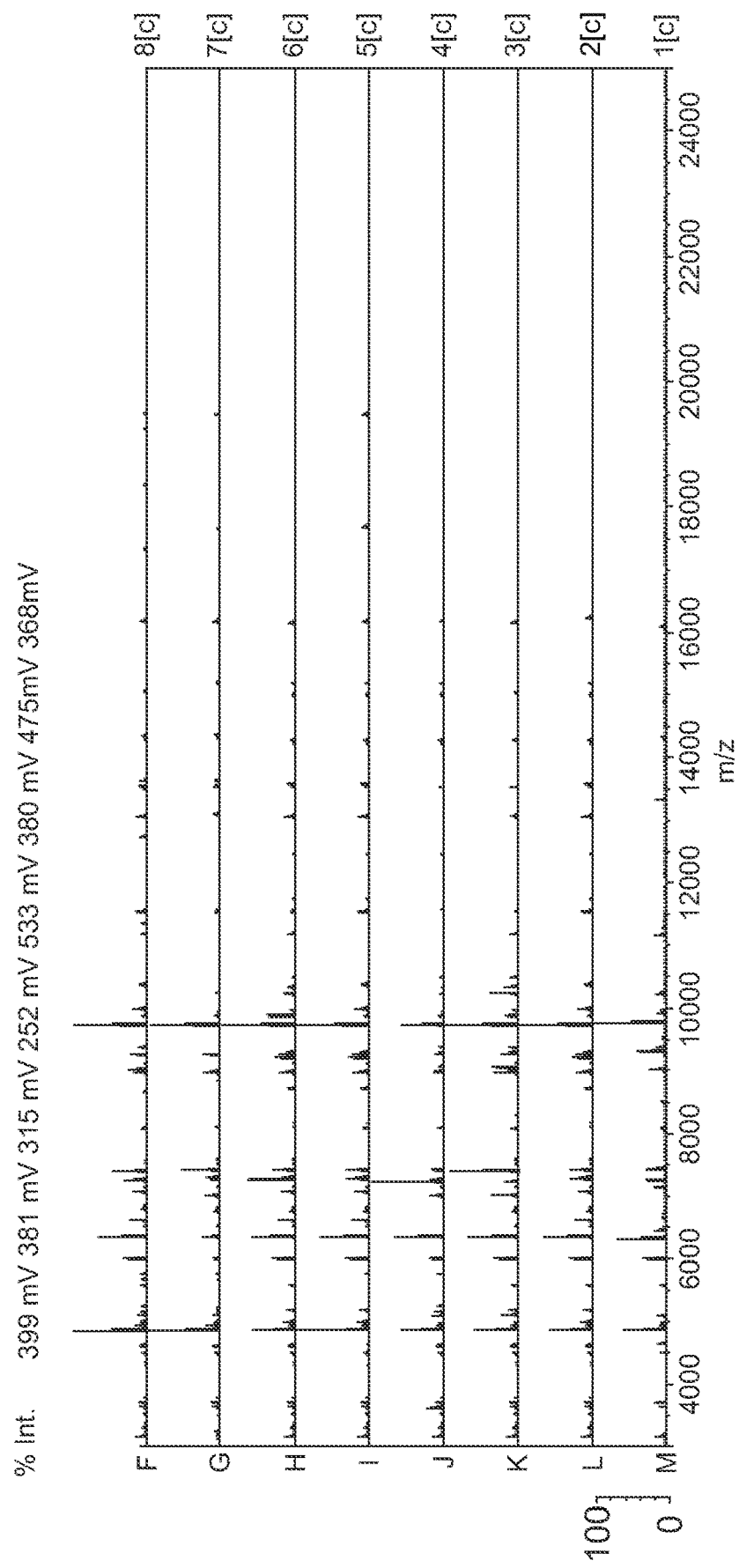
FIG. 9B is a chart obtained by MALDI-TOF MS measurement (part 2)

(8) Comparison of Discrimination Results using SARAMIS and Discrimination Results by Cluster Analysis The species of the genus *Listeria* was discriminated using SARAMIS and the species of the genus *Listeria* was discriminated by cluster analysis using the theoretical mass values of 8 ribosomal proteins shown in FIG. 8 as an index and the results were compared. FIGS. 9A and 9B show charts obtained by MALDI-TOF MS measurements. FIG. 9A is a chart of bacterial species or strains of groups A to E, and FIG. 9B is a chart of bacterial species or strains of groups F to M. When these charts were analyzed using SARAMIS, the discrimination result shown in FIG. 10 was obtained. As can be seen from FIG. 10, two strains of *Listeria innocua*, one strain of *Listeria ivanovii*, *Listeria seeligeri* ATCC 35967, and *Listeria welshimeri* were all discriminated as "*Listeria* sp." and their species could not be identified. The *Listeria ivanovii* JCM7681 strain and *Listeria seeligeri* JCM7679 and JCM7682 strains were misidentified as *L. monocytogenes*. For *Listeria seeligeri* JCM7679 and JCM7682 strains, a biochemical test and sequence analysis of 16S RNA were carried out so that *Listeria seeligeri* could be identified. *Listeria rocourtiae* was not identified as a species because the theoretical mass value corresponding to its mass peak was not stored in the database of SARAMIS. On the other hand, *Listeria grayi* was correctly identified up to the species level by SARAMIS. Because *Listeria grayi* is systematically distant from other *Listeria* bacteria, *Listeria grayi* is considered to have been identifiable by the existing fingerprint method.

Next, based on the database of theoretical mass values shown in FIG. 8, attempts were made to discriminate the species of the genus *Listeria*. For m/z 15797.08, 15797.03, and 15796.09 of L15 with a small difference in mass value, these mass-to-charge ratios are considered to be not discriminable by actual measurements and so were all attributed by regarding as having the theoretical mass value m/z 15797.08. FIGS. 11A-1, 11A-2, 11B-1 and 11B-2 are enlarged views of the biomarker peak portions of the charts of FIGS. 9A and 9B. As can be seen from FIGS. 11A-1, 11A-2, 11B-1 and 11B-2, the biomarker mass was shifted by the species of the genus *Listeria* and peaks could be distinguished.

When the actual measurement values of 8 ribosomal proteins were compared with the theoretical values and attributed, the results shown in FIG. 12A were obtained. FIG. 12B is a table showing the correspondence relationship between the attribution number of the biomarker and the theoretical mass value in FIG. 12A. Incidentally, the numerals 1 to 5 shown on the charts in FIGS. 11A-1, 11A-2, 11B-1 and 11B-2 represent the attribution number of each biomarker.

As can be seen from FIGS. 8 and 12A, for *Listeria rocourtiae* and *Listeria grayi*, a difference between the theoretical value and the actual measurement value was found in sonic ribosomal proteins, but for other bacterial species of the genus *Listeria*, a difference in mass value of the ribosomal proteins could be discriminated.

Figure 13A:
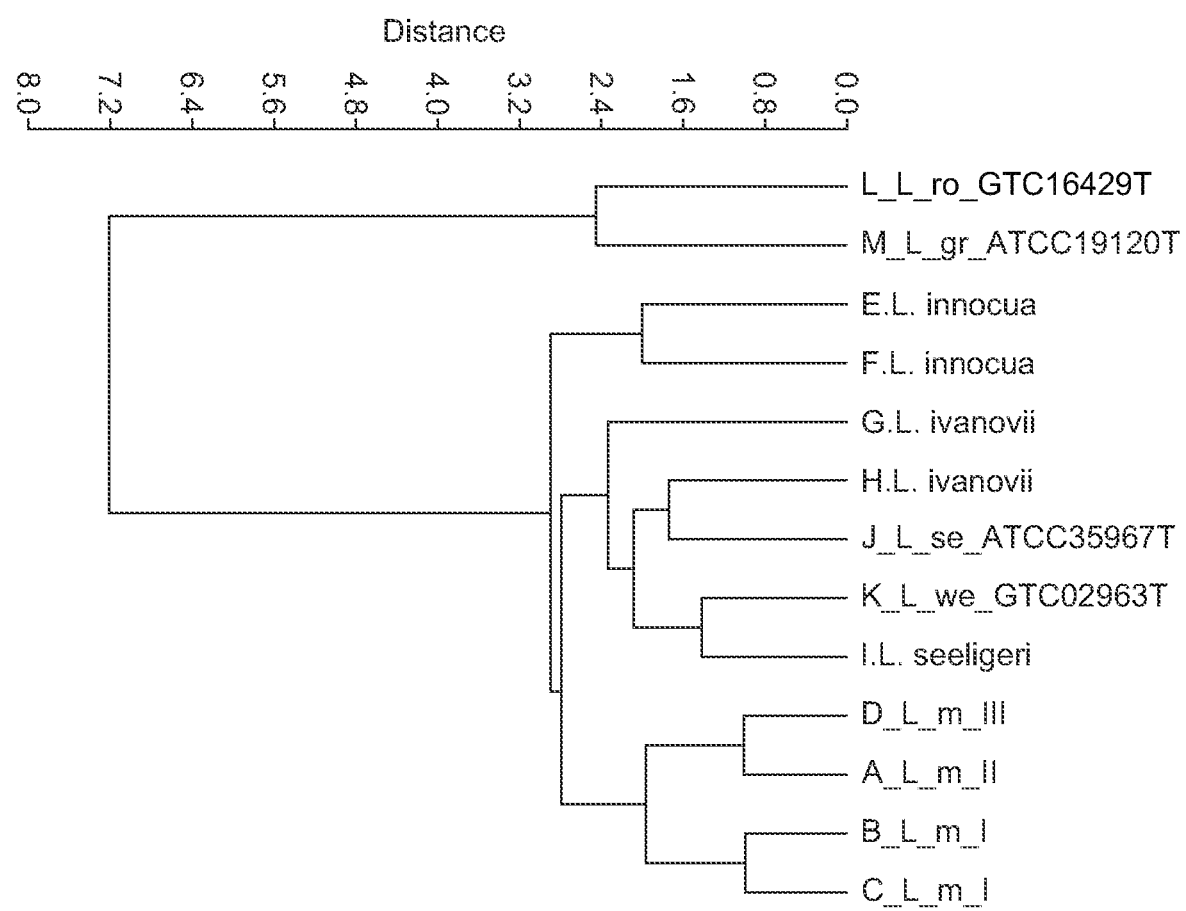
FIG. 13A is a dendrogram created using 8 ribosomal proteins.
Figure 13B:
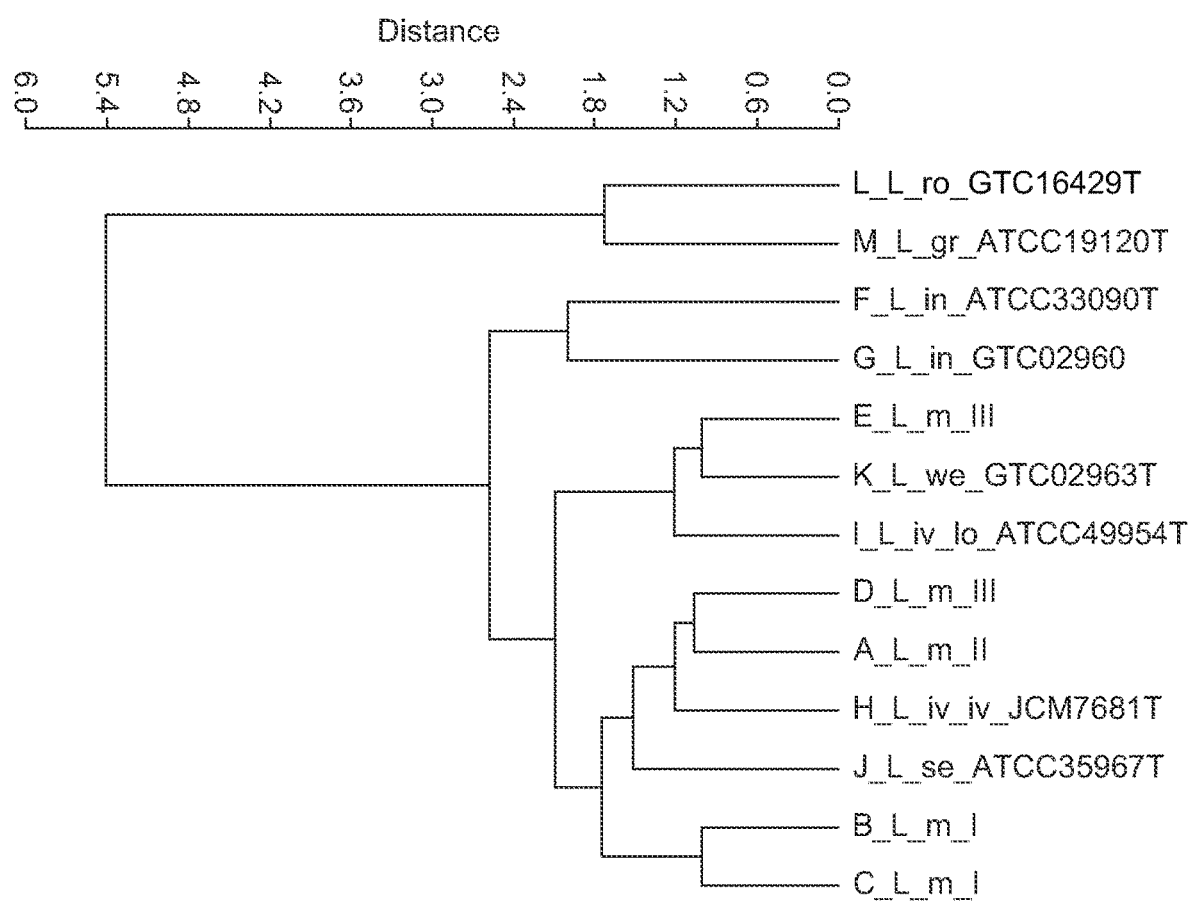
FIG. 13B is a dendrogram created using 5 ribosomal proteins.

A dendrogram (lineage diagram) showing the attribution result using the 8 ribosomal proteins shown in FIG. 12A and a dendrogram of the attribution result using five ribosomal proteins L24, S9, L6, L18, and S16 out of the 8 ribosomal proteins are shown in FIGS. 13A and 13B. In both cases, it is clear that the species of the genus *Listeria* can be discriminated and the lineage of *Listeria monocytogenes* can be discriminated. From the above, it was found that the discrimination method of the genus *Listeria* using the ribosomal proteins found in the present embodiment as marker proteins is a very effective method.

In the above embodiment, the second database 36 was caused to store the mass-to-charge ratios of 8 ribosomal proteins as marker proteins to discriminate which of the 7 bacterial species of the genus *Listeria* the test microorganism belongs to, but in the above embodiment, the second database 36 may also be caused to store the total of 17 ribosomal proteins, 15 ribosomal proteins (L3, L4, L23, L2, L24, L6, L18, S5, L15, S13, S11, L10, L21, L13, and S9) found in the process of constructing a protein mass database to discriminate *Listeria monocytogenes* and two ribosomal proteins (L31 (L31 type B), and S16) found in the process of constructing a protein mass database to discriminate the bacterial species other than *Listeria monocytogenes*, so that the subclass determination program 35 uses at least one of 17 ribosomal proteins to discriminate which of the bacterial species of the genus *Listeria* the test microorganism belongs to.

Further, in the above embodiment, the lineage of *Listeria monocytogenes* is discriminated by cluster analysis, but the lineage may also be discriminated by comparing the actual measurement value of one or more ribosomal proteins with the theoretical mass value. For example, the lineage may be discriminated from actual measurement values of mass peaks corresponding to the ribosomal proteins L24, L6, and S9. In particular, the ribosomal proteins L24 and L6 are useful as marker proteins to distinguish between a lineage I and other lineages, because a unique mass shift was observed in the lineage I of *Listeria monocytogenes*.

Further, distinct peaks could be detected in MALDI-TOF MS measurements of the ribosomal protein L18 and a unique mass shift was observed in *Listeria seeligeri*. Therefore, the ribosomal protein L18 may be used as a marker protein to discriminate *Listeria seeligeri*.

Also, the ribosomal protein S16 having a mass-to-charge ratio characteristic of *L. innocua* and the ribosomal protein S9 capable of discriminating a strain of *Listeria seeligeri* are useful as biomarkers to discriminate species of the genus *Listeria*. In addition, the ribosomal proteins L18, L15 become useful marker proteins to discriminate subspecies of *Listeria ivanovii*, and the ribosomal protein S11 becomes a useful marker protein to discriminate *Listeria welshimeri*.

REFERENCE SIGNS LIST

10 . . . Mass spectrometry unit
11 . . . Ionization unit
12 . . . TOF
13 . . . Extraction electrode
14 . . . Detector
20 . . . Microorganism determination unit
21 . . . CPU
22 . . . Memory
23 . . . Display unit
24 . . . Input unit
25 . . . I/F
30 . . . Storage unit
31 . . . OS
32 . . . Spectrum creation program
33 . . . Genus/species determination program
34 . . . First database
35 . . . Subclass determination program
36 . . . Second database
37 . . . Spectrum acquisition unit
38 . . . m/z reading unit
39 . . . Subclass determination unit
40 . . . Cluster analysis unit
41 . . . Dendrogram creation unit

The invention claimed is:

1. A method for discriminating a microorganism, the method comprising:
   a) a step of subjecting a sample containing a microorganism to mass spectrometry to obtain a mass spectrum;
   b) a reading step of reading a mass-to-charge ratio m/z of a peak derived from a marker protein from the mass spectrum; and
   c) a discrimination step of discriminating which bacterial species of *Listeria* bacteria is contained in the sample based on the mass-to-charge ratio m/z,
   wherein
   at least one of ribosomal proteins L24, L6, L18, L15, S11, S9, L31, and S16 is used as the marker protein;
   wherein a bacterial species of the *Listeria* bacteria is one of *Listeria innocua*, *Listeria welshimeri*, *Listeria seeligeri*, *Listeria ivanovii*, *Listeria grayi*, and *Listeria rocourtiae*; and
   wherein the discrimination step discriminates whether the bacterial species of the *Listeria* bacteria contained in the microorganism is *Listeria grayi* or *Listeria rocourtiae* based on a mass-to-charge ratio m/z of a peak derived from at least one of the ribosomal proteins L6, L15, S11, S9, L31, and S16.

2. A non-transitory computer-readable medium storing a program for causing a computer to execute each step according to claim 1.

* * * * *

```
                        SEQUENCE LISTING

<160> NUMBER OF SEQ ID NOS: 341

<210> SEQ ID NO 1
<211> LENGTH: 630
<212> TYPE: DNA
<213> ORGANISM: Listeria monocytogenes

<400> SEQUENCE: 1
atgaccaaag gaatcttagg tagaaaagta gggatgacac aagttttcac tgaaaacggc      60
gaacttattc cagtaacagt aatcgaagca gcacaaaacg tggtacttca aaagaaaact     120
gttgaaactg acggctatga agctgtacaa atcggtttcg aagataagag agcaattttg     180
tcaaacaaac ccgaacaagg tcatgtagca aaagccaata ctactcctaa gcgcttcatt     240
cgcgaattcc gcgatgtaaa cttagacgag tatgagattg gtgcagaagt aaaagtagat     300
gtattcgcag aaggtgacat catcgacgcg acaggcgtat cgaaaggtaa aggattccaa     360
ggtgttatta aacgccacgg acaatcacgc ggccctatgg cccacggttc ccgttaccat     420
cgtcgcccag gttcaatggg tccagtagca cctaaccgtg ttttcaaaaa taaactactt     480
ccaggtcgta tgggtggaga acaaatcact atccaaaacc tcgaaatcgt taaagtagac     540
gttgaaaaga acgttctttt agtaaaaggt aacgttccag gcgctaaaaa agcattagtt     600
caaattaaaa ctgctactaa agcaaaataa                                     630

<210> SEQ ID NO 2
<211> LENGTH: 630
<212> TYPE: DNA
<213> ORGANISM: Listeria monocytogenes

<400> SEQUENCE: 2
atgaccaaag gaatcttagg tagaaaagta gggatgacac aagttttcac tgaaaacggc      60
gaacttattc cagtaacagt aatcgaagca gcacaaaacg tggtacttca aaagaagact     120
gttgaaactg acggctatga agctgtacaa atcggtttcg aagataagag agcaattttg     180
tcaaacaaac ccgaacaagg tcatgtagca aaagccaata ctactcctaa gcgcttcatt     240
cgcgaattcc gcgatgtaaa cttagacgag tatgagattg gtgcagaagt aaaagtagac     300
gtattcgcag aaggtgacat catcgacgcg acaggcgtat cgaaaggtaa aggattccaa     360
ggtgttatta aacgccacgg acaatcacgc ggccctatgg cccacggttc ccgttaccat     420
```

| cgtcgcccag gttcaatggg tccagtagca cctaaccgtg ttttcaaaaa taaactactt | 480 |
| ccaggtcgta tgggtggaga acaaatcact atccaaaacc tagaaatcgt taaagtagac | 540 |
| gttgaaaaga acgttctttt agtaaaaggt aacgttccag gcgctaaaaa agcattagtt | 600 |
| caaattaaaa ctgctactaa agcaaaataa | 630 |

<210> SEQ ID NO 3
<211> LENGTH: 630
<212> TYPE: DNA
<213> ORGANISM: Listeria monocytogenes

<400> SEQUENCE: 3

| atgaccaaag gaatcttagg tagaaaagta gggatgacac aagttttcac tgaaaacggc | 60 |
| gaacttattc cagtaacagt aatcgaagca gcacaaaacg tggtacttca aaagaaaact | 120 |
| gttgaaactg acggctatga agctgtacaa atcggtttcg aagataagag agcaattttg | 180 |
| tcaaacaaac ccgaacaagg tcatgtagca aaagccaata ctactcctaa gcgcttcatt | 240 |
| cgcgaattcc gcgatgtaaa cttagacgag tatgagattg gtgcagaagt aaaagtagat | 300 |
| gtattcgcag aaggtgacat catcgacgcg acaggcgtat cgaaaggtaa aggattccaa | 360 |
| ggtgttatta aacgccacgg acaatcacgc ggccctatgg cccacggttc ccgttaccat | 420 |
| cgtcgcccag gttcaatggg tccagtagca cctaaccgtg ttttcaaaaa taaactactt | 480 |
| ccaggtcgta tgggtggaga acaaatcact atccaaaacc tcgaaatcgt taaagtagac | 540 |
| gttgaaaaga acgttctttt agtaaaaggt aacgttccag gcgctaaaaa agcattagtt | 600 |
| caaattaaaa ctgctactaa agcaaaataa | 630 |

<210> SEQ ID NO 4
<211> LENGTH: 630
<212> TYPE: DNA
<213> ORGANISM: Listeria monocytogenes

<400> SEQUENCE: 4

| atgaccaaag gaatcttagg tagaaaagta gggatgacac aagttttcac tgaaaacggc | 60 |
| gaacttattc cagtaacagt aatcgaagca gcacaaaacg tggtacttca aaagaaaact | 120 |
| gttgaaactg acggctatga agctgtacaa atcggtttcg aagataagag agcaattttg | 180 |
| tcaaacaaac ccgaacaagg tcatgtagca aaagccaata ctactcctaa gcgcttcatt | 240 |
| cgcgaattcc gcgatgtaaa cttagacgag tatgagattg gtgcagaagt aaaagtagac | 300 |
| gtattcgcag aaggtgacat catcgacgcg acaggcgtat cgaaaggtaa aggattccaa | 360 |
| ggtgttatta aacgccacgg acaatcacgc ggccctatgg cccacggttc ccgttaccat | 420 |
| cgtcgcccag gttcaatggg tccagtagca cctaaccgtg ttttcaaaaa taaactactt | 480 |
| ccaggtcgta tgggtggaga acaaatcact atccaaaacc tcgaaatcgt taaagtagac | 540 |
| gttgaaaaga acgttctttt agtaaaaggt aacgttccag gcgctaaaaa agcattagtt | 600 |
| caaattaaaa ctgctactaa agcaaaataa | 630 |

<210> SEQ ID NO 5
<211> LENGTH: 630
<212> TYPE: DNA
<213> ORGANISM: Listeria monocytogenes

<400> SEQUENCE: 5

```
atgaccaaag gaatcttagg tagaaaagta gggatgacac aagttttcac tgaaaacggc      60
gaacttattc cagtaacagt aatcgaagca gcacaaaacg tggtacttca aaagaaaact     120
gttgaaactg acggctatga agctgtacaa atcggtttcg aagataagag agcaattttg     180
tcaaacaaac ccgaacaagg tcatgtagca aaagccaata ctactcctaa gcgcttcatt     240
cgcgaattcc gcgatgtaaa cttagacgag tatgagattg gtgcagaagt aaaagtagat     300
gtattcgcag aaggtgacat catcgacgcg acaggcgtat cgaaaggtaa aggattccaa     360
ggtgttatta acgccacgg acaatcacgc ggccctatgg cccacggttc ccgttaccat      420
cgtcgcccag gttcaatggg tccagtagca cctaaccgtg ttttcaaaaa taaactactt     480
ccaggtcgta tgggtggaga acaaatcact atccaaaacc tcgaaatcgt taaagtagac     540
gttgaaaaga acgttctttt agtaaaaggt aacgttccag gcgctaaaaa agcattagtt     600
caaattaaaa ctgctactaa agcaaaataa                                      630
```

<210> SEQ ID NO 6
<211> LENGTH: 630
<212> TYPE: DNA
<213> ORGANISM: Listeria monocytogenes

<400> SEQUENCE: 6

```
atgaccaaag gaatcttagg tagaaaagta gggatgacac aagttttcac tgaaaacggc      60
gaacttattc cagtaacagt aatcgaagca gcacaaaacg tggtacttca aaagaaaact     120
gttgaaactg acggctatga agctgtacaa atcggtttcg aagataagag agcaattttg     180
tcaaacaaac ccgaacaagg tcatgtagca aaagccaata ctactcctaa gcgcttcatt     240
cgcgaattcc gcgatgtaaa cttagacgag tatgagattg gtgcagaagt aaaagtagac     300
gtattcgcag aaggtgacat catcgacgcg acaggcgtat cgaaaggtaa aggattccaa     360
ggtgttatta acgccacgg acaatcacgc ggccctatgg cccatggttc ccgttaccat      420
cgtcgcccag gttcaatggg tccagtagca cctaaccgtg ttttcaaaaa taaactactt     480
ccaggtcgta tgggtggaga acaaatcact atccaaaacc tagaaatcgt taaagtagac     540
gttgaaaaga acgttctttt agtaaaaggt aacgttccag gcgctaaaaa agcattagtt     600
caaattaaaa ctgctactaa agcaaaataa                                      630
```

<210> SEQ ID NO 7
<211> LENGTH: 630
<212> TYPE: DNA
<213> ORGANISM: Listeria monocytogenes

<400> SEQUENCE: 7

```
atgaccaaag gaatcttagg tagaaaagta gggatgacac aagttttcac tgaaaacggc      60
gaacttattc cagtaacagt aatcgaagca gcacaaaacg tggtacttca aaagaaaact     120
gttgaaactg acggctatga agctgtacaa atcggtttcg aagataagag agcaattttg     180
tcaaacaaac ccgaacaagg tcatgtagca aaagccaata ctactcctaa gcgcttcatt     240
cgcgaattcc gcgatgtaaa cttagacgag tatgagattg gtgcagaagt aaaagtagac     300
gtattcgcag aaggtgacat catcgacgcg acaggcgtat cgaaaggtaa aggattccaa     360
ggtgttatta acgccacgg acaatcacgc ggccctatgg cccacggttc ccgttaccat      420
cgtcgcccag gttcaatggg tccagtagca cctaaccgtg ttttcaaaaa taaactactt     480
```

| | |
|---|---:|
| ccaggtcgta tgggtggaga acaaatcact atccaaaacc tagaaatcgt taaagtagac | 540 |
| gttgaaaaga acgttctttt agtaaaaggt aacgttccag gcgctaaaaa agcattagtt | 600 |
| caaattaaaa ctgctactaa agcaaaataa | 630 |

<210> SEQ ID NO 8
<211> LENGTH: 630
<212> TYPE: DNA
<213> ORGANISM: Listeria monocytogenes

<400> SEQUENCE: 8

| | |
|---|---:|
| atgaccaaag gaatcttagg tagaaaagta gggatgacac aagttttcac tgaaaacggc | 60 |
| gaacttattc cagtaacagt aatcgaagca gcacaaaacg tggtacttca aaagaaaact | 120 |
| gttgaaactg acggctatga agctgtacaa atcggtttcg aagataagag agcaattttg | 180 |
| tcaaacaaac ccgaacaagg tcatgtagca aaagccaata ctactcctaa gcgcttcatt | 240 |
| cgcgaattcc gcgatgtaaa cttagacgag tatgagattg gtgcagaagt aaaagtagac | 300 |
| gtattcgcag aaggtgacat catcgacgcg acaggcgtat cgaaaggtaa aggattccaa | 360 |
| ggtgttatta acgccacgg acaatcacgc ggccctatgg cccacggttc ccgttaccat | 420 |
| cgtcgcccag gttcaatggg tccagtagca cctaaccgtg ttttcaaaaa taaactactt | 480 |
| ccaggtcgta tgggtggaga acaaatcact atccaaaacc tagaaatcgt taaagtagac | 540 |
| gttgaaaaga acgttctttt agtaaaaggt aacgttccag gcgctaaaaa agcattagtt | 600 |
| caaattaaaa ctgctactaa agcaaaataa | 630 |

<210> SEQ ID NO 9
<211> LENGTH: 630
<212> TYPE: DNA
<213> ORGANISM: Listeria monocytogenes

<400> SEQUENCE: 9

| | |
|---|---:|
| atgaccaaag gaatcttagg tagaaaagta gggatgacac aagttttcac tgaaaacggc | 60 |
| gaacttattc cagtaacagt aatcgaagca gcacaaaacg tggtacttca aaagaagact | 120 |
| gttgaaactg acggctatga agctgtacaa atcggtttcg aagataagag agcaattttg | 180 |
| tcaaacaaac ccgaacaagg tcatgtagca aaagccaata ctactcctaa gcgcttcatt | 240 |
| cgcgaattcc gcgatgtaaa cttagacgag tatgagattg gggcagaagt aaaagtagac | 300 |
| gtattcgcag aaggtgacat catcgacgcg acaggcgtat cgaaaggtaa aggattccaa | 360 |
| ggtgttatta acgccacgg acaatcacgc ggccctatgg cccacggttc ccgttaccat | 420 |
| cgtcgcccag gttcaatggg tccagtagca cctaaccgtg ttttcaaaaa taaactactt | 480 |
| ccaggtcgta tgggtggaga acaaatcact atccaaaacc tagaaatcgt taaagtagac | 540 |
| gttgaaaaga acgttctttt agtaaaaggt aacgttccag gcgctaaaaa agcattagtt | 600 |
| caaattaaaa ctgctactaa agcaaaataa | 630 |

<210> SEQ ID NO 10
<211> LENGTH: 630
<212> TYPE: DNA
<213> ORGANISM: Listeria monocytogenes

<400> SEQUENCE: 10

| | |
|---|---:|
| atgaccaaag gaatcttagg tagaaaagta gggatgacac aagttttcac tgaaaacggc | 60 |
| gaacttattc cagtaacagt aatcgaagca gcacaaaacg tggtacttca aaagaaaact | 120 |
| gttgaaactg acggctatga agctgtacaa atcggtttcg aagataagag agcaattttg | 180 |

```
tcaaacaaac ccgaacaagg tcatgtagca aaagccaata ctactcctaa gcgcttcatt      240
cgcgaattcc gcgatgtaaa cttagacgag tatgagattg gtgcagaagt aaaagtagac      300
gtattcgcag aaggtgacat catcgacgcg acaggcgtat cgaaaggtaa aggattccaa      360
ggtgttatta aacgccacgg acaatcacgc ggccctatgg cccacggttc ccgttaccat      420
cgtcgcccag gttcaatggg tccagtagca cctaaccgtg ttttcaaaaa taaactactt      480
ccaggtcgta tgggtggaga acaaatcact atccaaaacc tcgaaatcgt taagtagac       540 gttgaaaaga acgttctttt agtaaaaggt aacgttccag gcgctaaaaa agcattagtt      600
caaattaaaa ctgctactaa agcaaaataa                                      630
```

<210> SEQ ID NO 11
<211> LENGTH: 630
<212> TYPE: DNA
<213> ORGANISM: Listeria monocytogenes

<400> SEQUENCE: 11

```
atgaccaaag gaatcttagg tagaaaagta gggatgacac aagttttcac tgaaaacggc       60
gaacttattc cagtaacagt tatcgaagcg cacaaaacg tggtacttca aagaaaact       120 gttgaaactg acggctacga agctgtacaa atcggtttcg aagataagag agcaaaattg      180
tcaaacaaac ccgaacaagg tcatgtagca aaagccaata ctactcctaa gcgcttcatt      240
cgcgaattcc gcgatgtaaa cttagacgag tatgagattg gtgcagaagt aaaagtagac      300
gtattcgcag aaggtgacat catcgacgcg acaggcgtat cgaaaggtaa aggattccaa      360
ggtgttatta aacgccacgg acaatcacgc ggccctatgg cccacggttc ccgttaccat      420
cgtcgcccag gttcaatggg tccagtagca cctaaccgtg ttttcaaaaa taaactactt      480
ccaggtcgta tgggtggaga acaaatcact atccaaaacc tagaaatcgt taagtagac       540 gttgaaaaga acgttctttt agtaaaaggt aacgttccag gcgctaaaaa agcattagtt      600
caaattaaaa ctgctactaa agcaaaataa                                      630
```

<210> SEQ ID NO 12
<211> LENGTH: 630
<212> TYPE: DNA
<213> ORGANISM: Listeria monocytogenes

<400> SEQUENCE: 12

```
atgaccaaag gaatcttagg tagaaaagta gggatgacac aagttttcac tgaaaacggc       60
gaacttattc cagtaacagt aatcgaagca gcacaaaacg tggtacttca aagaaaact      120 gttgaaactg acggctatga agctgtacaa atcggtttcg aagataagag agcaatttg       180 tcaaacaaac ccgaacaagg tcatgtagca aaagccaata ctactcctaa gcgcttcatt      240
cgcgaattcc gcgatgtaaa cttagacgag tatgagattg gtgcagaagt aaaagtagac      300
gtattcgcag aaggtgacat catcgacgcg acaggcgtat cgaaaggtaa aggattccaa      360
ggtgttatta aacgccacgg acaatcacgc ggccctatgg cccacggttc ccgttaccat      420
cgtcgcccag gttcaatggg tccagtagca cctaaccgtg ttttcaaaaa taaactactt      480
ccaggtcgta tgggtggaga acaaatcact atccaaaacc tagaaatcgt taagtagac       540 gttgaaaaga acgttctttt agtaaaaggt aacgttccag gcgctaaaaa agcattagtt      600
caaattaaaa ctgctactaa agcaaaataa                                      630
```

<210> SEQ ID NO 13

<211> LENGTH: 630
<212> TYPE: DNA
<213> ORGANISM: Listeria monocytogenes

<400> SEQUENCE: 13

```
atgaccaaag gaatcttagg tagaaaagta gggatgacac aagttttcac tgaaaacggc    60
gaacttatt

```
cgtcgcccag gttcaatggg tccagtagca cctaaccgtg ttttcaaaaa taaactactt    480
ccaggtcgta tgggtggaga acaaatcact atccaaaacc tcgaaatcgt taaagtagac    540
gttgaaaaga acgttctttt agtaaaaggt aacgttccag gcgctaaaaa agcattagtt    600
caaattaaaa ctgctactaa agcaaaataa                                     630
```

<210> SEQ ID NO 16
<211> LENGTH: 630
<212> TYPE: DNA
<213> ORGANISM: Listeria monocytogenes

<400> SEQUENCE: 16

```
atgaccaaag gaatcttagg tagaaaagta gggatgacac aagttttcac tgaaaacggc     60
gaacttattc cagtaacagt aatcgaagca gcacaaaacg tggtacttca aaagaaaact    120
gttgaaactg acggctatga agctgtacaa atcggtttcg aagataagag agcaattttg    180
tcaaacaaac ccgaacaagg tcatgtagca aaagccaata ctactcctaa gcgcttcatt    240
cgcgaattcc gcgatgtaaa cttagacgag tatgagattg gtgcagaagt aaaagtagac    300
gtattcgcag aaggtgacat catcgacgcg acaggcgtat cgaaaggtaa aggattccaa    360
ggtgttatta acgccacgg acaatcacgc ggccctatgg cccacggttc ccgttaccat    420
cgtcgcccag gttcaatggg tccagtagca cctaaccgtg ttttcaaaaa taaactactt    480
ccaggtcgta tgggtggaga acaaatcact atccaaaacc tagaaatcgt taaagtagac    540
gttgaaaaga acgttctttt agtaaaaggt aacgttccag gcgctaaaaa agcattagtt    600
caaattaaaa ctgctactaa agcaaaataa                                     630
```

<210> SEQ ID NO 17
<211> LENGTH: 624
<212> TYPE: DNA
<213> ORGANISM: Listeria monocytogenes

<400> SEQUENCE: 17

```
atgccaaaat taagcttact taaacaagat ggaacaaacg ctggcgaaat tactttaaac     60
gacactgttt tcggtatcga accaaatgaa aaagttgttg ttgatgtgat tttgagccaa    120
cgtgcatccc tacgtcaagg gactcacaaa gtaaaaaatc gttcagaagt acgtggtggc    180
ggacgtaaac catggcgtca aaaaggtaca ggtcgtgccc gtcaaggttc aatccgttcc    240
ccgcaatggc gtggcggtgg tgtcgtattc ggcccaacac ctcgttcata tgcttacaaa    300
ttacctaaga aagttcgtcg tttagcgatt aaatcaattc tttcttctaa agtaaatgaa    360
gaaaaattag ttgtacttga aggtttgact tcgatgcac ctaaaacaaa gaatttgcg    420 gcttttctta aaaatatctc tgtagatact aaggcactaa tcgtagttgc tggtgaaagt    480
gaaaatgtag aattatctgc acgcaactta caaggcatta cagttattcc ggctgaaagt    540
atctcagtac tagaagttgc taaacatgat aaattaatta tcactaaagc agctgtcgaa    600
aaagtagagg aggtgctcgc ataa                                           624
```

<210> SEQ ID NO 18
<211> LENGTH: 624
<212> TYPE: DNA
<213> ORGANISM: Listeria monocytogenes

<400> SEQUENCE: 18

```
atgccaaaat taagcttact taaacaagat ggaacaaacg ctggcgaaat tactttaaac    60
gacactgttt tcggtatcga accaaatgaa aaagttgttg ttgatgtgat tttgagccaa   120
cgtgcatccc tacgtcaagg gactcacaaa gtaaaaaatc gttcagaagt acgtggtggc   180
ggacgtaaac catggcgtca aaaaggtaca ggtcgtgccc gtcaaggttc aatccgttcc   240
ccgcaatggc gtggcggtgg tgtcgtattc ggcccaacac ctcgttcata tgcatacaaa   300
ttacctaaga aagttcgtcg tttagcgatt aaatcaattc tttcttctaa agtaaatgaa   360
gaaaaattag ttgtacttga aggtttgact ttcgatgcac ctaaaacaaa agaatttgcg   420
gcttttctta aaaatatctc tgtagatact aaggcactaa tcgtagttgc cggtgaaagt   480
gaaaatgtag aattatctgc acgcaactta caaggcatta cagttattcc agctgaaagt   540
atctcagtac tagaagttgc taaacatgat aaattaatta tcactaaagc agctgtcgaa   600
aaagtagagg aggtgctcgc ataa                                          624
```

<210> SEQ ID NO 19
<211> LENGTH: 624
<212> TYPE: DNA
<213> ORGANISM: Listeria monocytogenes

<400> SEQUENCE: 19

```
atgccaaaat taagcttact taaacaagat ggaacaaacg ctggcgaaat tactttaaac    60
gacactgttt tcggtatcga accaaatgaa aaagttgttg ttgatgtgat tttgagccaa   120
cgtgcatccc tacgtcaagg gactcacaaa gtaaaaaatc gttcagaagt acgtggtggc   180
ggacgtaaac catggcgtca aaaaggtaca ggtcgtgccc gtcaaggttc aatccgttcc   240
ccgcaatggc gtggcggtgg tgtcgtattc ggcccaacac ctcgttcata tgcttacaaa   300
ttacctaaga aagttcgtcg tttagcgatt aaatcaattc tttcttctaa agtaaatgaa   360
gaaaaattag ttgtacttga aggtttgact ttcgatgcac ctaaaacaaa agaatttgcg   420
gcttttctta aaaatatctc tgtagatact aaggcactaa tcgtagttgc tggtgaaagt   480
gaaaatgtag aattatctgc acgcaactta caaggcatta cagttattcc ggctgaaagt   540
atctcagtac tagaagttgc taaacatgat aaattaatta tcactaaagc agctgtcgaa   600
aaagtagagg aggtgctcgc ataa                                          624
```

<210> SEQ ID NO 20
<211> LENGTH: 624
<212> TYPE: DNA
<213> ORGANISM: Listeria monocytogenes

<400> SEQUENCE: 20

```
atgccaaaat taagcttact taaacaagat ggaacaaacg ctggcgaaat tactttaaac    60
gacactgttt tcggtatcga accaaatgaa aaagttgttg ttgatgtgat tttgagccaa   120
cgtgcatccc tacgtcaagg gactcacaaa gtaaaaaatc gttcagaagt acgtggtggc   180
ggacgtaaac catggcgtca aaaaggtaca ggtcgtgccc gtcaaggttc aatccgttcc   240
ccgcaatggc gtggcggtgg tgtcgtattc ggcccaacac ctcgttcata tgcttacaaa   300
ttacctaaga aagttcgtcg tttagcgatt aaatcaattc tttcttctaa agtaaatgaa   360
gaaaaattag ttgtacttga aggtttgact ttcgatgcac ctaaaacaaa agaatttgcg   420
gcttttctta aaaatatctc tgtagatact aaggcactaa tcgtagttgc tggtgaaagt   480
```

```
gaaaatgtag aattatctgc acgcaactta caaggcatta cagttattcc ggctgaaagt      540
atctcagtac tagaagttgc taaacatgat aaattaatta tcactaaagc agctgtcgaa      600
aaagtagagg aggtgctcgc ataa                                             624
```

<210> SEQ ID NO 21
<211> LENGTH: 624
<212> TYPE: DNA
<213> ORGANISM: Listeria monocytogenes

<400> SEQUENCE: 21

```
atgccaaaat taagcttact taaacaagat ggaacaaacg ctggcgaaat tactttaaac       60
gacactgttt tcggtatcga accaaatgaa aaagttgttg ttgatgtgat tttgagccaa      120
cgtgcatccc tacgtcaagg gactcacaaa gtaaaaaatc gttcagaagt acgtggtggc      180
ggacgtaaac catggcgtca aaaaggtaca ggtcgtgccc gtcaaggttc aatccgttcc      240
ccgcaatggc gtggcggtgg tgtcgtattc ggcccaacac ctcgttcata tgcttacaaa      300
ttacctaaga aagttcgtcg tttagcgatt aaatcaattc tttcttctaa agtaaatgaa      360
gaaaaattag ttgtacttga aggtttgact ttcgatgcac taaaacaaa agaatttgcg      420 gcttttctta aaaatatctc tgtagatact aaggcactaa tcgtagttgc tggtgaaagt      480
gaaaatgtag aattatctgc acgcaactta caaggcatta cagttattcc ggctgaaagt      540
atctcagtac tagaagttgc taaacatgat aaattaatta tcactaaagc agctgtcgaa      600
aaagtagagg aggtgctcgc ataa                                             624
```

<210> SEQ ID NO 22
<211> LENGTH: 624
<212> TYPE: DNA
<213> ORGANISM: Listeria monocytogenes

<400> SEQUENCE: 22

```
atgccaaaat taagcttact taaacaagat ggaacaaacg ctggcgaaat tactttaaac       60
gacactgttt tcggtatcga accaaatgaa aaagttgttg ttgatgtgat tttgagccaa      120
cgtgcatccc tacgtcaagg gactcacaaa gtaaaaaatc gttcagaagt acgtggtggc      180
ggacgtaaac catggcgtca aaaaggtaca ggtcgtgccc gtcaaggttc aatccgttcc      240
ccacaatggc gcggcggtgg tgtcgtattc ggcccaacac ctcgttcata tgcttacaaa      300
ttacctaaga aagttcgtcg tttagcgatt aaatcaattc tttcttctaa agtaaatgaa      360
gaaaaattag ttgtacttga aggtttgact ttcgatgcac taaaacaaa agaatttgcg      420 gcttttctta aaaatatctc tgtagatact aaggcactaa tcgtagttgc tggtgaaagt      480
gaaaatgtag aattatctgc acgcaactta caaggcatta cagttattcc agctgaaagt      540
atctcagtac tagaagttgc taaacatgat aaattaatta tcactaaagc agctgtcgaa      600
aaagtagagg aggtgctcgc ataa                                             624
```

<210> SEQ ID NO 23
<211> LENGTH: 624
<212> TYPE: DNA
<213> ORGANISM: Listeria monocytogenes

<400> SEQUENCE: 23

```
atgccaaaat taagcttact taaacaagat ggaacaaacg ctggcgaaat tactttaaac       60
gacactgttt tcggtatcga accaaatgaa aaagttgttg ttgatgtgat tttgagccaa      120
cgtgcatccc tacgtcaagg gactcacaaa gtaaaaaatc gttcagaagt acgtggtggc      180
```

```
ggacgtaaac catggcgtca aaaaggtaca ggtcgtgccc gtcaaggttc aatccgttcc      240
ccgcaatggc gtggcggtgg tgtcgtattc ggcccaacac ctcgttcata tgcatacaaa      300
ttacctaaga aagttcgtcg tttagcgatt aaatcaattc tttcttctaa agtaaatgaa      360
gaaaaattag ttgtacttga aggtttgact ttcgatgcac ctaaaacaaa agaatttgcg      420
gcttttctta aaaatatctc tgtagatact aaggcactaa tcgtagttgc cggtgaaagt      480
gaaaatgtag aattatctgc acgcaactta caaggcatta cagttattcc agctgaaagt      540
atctcagtac tagaagttgc taaacatgat aaattaatta tcactaaagc agctgtcgaa      600
aaagtagagg aggtgctcgc ataa                                             624

<210> SEQ ID NO 24
<211> LENGTH: 624
<212> TYPE: DNA
<213> ORGANISM: Listeria monocytogenes

<400> SEQUENCE: 24
atgccaaaat taagcttact taaacaagat ggaacaaacg ctggcgaaat tactttaaac       60
gacactgttt tcggtatcga accaaatgaa aaagttgttg ttgatgtgat tttgagccaa      120
cgtgcatccc tacgtcaagg gactcacaaa gtaaaaaatc gttcagaagt acgtggtggc      180
ggacgtaaac catggcgtca aaaaggtaca ggtcgtgccc gtcaaggttc aatccgttcc      240
ccgcaatggc gtggcggtgg tgtcgtattc ggcccaacac ctcgttcata tgcatacaaa      300
ttacctaaga aagttcgtcg tttagcgatt aaatcaattc tttcttctaa agtaaatgaa      360
gaaaaattag ttgtacttga aggtttgact ttcgatgcac ctaaaacaaa agaatttgcg      420
gcttttctta aaaatatctc tgtagatact aaggcactaa tcgtagttgc cggtgaaagt      480
gaaaatgtag aattatctgc acgcaactta caaggcatta cagttattcc agctgaaagt      540
atctcagtac tagaagttgc taaacatgat aaattaatta tcactaaagc agctgtcgaa      600
aaagtagagg aggtgctcgc ataa                                             624

<210> SEQ ID NO 25
<211> LENGTH: 624
<212> TYPE: DNA
<213> ORGANISM: Listeria monocytogenes

<400> SEQUENCE: 25
atgccaaaat taagcttact taaacaagat ggaacaaacg ctggcgaaat tactttaaac       60
gacactgttt tcggtatcga accaaatgaa aaagttgttg ttgatgtgat tttgagccaa      120
cgtgcatccc tacgtcaagg gactcacaaa gtaaaaaatc gttcagaagt acgtggtggc      180
ggacgtaaac catggcgtca aaaaggtaca ggtcgtgccc gtcaaggttc aatccgttcc      240
ccgcaatggc gtggcggtgg tgtcgtattc ggcccaacac ctcgttcata tgcatacaaa      300
ttacctaaga aagttcgtcg tttagcgatt aaatcaattc tttcttctaa agtaaatgaa      360
gaaaaattag ttgtacttga aggtttgact ttcgatgcac ctaaaacaaa agaatttgcg      420
gcttttctta aaaatatctc tgtagatact aaggcactaa tcgtagttgc cggtgaaagt      480
gaaaatgtag aattatctgc acgcaactta caaggcatta cagttattcc agctgaaagt      540
atctcagtac tagaagttgc taaacatgat aaattaatta tcactaaagc agctgtcgaa      600
aaagtagagg aggtgctcgc ataa                                             624

<210> SEQ ID NO 26
```

<211> LENGTH: 624
<212> TYPE: DNA
<213> ORGANISM: Listeria monocytogenes

<400> SEQUENCE: 26

| | | | | | |
|---|---|---|---|---|---|
| atgccaaaat | taagcttact | taaacaagat | ggaacaaacg | ctggcgaaat | tactttaaac | 60 |
| gacactgttt | tcggtatcga | accaaatgaa | aaagttgttg | ttgatgtgat | tttgagccaa | 120 |
| cgtgcatccc | tacgtcaagg | gactcacaaa | gtaaaaaatc | gttcagaagt | acgtggtggc | 180 |
| ggacgtaaac | catggcgtca | aaaaggtaca | ggtcgtgccc | gtcaaggttc | aatccgttcc | 240 |
| ccgcaatggc | gtggcggtgg | tgtcgtattc | ggcccaacac | ctcgttcata | tgcttacaaa | 300 |
| ttacctaaga | aagttcgtcg | tttagcgatt | aaatcaattc | tttcttctaa | agtaaatgaa | 360 |
| gaaaaattag | ttgtacttga | aggtttgact | ttcgatgcac | ctaaaacaaa | agaatttgcg | 420 |
| gcttttctta | aaatatctc | tgtagatact | aaggcactaa | tcgtagttgc | tggtgaaagt | 480 |
| gaaaatgtag | aattatctgc | acgcaactta | caaggcatta | cagttattcc | ggctgaaagt | 540 |
| atctcagtac | tagaagttgc | taaacatgat | aaattaatta | tcactaaagc | agctgtcgaa | 600 |
| aaagtagagg | aggtgctcgc | ataa | | | | 624 |

<210> SEQ ID NO 27
<211> LENGTH: 624
<212> TYPE: DNA
<213> ORGANISM: Listeria monocytogenes

<400> SEQUENCE: 27

| | | | | | |
|---|---|---|---|---|---|
| atgccaaaat | taagcttact | taaacaagat | ggaacaaacg | ctggcgaaat | tactttaaac | 60 |
| gacactgttt | tcggtatcga | accaaatgaa | aaagttgttg | ttgatgtgat | tttgagccaa | 120 |
| cgtgcatccc | ttcgtcaagg | gactcacaaa | gtaaaaaatc | gttcagaagt | acgtggtggc | 180 |
| ggacgtaaac | catggcgtca | aaaaggtaca | ggtcgtgccc | gtcaaggttc | aatccgttcc | 240 |
| ccacaatggc | gtggcggtgg | tgtcgtattc | ggcccaacac | ctcgttcata | tgcttacaaa | 300 |
| ttacctaaga | aagttcgtcg | tttagcgatt | aaatcaattc | tttcttctaa | agtaaatgaa | 360 |
| gaaaaattag | ttgtacttga | aggtttaact | ttcgatgctc | ctaaaacaaa | agaatttgcg | 420 |
| gcttttctta | aaatatctc | tgtagatact | aaggcactaa | tcgtagttgc | tagtgaaagt | 480 |
| gaaaatgtag | aattatctgc | acgcaactta | caaggcatta | cagttattcc | agctgaaagt | 540 |
| atctcagtac | tagaagttgc | taaacatgat | aagttaatta | tcactaaagc | agctgtcgaa | 600 |
| aaagtagagg | aggtgctcgc | ataa | | | | 624 |

<210> SEQ ID NO 28
<211> LENGTH: 624
<212> TYPE: DNA
<213> ORGANISM: Listeria monocytogenes

<400> SEQUENCE: 28

| | | | | | |
|---|---|---|---|---|---|
| atgccaaaat | taagcttact | taaacaagat | ggaacaaacg | ctggcgaaat | tactttaaac | 60 |
| gacactgttt | tcggtatcga | accaaatgaa | aaagttgttg | ttgatgtgat | tttgagccaa | 120 |
| cgtgcatccc | tacgtcaagg | gactcacaaa | gtaaaaaatc | gttcagaagt | acgtggtggc | 180 |
| ggacgtaaac | catggcgtca | aaaaggtaca | ggtcgtgccc | gtcaaggttc | aatccgttcc | 240 |
| ccgcaatggc | gtggcggtgg | tgtcgtattc | ggcccaacac | ctcgttcata | tgcatacaaa | 300 |
| ttacctaaga | aagttcgtcg | tttagcgatt | aaatcaattc | tttcttctaa | agtaaatgaa | 360 |
| gaaaaattag | ttgtacttga | aggtttgact | ttcgatgcac | ctaaaacaaa | agaatttgcg | 420 |

```
gcttttctta aaaatatctc tgtagatact aaggcactaa tcgtagttgc cggtgaaagt    480
gaaaatgtag aattatctgc acgcaactta caaggcatta cagttattcc agctgaaagt    540
atctcagtac tagaagttgc taaacatgat aaattaatta tcactaaagc agctgtcgaa    600
aaagtagagg aggtgctcgc ataa                                           624
```

<210> SEQ ID NO 29
<211> LENGTH: 624
<212> TYPE: DNA
<213> ORGANISM: Listeria monocytogenes

<400> SEQUENCE: 29

```
atgccaaaat taagcttact taaacaagat ggaacaaacg ctggcgaaat tactttaaac    60
gacactgttt tcggtatcga accaaatgaa aaagttgttg ttgatgtgat tttgagccaa   120
cgtgcatccc ttcgtcaagg gactcacaaa gtaaaaaatc gttcagaagt acgtggtggc   180
ggacgtaaac catggcgtca aaaaggtaca ggtcgtgccc gtcaaggttc aatccgttcc   240
ccacaatggc gtggcggtgg tgtcgtattc ggcccaacac ctcgttcata tgcttacaaa   300
ttacctaaga aagttcgtcg tttagcgatt aaatcaattc tttcttctaa agtaaatgaa   360
gaaaaattag ttgtacttga aggtttaact ttcgatgctc ctaaaacaaa gaatttgcg    420 gcttttctta aaatatctc tgtagatact aaggcactaa tcgtagttgc tagtgaaagt    480
gaaaatgtag aattatctgc acgcaactta caaggcatta cagttattcc agctgaaagt    540
atctcagtac tagaagttgc taaacatgat aagttaatta tcactaaagc agctgtcgaa    600
aaagtagagg aggtgctcgc ataa                                           624
```

<210> SEQ ID NO 30
<211> LENGTH: 624
<212> TYPE: DNA
<213> ORGANISM: Listeria monocytogenes

<400> SEQUENCE: 30

```
atgccaaaat taagcttact taaacaagat ggaacaaacg ctggcgaaat tactttaaac    60
gacactgttt tcggtatcga accaaatgaa aaagttgttg ttgatgtgat tttgagccaa   120
cgtgcatccc tacgtcaagg gactcacaaa gtaaaaaatc gttcagaagt acgtggtggc   180
ggacgtaaac catggcgtca aaaaggtaca ggtcgtgccc gtcaaggttc aatccgttcc   240
ccgcaatggc gtggcggtgg tgtcgtattc ggcccaacac ctcgttcata tgcatacaaa   300
ttacctaaga aagttcgtcg tttagcgatt aaatcaattc tttcttctaa agtaaatgaa   360
gaaaaattag ttgtacttga aggtttgact ttcgatgcac ctaaaacaaa gaatttgcg    420 gcttttctta aaatatctc tgtagatact aaggcactaa tcgtagttgc cggtgaaagt    480
gaaaatgtag aattatctgc acgcaactta caaggcatta cagttattcc agctgaaagt    540
atctcagtac tagaagttgc taaacatgat aaattaatta tcactaaagc agctgtcgaa    600
aaagtagagg aggtgctcgc ataa                                           624
```

<210> SEQ ID NO 31
<211> LENGTH: 624
<212> TYPE: DNA
<213> ORGANISM: Listeria monocytogenes

<400> SEQUENCE: 31

```
atgccaaaat taagcttact taaacaagat ggaacaaacg ctggcgaaat tactttaaac    60
gacactgttt tcggtatcga accaaatgaa aaagttgttg ttgatgtgat tttgagccaa   120
cgtgcatccc tacgtcaagg gactcacaaa gtaaaaaatc gttcagaagt acgtggtggc   180
ggacgtaaac catggcgtca aaaaggtaca ggtcgtgccc gtcaaggttc aatccgttcc   240
ccgcaatggc gtggcggtgg tgtcgtattc ggcccaacac ctcgttcata tgcttacaaa   300
ttacctaaga aagttcgtcg tttagcgatt aaatcaattc tttcttctaa agtaaatgaa   360
gaaaaattag ttgtacttga aggtttgact ttcgatgcac ctaaaacaaa gaatttgcg    420
gcttttctta aaaatatctc tgtagatact aaggcactaa tcgtagttgc tggtgaaagt   480
gaaaatgtag aattatctgc acgcaactta caaggcatta cagttattcc ggctgaaagt   540
atctcagtac tagaagttgc taaacatgat aaattaatta tcactaaagc agctgtcgaa   600
aaagtagagg aggtgctcgc ataa                                          624
```

<210> SEQ ID NO 32
<211> LENGTH: 624
<212> TYPE: DNA
<213> ORGANISM: Listeria monocytogenes

<400> SEQUENCE: 32

```
atgccaaaat taagcttact taaacaagat ggaacaaacg ctggcgaaat tactttaaac    60
gacactgttt tcggtatcga accaaatgaa aaagttgttg ttgatgtgat tttgagccaa   120
cgtgcatccc tacgtcaagg gactcacaaa gtaaaaaatc gttcagaagt acgtggtggc   180
ggacgtaaac catggcgtca aaaaggtaca ggtcgtgccc gtcaaggttc aatccgttcc   240
ccgcaatggc gtggcggtgg tgtcgtattc ggcccaacac ctcgttcata tgcatacaaa   300
ttacctaaga aagttcgtcg tttagcgatt aaatcaattc tttcttctaa agtaaatgaa   360
gaaaaattag ttgtacttga aggtttgact ttcgatgcac ctaaaacaaa gaatttgcg    420
gcttttctta aaaatatctc tgtagatact aaggcactaa tcgtagttgc cggtgaaagt   480
gaaaatgtag aattatctgc acgcaactta caaggcatta cagttattcc agctgaaagt   540
atctcagtac tagaagttgc taaacatgat aaattaatta tcactaaagc agctgtcgaa   600
aaagtagagg aggtgctcgc ataa                                          624
```

<210> SEQ ID NO 33
<211> LENGTH: 285
<212> TYPE: DNA
<213> ORGANISM: Listeria monocytogenes

<400> SEQUENCE: 33

```
atggatgcac gcgacatcat taagcgccca gttgtaactg aagaatctac aagcattctc    60
gacgataaga aatatacatt tgaagtagat actcgcgcaa ctaaaacgca agtaaaatac   120
gcagttgaag aaattttcga cgtaaaagtt gctaaagtaa acgtaatgaa ttacaaaggc   180
aaacttaaac gtatgggccg ttatgcaggt tacactaaca aacgccgtaa agcgattgtt   240
actgttacag ctgacagcaa agaaattcaa ttctttgaag tataa                   285
```

<210> SEQ ID NO 34
<211> LENGTH: 285
<212> TYPE: DNA
<213> ORGANISM: Listeria monocytogenes

<400> SEQUENCE: 34
atggatgcac gcgacatcat taagcgccca gttgtaactg aagaatctac aagtattctc    60
gacgataaga aatatacatt tgaagtagat actcgcgcaa ctaaaacgca agtaaaatac   120
gcagttgaag aaattttcga cgtaaaagtt gctaaagtaa acgtaatgaa ttacaaaggc   180
aaacttaaac gtatgggccg ttatgcaggt tacactaaca aacgccgtaa agcgattgtt   240
actgttacag ctgacagcaa agaaattcaa ttctttgaag tataa                  285

<210> SEQ ID NO 35
<211> LENGTH: 285
<212> TYPE: DNA
<213> ORGANISM: Listeria monocytogenes

<400> SEQUENCE: 35
atggatgcac gcgacatcat taagcgccca gttgtaactg aagaatctac aagcattctc    60
gacgataaga aatatacatt tgaagtagat actcgcgcaa ctaaaacgca agtaaaatac   120
gcagttgaag aaattttcga cgtaaaagtt gctaaagtaa acgtaatgaa ttacaaaggc   180
aaacttaaac gtatgggccg ttatgcaggt tacactaaca aacgccgtaa agcgattgtt   240
actgttacag ctgacagcaa agaaattcaa ttctttgaag tataa                  285

<210> SEQ ID NO 36
<211> LENGTH: 285
<212> TYPE: DNA
<213> ORGANISM: Listeria monocytogenes

<400> SEQUENCE: 36
atggatgcac gcgacatcat taagcgccca gttgtaactg aagaatctac aagcattctc    60
gacgataaga aatatacatt tgaagtagat actcgcgcaa ctaaaacgca agtaaaatac   120
gcagttgaag aaattttcga cgtaaaagtt gctaaagtaa acgtaatgaa ttacaaaggc   180
aaacttaaac gtatgggccg ttatgcaggt tacactaaca aacgccgtaa agcgattgtt   240
actgttacag ctgacagcaa agaaattcaa ttctttgaag tataa                  285

<210> SEQ ID NO 37
<211> LENGTH: 285
<212> TYPE: DNA
<213> ORGANISM: Listeria monocytogenes

<400> SEQUENCE: 37
atggatgcac gcgacatcat taagcgccca gttgtaactg aagaatctac aagcattctc    60
gacgataaga aatatacatt tgaagtagat actcgcgcaa ctaaaacgca agtaaaatac   120
gcagttgaag aaattttcga cgtaaaagtt gctaaagtaa acgtaatgaa ttacaaaggc   180
aaacttaaac gtatgggccg ttatgcaggt tacactaaca aacgccgtaa agcgattgtt   240
actgttacag ctgacagcaa agaaattcaa ttctttgaag tataa                  285

<210> SEQ ID NO 38
<211> LENGTH: 285
<212> TYPE: DNA
<213> ORGANISM: Listeria monocytogenes

<400> SEQUENCE: 38
atggatgcac gcgacatcat taagcgccca gttgtaactg aagaatctac aagcattctc    60
gacgataaga aatatacatt tgaagtagat actcgcgcaa ctaaaacgca agtaaaatac   120
gcaattgaag aaattttcga cgtaaaagtt gctaaagtaa acgtaatgaa ttacaaaggc   180

```
aaacttaaac gtatgggccg ttatgcaggt tacactaaca aacgccgtaa agcgattgtt    240
actgttacag ctgacagcaa agaaattcaa ttctttgaag tataa                    285

<210> SEQ ID NO 39
<211> LENGTH: 285
<212> TYPE: DNA
<213> ORGANISM: Listeria monocytogenes

<400> SEQUENCE: 39
atggatgcac gcgacatcat taagcgccca gttgtaactg aagaatctac aagtattctc    60
gacgataaga aatatacatt tgaagtagat actcgcgcaa ctaaaacgca agtaaaatac   120
gcagttgaag aaattttcga cgtaaaagtt gctaaagtaa acgtaatgaa ttacaaaggc   180
aaacttaaac gtatgggccg ttatgcaggt tacactaaca aacgccgtaa agcgattgtt   240
actgttacag ctgacagcaa agaaattcaa ttctttgaag tataa                   285

<210> SEQ ID NO 40
<211> LENGTH: 285
<212> TYPE: DNA
<213> ORGANISM: Listeria monocytogenes

<400> SEQUENCE: 40
atggatgcac gcgacatcat taagcgccca gttgtaactg aagaatctac aagtattctc    60
gacgataaga aatatacatt tgaagtagat actcgcgcaa ctaaaacgca agtaaaatac   120
gcagttgaag aaattttcga cgtaaaagtt gctaaagtaa acgtaatgaa ttacaaaggc   180
aaacttaaac gtatgggccg ttatgcaggt tacactaaca aacgccgtaa agcgattgtt   240
actgttacag ctgacagcaa agaaattcaa ttctttgaag tataa                   285

<210> SEQ ID NO 41
<211> LENGTH: 285
<212> TYPE: DNA
<213> ORGANISM: Listeria monocytogenes

<400> SEQUENCE: 41
atggatgcac gcgacatcat taagcgccca gttgtaactg aagaatctac aagtattctc    60
gacgataaga aatatacatt tgaagtagat actcgcgcaa ctaaaacgca agtaaaatac   120
gcagttgaag aaattttcga cgtaaaagtt gctaaagtaa acgtaatgaa ttacaaaggc   180
aaacttaaac gtatgggccg ttatgcaggt tacactaaca aacgccgtaa agcgattgtt   240
actgttacag ctgacagcaa agaaattcaa ttctttgaag tataa                   285

<210> SEQ ID NO 42
<211> LENGTH: 285
<212> TYPE: DNA
<213> ORGANISM: Listeria monocytogenes

<400> SEQUENCE: 42
atggatgcac gcgacatcat taagcgccca gttgtaactg aagaatctac aagcattctc    60
gacgataaga aatatacatt tgaagtagat actcgcgcaa ctaaaacgca agtaaaatac   120
gcagttgaag aaattttcga cgtaaaagtt gctaaagtaa acgtaatgaa ttacaaaggc   180
aaacttaaac gtatgggccg ttatgcaggt tacactaaca aacgccgtaa agcgattgtt   240
actgttacag ctgacagcaa agaaattcaa ttctttgaag tataa                   285

<210> SEQ ID NO 43
```

<211> LENGTH: 285
<212> TYPE: DNA
<213> ORGANISM: Listeria monocytogenes

<400> SEQUENCE: 43

| atggatgcac gcgacatcat taagcgcccg gttgtaactg aagaatctac aagcattctc | 60 |
| gacgataaga aatatacttt tgaagtagat actcgcgcaa ctaaaacgca agtaaaatac | 120 |
| gcagttgaag aaattttga cgtaaaagtt gctaaagtaa acgtaatgaa ttacaaaggc | 180 |
| aaacttaaac gtatgggccg ttatgcaggt tacactaaca aacgccgtaa agcgattgtt | 240 |
| actgttacag ctgacagcaa agaaattcaa ttctttgaag tataa | 285 |

<210> SEQ ID NO 44
<211> LENGTH: 285
<212> TYPE: DNA
<213> ORGANISM: Listeria monocytogenes

<400> SEQUENCE: 44

| atggatgcac gcgacatcat taagcgccca gttgtaactg aagaatctac aagtattctc | 60 |
| gacgataaga aatatacatt tgaagtagat actcgcgcaa ctaaaacgca agtaaaatac | 120 |
| gcagttgaag aaattttcga cgtaaaagtt gctaaagtaa acgtaatgaa ttacaaaggc | 180 |
| aaacttaaac gtatgggccg ttatgcaggt tacactaaca aacgccgtaa agcgattgtt | 240 |
| actgttacag ctgacagcaa agaaattcaa ttctttgaag tataa | 285 |

<210> SEQ ID NO 45
<211> LENGTH: 285
<212> TYPE: DNA
<213> ORGANISM: Listeria monocytogenes

<400> SEQUENCE: 45

| atggatgcac gcgacatcat taagcgcccg gttgtaactg aagaatctac aagcattctc | 60 |
| gacgataaga aatatacttt tgaagtagat actcgcgcaa ctaaaacgca agtaaaatac | 120 |
| gcagttgaag aaattttga cgtaaaagtt gctaaagtaa acgtaatgaa ttacaaaggc | 180 |
| aaacttaaac gtatgggccg ttatgcaggt tacactaaca aacgccgtaa agcgattgtt | 240 |
| actgttacag ctgacagcaa agaaattcaa ttctttgaag tataa | 285 |

<210> SEQ ID NO 46
<211> LENGTH: 285
<212> TYPE: DNA
<213> ORGANISM: Listeria monocytogenes

<400> SEQUENCE: 46

| atggatgcac gcgacatcat taagcgccca gttgtaactg aagaatctac aagtattctc | 60 |
| gacgataaga aatatacatt tgaagtagat actcgcgcaa ctaaaacgca agtaaaatac | 120 |
| gcagttgaag aaattttcga cgtaaaagtt gctaaagtaa acgtaatgaa ttacaaaggc | 180 |
| aaacttaaac gtatgggccg ttatgcaggt tacactaaca aacgccgtaa agcgattgtt | 240 |
| actgttacag ctgacagcaa agaaattcaa ttctttgaag tataa | 285 |

<210> SEQ ID NO 47
<211> LENGTH: 285
<212> TYPE: DNA
<213> ORGANISM: Listeria monocytogenes

<400> SEQUENCE: 47

```
atggatgcac gcgacatcat taagcgccca gttgtaactg aagaatctac aagcattctc    60
gacgataaga aatatacatt tgaagtagat actcgcgcaa ctaaaacgca agtaaaatac   120
gcagttgaag aaattttcga cgtaaaagtt gctaaagtaa acgtaatgaa ttacaaaggc   180
aaacttaaac gtatgggccg ttatgcaggt tacactaaca acgccgtaa  agcgattgtt   240
actgttacag ctgacagcaa agaaattcaa ttctttgaag tataa                   285
```

<210> SEQ ID NO 48
<211> LENGTH: 285
<212> TYPE: DNA
<213> ORGANISM: Listeria monocytogenes

<400> SEQUENCE: 48

```
atggatgcac gcgacatcat taagcgccca gttgtaactg aagaatctac aagtattctc    60
gacgataaga aatatacatt tgaagtagat actcgcgcaa ctaaaacgca agtaaaatac   120
gcagttgaag aaattttcga cgtaaaagtt gctaaagtaa acgtaatgaa ttacaaaggc   180
aaacttaaac gtatgggccg ttatgcaggt tacactaaca acgccgtaa  agcgattgtt   240
actgttacag ctgacagcaa agaaattcaa ttctttgaag tataa                   285
```

<210> SEQ ID NO 49
<211> LENGTH: 834
<212> TYPE: DNA
<213> ORGANISM: Listeria monocytogenes

<400> SEQUENCE: 49

```
atggcgatca aaaagtataa acctaccact aacgggcgcc ggcacatgac tagttctgat    60
ttcgctgaga ttactacaag tactccagaa aaatctttac tacgtcctct taaaagaaa   120
gccggacgca ataaccaagg taagttaact gttcgtcatc acggcggtgg ccataaacgc   180
caataccgcg tgattgattt caaacgtaac aaagatggta ttcctggacg cgttgcaacg   240
atcgagtacg atccaaaccg ttctgctaat attgctctaa tcaactatgc tgatggagaa   300
aaacgctaca tcatcgcagc gaaaggcctt gaagtaggcc aaacaattta ttcaggagca   360
gaagctgaca tcaaagtcgg taatgcacta gaattaaaag atattccagt gggtactgtt   420
atccacaata tcgaaatgaa acctggtaaa ggtggacaat tagtacgttc tgctggaaca   480
agtgctcaag tgcttggtaa agaaggtaaa tacgtattaa tccgcttaaa ctctggtgaa   540
gttcgcatga ttcttgctac ttgccgtgct acaatcggtc aagttggtaa cgaacaacac   600
gaacttatca acatcggtaa agcaggtcgt tcacgttgga tgggtaaacg cccaactgtt   660
cgtggatctg taatgaaccc gaacgatcac ccacacggtg gtggtgaagg taaagctcca   720
atcggccgta aatcgccaat gtctccatgg ggtaaaccaa ctcttggata caaaacacgt   780
aagaaaaaca caactccgga taaatttatc gtacgtcgtc gtaagaaaaa ataa         834
```

<210> SEQ ID NO 50
<211> LENGTH: 834
<212> TYPE: DNA
<213> ORGANISM: Listeria monocytogenes

<400> SEQUENCE: 50

```
atggcgatca aaaagtataa acctaccact aacgggcgcc ggcacatgac tagttctgat    60
ttcgctgaga ttactacaag tactccagaa aaatctttac tacgtcctct taaaagaaa   120
```

-continued

```
gccggacgca ataaccaagg taagttaact gttcgtcatc acggcggtgg ccataaacgc      180
caataccgcg tgattgattt caaacgtaac aaagatggta ttcctggacg cgttgcaacg      240
atcgagtacg atccaaaccg ttctgctaat attgctctaa tcaactatgc tgatggagaa      300
aaacgctaca tcatcgcagc aaaaggcctt gaagtaggtc aaacaattta ttcaggagca      360
gaagctgata tcaaagtcgg taatgcacta gaattaaaag atattccagt gggtactgtt      420
atccacaata tcgaaatgaa acctggtaaa ggtggacaat tagtacgttc tgctggaaca      480
agtgctcaag tgcttggtaa agaaggtaaa tacgtattaa tccgcttaaa ctctggtgaa      540
gttcgcatga ttcttgctac ttgccgtgct acaatcggtc aagttggtaa cgaacaacac      600
gaacttatca acatcggtaa agcaggtcgt tcacgttgga tgggtaaacg cccaactgtt      660
cgtggatctg taatgaaccc gaacgatcac ccacacggtg gtggtgaagg taaagctcca      720
atcggccgta atcgccaat gtctccatgg ggtaaaccaa ctcttggata caaaacacgt      780
aagaaaaaca acaactccga taaatttatc gtacgtcgtc gtaagaaaaa ataa           834
```

<210> SEQ ID NO 51
<211> LENGTH: 834
<212> TYPE: DNA
<213> ORGANISM: Listeria monocytogenes

<400> SEQUENCE: 51

```
atggcgatca aaagtataaa acctaccact aacgggcgcc ggcacatgac tagttctgat       60
ttcgctgaga ttactacaag tactccagaa aaatctttac tacgtcctct taaaaagaaa      120
gccggacgca ataaccaagg taagttaact gttcgtcatc acggcggtgg ccataaacgc      180
caataccgcg tgattgattt caaacgtaac aaagatggta ttcctggacg cgttgcaacg      240
atcgagtacg atccaaaccg ttctgctaat attgctctaa tcaactatgc tgatggagaa      300
aaacgctaca tcatcgcagc gaaaggcctt gaagtaggcc aaacaattta ttcaggagca      360
gaagctgaca tcaaagtcgg taatgcacta gaattaaaag atattccagt gggtactgtt      420
atccacaata tcgaaatgaa acctggtaaa ggtggacaat tagtacgttc tgctggaaca      480
agtgctcaag tgcttggtaa agaaggtaaa tacgtattaa tccgcttaaa ctctggtgaa      540
gttcgcatga ttcttgctac ttgccgtgct acaatcggtc aagttggtaa cgaacaacac      600
gaacttatca acatcggtaa agcaggtcgt tcacgttgga tgggtaaacg cccaactgtt      660
cgtggatctg taatgaaccc gaacgatcac ccacacggtg gtggtgaagg taaagctcca      720
atcggccgta atcgccaat gtctccatgg ggtaaaccaa ctcttggata caaaacacgt      780
aagaaaaaca acaactccga taaatttatc gtacgtcgtc gtaagaaaaa ataa           834
```

<210> SEQ ID NO 52
<211> LENGTH: 834
<212> TYPE: DNA
<213> ORGANISM: Listeria monocytogenes

<400> SEQUENCE: 52

```
atggcgatca aaagtataaa acctaccact aacgggcgcc ggcacatgac tagttctgat       60
ttcgctgaga ttactacaag tactccagaa aaatctttac tacgtcctct taaaaagaaa      120
gccggacgca ataaccaagg taagttaact gttcgtcatc acggcggtgg ccataaacgc      180
caataccgcg tgattgattt caaacgtaac aaagatggta ttcctggacg cgttgcaacg      240
atcgagtacg atccaaaccg ttctgctaat attgctctaa tcaactatgc tgatggagaa      300
aaacgctaca tcatcgcagc aaaaggcctt gaagtaggtc aaacaattta ttcaggagca      360
```

```
gaagctgaca ttaaagtcgg taatgcacta gaattaaaag atattccagt gggtactgtt    420
atccacaata tcgaaatgaa acctggtaaa ggtggacaat tagtacgttc tgctggaaca    480
agtgctcaag tacttggtaa agaaggcaaa tacgtattaa tccgcttaaa ctctggtgaa    540
gttcgcatga tccttgctac ttgccgtgct acaatcggtc aagttggtaa cgaacaacac    600
gaacttatca acatcggtaa agcaggtcgt tcacgttgga tgggtaaacg cccaactgtt    660
cgtggatctg taatgaaccc gaacgatcac ccacacggtg gtggtgaagg taaagctcca    720
atcggccgta atcgccaat gtctccatgg ggtaaaccaa ctcttggata caaaacacgt    780
aagaaaaaca acaactccga taaatttatc gtacgtcgtc gtaagaaaaa ataa         834
```

<210> SEQ ID NO 53
<211> LENGTH: 834
<212> TYPE: DNA
<213> ORGANISM: Listeria monocytogenes

<400> SEQUENCE: 53

```
atggcgatca aaagtataa acctaccact aacgggcgcc ggcacatgac tagttctgat     60
ttcgctgaga ttactacaag tactccagaa aaatctttac tacgtcctct taaaaagaaa    120
gccggacgca ataaccaagg taagttaact gttcgtcatc acggcggtgg ccataaacgc    180
caataccgcg tgattgattt caaacgtaac aaagatggta ttcctggacg cgttgcaacg    240
atcgagtacg atccaaaccg ttctgctaat attgctctaa tcaactatgc tgatggagaa    300
aaacgctaca tcatcgcagc gaaaggcctt gaagtaggcc aaacaattta ttcaggagca    360
gaagctgaca tcaaagtcgg taatgcacta gaattaaaag atattccagt gggtactgtt    420
atccacaata tcgaaatgaa acctggtaaa ggtggacaat tagtacgttc tgctggaaca    480
agtgctcaag tgcttggtaa agaaggtaaa tacgtattaa tccgcttaaa ctctggtgaa    540
gttcgcatga ttcttgctac ttgccgtgct acaatcggtc aagttggtaa cgaacaacac    600
gaacttatca acatcggtaa agcaggtcgt tcacgttgga tgggtaaacg cccaactgtt    660
cgtggatctg taatgaaccc gaacgatcac ccacacggtg gtggtgaagg taaagctcca    720
atcggccgta atcgccaat gtctccatgg ggtaaaccaa ctcttggata caaaacacgt    780
aagaaaaaca acaactccga taaatttatc gtacgtcgtc gtaagaaaaa ataa         834
```

<210> SEQ ID NO 54
<211> LENGTH: 834
<212> TYPE: DNA
<213> ORGANISM: Listeria monocytogenes

<400> SEQUENCE: 54

```
atggcgatca aaagtataa acctaccact aacgggcgcc ggcacatgac tagttctgat     60
ttcgctgaga ttactacaag tactccagaa aaatctttac tacgtcctct taaaaagaaa    120
gccggacgca ataaccaagg taagttaact gttcgtcatc acggcggtgg ccataaacgc    180
caataccgcg tgattgattt caaacgtaac aaagatggta ttcctggacg cgttgcaacg    240
atcgagtacg atccaaaccg ttctgctaat attgctctaa tcaactatgc tgatggagaa    300
aaacgctaca tcatcgcagc aaaaggcctt gaagtaggtc aaacaattta ttcaggagca    360
gaagctgaca tcaaagtcgg taatgcacta gaattaaaag atattccagt gggtactgtt    420
atccacaata tcgaaatgaa acctggtaaa ggtggacaat tagtacgttc tgctggaaca    480
agtgctcaag tacttggtaa agaaggcaaa tacgtattaa tccgcttaaa ctctggtgaa    540
```

```
gttcgcatga tccttgctac ttgccgtgct acaatcggtc aagttggtaa cgaacaacac    600
gaacttatca acatcggtaa agcaggtcgt tcacgttgga tgggtaaacg cccaactgtt    660
cgtggatctg taatgaaccc gaacgatcac ccacacggtg gtggtgaagg taaagctcca    720
atcggccgta atcgccaat gtctccatgg ggtaaaccaa ctcttggata caaaacacgt    780
aagaaaaaca acaactccga taaatttatc gtacgtcgtc gtaagaaaaa ataa          834
```

<210> SEQ ID NO 55
<211> LENGTH: 834
<212> TYPE: DNA
<213> ORGANISM: Listeria monocytogenes

<400> SEQUENCE: 55

```
atggcgatca aaaagtataa acctaccact aacgggcgcc ggcacatgac tagttctgat     60
ttcgctgaga ttactacaag tactccagaa aaatctttac tacgtcctct taaaaagaaa    120
gccggacgca ataaccaagg taagttaact gttcgtcatc acggcggtgg ccataaacgc    180
caataccgcg tgattgattt caaacgtaac aaagatggta ttcctggacg cgttgcaacg    240
atcgagtacg atccaaaccg ttctgctaat attgctctaa tcaactatgc tgatggagaa    300
aaacgctaca tcatcgcagc aaaaggcctt gaagtaggta aacaatttta ttcaggagca    360
gaagctgata tcaaagtcgg taatgcacta gaattaaaag atattccagt gggtactgtt    420
atccacaata tcgaaatgaa acctggtaaa ggtggacaat tagtacgttc tgctggaaca    480
agtgctcaag tgcttggtaa agaaggtaaa tacgtattaa tccgcttaaa ctctggtgaa    540
gttcgcatga ttcttgctac ttgccgtgct acaatcggtc aagttggtaa cgaacaacac    600
gaacttatca acatcggtaa agcaggtcgt tcacgttgga tgggtaaacg cccaactgtt    660
cgtggatctg taatgaaccc gaacgatcac ccacacggtg gtggtgaagg taaagctcca    720
atcggccgta atcgccaat gtctccatgg ggcaaaccaa ctcttggata caaaacacgt    780
aagaaaaaca acaactccga taaatttatc gtacgtcgtc gtaagaaaaa ataa          834
```

<210> SEQ ID NO 56
<211> LENGTH: 834
<212> TYPE: DNA
<213> ORGANISM: Listeria monocytogenes

<400> SEQUENCE: 56

```
atggcgatca aaaagtataa acctaccact aacgggcgcc ggcacatgac tagttctgat     60
ttcgctgaga ttactacaag tactccagaa aaatctttac tacgtcctct taaaaagaaa    120
gccggacgca ataaccaagg taagttaact gttcgtcatc acggcggtgg ccataaacgc    180
caataccgcg tgattgattt caaacgtaac aaagatggta ttcctggacg cgttgcaacg    240
atcgagtacg atccaaaccg ttctgctaat attgctctaa tcaactatgc tgatggagaa    300
aaacgctaca tcatcgcagc aaaaggcctt gaagtaggtc aaacaatttta ttcaggagca    360 gaagctgata tcaaagtcgg taatgcacta gaattaaaag atattccagt gggtactgtt    420
atccacaata tcgaaatgaa acctggtaaa ggtggacaat tagtacgttc tgctggaaca    480
agtgctcaag tgcttggtaa agaaggtaaa tacgtattaa tccgcttaaa ctctggtgaa    540
gttcgcatga ttcttgctac ttgccgtgct acaatcggtc aagttggtaa cgaacaacac    600
gaacttatca acatcggtaa agcaggtcgt tcacgttgga tgggtaaacg cccaactgtt    660
cgtggatctg taatgaaccc gaacgatcac ccacacggtg gtggtgaagg taaagctcca    720
```

```
atcggccgta aatcgccaat gtctccatgg ggtaaaccaa ctcttggata caaaacacgt    780
aagaaaaaca acaactccga taaatttatc gtacgtcgtc gtaagaaaaa ataa          834

<210> SEQ ID NO 57
<211> LENGTH: 834
<212> TYPE: DNA
<213> ORGANISM: Listeria monocytogenes

<400> SEQUENCE: 57
atggcgatca aaagtataa acctaccact aacgggcgcc ggcacatgac tagttctgat      60
ttcgctgaga ttactacaag tactccagaa aaatctttac tacgtcctct taaaaagaaa   120
gccggacgca ataaccaagg taagttaact gttcgtcatc acggcggtgg ccataaacgc   180
caataccgcg tgattgattt caaacgtaac aaagatggta ttcctggacg cgttgcaacg   240
atcgagtacg atccaaaccg ttctgctaat attgctctaa tcaactatgc tgatggagaa   300
aaacgctaca tcatcgcagc aaaaggcctt gaagtaggtc aaacaattta ttcaggagca   360
gaagctgata tcaaagtcgg taatgcacta gaattaaaag atattccagt gggtactgtt   420
atccacaata tcgaaatgaa acctggtaaa ggtggacaat tagtacgttc tgctggaaca   480
agtgctcaag tgcttggtaa agaaggtaaa tacgtattaa tccgcttaaa ctctggtgaa   540
gttcgcatga ttcttgctac ttgccgtgct acaatcggtc aagttggtaa cgaacaacac   600
gaacttatca acatcggtaa agcaggtcgt tcacgttgga tgggtaaacg cccaactgtt   660
cgtggatctg taatgaaccc gaacgatcac ccacacggtg gtggtgaagg taaagctcca   720
atcggccgta aatcgccaat gtctccatgg ggtaaaccaa ctcttggata caaaacacgt   780
aagaaaaaca acaactccga taaatttatc gtacgtcgtc gtaagaaaaa ataa          834

<210> SEQ ID NO 58
<211> LENGTH: 834
<212> TYPE: DNA
<213> ORGANISM: Listeria monocytogenes

<400> SEQUENCE: 58
atggcgatca aaagtataa acctaccact aacgggcgcc ggcacatgac tagttctgat      60
ttcgctgaga ttactacaag tactccagaa aaatctttac tacgtcctct taaaaagaaa   120
gccggacgca ataaccaagg taagttaact gttcgtcatc acggcggtgg ccataaacgc   180
caataccgcg tgattgattt caaacgtaac aaagatggta ttcctggacg cgttgcaacg   240
atcgagtacg atccaaaccg ttctgctaat attgctctaa tcaactatgc tgatggagaa   300
aaacgctaca tcatcgcagc aaaaggcctt gaagtaggtc aaacaattta ttcaggagca   360
gaagctgaca ttaaagtcgg taatgcacta gaattaaaag atattccagt gggtactgtt   420
atccacaata tcgaaatgaa acctggtaaa ggtggacaat tagtacgttc tgctggaaca   480
agtgctcaag tacttggtaa agaaggcaaa tacgtattaa tccgcttaaa ctctggtgaa   540
gttcgcatga tccttgctac ttgccgtgct acaatcggtc aagttggtaa cgaacaacac   600
gaacttatca acatcggtaa agcaggtcgt tcacgttgga tgggtaaacg cccaactgtt   660
cgtggatctg taatgaaccc gaacgatcac ccacacggtg gtggtgaagg taaagctcca   720
atcggccgta aatcgccaat gtctccatgg ggtaaaccaa ctcttggata caaaacacgt   780
aagaaaaaca acaactccga taaatttatc gtacgtcgtc gtaagaaaaa ataa          834

<210> SEQ ID NO 59
```

<211> LENGTH: 834
<212> TYPE: DNA
<213> ORGANISM: Listeria monocytogenes

<400> SEQUENCE: 59

```
atggcgatca aaagtataa acctaccaca acgggcgcc ggcatatgac tagttcagat      60
tttgctgaga ttactacaag tactccagaa aaatctttac tacgtcctct taaaaagaaa    120
gccggacgca ataaccaagg taagttaact gttcgtcatc acggcggtgg ccataaacgc    180
caataccgcg tgattgattt caaacgtaac aaagatggta ttcctggacg cgttgcaacg    240
atcgagtacg atccaaaccg ttctgctaat attgctctaa tcaactatgc tgatggagaa    300
aaacgctaca tcatcgcagc aaaaggcctt gaagtaggtc aaacaattta ttcaggagca    360
gaagccgaca tcaaaatcgg taatgcacta gaattaaaag atattccagt gggtactgtt    420
atccacaata tcgaaatgaa acctggtaaa ggtggacaat tagtacgttc agctggaaca    480
agtgctcaag tgcttggtaa agaaggtaaa tacgtattaa tccgcttaaa ctctggtgaa    540
gttcgcatga ttcttgctac ttgccgcgct acaatcggtc aagttggtaa cgaacaacac    600
gaacttatca acattggtaa agcaggtcgt tcacgttgga tgggtaaacg cccaactgtt    660
cgtggatctg taatgaaccc taacgatcac ccgcacggtg gtggtgaagg taaagctcca    720
atcggtcgta atctccaat gtctccatgg ggtaaaccaa ctcttggata caaaacacgt    780
aagaaaaata caactccga taaatttatc gtacgtcgtc gtaagaaaaa ataa            834
```

<210> SEQ ID NO 60
<211> LENGTH: 834
<212> TYPE: DNA
<213> ORGANISM: Listeria monocytogenes

<400> SEQUENCE: 60

```
atggcgatca aaagtataa acctaccact acgggcgcc ggcacatgac tagttctgat      60
ttcgctgaga ttactacaag tactccagaa aaatctttac tacgtcctct taaaaagaaa    120
gccggacgca ataaccaagg taagttaact gttcgtcatc acggcggtgg ccataaacgc    180
caataccgcg tgattgattt caaacgtaac aaagatggta ttcctggacg cgttgcaacg    240
atcgagtacg atccaaaccg ttctgctaat attgctctaa tcaactatgc tgatggagaa    300
aaacgctaca tcatcgcagc aaaaggcctt gaagtaggtc aaacaattta ttcaggagca    360
gaagctgata tcaaagtcgg taatgcacta gaattaaaag atattccagt gggtactgtt    420
atccacaata tcgaaatgaa acctggtaaa ggtggacaat tagtacgttc tgctggaaca    480
agtgctcaag tgcttggtaa agaaggtaaa tacgtattaa tccgcttaaa ctctggtgaa    540
gttcgcatga ttcttgctac ttgccgtgct acaatcggtc aagttggtaa cgaacaacac    600
gaacttatca acattggtaa agcaggtcgt tcacgttgga tgggtaaacg cccaactgtt    660
cgtggatctg taatgaaccc gaacgatcac ccacacggtg gtggtgaagg taaagctcca    720
atcggccgta atctccaat gtctccatgg ggcaaaccaa ctcttggata caaaacacgt    780
aagaaaaaca caactccga taaatttatc gtacgtcgtc gtaagaaaaa ataa            834
```

<210> SEQ ID NO 61
<211> LENGTH: 834
<212> TYPE: DNA
<213> ORGANISM: Listeria monocytogenes

<400> SEQUENCE: 61

```
atggcgatca aaaagtataa acctaccaca acgggcgcc ggcatatgac tagttcagat      60
tttgctgaga ttactacaag tactccagaa aaatctttac tacgtcctct taaaaagaaa    120
gccggacgca ataaccaagg taagttaact gttcgtcatc acggcggtgg ccataaacgc    180
caataccgcg tgattgattt caaacgtaac aaagatggta ttcctggacg cgttgcaacg    240
atcgagtacg atccaaaccg ttctgctaat attgctctaa tcaactatgc tgatggagaa    300
aaacgctaca tcatcgcagc aaaaggcctt gaagtaggtc aaacaattta ttcaggagca    360
gaagccgaca tcaaaatcgg taatgcacta gaattaaaag atattccagt gggtactgtt    420
atccacaata tcgaaatgaa acctggtaaa ggtggacaat tagtacgttc agctggaaca    480
agtgctcaag tgcttggtaa agaaggtaaa tacgtattaa tccgcttaaa ctctggtgaa    540
gttcgcatga ttcttgctac ttgccgcgct acaatcggtc aagttggtaa cgaacaacac    600
gaacttatca acattggtaa agcaggtcgt tcacgttgga tgggtaaacg cccaactgtt    660
cgtggatctg taatgaaccc taacgatcac ccgcacggtg gtggtgaagg taaagctcca    720
atcggtcgta atctccaat gtctccatgg ggtaaaccaa ctcttggata caaaacacgt    780
aagaaaaata caaactccga taaatttatc gtacgtcgtc gtaagaaaaa ataa          834
```

<210> SEQ ID NO 62
<211> LENGTH: 834
<212> TYPE: DNA
<213> ORGANISM: Listeria monocytogenes

<400> SEQUENCE: 62

```
atggcgatca aaaagtataa acctaccact aacgggcgcc ggcacatgac tagttctgat     60
ttcgctgaga ttactacaag tactccagaa aaatctttac tacgtcctct taaaaagaaa    120
gccggacgca ataaccaagg taagttaact gttcgtcatc acggcggtgg ccataaacgc    180
caataccgcg tgattgattt caaacgtaac aaagatggta ttcctggacg cgttgcaacg    240
atcgagtacg atccaaaccg ttctgctaat attgctctaa tcaactatgc tgatggagaa    300
aaacgctaca tcatcgcagc aaaaggcctt gaagtaggtc aaacaattta ttcaggagca    360
gaagctgata tcaaagtcgg taatgcacta gaattaaaag atattccagt gggtactgtt    420
atccacaata tcgaaatgaa acctggtaaa ggtggacaat tagtacgttc tgctggaaca    480
agtgctcaag tgcttggtaa agaaggtaaa tacgtattaa tccgcttaaa ctctggtgaa    540
gttcgcatga ttcttgctac ttgccgtgct acaatcggtc aagttggtaa cgaacaacac    600
gaacttatca acatcggtaa agcaggtcgt tcacgttgga tgggtaaacg cccaactgtt    660
cgtggatctg taatgaaccc gaacgatcac ccacacggtg gtggtgaagg taaagctcca    720
atcggccgta atcgccaat gtctccatgg ggtaaaccaa ctcttggata caaaacacgt    780
aagaaaaaca caaactccga taaatttatc gtacgtcgtc gtaagaaaaa ataa          834
```

<210> SEQ ID NO 63
<211> LENGTH: 834
<212> TYPE: DNA
<213> ORGANISM: Listeria monocytogenes

<400> SEQUENCE: 63

```
atggcgatca aaaagtataa acctaccact aacgggcgcc ggcacatgac tagttctgat     60
ttcgctgaga ttactacaag tactccagaa aaatctttac tacgtcctct taaaaagaaa    120
```

| | |
|---|---|
| gccggacgca ataaccaagg taagttaact gttcgtcatc acggcggtgg ccataaacgc | 180 |
| caataccgcg tgattgattt caaacgtaac aaagatggta ttcctggacg cgttgcaacg | 240 |
| atcgagtacg atccaaaccg ttctgctaat attgctctaa tcaactatgc tgatggagaa | 300 |
| aaacgctaca tcatcgcagc aaaaggcctt gaagtaggtc aaacaattta ttcaggagca | 360 |
| gaagctgaca ttaaagtcgg taatgcacta gaattaaaag atattccagt gggtactgtt | 420 |
| atccacaata tcgaaatgaa acctggtaaa ggtggacaat tagtacgttc tgctggaaca | 480 |
| agtgctcaag tacttggtaa agaaggcaaa tacgtattaa tccgcttaaa ctctggtgaa | 540 |
| gttcgcatga tccttgctac ttgccgtgct acaatcggtc aagttggtaa cgaacaacac | 600 |
| gaacttatca acatcggtaa agcaggtcgt tcacgttgga tgggtaaacg cccaactgtt | 660 |
| cgtggatctg taatgaaccc gaacgatcac ccacacggtg gtggtgaagg taaagctcca | 720 |
| atcggccgta atcgccaat gtctccatgg ggtaaaccaa ctcttggata caaaacacgt | 780 |
| aagaaaaaca acaactccga taaatttatc gtacgtcgtc gtaagaaaaa ataa | 834 |

<210> SEQ ID NO 64
<211> LENGTH: 834
<212> TYPE: DNA
<213> ORGANISM: Listeria monocytogenes

<400> SEQUENCE: 64

| | |
|---|---|
| atggcgatca aaagtataa acctaccact aacgggcgcc ggcacatgac tagttctgat | 60 |
| ttcgctgaga ttactacaag tactccagaa aaatctttac tacgtcctct taaaaagaaa | 120 |
| gccggacgca ataaccaagg taagttaact gttcgtcatc acggcggtgg ccataaacgc | 180 |
| caataccgcg tgattgattt caaacgtaac aaagatggta ttcctggacg cgttgcaacg | 240 |
| atcgagtacg atccaaaccg ttctgctaat attgctctaa tcaactatgc tgatggagaa | 300 |
| aaacgctaca tcatcgcagc aaaaggcctt gaagtaggtc aaacaattta ttcaggagca | 360 |
| gaagctgata tcaaagtcgg taatgcacta gaattaaaag atattccagt gggtactgtt | 420 |
| atccacaata tcgaaatgaa acctggtaaa ggtggacaat tagtacgttc tgctggaaca | 480 |
| agtgctcaag tgcttggtaa agaaggtaaa tacgtattaa tccgcttaaa ctctggtgaa | 540 |
| gttcgcatga ttcttgctac ttgccgtgct acaatcggtc aagttggtaa cgaacaacac | 600 |
| gaacttatca acatcggtaa agcaggtcgt tcacgttgga tgggtaaacg cccaactgtt | 660 |
| cgtggatctg taatgaaccc gaacgatcac ccacacggtg gtggtgaagg taaagctcca | 720 |
| atcggccgta atcgccaat gtctccatgg ggcaaaccaa ctcttggata caaaacacgt | 780 |
| aagaaaaaca acaactccga taaatttatc gtacgtcgtc gtaagaaaaa ataa | 834 |

<210> SEQ ID NO 65
<211> LENGTH: 312
<212> TYPE: DNA
<213> ORGANISM: Listeria monocytogenes

<400> SEQUENCE: 65

| | |
|---|---|
| atgcatgtca aaaaggtga taaagtaaaa gttattactg gtaaagataa aggcaaatcc | 60 |
| ggcaaagtgc tcgcagcatt tccgaaaaag gatcgcgtac ttatcgaagg aatcaatatg | 120 |
| gttaaaaaac atacaaaacc ttccaacgtc aacccgcaag gcggaatctt gaatgttgaa | 180 |
| gcaccaatcc acgtttcaaa cgtaatgcta cttgacccta aaacaggcga acctactcgt | 240 |
| gtaggatacg aagttaaagg cgacaagaaa gtacgcgtag caaaaaaatc cggtgaagta | 300 |
| atagataaat aa | 312 |

<210> SEQ ID NO 66
<211> LENGTH: 312
<212> TYPE: DNA
<213> ORGANISM: Listeria monocytogenes

<400> SEQUENCE: 66

```
atgcatgtca aaaaggtga taaagtaaaa gttattactg gtaaagataa aggcaaattc      60
ggcaaagtgc tcgcagcatt tccgaaaaag accgcgtac ttatcgaagg aatcaatatg     120
gttaaaaaac atacaaaacc ttccaacatc aacccgcaag gcggaatctt gaatgttgaa    180
gcaccaatcc acgtttcaaa cgtaatgcta attgacccta aaacaggcga acctactcgt    240
gtaggatacg aagttaaagg cgataaaaaa gtacgcgtag caaaaaaatc cggtgaagta    300
atagataaat aa                                                        312
```

<210> SEQ ID NO 67
<211> LENGTH: 312
<212> TYPE: DNA
<213> ORGANISM: Listeria monocytogenes

<400> SEQUENCE: 67

```
atgcatgtca aaaaggtga taaagtaaaa gttattactg gtaaagataa aggcaaatcc      60
ggcaaagtgc tcgcagcatt tccgaaaaag gatcgcgtac ttatcgaagg aatcaatatg    120
gttaaaaaac atacaaaacc ttccaacgtc aacccgcaag gcggaatctt gaatgttgaa    180
gcaccaatcc acgtttcaaa cgtaatgcta cttgacccta aaacaggcga acctactcgt    240
gtaggatacg aagttaaagg cgacaagaaa gtacgcgtag caaaaaaatc cggtgaagta    300
atagataaat aa                                                        312
```

<210> SEQ ID NO 68
<211> LENGTH: 312
<212> TYPE: DNA
<213> ORGANISM: Listeria monocytogenes

<400> SEQUENCE: 68

```
atgcatgtca aaaaggtga taaagtaaaa gttattactg gtaaagataa aggcaaatcc      60
ggcaaagtgc tcgcagcatt tccgaaaaag gatcgcgtac ttatcgaagg aatcaatatg    120
gttaaaaaac atacaaaacc ttccaacgtc aacccgcaag gcggaatctt gaatgttgaa    180
gcaccaatcc acgtttcaaa cgtaatgcta attgacccta aaacaggtga acctactcgt    240
gtaggatacg aagttaaagg cgacaaaaaa gtacgcgtag caaaaaaatc cggtgaagta    300
atagataaat aa                                                        312
```

<210> SEQ ID NO 69
<211> LENGTH: 312
<212> TYPE: DNA
<213> ORGANISM: Listeria monocytogenes

<400> SEQUENCE: 69

```
atgcatgtca aaaaggtga taaagtaaaa gttattactg gtaaagataa aggcaaatcc      60
ggcaaagtgc tcgcagcatt tccgaaaaag gatcgcgtac ttatcgaagg aatcaatatg    120
gttaaaaaac atacaaaacc ttccaacgtc aacccgcaag gcggaatctt gaatgttgaa    180
```

```
gcaccaatcc acgtttcaaa cgtaatgcta cttgacccta aaacaggcga acctactcgt      240
gtaggatacg aagttaaagg cgacaagaaa gtacgcgtag caaaaaaatc cggtgaagta      300
atagataaat aa                                                          312
```

<210> SEQ ID NO 70
<211> LENGTH: 312
<212> TYPE: DNA
<213> ORGANISM: Listeria monocytogenes

<400> SEQUENCE: 70

```
atgcatgtca aaaaggtga taaagtaaaa gttattactg gtaaagataa aggcaaatcc       60
ggcaaagtgc tcgcagcatt tccgaaaaag gatcgcgtac ttatcgaagg aatcaatatg      120
gttaaaaaac atacaaaacc ttccaacgtc aacccgcaag gcggaatctt gaatgttgaa      180
gcaccaatcc acgtttcaaa cgtaatgcta attgacccta aaacaggcga acctactcgt      240
gtaggatacg aagttaaagg cgacaaaaaa gtacgcgtag caaaaaaatc cggtgaagta      300
atagataaat aa                                                          312
```

<210> SEQ ID NO 71
<211> LENGTH: 312
<212> TYPE: DNA
<213> ORGANISM: Listeria monocytogenes

<400> SEQUENCE: 71

```
atgcatgtca aaaaggtga taaagtaaaa gttattactg gtaaagataa aggcaaatcc       60
ggcaaagtgc tcgcagcatt tccgaaaaag gaccgcgtac ttatcgaagg aatcaatatg      120
gttaaaaaac atacaaaacc ttccaacatc aacccgcaag gcgggatctt gaatgttgaa      180
gcaccaatcc acgtttcaaa cgtaatgcta attgacccta aaacaggcga acctactcgt      240
gtaggatacg aagttaaagg cgataaaaaa gtacgcgtag caaaaaaatc cggtgaagta      300
atagataaat aa                                                          312
```

<210> SEQ ID NO 72
<211> LENGTH: 312
<212> TYPE: DNA
<213> ORGANISM: Listeria monocytogenes

<400> SEQUENCE: 72

```
atgcatgtca aaaaggtga taaagtaaaa gttattactg gtaaagataa aggcaaatcc       60
ggcaaagtgc tcgcagcatt tccgaaaaag gaccgcgtac ttatcgaagg aatcaatatg      120
gttaaaaaac atacaaaacc ttccaacatc aacccgcaag gcggaatctt gaatgttgaa      180
gcaccaatcc acgtttcaaa cgtaatgcta attgacccta aaacaggcga acctactcgt      240
gtaggatacg aagttaaagg cgataaaaaa gtacgcgtag caaaaaaatc cggtgaagta      300
atagataaat aa                                                          312
```

<210> SEQ ID NO 73
<211> LENGTH: 312
<212> TYPE: DNA
<213> ORGANISM: Listeria monocytogenes

<400> SEQUENCE: 73

```
atgcatgtca aaaaggtga taaagtaaaa gttattactg gtaaagataa aggcaaatcc       60
ggcaaagtgc tcgcagcatt tccgaaaaag gaccgcgtac ttatcgaagg aatcaatatg      120
```
gttaaaaaac atacaaaacc ttccaacatc aacccgcaag gcggaatctt gaatgttgaa    180
gcaccaatcc acgtttcaaa cgtaatgcta attgaccta aaacaggcga acctactcgt     240
gtaggatacg aagttaaagg cgataaaaaa gtacgcgtag caaaaaaatc cggtgaagta    300
atagataaat aa                                                        312

<210> SEQ ID NO 74
<211> LENGTH: 312
<212> TYPE: DNA
<213> ORGANISM: Listeria monocytogenes

<400> SEQUENCE: 74
atgcatgtca aaaaggtga taaagtaaaa gttattactg gtaaagataa aggcaaatcc     60
ggcaaagtgc tcgcagcatt tccgaaaaag gatcgcgtac ttatcgaagg aatcaatatg    120
gttaaaaaac atacaaaacc ttccaacgtc aacccgcaag gcggaatctt gaatgttgaa    180
gcaccaatcc acgtttcaaa cgtaatgcta attgaccta aaacaggtga acctactcgt     240
gtaggatacg aagttaaagg cgacaaaaaa gtacgcgtag caaaaaaatc cggtgaagta    300
atagataaat aa                                                        312

<210> SEQ ID NO 75
<211> LENGTH: 312
<212> TYPE: DNA
<213> ORGANISM: Listeria monocytogenes

<400> SEQUENCE: 75
atgcatgtca aaaaggtga taaagtaaaa gttattactg gtaaagataa aggcaaatcc     60
ggcaaagtgc tcgcagcatt tccgaagaag gatcgcgtac ttattgaagg aattaatatg    120
gtcaaaaaac atacaaaacc ttccaacatc aacccgcaag gcggaatctt gaatgttgaa    180
gcaccaatcc atgtttcaaa cgtaatgcta attgaccta aaacaggcga acctactcgt     240
gtaggctacg aagttaaagg cgataaaaaa gtacgcgtag caaaaaaatc cggtgaagta    300
atagataaat aa                                                        312

<210> SEQ ID NO 76
<211> LENGTH: 312
<212> TYPE: DNA
<213> ORGANISM: Listeria monocytogenes

<400> SEQUENCE: 76
atgcatgtca aaaaggtga taaagtaaaa gttattactg gtaaagataa aggcaaatcc     60
ggcaaagtgc tcgcagcatt tccgaaaaag gaccgcgtac ttatcgaagg aatcaatatg    120
gttaaaaaac atacaaaacc ttccaacatc aacccgcaag gcgggatctt gaatgttgaa    180
gcaccaatcc acgtttcaaa cgtaatgcta attgaccta aaacaggcga acctactcgt     240
gtaggatacg aagttaaagg cgataaaaaa gtacgcgtag caaaaaaatc cggtgaagta    300
atagataaat aa                                                        312

<210> SEQ ID NO 77
<211> LENGTH: 312
<212> TYPE: DNA
<213> ORGANISM: Listeria monocytogenes

<400> SEQUENCE: 77
atgcatgtca aaaaggtga taaagtaaaa gttattactg gtaaagataa aggcaaatcc     60
ggcaaagtgc tcgcagcatt tccgaagaag gatcgcgtac ttattgaagg aattaatatg    120

-continued

```
gtcaaaaaac atacaaaacc ttccaacatc aacccgcaag gcggaatctt gaatgttgaa      180
gcaccaatcc atgtttcaaa cgtaatgcta attgaccota aaacaggcga acctactcgt      240
gtaggctacg aagttaaagg cgataaaaaa gtacgcgtag caaaaaaatc cggtgaagta      300
atagataaat aa                                                          312
```

<210> SEQ ID NO 78
<211> LENGTH: 312
<212> TYPE: DNA
<213> ORGANISM: Listeria monocytogenes

<400> SEQUENCE: 78

```
atgcatgtca aaaaggtga taaagtaaaa gttattactg gtaaagataa aggcaaatcc       60
ggcaaagtgc tcgcagcatt tccgaaaaag gaccgcgtac ttatcgaagg aatcaatatg     120
gttaaaaaac atacaaaacc ttccaacatc aacccgcaag gcggaatctt gaatgttgaa     180
gcaccaatcc acgtttcaaa cgtaatgcta attgacccta aaacaggcga acctactcgt     240
gtaggatacg aagttaaagg cgataaaaaa gtacgcgtag caaaaaaatc cggtgaagta     300
atagataaat aa                                                         312
```

<210> SEQ ID NO 79
<211> LENGTH: 312
<212> TYPE: DNA
<213> ORGANISM: Listeria monocytogenes

<400> SEQUENCE: 79

```
atgcatgtca aaaaggtga taaagtaaaa gttattactg gtaaagataa aggcaaatcc       60
ggcaaagtgc tcgcagcatt tccgaaaaag gatcgcgtac ttatcgaagg aatcaatatg     120
gttaaaaaac atacaaaacc ttccaacgtc aacccgcaag gcggaatctt gaatgttgaa     180
gcaccaatcc acgtttcaaa cgtaatgcta attgacccta aaacaggtga acctactcgt     240
gtaggatacg aagttaaagg cgacaaaaaa gtacgcgtag caaaaaaatc cggtgaagta     300
atagataaat aa                                                         312
```

<210> SEQ ID NO 80
<211> LENGTH: 312
<212> TYPE: DNA
<213> ORGANISM: Listeria monocytogenes

<400> SEQUENCE: 80

```
atgcatgtca aaaaggtga taaagtaaaa gttattactg gtaaagataa aggcaaatcc       60
ggcaaagtgc tcgcagcatt tccgaaaaag gaccgcgtac ttatcgaagg aatcaatatg     120
gttaaaaaac atacaaaacc ttccaacatc aacccgcaag gcgggatctt gaatgttgaa     180
gcaccaatcc acgtttcaaa cgtaatgcta attgacccta aaacaggcga acctactcgt     240
gtaggatacg aagttaaagg cgataaaaaa gtacgcgtag caaaaaaatc cggtgaagta     300
atagataaat aa                                                         312
```

<210> SEQ ID NO 81
<211> LENGTH: 537
<212> TYPE: DNA
<213> ORGANISM: Listeria monocytogenes

<400> SEQUENCE: 81

```
atgtcccgta taggtaaaaa aactattgtg attcctgcag gtgtaacagt tacacttaat    60
ggatcaacag caacagttaa aggtcctaaa ggtgaacttg taaaagagtt caacccagaa   120
attactatta aaatcgaagg caacgaaatt aacgtttctc gcccgactga taataaaaac   180
caccgtgcac ttcatggtac aactcgtgct attcttaata acatggttgt cggagtttcc   240
gagggttatg aaaagaaatt agaacttatc ggtgttggtt accgtgcgca aaaacaaggc   300
gataagcttg ttcttaacgt agggtactct catccagtag agtttgttgc tcctaaaggc   360
gtagatattg aagttcctgc aaacacacaa gtgattgtta aaggatacaa caaggaacac   420
gttggcgagt tagctgcaaa cattcgtgcc gtacgtccac cagagccata taaggtaaa    480
ggtattcgtt acgaaggcga acatgtacgc cgtaaagaag gtaaaactgg taaataa      537
```

<210> SEQ ID NO 82
<211> LENGTH: 537
<212> TYPE: DNA
<213> ORGANISM: Listeria monocytogenes

<400> SEQUENCE: 82

```
atgtcccgta taggtaaaaa aactattgtg attcctgcag gtgtaacagt tacacttaat    60
ggatcaacag caacagttaa aggtcctaaa ggtgaacttg taaaagagtt caacccagaa   120
attactatta atattgaagg caacgaaatt aacgtttctc gcccgactga taataaaaac   180
caccgtgcac ttcatggtac aactcgtgct attcttaata acatggttgt cggagtttcc   240
gagggttatg aaaagaaatt agaacttatc ggtgttggtt accgtgcgca aaaacaaggc   300
gacaagcttg ttcttaacgt agggtactct catccagtag agtttgttgc tcctaaaggc   360
gtagatattg aagttcctgc aaacacacaa gtgattgtta aaggatacaa caagaacac    420
gttggcgagt tagctgcaaa cattcgtgcc gtacgtccac cagagccata taaggtaaa    480
ggtattcgtt acgaaggcga acatgtacgc cgtaaagaag gtaaaactgg taaataa      537
```

<210> SEQ ID NO 83
<211> LENGTH: 537
<212> TYPE: DNA
<213> ORGANISM: Listeria monocytogenes

<400> SEQUENCE: 83

```
atgtcccgta taggtaaaaa aactattgtg attcctgcag gtgtaacagt tacacttaat    60
ggatcaacag caacagttaa aggtcctaaa ggtgaacttg taaaagagtt caacccagaa   120
attactatta aaatcgaagg caacgaaatt aacgtttctc gcccgactga taataaaaac   180
caccgtgcac ttcatggtac aactcgtgct attcttaata acatggttgt cggagtttcc   240
gagggttatg aaaagaaatt agaacttatc ggtgttggtt accgtgcgca aaaacaaggc   300
gataagcttg ttcttaacgt agggtactct catccagtag agtttgttgc tcctaaaggc   360
gtagatattg aagttcctgc aaacacacaa gtgattgtta aaggatacaa caaggaacac   420
gttggcgagt tagctgcaaa cattcgtgcc gtacgtccac cagagccata taaggtaaa    480
ggtattcgtt acgaaggcga acatgtacgc cgtaaagaag gtaaaactgg taaataa      537
```

<210> SEQ ID NO 84
<211> LENGTH: 537
<212> TYPE: DNA
<213> ORGANISM: Listeria monocytogenes

<400> SEQUENCE: 84

```
atgtcccgta taggtaaaaa aactattgtg attcctgcag gtgtaacagt tacacttaat    60
ggatcaacag caacagttaa aggtcctaaa ggtgaacttg taaaagagtt caacccagaa   120
attactatta aaatcgaagg caacgaaatt aacgtttctc gcccgactga taataaaaac   180
caccgtgcac ttcatggtac aactcgtgct attcttaata acatggttgt cggagtttcc   240
gagggttatg aaaagaaatt agaacttatc ggtgttggtt accgtgcgca aaaacaaggc   300
gataagcttg ttcttaacgt agggtactct catccagtag agtttgttgc tcctaaaggc   360
gtagatattg aagttcctgc aaacacacaa gtgattgtta aaggatacaa caaggaacac   420
gttggcgagt tagctgcaaa cattcgtgcc gtacgtccac cagagccata taaggtaaa   480
ggtattcgtt acgaaggcga acatgtacgc cgtaaagaag gtaaaactgg taaataa     537
```

<210> SEQ ID NO 85
<211> LENGTH: 537
<212> TYPE: DNA
<213> ORGANISM: Listeria monocytogenes

<400> SEQUENCE: 85

```
atgtcccgta taggtaaaaa aactattgtg attcctgcag gtgtaacagt tacacttaat    60
ggatcaacag caacagttaa aggtcctaaa ggtgaacttg taaaagagtt caacccagaa   120
attactatta aaatcgaagg caacgaaatt aacgtttctc gcccgactga taataaaaac   180
caccgtgcac ttcatggtac aactcgtgct attcttaata acatggttgt cggagtttcc   240
gagggttatg aaaagaaatt agaacttatc ggtgttggtt accgtgcgca aaaacaaggc   300
gataagcttg ttcttaacgt agggtactct catccagtag agtttgttgc tcctaaaggc   360
gtagatattg aagttcctgc aaacacacaa gtgattgtta aaggatacaa caaggaacac   420
gttggcgagt tagctgcaaa cattcgtgcc gtacgtccac cagagccata taaggtaaa   480
ggtattcgtt acgaaggcga acatgtacgc cgtaaagaag gtaaaactgg taaataa     537
```

<210> SEQ ID NO 86
<211> LENGTH: 537
<212> TYPE: DNA
<213> ORGANISM: Listeria monocytogenes

<400> SEQUENCE: 86

```
atgtcccgta taggtaaaaa aactattgtg attcctgcag gtgtaacagt tacacttaat    60
ggatcaacag caacagttaa aggtcctaaa ggtgaacttg taaaagagtt caacccagaa   120
attactatta aaatcgaagg caacgaaatt aacgtttctc gcccgactga taataaaaac   180
caccgtgcac ttcatggtac aactcgtgct attcttaata acatggttgt cggagtttcc   240
gagggttatg aaaagaaatt agaacttatc ggtgttggtt accgtgcgca aaaacaaggc   300
gacaagcttg ttcttaacgt agggtactct catccagtag agtttgttgc tcctaaaggc   360
gtagatattg aagttcctgc aaacacacaa gtgattgtta aaggatacaa caagaacac   420
gttggcgagt tagctgcaaa cattcgtgcc gtacgtccac cagagccata taaggtaaa   480
ggtattcgtt acgaaggcga acatgtacgc cgtaaagaag gtaaaactgg taaataa     537
```

<210> SEQ ID NO 87
<211> LENGTH: 537
<212> TYPE: DNA
<213> ORGANISM: Listeria monocytogenes

<400> SEQUENCE: 87

```
atgtcccgta taggtaaaaa aactattgtg attcctgcag gtgtaacagt tacacttaat      60
ggatcaacag caacagttaa aggtcctaaa ggtgaacttg taaaagagtt caacccagaa     120
attactatta atattgaagg caacgaaatt aacgtttctc gcccgactga taataaaaac     180
caccgtgcac ttcatggtac aactcgtgct attcttaata acatggttgt cggagtttcc     240
gagggttatg aaaagaaatt agaacttatc ggtgttggtt accgtgcgca aaaacaaggc     300
gacaagcttg ttcttaacgt agggtactct catccagtag agtttgttgc tcctaaaggc     360
gtagatattg aagttcctgc aaacacacaa gtgattgtta aaggatacaa caaagaacac     420
gttggcgagt tagctgcaaa cattcgtgcc gtacgtccac cagagccata taaggtaaa      480
ggtattcgtt acgaaggcga acatgtacgc cgtaaagaag gtaaaactgg taaataa       537
```

<210> SEQ ID NO 88
<211> LENGTH: 537
<212> TYPE: DNA
<213> ORGANISM: Listeria monocytogenes

<400> SEQUENCE: 88

```
atgtcccgta taggtaaaaa aactattgtg attcctgcag gtgtaacagt tacacttaat      60
ggatcaacag caacagttaa aggtcctaaa ggtgaacttg taaaagagtt caacccagaa     120
attactatta atattgaagg caacgaaatt aacgtttctc gcccgactga taataaaaac     180
caccgtgcac ttcatggtac aactcgtgct attcttaata acatggttgt cggagtttcc     240
gagggttatg aaaagaaatt agaacttatc ggtgttggtt accgtgcgca aaaacaaggc     300
gacaagcttg ttcttaacgt agggtactct catccagtag agtttgttgc tcctaaaggc     360
gtagatattg aagttcctgc aaacacacaa gtgattgtta aaggatacaa caaagaacac     420
gttggcgagt tagctgcaaa cattcgtgcc gtacgtccac cagagccata taaggtaaa      480
ggtattcgtt acgaaggcga acatgtacgc cgtaaagaag gtaaaactgg taaataa       537
```

<210> SEQ ID NO 89
<211> LENGTH: 537
<212> TYPE: DNA
<213> ORGANISM: Listeria monocytogenes

<400> SEQUENCE: 89

```
atgtcccgta taggtaaaaa aactattgtg attcctgcag gtgtaacagt tacacttaat      60
ggatcaacag caacagttaa aggtcctaaa ggtgaacttg taaaagagtt caacccagaa     120
attactatta atattgaagg caacgaaatt aacgtttctc gcccgactga taataaaaac     180
caccgtgcac ttcatggtac aactcgtgct attcttaata acatggttgt cggagtttcc     240
gagggttatg aaaagaaatt agaacttatc ggtgttggtt accgtgcgca aaaacaaggc     300
gacaagcttg ttcttaacgt agggtactct catccagtag agtttgttgc tcctaaaggc     360
gtagatattg aagttcctgc aaacacacaa gtgattgtta aaggatacaa caaagaacac     420
gttggcgagt tagctgcaaa cattcgtgcc gtacgtccac cagagccata taaggtaaa      480
ggtattcgtt acgaaggcga acatgtacgc cgtaaagaag gtaaaactgg taaataa       537
```

<210> SEQ ID NO 90
<211> LENGTH: 537
<212> TYPE: DNA
<213> ORGANISM: Listeria monocytogenes

<400> SEQUENCE: 90

```
atgtcccgta taggtaaaaa aactattgtg attcctgcag gtgtaacagt tacacttaat    60
ggatcaacag caacagttaa aggtcctaaa ggtgaacttg taaaagagtt caacccagaa   120
attactatta aaatcgaagg caacgaaatt aacgtttctc gcccgactga taataaaaac   180
caccgtgcac ttcatggtac aactcgtgct attcttaata acatggttgt cggagtttcc   240
gagggttatg aaaagaaatt agaacttatc ggtgttggtt accgtgcgca aaaacaaggc   300
gataagcttg ttcttaacgt agggtactct catccagtag agtttgttgc tcctaaaggc   360
gtagatattg aagttcctgc aaacacacaa gtgattgtta aaggatacaa caaggaacac   420
gttggcgagt tagctgcaaa cattcgtgcc gtacgtccac cagagccata taaaggtaaa   480
ggtattcgtt acgaaggcga acatgtacgc cgtaaagaag gtaaaactgg taaataa     537
```

<210> SEQ ID NO 91
<211> LENGTH: 537
<212> TYPE: DNA
<213> ORGANISM: Listeria monocytogenes

<400> SEQUENCE: 91

```
atgtcccgta taggtaaaaa aactattgtg attcctgcag gtgtaacagt tacacttaat    60
ggatcaacag caacagttaa aggtcctaaa ggtgaacttg taaaagagtt caacccagaa   120
attactatta atattgaagg caatgaaatt aacgtttctc gcccgactga taataaaaac   180
caccgcgcgc ttcatggtac aactcgtgct attctaaata acatggttgt cggagtttcc   240
gagggttatg aaaagaaatt agaacttatc ggtgttggtt accgtgcgca aaaacaaggc   300
gacaagcttg ttcttaacgt agggtactct catccagtag aatttgttgc tccgaaaggc   360
gtagaaattg aagttcctgc aaacacacaa gtgattgtta aaggatacaa caagaacac   420
gttggagaat tagctgcaaa cattcgtgcc gtacgtccac cagagccgta taaaggtaaa   480
ggtattcgtt acgaaggcga acatgtacgc cgtaaagaag gtaaaactgg taaataa     537
```

<210> SEQ ID NO 92
<211> LENGTH: 537
<212> TYPE: DNA
<213> ORGANISM: Listeria monocytogenes

<400> SEQUENCE: 92

```
atgtcccgta taggtaaaaa aactattgtg attcctgcag gtgtaacagt tacacttaat    60
ggatcaacag caacagttaa aggtcctaaa ggtgaacttg taaaagagtt caacccagaa   120
attactatta atattgaagg caacgaaatt aacgtttctc gcccgactga taataaaaac   180
caccgtgcac ttcatggtac aactcgtgct attcttaata acatggttgt cggagtttcc   240
gagggttatg aaaagaaatt agaacttatc ggtgttggtt accgtgcgca aaaacaaggc   300
gacaagcttg ttcttaacgt agggtactct catccagtag agtttgttgc tcctaaaggc   360
gtagatattg aagttcctgc aaacacacaa gtgattgtta aaggatacaa caagaacac   420
gttggcgagt tagctgcaaa cattcgtgcc gtacgtccac cagagccata taaaggtaaa   480
ggtattcgtt acgaaggcga acatgtacgc cgtaaagaag gtaaaactgg taaataa     537
```

<210> SEQ ID NO 93
<211> LENGTH: 537
<212> TYPE: DNA
<213> ORGANISM: Listeria monocytogenes

<400> SEQUENCE: 93

```
atgtcccgta taggtaaaaa aactattgtg attcctgcag gtgtaacagt tacacttaat    60
ggatcaacag caacagttaa aggtcctaaa ggtgaacttg taaaagagtt caacccagaa   120
attactatta atattgaagg caacgaaatt aacgtttctc gcccgactga taataaaaac   180
caccgcgcgc ttcatggtac aactcgtgct attctaaata acatggttgt cggagttttcc  240
gagggttatg aaaagaaatt agaacttatc ggtgttggtt accgtgcgca aaaacaaggc   300
gacaagcttg ttcttaacgt agggtactct catccagtag aatttgttgc tccgaaaggc   360
gtagaaattg aagttcctgc aaacacacaa gtgattgtta aaggatacaa caagaacac    420
gttggagaat tagctgcaaa cattcgtgcc gtacgtccac cagagccgta taaggtaaa    480
ggtattcgtt acgaaggcga acatgtacgc cgtaaagaag gtaaaactgg taaataa      537
```

<210> SEQ ID NO 94
<211> LENGTH: 537
<212> TYPE: DNA
<213> ORGANISM: Listeria monocytogenes

<400> SEQUENCE: 94

```
atgtcccgta taggtaaaaa aactattgtg attcctgcag gtgtaacagt tacacttaat    60
ggatcaacag caacagttaa aggtcctaaa ggtgaacttg taaaagagtt caacccagaa   120
attactatta atattgaagg caacgaaatt aacgtttctc gcccgactga taataaaaac   180
caccgtgcac ttcatggtac aactcgtgct attcttaata acatggttgt cggagttttcc  240
gagggttatg aaaagaaatt agaacttatc ggtgttggtt accgtgcgca aaaacaaggc   300
gacaagcttg ttcttaacgt agggtactct catccagtag agtttgttgc tcctaaaggc   360
gtagatattg aagttcctgc aaacacacaa gtgattgtta aaggatacaa caagaacac    420
gttggcgagt tagctgcaaa cattcgtgcc gtacgtccac cagagccata taaggtaaa    480
ggtattcgtt acgaaggcga acatgtacgc cgtaaagaag gtaaaactgg taaataa      537
```

<210> SEQ ID NO 95
<211> LENGTH: 537
<212> TYPE: DNA
<213> ORGANISM: Listeria monocytogenes

<400> SEQUENCE: 95

```
atgtcccgta taggtaaaaa aactattgtg attcctgcag gtgtaacagt tacacttaat    60
ggatcaacag caacagttaa aggtcctaaa ggtgaacttg taaaagagtt caacccagaa   120
attactatta aaatcgaagg caacgaaatt aacgtttctc gcccgactga taataaaaac   180
caccgtgcac ttcatggtac aactcgtgct attcttaata acatggttgt cggagttttcc  240
gagggttatg aaaagaaatt agaacttatc ggtgttggtt accgtgcgca aaaacaaggc   300
gataagcttg ttcttaacgt agggtactct catccagtag agtttgttgc tcctaaaggc   360
gtagatattg aagttcctgc aaacacacaa gtgattgtta aaggatacaa caaggaacac   420
gttggcgagt tagctgcaaa cattcgtgcc gtacgtccac cagagccata taaggtaaa    480
ggtattcgtt acgaaggcga acatgtacgc cgtaaagaag gtaaaactgg taaataa      537
```

<210> SEQ ID NO 96
<211> LENGTH: 537
<212> TYPE: DNA
<213> ORGANISM: Listeria monocytogenes

<400> SEQUENCE: 96

```
atgtcccgta taggtaaaaa aactattgtg attcctgcag gtgtaacagt tacacttaat    60
ggatcaacag caacagttaa aggtcctaaa ggtgaacttg taaaagagtt caacccagaa   120
attactatta atattgaagg caacgaaatt aacgtttctc gcccgactga taataaaaac   180
caccgtgcac ttcatggtac aactcgtgct attcttaata acatggttgt cggagtttcc   240
gagggttatg aaaagaaatt agaacttatc ggtgttggtt accgtgcgca aaaacaaggc   300
gacaagcttg ttcttaacgt agggtactct catccagtag agtttgttgc tcctaaaggc   360
gtagatattg aagttcctgc aaacacacaa gtgattgtta aaggatacaa caaagaacac   420
gttggcgagt tagctgcaaa cattcgtgcc gtacgtccac cagagccata taaaggtaaa   480
ggtattcgtt acgaaggcga acatgtacgc cgtaaagaag gtaaaactgg taaataa      537
```

<210> SEQ ID NO 97
<211> LENGTH: 360
<212> TYPE: DNA
<213> ORGANISM: Listeria monocytogenes

<400> SEQUENCE: 97

```
gtgattacca aaatcgacaa aaataaagta cgtaaaaaaa gacatgctcg tgttcgttct    60
aagatttctg gaactgaaag tcgtccacgt ttaaacgtat tccgttcaaa caaaaacatt   120
tatgctcaaa ttattgatga tgtaaatggt gtgacacttg caagtgcgtc taatttagat   180
aaagatttcg gttctgctga atccaaagtt gatgcagcaa gcaaagttgg cgaactagtt   240
gctaaacgtg cttccgaaaa aggtattact tctgtcactt ttgaccgtgg aggatactta   300
tatcatggcc gcgtgaaagc tcttgctgaa gcagctcgcg aaaatggact agaattttaa   360
```

<210> SEQ ID NO 98
<211> LENGTH: 360
<212> TYPE: DNA
<213> ORGANISM: Listeria monocytogenes

<400> SEQUENCE: 98

```
gtgattacca aaatcgacaa aaataaagta cgtaaaaaaa gacatgctcg tgttcgttct    60
aagatttctg gaactgaaag tcgtccacgt ttaaacgtat tccgttcaaa caaaaacatt   120
tatgctcaaa ttattgatga tgtaaatggt gtgacacttg caagtgcgtc taatttagat   180
aaagatttcg gttctgctga atccaaagtt gatgcagcaa gcaaagttgg cgaactagtt   240
gctaaacgtg cttccgaaaa aggtattact tctgtcactt ttgaccgtgg aggatactta   300
tatcatggcc gcgtgaaagc tcttgctgaa gcagctcgcg aaaatggact agaattttaa   360
```

<210> SEQ ID NO 99
<211> LENGTH: 360
<212> TYPE: DNA
<213> ORGANISM: Listeria monocytogenes

<400> SEQUENCE: 99

```
gtgattacca aaatcgacaa aaataaagta cgtaaaaaaa gacatgctcg tgttcgttct    60
aagatttctg gaactgaaag tcgtccacgt ttaaacgtat tccgttcaaa caaaaacatt   120
tatgctcaaa ttattgatga tgtaaatggt gtgacacttg caagtgcgtc taatttagat   180
aaagatttcg gttctgctga atccaaagtt gatgcagcaa gcaaagttgg cgaactagtt   240
gctaaacgtg cttccgaaaa aggtattact tctgtcactt ttgaccgtgg aggatactta   300
tatcatggcc gcgtgaaagc tcttgctgaa gcagctcgcg aaaatggact agaattttaa   360
```

<210> SEQ ID NO 100
<211> LENGTH: 360
<212> TYPE: DNA
<213> ORGANISM: Listeria monocytogenes

<400> SEQUENCE: 100

```
gtgattacca aaatcgacaa aaataaagta cgtaaaaaaa gacatgctcg tgttcgttct      60
aagatttctg gaactgaaag tcgtccacgt ttaaacgtat tccgttcaaa caaaaacatt     120
tatgctcaaa ttattgatga tgtaaatggt gtgacacttg caagtgcgtc taatttagat     180
aaagatttcg gttctgctga atccaaagtt gatgcagcaa gcaaagttgg cgaactagtt     240
gctaaacgtg cttccgaaaa aggtattact tctgtcactt ttgaccgtgg aggatactta     300
tatcatggcc gcgtgaaagc tcttgctgaa gcagctcgcg aaaatggact agaattttaa     360
```

<210> SEQ ID NO 101
<211> LENGTH: 360
<212> TYPE: DNA
<213> ORGANISM: Listeria monocytogenes

<400> SEQUENCE: 101

```
gtgattacca aaatcgacaa aaataaagta cgtaaaaaaa gacatgctcg tgttcgttct      60
aagatttctg gaactgaaag tcgtccacgt ttaaacgtat tccgttcaaa caaaaacatt     120
tatgctcaaa ttattgatga tgtaaatggt gtgacacttg caagtgcgtc taatttagat     180
aaagatttcg gttctgctga atccaaagtt gatgcagcaa gcaaagttgg cgaactagtt     240
gctaaacgtg cttccgaaaa aggtattact tctgtcactt ttgaccgtgg aggatactta     300
tatcatggcc gcgtgaaagc tcttgctgaa gcagctcgcg aaaatggact agaattttaa     360
```

<210> SEQ ID NO 102
<211> LENGTH: 360
<212> TYPE: DNA
<213> ORGANISM: Listeria monocytogenes

<400> SEQUENCE: 102

```
gtgattacca aaatcgacaa aaataaagta cgtaaaaaaa gacatgctcg tgttcgttct      60
aagatttctg gaactgaaag tcgtccacgt ttaaacgtat tccgttcaaa caaaaacatt     120
tatgctcaaa ttattgatga tgtaaatggt gtgacacttg caagtgcgtc taatttagat     180
aaagatttcg gttctgctga atccaaagtt gatgcagcaa gcaaagttgg cgaactagtt     240
gctaaacgtg cttccgaaaa aggtattact tctgtcactt ttgaccgtgg aggatactta     300
tatcatggcc gcgtgaaagc tcttgctgaa gcagctcgcg aaaatggact agaattttaa     360
```

<210> SEQ ID NO 103
<211> LENGTH: 360
<212> TYPE: DNA
<213> ORGANISM: Listeria monocytogenes

<400> SEQUENCE: 103

```
gtgattacca aaatcgacaa aaataaagta cgtaaaaaaa gacatgctcg tgttcgttct      60
aagatttctg gaactgaaag tcgtccacgt ttaaacgtat tccgttcaaa caaaaacatt     120
tatgctcaaa ttattgatga tgtaaatggt gtgacacttg caagtgcgtc taatttagat     180
```
aaagatttcg gttctgctga atccaaagtt gatgcagcaa gcaaagttgg cgaactagtt    240
gctaaacgtg cttccgaaaa aggtattact tctgtcactt ttgaccgtgg aggatactta    300
tatcatggcc gcgtgaaagc tcttgctgaa gcagctcgcg aaaatggact agaattttaa    360

<210> SEQ ID NO 104
<211> LENGTH: 360
<212> TYPE: DNA
<213> ORGANISM: Listeria monocytogenes

<400> SEQUENCE: 104
gtgattacca aaatcgacaa aaataaagta cgtaaaaaaa gacatgctcg tgttcgttct     60
aagatttctg gaactgaaag tcgtccacgt ttaaacgtat tccgttcaaa caaaaacatt    120
tatgctcaaa ttattgatga tgtaaatggt gtgacacttg caagtgcgtc taatttagat    180
aaagatttcg gttctgctga atccaaagtt gatgcagcaa gcaaagttgg cgaactagtt    240
gctaaacgtg cttccgaaaa aggtattact tctgtcactt ttgaccgtgg aggatactta    300
tatcatggcc gcgtgaaagc tcttgctgaa gcagctcgcg aaaatggact agaattttaa    360

<210> SEQ ID NO 105
<211> LENGTH: 360
<212> TYPE: DNA
<213> ORGANISM: Listeria monocytogenes

<400> SEQUENCE: 105
gtgattacca aaatcgacaa aaataaagta cgtaaaaaaa gacatgctcg tgttcgttct     60
aagatttctg gaactgaaag tcgtccacgt ttaaacgtat tccgttcaaa caaaaacatt    120
tatgctcaaa ttattgatga tgtaaatggt gtgacacttg caagtgcgtc taatttagat    180
aaagatttcg gttctgctga atccaaagtt gatgcagcaa gcaaagttgg cgaactagtt    240
gctaaacgtg cttccgaaaa aggtattact tctgtcactt ttgaccgtgg aggatactta    300
tatcatggcc gcgtgaaagc tcttgctgaa gcagctcgcg aaaatggact agaattttaa    360

<210> SEQ ID NO 106
<211> LENGTH: 360
<212> TYPE: DNA
<213> ORGANISM: Listeria monocytogenes

<400> SEQUENCE: 106
gtgattacca aaatcgacaa aaataaagta cgtaaaaaaa gacatgctcg tgttcgttct     60
aagatttctg gaactgaaag tcgtccacgt ttaaacgtat tccgttcaaa caaaaacatt    120
tatgctcaaa ttattgatga tgtaaatggt gtgacacttg caagtgcgtc taatttagat    180
aaagatttcg gttctgctga atccaaagtt gatgcagcaa gcaaagttgg cgaactagtt    240
gctaaacgtg cttccgaaaa aggtattact tctgtcactt ttgaccgtgg aggatactta    300
tatcatggcc gcgtgaaagc tcttgctgaa gcagctcgcg aaaatggact agaattttaa    360

<210> SEQ ID NO 107
<211> LENGTH: 360
<212> TYPE: DNA
<213> ORGANISM: Listeria monocytogenes

<400> SEQUENCE: 107
gtgattacca aaatcgacaa aaataaagta cgtaaaaaaa gacatgctcg tgttcgttct     60
aagatttccg gaactgaaag tcgtccacgt ttaaacgtat tccgttcaaa caaaaacatt    120

```
tatgctcaag taattgatga tgtaaatggt gtgacacttg caagtgcgtc taatttagat    180
aaagatttcg gttctgttga atcaaaagtt gatgcagcaa gcaaagttgg cgaactagtt    240
gctaaacgtg cttccgaaaa aggtattact tctgtcactt ttgaccgtgg aggatactta    300
tatcatggcc gcgtaaaagc tcttgctgaa gcagctcgcg aaaatggact agaattttaa    360
```

<210> SEQ ID NO 108
<211> LENGTH: 360
<212> TYPE: DNA
<213> ORGANISM: Listeria monocytogenes

<400> SEQUENCE: 108

```
gtgattacca aaatcgacaa aaataaagta cgtaaaaaaa gacatgctcg tgttcgttct     60
aagatttctg gaactgaaag tcgtccacgt ttaaacgtat tccgttcaaa caaaaacatt    120
tatgctcaaa ttattgatga tgtaaatggt gtgacacttg caagtgcgtc taatttagat    180
aaagatttcg gttctgctga atccaaagtt gatgcagcaa gcaaagttgg cgaactagtt    240
gctaaacgtg cttccgaaaa aggtattact tctgtcactt ttgaccgtgg aggatactta    300
tatcatggcc gcgtgaaagc tcttgctgaa gcagctcgcg aaaatggact agaattttaa    360
```

<210> SEQ ID NO 109
<211> LENGTH: 360
<212> TYPE: DNA
<213> ORGANISM: Listeria monocytogenes

<400> SEQUENCE: 109

```
gtgattacca aaatcgacaa aaataaagta cgtaaaaaaa gacatgctcg tgttcgttct     60
aagatttccg gaactgaaag tcgtccacgt ttaaacgtat tccgttcaaa caaaaacatt    120
tatgctcaag taattgatga tgtaaatggt gtgacacttg caagtgcgtc taatttagat    180
aaagatttcg gttctgttga atcaaaagtt gatgcagcaa gcaaagttgg cgaactagtt    240
gctaaacgtg cttccgaaaa aggtattact tctgtcactt ttgaccgtgg aggatactta    300
tatcatggcc gcgtaaaagc tcttgctgaa gcagctcgcg aaaatggact agaattttaa    360
```

<210> SEQ ID NO 110
<211> LENGTH: 360
<212> TYPE: DNA
<213> ORGANISM: Listeria monocytogenes

<400> SEQUENCE: 110

```
gtgattacca aaatcgacaa aaataaagta cgtaaaaaaa gacatgctcg tgttcgttct     60
aagatttctg gaactgaaag tcgtccacgt ttaaacgtat tccgttcaaa caaaaacatt    120
tatgctcaaa ttattgatga tgtaaatggt gtgacacttg caagtgcgtc taatttagat    180
aaagatttcg gttctgctga atccaaagtt gatgcagcaa gcaaagttgg cgaactagtt    240
gctaaacgtg cttccgaaaa aggtattact tctgtcactt ttgaccgtgg aggatactta    300
tatcatggcc gcgtgaaagc tcttgctgaa gcagctcgcg aaaatggact agaattttaa    360
```

<210> SEQ ID NO 111
<211> LENGTH: 360
<212> TYPE: DNA
<213> ORGANISM: Listeria monocytogenes

<400> SEQUENCE: 111

```
gtgattacca aaatcgacaa aaataaagta cgtaaaaaaa gacatgctcg tgttcgttct     60
aagatttctg gaactgaaag tcgtccacgt ttaaacgtat tccgttcaaa caaaaacatt    120
```

| tatgctcaaa ttattgatga tgtaaatggt gtgacacttg caagtgcgtc taatttagat | 180 |
| aaagatttcg gttctgctga atccaaagtt gatgcagcaa gcaaagttgg cgaactagtt | 240 |
| gctaaacgtg cttccgaaaa aggtattact tctgtcactt ttgaccgtgg aggatactta | 300 |
| tatcatggcc gcgtgaaagc tcttgctgaa gcagctcgcg aaaatggact agaattttaa | 360 |

<210> SEQ ID NO 112
<211> LENGTH: 360
<212> TYPE: DNA
<213> ORGANISM: Listeria monocytogenes

<400> SEQUENCE: 112

| gtgattacca aaatcgacaa aaataaagta cgtaaaaaaa gacatgctcg tgttcgttct | 60 |
| aagatttctg gaactgaaag tcgtccacgt ttaaacgtat tccgttcaaa caaaaacatt | 120 |
| tatgctcaaa ttattgatga tgtaaatggt gtgacacttg caagtgcgtc taatttagat | 180 |
| aaagatttcg gttctgctga atccaaagtt gatgcagcaa gcaaagttgg cgaactagtt | 240 |
| gctaaacgtg cttccgaaaa aggtattact tctgtcactt ttgaccgtgg aggatactta | 300 |
| tatcatggcc gcgtgaaagc tcttgctgaa gcagctcgcg aaaatggact agaattttaa | 360 |

<210> SEQ ID NO 113
<211> LENGTH: 504
<212> TYPE: DNA
<213> ORGANISM: Listeria monocytogenes

<400> SEQUENCE: 113

| atgcctgagc aaattgatgg aaacaaatta gatttagaag aacgcgttgt tacaatcaac | 60 |
| cgtgttgcta agtagttaa aggtggacgt cgtttccgtt tcacagcact tgttgttgtt | 120 |
| ggagacaaaa atggtcatgt tggtttcggt actggtaaag cgcaagaagt tccagatgct | 180 |
| atccgtaaag ctgttgagga tgctaaaaag aacatggtgc ttgtaccaac tgtagacaca | 240 |
| actattccac acactgtagt cggacatttt ggtggcggag aaattcttct taaacctgct | 300 |
| agtgccggtt ctggtgtaac tgctggtggt cccgttcgtg cggtcctaga acttgctggt | 360 |
| gttgctgatg tatcttccaa atcgcttgga tctaatacac caattaacat ggtacgtgct | 420 |
| acaatcgacg gaattaaaca actgaaaaac gctgaagatg ttgcgaaact tcgtggcaaa | 480 |
| acagtagaag aattgttagg ataa | 504 |

<210> SEQ ID NO 114
<211> LENGTH: 504
<212> TYPE: DNA
<213> ORGANISM: Listeria monocytogenes

<400> SEQUENCE: 114

| atgcctgagc aaattgatgg aaacaaatta gatttagaag aacgcgttgt tacaatcaac | 60 |
| cgtgttgcta agtagttaa aggtggacgt cgtttccgtt tcacagcact tgttgttgtt | 120 |
| ggagacaaaa atggtcatgt tggtttcggt actggtaaag cgcaagaagt tccagatgct | 180 |
| atccgtaaag ctgttgagga tgctaaaaag aacatggtgc ttgtaccaac tgtagacaca | 240 |
| actattccac acactgtagt cggacatttt ggtggcggag aaattcttct taaaccagct | 300 |
| agtgccggtt ctggtgtaac tgctggtggt cccgttcgtg cggtcctaga acttgccggt | 360 |
| gttgctgatg tatcttccaa atcgcttgga tctaatacac caattaacat ggtacgtgct | 420 |

```
acaatcgacg gaattaaaca actgaaaaac gctgaagatg ttgcgaaact tcgtggcaaa    480
acagtagaag aattgttagg ataa                                           504

<210> SEQ ID NO 115
<211> LENGTH: 504
<212> TYPE: DNA
<213> ORGANISM: Listeria monocytogenes

<400> SEQUENCE: 115
atgcctgagc aaattgatgg aaacaaatta gatttagaag aacgcgttgt tacaatcaac     60
cgtgttgcta aagtagttaa aggtggacgt cgtttccgtt tcacagcact tgttgttgtt    120
ggagacaaaa atggtcatgt tggtttcggt actggtaaag cgcaagaagt tccagatgct    180
atccgtaaag ctgttgagga tgctaaaaag aacatggtgc ttgtaccaac tgtagacaca    240
actattccac acactgtagt cggacatttt ggtggcggag aaattcttct taaacctgct    300
agtgccggtt ctggtgtaac tgctggtggt cccgttcgtg cggtcctaga acttgctggt    360
gttgctgatg tatcttccaa atcgcttgga tctaatacac caattaacat ggtacgtgct    420
acaatcgacg gaattaaaca actgaaaaac gctgaagatg ttgcgaaact tcgtggcaaa    480
acagtagaag aattgttagg ataa                                           504

<210> SEQ ID NO 116
<211> LENGTH: 504
<212> TYPE: DNA
<213> ORGANISM: Listeria monocytogenes

<400> SEQUENCE: 116
atgcctgagc aaattgatgg aaacaaatta gatttagaag aacgcgttgt tacaatcaac     60
cgtgttgcta aagtagttaa aggtggacgt cgtttccgtt tcacagcact tgttgttgtt    120
ggagacaaaa atggtcatgt tggtttcggt actggtaaag cgcaagaagt tccagatgct    180
atccgtaaag ctgttgagga tgctaaaaag aacatggtgc ttgtaccaac tgtagacaca    240
actattccac acactgtagt cggacatttt ggtggcggag aaattcttct taaacctgct    300
agtgccggtt ctggtgtaac tgctggtggt cccgttcgtg cggtcctaga acttgctggt    360
gttgctgatg tatcttccaa atcgcttgga tctaatacac caattaacat ggtacgtgct    420
acaatcgacg gaattaaaca actgaaaaac gctgaagatg ttgcgaaact tcgtggcaaa    480
acagtagaag aattgttagg ataa                                           504

<210> SEQ ID NO 117
<211> LENGTH: 504
<212> TYPE: DNA
<213> ORGANISM: Listeria monocytogenes

<400> SEQUENCE: 117
atgcctgagc aaattgatgg aaacaaatta gatttagaag aacgcgttgt tacaatcaac     60
cgtgttgcta aagtagttaa aggtggacgt cgtttccgtt tcacagcact tgttgttgtt    120
ggagacaaaa atggtcatgt tggtttcggt actggtaaag cgcaagaagt tccagatgct    180
atccgtaaag ctgttgagga tgctaaaaag aacatggtgc ttgtaccaac tgtagacaca    240
actattccac acactgtagt cggacatttt ggtggcggag aaattcttct taaacctgct    300
agtgccggtt ctggtgtaac tgctggtggt cccgttcgtg cggtcctaga acttgctggt    360
gttgctgatg tatcttccaa atcgcttgga tctaatacac caattaacat ggtacgtgct    420
```

```
acaatcgacg gaattaaaca actgaaaaac gctgaagatg ttgcgaaact tcgtggcaaa    480
acagtagaag aattgttagg ataa                                          504

<210> SEQ ID NO 118
<211> LENGTH: 504
<212> TYPE: DNA
<213> ORGANISM: Listeria monocytogenes

<400> SEQUENCE: 118
atgcctgagc aaattgatgg aaacaaatta gatttagaag aacgcgttgt tacaatcaac     60
cgtgttgcta agtagttaa aggtggacgt cgtttccgtt tcacagcact tgttgttgtt    120
ggagacaaaa atggtcatgt tggtttcggt actggtaaag cacaagaagt tccagatgct    180
atccgtaaag ctgttgagga tgctaaaaag aacatggtgc ttgtaccaac tgtagacaca    240
actattccac acactgtagt cggacatttt ggtggcggag aaattcttct taaaccagct    300
agtgccggtt ctggtgtaac tgctggtggt cccgttcgtg cggtcctaga acttgccggt    360
gttgctgatg tatcttccaa atcgcttgga tctaatacac caattaacat ggtacgtgct    420
acaatcgacg gaattaaaca actgaaaaac gctgaagatg ttgcgaaact tcgtggcaaa    480
acagtagaag aattgttagg ataa                                          504

<210> SEQ ID NO 119
<211> LENGTH: 504
<212> TYPE: DNA
<213> ORGANISM: Listeria monocytogenes

<400> SEQUENCE: 119
atgcctgagc aaattgatgg aaacaaatta gatttagaag aacgcgttgt tacaatcaac     60
cgtgttgcta agtagttaa aggtggacgt cgtttccgtt tcacagcact tgttgttgtt    120
ggagacaaaa atggtcatgt tggtttcggt actggtaaag cgcaagaagt tccagatgct    180
atccgtaaag ctgttgagga tgctaaaaag aacatggtgc ttgtaccaac tgtagacaca    240
actattccac acactgtagt cggacatttt ggtggcggag aaattcttct taaaccagct    300
agtgccggtt ctggtgtaac tgctggtggt cccgttcgtg cggtcctaga acttgccggt    360
gttgctgatg tatcttccaa atcgcttgga tctaatacac caattaacat ggtacgtgct    420
acaatcgacg gaattaaaca actgaaaaac gctgaagatg ttgcgaaact tcgtggcaaa    480
acagtagaag aattgttagg ataa                                          504

<210> SEQ ID NO 120
<211> LENGTH: 504
<212> TYPE: DNA
<213> ORGANISM: Listeria monocytogenes

<400> SEQUENCE: 120
atgcctgagc aaattgatgg aaacaaatta gatttagaag aacgcgttgt tacaatcaac     60
cgtgttgcta agtagttaa aggtggacgt cgtttccgtt tcacagcact tgttgttgtt    120
ggagacaaaa atggtcatgt tggtttcggt actggtaaag cgcaagaagt tccagatgct    180
atccgtaaag ctgttgagga tgctaaaaag aacatggtgc ttgtaccaac tgtagacaca    240
actattccac acactgtagt cggacatttt ggtggcggag aaattcttct taaaccagct    300
agtgccggtt ctggtgtaac tgctggtggt cccgttcgtg cggtcctaga acttgccggt    360
gttgctgatg tatcttccaa atcgcttgga tctaatacac caattaacat ggtacgtgct    420
```

```
acaatcgacg gaattaaaca actgaaaaac gctgaagatg ttgcgaaact tcgtggcaaa    480
acagtagaag aattgttagg ataa                                          504

<210> SEQ ID NO 121
<211> LENGTH: 504
<212> TYPE: DNA
<213> ORGANISM: Listeria monocytogenes

<400> SEQUENCE: 121
atgcctgagc aaattgatgg aaacaaatta gatttagaag aacgcgttgt tacaatcaac    60
cgtgttgcta aagtagttaa aggtggacgt cgtttccgtt tcacagcact tgttgttgtt    120
ggagacaaaa atggtcatgt tggtttcggt actggtaaag cgcaagaagt tccagatgct    180
atccgtaaag ctgttgagga tgctaaaaag aacatggtgc ttgtaccaac tgtagacaca    240
actattccac acactgtagt cggacatttt ggtggcggag aaattcttct taaaccagct    300
agtgccggtt ctggtgtaac tgctggtggt cccgttcgtg cggtcctaga acttgccggt    360
gttgctgatg tatcttccaa atcgcttgga tctaatacac caattaacat ggtacgtgct    420
acaatcgacg gaattaaaca actgaaaaac gctgaagatg ttgcgaaact tcgtggcaaa    480
acagtagaag aattgttagg ataa                                          504

<210> SEQ ID NO 122
<211> LENGTH: 504
<212> TYPE: DNA
<213> ORGANISM: Listeria monocytogenes

<400> SEQUENCE: 122
atgcctgagc aaattgatgg aaacaaatta gatttagaag aacgcgttgt tacaatcaac    60
cgtgttgcta aagtagttaa aggtggacgt cgtttccgtt tcacagcact tgttgttgtt    120
ggagacaaaa atggtcatgt tggtttcggt actggtaaag cgcaagaagt tccagatgct    180
atccgtaaag ctgttgagga tgctaaaaag aacatggtgc ttgtaccaac tgtagacaca    240
actattccac acactgtagt cggacatttt ggtggcggag aaattcttct taaacctgct    300
agtgccggtt ctggtgtaac tgctggtggt cccgttcgtg cggtcctaga acttgctggt    360
gttgctgatg tatcttccaa atcgcttgga tctaatacac caattaacat ggtacgtgct    420
acaatcgacg gaattaaaca actgaaaaac gctgaagatg ttgcgaaact tcgtggcaaa    480
acagtagaag aattgttagg ataa                                          504

<210> SEQ ID NO 123
<211> LENGTH: 504
<212> TYPE: DNA
<213> ORGANISM: Listeria monocytogenes

<400> SEQUENCE: 123
atgcctgagc aaattgatgg aaacaaatta gatttagaag aacgcgttgt tacaatcaac    60
cgtgttgcta aagtagttaa aggtggacgt cgtttccgtt tcacagcact tgttgttgtt    120
ggagacaaaa atggtcatgt tggtttcggt actggtaaag cacaagaagt tccagatgca    180
atccgcaaag ctgttgagga tgctaaaaag aacatggtgc ttgtaccaac tgtaaacaca    240
actattccac acactgtagt cggacatttt ggtggcggag aaattcttct taaacctgct    300
agtgccggtt ctggtgtaac tgctggtggt cccgttcgtg cggtcctaga acttgccggt    360
gttgctgatg tatcttccaa atcgcttgga tctaatacac caattaacat ggtacgtgct    420
```

```
acaatcgacg gaattaaaca acttaaaaac gctgaagatg ttgcgaaact tcgtggcaaa    480
acagtagaag aattgttagg ataa                                          504

<210> SEQ ID NO 124
<211> LENGTH: 504
<212> TYPE: DNA
<213> ORGANISM: Listeria monocytogenes

<400> SEQUENCE: 124
atgcctgagc aaattgatgg aaacaaatta gatttagaag aacgcgttgt tacaatcaac     60
cgtgttgcta aagtagttaa aggtggacgt cgtttccgtt tcacagcact tgttgttgtt    120
ggagacaaaa atggtcatgt tggtttcggt actggtaaag cgcaagaagt tccagatgct    180
atccgtaaag ctgttgagga tgctaaaaag aacatggtgc ttgtaccaac tgtagacaca    240
actattccac acactgtagt cggacatttt ggtggcggag aaattcttct taaaccagct    300
agtgccggtt ctggtgtaac tgctggtggt cccgttcgtg cggtcctaga acttgccggt    360
gttgctgatg tatcttccaa atcgcttgga tctaatacac caattaacat ggtacgtgct    420
acaatcgacg gaattaaaca actgaaaaac gctgaagatg ttgcgaaact tcgtggcaaa    480
acagtagaag aattgttagg ataa                                          504

<210> SEQ ID NO 125
<211> LENGTH: 504
<212> TYPE: DNA
<213> ORGANISM: Listeria monocytogenes

<400> SEQUENCE: 125
atgcctgagc aaattgatgg aaacaaatta gatttagaag aacgcgttgt tacaatcaac     60
cgtgttgcta aagtagttaa aggtggacgt cgtttccgtt tcacagcact tgttgttgtt    120
ggagacaaaa atggtcatgt tggtttcggt actggtaaag cacaagaagt tccagatgca    180
atccgcaaag ctgttgagga tgctaaaaag aacatggtgc ttgtaccaac tgtaaacaca    240
actattccac acactgtagt cggacatttt ggtggcggag aaattcttct taaacctgct    300
agtgccggtt ctggtgtaac tgctggtggt cccgttcgtg cggtcctaga acttgctggt    360
gttgctgatg tatcttccaa atcgcttgga tctaatacac caattaacat ggtacgtgct    420
acaatcgacg gaattaaaca acttaaaaac gctgaagatg ttgcgaaact tcgtggcaaa    480
acagtagaag aattgttagg ataa                                          504

<210> SEQ ID NO 126
<211> LENGTH: 504
<212> TYPE: DNA
<213> ORGANISM: Listeria monocytogenes

<400> SEQUENCE: 126
atgcctgagc aaattgatgg aaacaaatta gatttagaag aacgcgttgt tacaatcaac     60
cgtgttgcta aagtagttaa aggtggacgt cgtttccgtt tcacagcact tgttgttgtt    120
ggagacaaaa atggtcatgt tggtttcggt actggtaaag cgcaagaagt tccagatgct    180
atccgtaaag ctgttgagga tgctaaaaag aacatggtgc ttgtaccaac tgtagacaca    240
actattccac acactgtagt cggacatttt ggtggcggag aaattcttct taaaccagct    300
agtgccggtt ctggtgtaac tgctggtggt cccgttcgtg cggtcctaga acttgccggt    360
gttgctgatg tatcttccaa atcgcttgga tctaatacac caattaacat ggtacgtgct    420
```
acaatcgacg gaattaaaca actgaaaaac gctgaagatg ttgcgaaact tcgtggcaaa        480
acagtagaag aattgttagg ataa                                              504

<210> SEQ ID NO 127
<211> LENGTH: 504
<212> TYPE: DNA
<213> ORGANISM: Listeria monocytogenes

<400> SEQUENCE: 127
atgcctgagc aaattgatgg aaacaaatta gatttagaag aacgcgttgt tacaatcaac        60
cgtgttgcta agtagttaa aggtggacgt cgtttccgtt tcacagcact tgttgttgtt       120
ggagacaaaa atggtcatgt tggtttcggt actggtaaag cgcaagaagt tccagatgct       180
atccgtaaag ctgttgagga tgctaaaaag aacatggtgc ttgtaccaac tgtagacaca       240
actattccac acactgtagt cggacatttt ggtggcggaa aaattcttct taaacctgct       300
agtgccggtt ctggtgtaac tgctggtggt cccgttcgtg cggtcctaga acttgctggt       360
gttgctgatg tatcttccaa atcgcttgga tctaatacac aattaacat ggtacgtgct       420 acaatcgacg gaattaaaca actgaaaaac gctgaagatg ttgcgaaact tcgtggcaaa       480
acagtagaag aattgttagg ataa                                              504

<210> SEQ ID NO 128
<211> LENGTH: 504
<212> TYPE: DNA
<213> ORGANISM: Listeria monocytogenes

<400> SEQUENCE: 128
atgcctgagc aaattgatgg aaacaaatta gatttagaag aacgcgttgt tacaatcaac        60
cgtgttgcta agtagttaa aggtggacgt cgtttccgtt tcacagcact tgttgttgtt       120
ggagacaaaa atggtcatgt tggtttcggt actggtaaag cgcaagaagt tccagatgct       180
atccgtaaag ctgttgagga tgctaaaaag aacatggtgc ttgtaccaac tgtagacaca       240
actattccac acactgtagt cggacatttt ggtggcggaa aaattcttct taaaccagct       300
agtgccggtt ctggtgtaac tgctggtggt cccgttcgtg cggtcctaga acttgccggt       360
gttgctgatg tatcttccaa atcgcttgga tctaatacac aattaacat ggtacgtgct       420 acaatcgacg gaattaaaca actgaaaaac gctgaagatg ttgcgaaact tcgtggcaaa       480
acagtagaag aattgttagg ataa                                              504

<210> SEQ ID NO 129
<211> LENGTH: 441
<212> TYPE: DNA
<213> ORGANISM: Listeria monocytogenes

<400> SEQUENCE: 129
atgaaactac atgaacttaa gccttcagaa ggttctcgta agaacgtaa tcgtgttggt        60 cgtggaacag ctctggtaa cggcaaaact tcaggacgcg gtcataaagg acaaaaagct       120
cgttctggtg gtggcgtacg tttaggtttt gaaggtggac aacttccact tttccgtcgt       180
attccaaaac gtggattcac aaatatcaac cgtaaagaat ttgctatcgt gaacttagat       240
gttttaaacc gctttgaaga tggtacagaa gtaaccaccag aacttttagt tgaaactgga       300
attattcgta atgaaaaatc cggaatcaag attttatcta atggaaatat cgagaaaaaa       360

```
cttactgtga aagcgaacaa attctctgca gctgcgaaag aagcaattga agcagctggc    420
ggaaaaactg aggtgatcta a                                              441
```

<210> SEQ ID NO 130
<211> LENGTH: 441
<212> TYPE: DNA
<213> ORGANISM: Listeria monocytogenes

<400> SEQUENCE: 130

```
atgaaactac atgaacttaa gccttcagaa ggttctcgta agaacgtaa tcgtgttggt      60 cgtggaacag gctctggtaa cggcaaaact tcaggacgcg gtcataaagg acaaaaagct    120
cgttctggtg gtggcgtacg tttaggcttt gaaggtggac aacttccact tttccgtcgt    180
attccaaaac gtggattcac aaatatcaac cgtaaagaat ttgctatcgt gaacttagat    240
gttttaaacc gctttgaaga tggtacagaa gtaacaccag aactttagt tgaaactgga    300 attattcgta atgaaaaatc cggaatcaag attttatcta atggaaatat cgagaaaaaa    360
cttactgtga aagcgaacaa attctctgca gctgcgaaag aagcaattga agcggctggc    420
ggaaaaactg aggtgatcta a                                              441
```

<210> SEQ ID NO 131
<211> LENGTH: 441
<212> TYPE: DNA
<213> ORGANISM: Listeria monocytogenes

<400> SEQUENCE: 131

```
atgaaactac atgaacttaa gccttcagaa ggttctcgta agaacgtaa tcgtgttggt      60 cgtggaacag gctctggtaa cggcaaaact tcaggacgcg gtcataaagg acaaaaagct    120
cgttctggtg gtggcgtacg tttaggtttt gaaggtggac aacttccact tttccgtcgt    180
attccaaaac gtggattcac aaatatcaac cgtaaagaat ttgctatcgt gaacttagat    240
gttttaaacc gctttgaaga tggtacagaa gtaacaccag aactttagt tgaaactgga    300 attattcgta atgaaaaatc cggaatcaag attttatcta atggaaatat cgagaaaaaa    360
cttactgtga aagcgaacaa attctctgca gctgcgaaag aagcaattga agcagctggc    420
ggaaaaactg aggtgatcta a                                              441
```

<210> SEQ ID NO 132
<211> LENGTH: 441
<212> TYPE: DNA
<213> ORGANISM: Listeria monocytogenes

<400> SEQUENCE: 132

```
atgaaactac atgaacttaa gccttcagaa ggttctcgta agaacgtaa tcgtgttggt      60 cgtggaacag gctctggtaa cggcaaaact tcaggacgcg gtcataaagg acaaaaagct    120
cgttctggtg gtggcgtacg tttaggtttt gaaggtggac aacttccact tttccgtcgt    180
attccaaaac gtggattcac aaatatcaac cgtaaagaat ttgctatcgt gaacttagat    240
gttttaaacc gctttgaaga tggtacagaa gtaacaccag aactttagt tgaaactgga    300 attattcgta atgaaaaatc cggaatcaag attttatcta atggaaatat cgagaaaaaa    360
cttactgtga aagcgaacaa attctctgca gctgcgaaag aagcaattga agcagctggc    420
ggaaaaactg aggtgatcta a                                              441
```

<210> SEQ ID NO 133

<211> LENGTH: 441
<212> TYPE: DNA
<213> ORGANISM: Listeria monocytogenes

<400> SEQUENCE: 133

```
atgaaactac atgaacttaa gccttcagaa ggttctcgta aagaacgtaa tcgtgttggt      60
cgtggaacag gctctggtaa cggcaaaact tcaggacgcg gtcataaagg acaaaaagct     120
cgttctggtg gtggcgtacg tttaggtttt gaaggtggac aacttccact tttccgtcgt     180
attccaaaac gtggattcac aaatatcaac cgtaaagaat ttgctatcgt gaacttagat     240
gttttaaacc gctttgaaga tggtacagaa gtaacaccag aacttttagt tgaaactgga     300
attattcgta atgaaaaatc cggaatcaag attttatcta tggaaatat cgagaaaaaa      360
cttactgtga aagcgaacaa attctctgca gctgcgaaag aagcaattga agcagctggc     420
ggaaaaactg aggtgatcta a                                                441
```

<210> SEQ ID NO 134
<211> LENGTH: 441
<212> TYPE: DNA
<213> ORGANISM: Listeria monocytogenes

<400> SEQUENCE: 134

```
atgaaactac atgaacttaa gccttcagaa ggttctcgta aagaacgtaa tcgtgttggt      60
cgtggaacag gctctggtaa cggcaaaact tcaggacgcg gtcataaagg acaaaaagct     120
cgttctggtg gtggcgtacg tttaggtttt gaaggtggac aacttccact tttccgtcgt     180
attccaaaac gtggattcac aaatatcaac cgtaaagaat ttgctatcgt gaacttagat     240
gttttaaacc gctttgaaga tggtacagaa gtaacaccag aacttttagt tgaaactgga     300
attattcgta acgaaaaatc cggaatcaag attttatcta tggaaatat cgagaaaaaa      360
cttactgtga aagcgaacaa attctctgca gctgccaaag aagcaatcga agcagctggc     420
ggaaaaactg aggtgatcta a                                                441
```

<210> SEQ ID NO 135
<211> LENGTH: 441
<212> TYPE: DNA
<213> ORGANISM: Listeria monocytogenes

<400> SEQUENCE: 135

```
atgaaactac atgaacttaa gccttcagaa ggttctcgta aagaacgtaa tcgtgttggt      60
cgtggaacag gctctggtaa cggcaaaact tcaggacgcg gtcataaagg acaaaaagct     120
cgttctggtg gtggcgtacg tttaggcttt gaaggtggac aacttccact tttccgtcgt     180
attccaaaac gtggattcac aaatatcaac cgtaaagaat ttgctatcgt gaacttagat     240
gttttaaacc gctttgaaga tggtacagaa gtaacaccag aacttttagt tgaaactgga     300
attattcgta atgaaaaatc cggaatcaag attttatcta tggaaatat cgagaaaaaa      360
cttactgtga aagcgaacaa attctctgca gctgcgaaag aagcaattga agcggctggc     420
ggaaaaactg aggtgatcta a                                                441
```

<210> SEQ ID NO 136
<211> LENGTH: 441
<212> TYPE: DNA
<213> ORGANISM: Listeria monocytogenes

<400> SEQUENCE: 136

```
atgaaactac atgaacttaa gccttcagaa ggttctcgta aagaacgtaa tcgtgttggt    60
cgtggaacag gctctggtaa cggcaaaact tcaggacgcg gtcataaagg acaaaaagct   120
cgttctggtg gtggcgtacg tttaggcttt gaaggtggac aacttccact tttccgtcgt   180
attccaaaac gtggattcac aaatatcaac cgtaaagaat ttgctatcgt gaacttagat   240
gttttaaacc gctttgaaga tggtacagaa gtaacaccag aacttttagt tgaaactgga   300
attattcgta tgaaaaatc cggaatcaag attttatcta tggaaatat cgagaaaaaa   360
cttactgtga aagcgaacaa attctctgca gctgcgaaag aagcaattga agcggctggc   420
ggaaaaactg aggtgatcta a                                            441
```

<210> SEQ ID NO 137
<211> LENGTH: 441
<212> TYPE: DNA
<213> ORGANISM: Listeria monocytogenes

<400> SEQUENCE: 137

```
atgaaactac atgaacttaa gccttcagaa ggttctcgta aagaacgtaa tcgtgttggt    60
cgtggaacag gctctggtaa cggcaaaact tcaggacgcg gtcataaagg acaaaaagct   120
cgttctggtg gtggcgtacg tttaggcttt gaaggtggac aacttccact tttccgtcgt   180
attccaaaac gtggattcac aaatatcaac cgtaaagaat ttgctatcgt gaacttagat   240
gttttaaacc gctttgaaga tggtacagaa gtaacaccag aacttttagt tgaaactgga   300
attattcgta tgaaaaatc cggaatcaag attttatcta tggaaatat cgagaaaaaa   360
cttactgtga aagcgaacaa attctctgca gctgcgaaag aagcaattga agcggctggc   420
ggaaaaactg aggtgatcta a                                            441
```

<210> SEQ ID NO 138
<211> LENGTH: 441
<212> TYPE: DNA
<213> ORGANISM: Listeria monocytogenes

<400> SEQUENCE: 138

```
atgaaactac atgaacttaa gccttcagaa ggttctcgta aagaacgtaa tcgtgttggt    60
cgtggaacag gctctggtaa cggcaaaact tcaggacgcg gtcataaagg acaaaaagct   120
cgttctggtg gtggcgtacg tttaggtttt gaaggtggac aacttccact tttccgtcgt   180
attccaaaac gtggattcac aaatatcaac cgtaaagaat ttgctatcgt gaacttagat   240
gttttaaacc gctttgaaga tggtacagaa gtaacaccag aacttttagt tgaaactgga   300
attattcgta tgaaaaatc cggaatcaag attttatcta tggaaatat cgagaaaaaa   360
cttactgtga aagcgaacaa attctctgca gctgcgaaag aagcaattga agcagctggc   420
ggaaaaactg aggtgatcta a                                            441
```

<210> SEQ ID NO 139
<211> LENGTH: 441
<212> TYPE: DNA
<213> ORGANISM: Listeria monocytogenes

<400> SEQUENCE: 139

```
atgaaactac atgaacttaa gccttcagaa ggttctcgaa aagaacgtaa tcgtgttggt    60
cgtggaacag gctctggtaa cggcaaaact tcaggacgcg gtcataaagg acaaaaagct   120
```

```
cgttccggtg gtggcgtacg tttaggtttt gaaggtggac aacttccact tttccgtcgt    180
attccaaaac gtggattcac aaatatcaac cgtaaagaat ttgcaatcgt gaacttagat    240
gttttaaacc gctttgaaga cggtacagaa gtaacaccag aacttttaat tgaatctgga    300
attattcgta acgaaaaatc cggaatcaag attttatctg atggtaaaat cgagaaaaaa    360
cttactgtga aagcgaacaa attctctgca gctgcaaaag aagctattga agcggctggc    420
ggaaaaactg aggtgatcta a                                              441

<210> SEQ ID NO 140
<211> LENGTH: 441
<212> TYPE: DNA
<213> ORGANISM: Listeria monocytogenes

<400> SEQUENCE: 140
atgaaactac atgaacttaa gccttcagaa ggttctcgta agaacgtaaa tcgtgttggt     60
cgtggaacag gctctggtaa cggcaaaact tcaggacgcg gtcataaagg acaaaaagct    120
cgttctggtg gtggcgtacg tttaggcttt gaaggtggac aacttccact tttccgtcgt    180
attccaaaac gtggattcac aaatatcaac cgtaaagaat ttgctatcgt gaacttagat    240
gttttaaacc gctttgaaga tggtacagaa gtaacaccag aacttttagt tgaaactgga    300
attattcgta atgaaaaatc cggaatcaag attttatcta tggaaatat cgagaaaaaa    360 cttactgtga aagcgaacaa attctctgca gctgcgaaag aagcaattga agcggctggc    420
ggaaaaactg aggtgatcta a                                              441

<210> SEQ ID NO 141
<211> LENGTH: 441
<212> TYPE: DNA
<213> ORGANISM: Listeria monocytogenes

<400> SEQUENCE: 141
atgaaactac atgaacttaa gccttcagaa ggttctcgaa agaacgtaaa tcgtgttggt     60
cgtggaacag gctctggtaa cggcaaaact tcaggacgcg gtcataaagg acaaaaagct    120
cgttccggtg gtggcgtacg tttaggtttt gaaggtggac aacttccact tttccgtcgt    180
attccaaaac gtggattcac aaatatcaac cgtaaagaat ttgcaatcgt gaacttagat    240
gttttaaacc gctttgaaga cggtacagaa gtaacaccag aacttttaat tgaatctgga    300
attattcgta acgaaaaatc cggaatcaag attttatctg atggtaaaat cgagaaaaaa    360
cttactgtga aagcgaacaa attctctgca gctgcaaaag aagctattga agcggctggc    420
ggaaaaactg aggtgatcta a                                              441

<210> SEQ ID NO 142
<211> LENGTH: 441
<212> TYPE: DNA
<213> ORGANISM: Listeria monocytogenes

<400> SEQUENCE: 142
atgaaactac atgaacttaa gccttcagaa ggttctcgta agaacgtaaa tcgtgttggt     60
cgtggaacag gctctggtaa cggcaaaact tcaggacgcg gtcataaagg acaaaaagct    120
cgttctggtg gtggcgtacg tttaggcttt gaaggtggac aacttccact tttccgtcgt    180
attccaaaac gtggattcac aaatatcaac cgtaaagaat ttgctatcgt gaacttagat    240
gttttaaacc gctttgaaga tggtacagaa gtaacaccag aacttttagt tgaaactgga    300
attattcgta atgaaaaatc cggaatcaag attttatcta tggaaatat cgagaaaaaa    360
```

```
cttactgtga aagcgaacaa attctctgca gctgcgaaag aagcaattga agcggctggc    420
ggaaaaactg aggtgatcta a                                              441
```

<210> SEQ ID NO 143
<211> LENGTH: 441
<212> TYPE: DNA
<213> ORGANISM: Listeria monocytogenes

<400> SEQUENCE: 143

```
atgaaactac atgaacttaa gccttcagaa ggttctcgta agaacgtaa tcgtgttggt     60 cgtggaacag gctctggtaa cggcaaaact tcaggacgcg gtcataaagg acaaaaagct    120
cgttctggtg gtggcgtacg tttaggtttt gaaggtggac aacttccact tttccgtcgt    180
attccaaaac gtggattcac aaatatcaac cgtaaagaat ttgctatcgt gaacttagat    240
gttttaaacc gctttgaaga tggtacagaa gtaacaccag aacttttagt tgaaactgga    300
attattcgta tgaaaaaatc cggaatcaag attttatcta atggaaatat cgagaaaaaa    360
cttactgtga aagcgaacaa attctctgca gctgcgaaag aagcaattga agcagctggc    420
ggaaaaactg aggtgatcta a                                              441
```

<210> SEQ ID NO 144
<211> LENGTH: 441
<212> TYPE: DNA
<213> ORGANISM: Listeria monocytogenes

<400> SEQUENCE: 144

```
atgaaactac atgaacttaa gccttcagaa ggttctcgta agaacgtaa tcgtgttggt     60 cgtggaacag gctctggtaa cggcaaaact tcaggacgcg gtcataaagg acaaaaagct    120
cgttctggtg gtggcgtacg tttaggcttt gaaggtggac aacttccact tttccgtcgt    180
attccaaaac gtggattcac aaatatcaac cgtaaagaat ttgctatcgt gaacttagat    240
gttttaaacc gctttgaaga tggtacagaa gtaacaccag aacttttagt tgaaactgga    300
attattcgta tgaaaaaatc cggaatcaag attttatcta atggaaatat cgagaaaaaa    360
cttactgtga aagcgaacaa attctctgca gctgcgaaag aagcaattga agcggctggc    420
ggaaaaactg aggtgatcta a                                              441
```

<210> SEQ ID NO 145
<211> LENGTH: 366
<212> TYPE: DNA
<213> ORGANISM: Listeria monocytogenes

<400> SEQUENCE: 145

```
atggcacgta ttgcaggtgt ggacgttcca cgtgaaaaac gtattgttat ttccctgact     60
tacatttatg gtatcggtaa acaaacagct aaagaagttc ttgctgaagc tggcgtttct    120
gaagatactc gtactcgtga tttaactgaa gaagagctag gtaaaatccg tgaaatctta    180
gaccgtatta aagttgaagg tgaccttcgt cgtgaagtaa acttaaacat taaacgtcta    240
atcgaaatcg ttcttaccg tggcatgcgt caccgtcgtg acttccagt tcgcggacaa     300 aatacaaaaa ataatgcccg tactcgtaaa ggcccgtcca aacagtagc aggcaaaaag    360 aaataa                                                               366
```

<210> SEQ ID NO 146
<211> LENGTH: 366
<212> TYPE: DNA

<213> ORGANISM: Listeria monocytogenes

<400> SEQUENCE: 146

```
atggcacgta ttgcaggtgt ggacgttcca cgtgaaaaac gtattgttat ttccctgact      60
tacatttatg gtatcggtaa acaaacagct aaagaagttc ttgctgaagc tggcgtttct     120
gaagatactc gtactcgtga tttaactgaa gaagagctag gtaaaatccg tgaaatctta     180
gaccgtatta agttgaagg tgaccttcgt cgtgaagtaa acttaaacat taaacgtcta     240
atcgaaatcg gttcttaccg tggcatgcgt caccgtcgtg gacttccagt tcgcggacaa     300
aatacaaaaa ataatgcccg tactcgtaaa ggcccgtcca aaacagtagc aggcaaaaag     360
aaataa                                                                 366
```

<210> SEQ ID NO 147
<211> LENGTH: 366
<212> TYPE: DNA
<213> ORGANISM: Listeria monocytogenes

<400> SEQUENCE: 147

```
atggcacgta ttgcaggtgt ggacgttcca cgtgaaaaac gtattgttat ttccctgact      60
tacatttatg gtatcggtaa acaaacagct aaagaagttc ttgctgaagc tggcgtttct     120
gaagatactc gtactcgtga tttaactgaa gaagagctag gtaaaatccg tgaaatctta     180
gaccgtatta agttgaagg tgaccttcgt cgtgaagtaa acttaaacat taaacgtcta     240
atcgaaatcg gttcttaccg tggcatgcgt caccgtcgtg gacttccagt tcgcggacaa     300
aatacaaaaa ataatgcccg tactcgtaaa ggcccgtcca aaacagtagc aggcaaaaag     360
aaataa                                                                 366
```

<210> SEQ ID NO 148
<211> LENGTH: 366
<212> TYPE: DNA
<213> ORGANISM: Listeria monocytogenes

<400> SEQUENCE: 148

```
atggcacgta ttgcaggtgt ggacgttcca cgtgaaaaac gtattgttat ttccctgact      60
tacatttatg gtatcggtaa acaaacagct aaagaagttc ttgctgaagc tggcgtttct     120
gaagatactc gtactcgtga tttaactgaa gaagagctag gtaaaatccg tgaaatctta     180
gaccgtatta agttgaagg tgaccttcgt cgtgaagtaa acttaaacat taaacgtcta     240
atcgaaatcg gttcttaccg tggcatgcgt caccgtcgtg gacttccagt tcgcggacaa     300
aatacaaaaa ataatgcccg tactcgtaaa ggcccgtcca aaacagtagc aggcaaaaag     360
aaataa                                                                 366
```

<210> SEQ ID NO 149
<211> LENGTH: 366
<212> TYPE: DNA
<213> ORGANISM: Listeria monocytogenes

<400> SEQUENCE: 149

```
atggcacgta ttgcaggtgt ggacgttcca cgtgaaaaac gtattgttat ttccctgact      60
tacatttatg gtatcggtaa acaaacagct aaagaagttc ttgctgaagc tggcgtttct     120
gaagatactc gtactcgtga tttaactgaa gaagagctag gtaaaatccg tgaaatctta     180
gaccgtatta agttgaagg tgaccttcgt cgtgaagtaa acttaaacat taaacgtcta     240
atcgaaatcg gttcttaccg tggcatgcgt caccgtcgtg gacttccagt tcgcggacaa     300
```

```
aatacaaaaa ataatgcccg tactcgtaaa ggcccgtcca aaacagtagc aggcaaaaag    360
aaataa                                                                366

<210> SEQ ID NO 150
<211> LENGTH: 366
<212> TYPE: DNA
<213> ORGANISM: Listeria monocytogenes

<400> SEQUENCE: 150
atggcacgta ttgcaggtgt ggacgttcca cgtgaaaaac gtattgttat ttccctgact    60
tacatttatg gtatcggtaa acaaacagct aaagaagttc ttgctgaagc tggcgtttct   120
gaagatactc gtactcgtga tttaactgaa gaagagcttg gtaaaatccg tgaaatctta   180
gaccgtatta agttgaaggg tgaccttcgt cgtgaagtaa acttaaacat taaacgtcta   240
atcgaaatcg gttcttaccg tggcatgcgt caccgtcgtg gacttccagt tcgcggacaa   300
aatacaaaaa ataatgcccg tactcgtaaa ggcccgtcca aaacagtagc aggcaaaaag   360
aaataa                                                                366

<210> SEQ ID NO 151
<211> LENGTH: 366
<212> TYPE: DNA
<213> ORGANISM: Listeria monocytogenes

<400> SEQUENCE: 151
atggcacgta ttgcaggtgt ggacgttcca cgtgaaaaac gtattgttat ttccctgact    60
tacatttatg gtatcggtaa acaaacagct aaagaagttc ttgctgaagc tggcgtttct   120
gaagatactc gtactcgtga tttaactgaa gaagagctag gtaaaatccg tgaaatctta   180
gaccgtatta agttgaaggg tgaccttcgt cgtgaagtaa acttaaacat taaacgtcta   240
atcgaaatcg gttcttaccg tggcatgcgt caccgtcgtg gacttccagt tcgcggacaa   300
aatacaaaaa ataatgcccg tactcgtaaa ggcccgtcca aaacagtagc aggcaaaaag   360
aaataa                                                                366

<210> SEQ ID NO 152
<211> LENGTH: 366
<212> TYPE: DNA
<213> ORGANISM: Listeria monocytogenes

<400> SEQUENCE: 152
atggcacgta ttgcaggtgt ggacgttcca cgtgaaaaac gtattgttat ttccctgact    60
tacatttatg gtatcggtaa acaaacagct aaagaagttc ttgctgaagc tggcgtttct   120
gaagatactc gtactcgtga tttaactgaa gaagagctag gtaaaatccg tgaaatctta   180
gaccgtatta agttgaaggg tgaccttcgt cgtgaagtaa acttaaacat taaacgtcta   240
atcgaaatcg gttcttaccg tggcatgcgt caccgtcgtg gacttccagt tcgcggacaa   300
aatacaaaaa ataatgcccg tactcgtaaa ggcccgtcca aaacagtagc aggcaaaaag   360
aaataa                                                                366

<210> SEQ ID NO 153
<211> LENGTH: 366
<212> TYPE: DNA
<213> ORGANISM: Listeria monocytogenes
```

<400> SEQUENCE: 153

| atggcacgta ttgcaggtgt ggacgttcca cgtgaaaaac gtattgttat ttccctgact | 60 |
| tacatttatg gtatcggtaa acaaacagct aaagaagttc ttgctgaagc tggcgtttct | 120 |
| gaagatactc gtactcgtga tttaactgaa gaagagctag gtaaaatccg tgaaatctta | 180 |
| gaccgtatta aagttgaagg tgaccttcgt cgtgaagtaa acttaaacat taaacgtcta | 240 |
| atcgaaatcg gttcttaccg tggcatgcgt caccgtcgtg gacttccagt tcgcggacaa | 300 |
| aatacaaaaa ataatgcccg tactcgtaaa ggcccgtcca aaacagtagc aggcaaaaag | 360 |
| aaataa | 366 |

<210> SEQ ID NO 154
<211> LENGTH: 366
<212> TYPE: DNA
<213> ORGANISM: Listeria monocytogenes

<400> SEQUENCE: 154

| atggcacgta ttgcaggtgt ggacgttcca cgtgaaaaac gtattgttat ttccctgact | 60 |
| tacatttatg gtatcggtaa acaaacagct aaagaagttc ttgctgaagc tggcgtttct | 120 |
| gaagatactc gtactcgtga tttaactgaa gaagagctag gtaaaatccg tgaaatctta | 180 |
| gaccgtatta aagttgaagg tgaccttcgt cgtgaagtaa acttaaacat taaacgtcta | 240 |
| atcgaaatcg gttcttaccg tggcatgcgt caccgtcgtg gacttccagt tcgcggacaa | 300 |
| aatacaaaaa ataatgcccg tactcgtaaa ggcccgtcca aaacagtagc aggcaaaaag | 360 |
| aaataa | 366 |

<210> SEQ ID NO 155
<211> LENGTH: 366
<212> TYPE: DNA
<213> ORGANISM: Listeria monocytogenes

<400> SEQUENCE: 155

| atggcacgta ttgcaggtgt ggacgttcca cgtgaaaaac gtattgttat ttccctgact | 60 |
| tacatttatg gtatcggtaa acaaacagct agcaaagttc ttgctgaagc tggtgtttct | 120 |
| gaagatactc gtactcgtga tttaactgaa gaagagctag gtaaaatccg cgaaatctta | 180 |
| gaccgcatta aagttgaagg tgaccttcgt cgtgaagtaa acttaaacat taaacgtcta | 240 |
| attgaaatcg gttcttaccg tggcatgcgt caccgtcgtg gacttccagt tcgcggacaa | 300 |
| aatacaaaaa ataatgcccg tactcgtaaa ggcccgtcca aaacagtatc aggcaaaaag | 360 |
| aaataa | 366 |

<210> SEQ ID NO 156
<211> LENGTH: 366
<212> TYPE: DNA
<213> ORGANISM: Listeria monocytogenes

<400> SEQUENCE: 156

| atggcacgta ttgcaggtgt ggacgttcca cgtgaaaaac gtattgttat ttccctgact | 60 |
| tacatttatg gtatcggtaa acaaacagct aaagaagttc ttgctgaagc tggcgtttct | 120 |
| gaagatactc gtactcgtga tttaactgaa gaagagctag gtaaaatccg tgaaatctta | 180 |
| gaccgtatta aagttgaagg tgaccttcgt cgtgaagtaa acttaaacat taaacgtcta | 240 |

```
atcgaaatcg gttcttaccg tggcatgcgt caccgtcgtg acttccagt tcgcggacaa    300 aatacaaaaa ataatgcccg tactcgtaaa ggcccgtcca aaacagtagc aggcaaaaag    360
aaataa                                                                366
```

<210> SEQ ID NO 157
<211> LENGTH: 366
<212> TYPE: DNA
<213> ORGANISM: Listeria monocytogenes

<400> SEQUENCE: 157

```
atggcacgta ttgcaggtgt ggacgttcca cgtgaaaaac gtattgttat ttccctgact     60
tacatttatg gtatcggtaa acaaacagct agcaaagttc ttgctgaagc tggtgttcct    120
gaagatactc gtactcgtga tttaactgaa gaagagctag gtaaaatccg cgaaatctta    180
gaccgcatta agttgaagg tgaccttcgt cgtgaagtaa acttaaacat taaacgtcta    240
attgaaatcg gttcttaccg tggcatgcgt caccgtcgtg acttccagt tcgcggacaa    300 aatacaaaaa ataatgcccg tactcgtaaa ggcccgtcca aaacagtatc aggcaaaaag    360
aaataa                                                                366
```

<210> SEQ ID NO 158
<211> LENGTH: 366
<212> TYPE: DNA
<213> ORGANISM: Listeria monocytogenes

<400> SEQUENCE: 158

```
atggcacgta ttgcaggtgt ggacgttcca cgtgaaaaac gtattgttat ttccctgact     60
tacatttatg gtatcggtaa acaaacagct aaagaagttc ttgctgaagc tggcgtttct    120
gaagatactc gtactcgtga tttaactgaa gaagagctag gtaaaatccg tgaaatctta    180
gaccgtatta agttgaagg tgaccttcgt cgtgaagtaa acttaaacat taaacgtcta    240
atcgaaatcg gttcttaccg tggcatgcgt caccgtcgtg acttccagt tcgcggacaa    300 aatacaaaaa ataatgcccg tactcgtaaa ggcccgtcca aaacagtagc aggcaaaaag    360
aaataa                                                                366
```

<210> SEQ ID NO 159
<211> LENGTH: 366
<212> TYPE: DNA
<213> ORGANISM: Listeria monocytogenes

<400> SEQUENCE: 159

```
atggcacgta ttgcaggtgt ggacgttcca cgtgaaaaac gtattgttat ttccctgact     60
tacatttatg gtatcggtaa acaaacagct aaagaagttc ttgctgaagc tggcgtttct    120
gaagatactc gtactcgtga tttaactgaa gaagagctag gtaaaatccg tgaaatctta    180
gaccgtatta agttgaagg tgaccttcgt cgtgaagtaa acttaaacat taaacgtcta    240
atcgaaatcg gttcttaccg tggcatgcgt caccgtcgtg acttccagt tcgcggacaa    300 aatacaaaaa ataatgcccg tactcgtaaa ggcccgtcca aaacagtagc aggcaaaaag    360
aaataa                                                                366
```

<210> SEQ ID NO 160
<211> LENGTH: 366
<212> TYPE: DNA
<213> ORGANISM: Listeria monocytogenes

<400> SEQUENCE: 160

```
atggcacgta ttgcaggtgt ggacgttcca cgtgaaaaac gtattgttat ttccctgact    60
tacatttatg gtatcggtaa acaaacagct aaagaagttc ttgctgaagc tggcgtttct   120
gaagatactc gtactcgtga tttaactgaa gagagctag gtaaaatccg tgaaatctta    180
gaccgtatta agttgaagg tgaccttcgt cgtgaagtaa acttaaacat taaacgtcta    240
atcgaaatcg gttcttaccg tggcatgcgt caccgtcgtg acttccagt tcgcggacaa    300
aatacaaaaa ataatgcccg tactcgtaaa ggcccgtcca aacagtagc aggcaaaaag    360
aaataa                                                              366
```

<210> SEQ ID NO 161
<211> LENGTH: 390
<212> TYPE: DNA
<213> ORGANISM: Listeria monocytogenes

<400> SEQUENCE: 161

```
atggctcgta aacaaatac tcgtaaacgc cgtgtgaaaa agaatatcga atctggtatt    60
gcacacatcc gttctacatt taataatacg atcgtaatga ttactgacac acatggtaat   120
gctttagctt ggtcaagtgc aggttcccta ggatttaaag gttctcgtaa atctactcct   180
ttcgcagcgc aaatggcagc tgaaagtgca gcaaaatcag cacaagaaca tggtttgaaa   240
acattagaag taactgttaa aggtcctggt tcaggtcgtg aagcggctat ccgtgcacta   300
caagcagctg gtcttgaagt aacagctatt aaagatgtaa ctccagttcc acataacgga   360
tgtcgtcctc caaaacgtcg tcgcgtataa                                    390
```

<210> SEQ ID NO 162
<211> LENGTH: 390
<212> TYPE: DNA
<213> ORGANISM: Listeria monocytogenes

<400> SEQUENCE: 162

```
atggctcgta aacaaatac tcgtaaacgc cgtgtgaaaa agaatatcga atctggtatt    60
gcacacatcc gttctacatt taataatacg atcgtaatga ttactgacac acatggtaat   120
gctttagctt ggtcaagtgc aggttcccta ggatttaaag gttctcgtaa atctactcct   180
ttcgcagcgc aaatggcagc tgaaagtgca gcaaaatcag cacaagaaca tggtttaaaa   240
acattagaag taactgttaa aggtcctggt tcaggtcgtg aagcggctat ccgtgcacta   300
caagcagctg gtcttgaagt aacagctatt aaagatgtaa ctccagttcc acataacgga   360
tgtcgtcctc caaaacgtcg tcgcgtataa                                    390
```

<210> SEQ ID NO 163
<211> LENGTH: 390
<212> TYPE: DNA
<213> ORGANISM: Listeria monocytogenes

<400> SEQUENCE: 163

```
atggctcgta aacaaatac tcgtaaacgc cgtgtgaaaa agaatatcga atctggtatt    60
gcacacatcc gttctacatt taataatacg atcgtaatga ttactgacac acatggtaat   120
gctttagctt ggtcaagtgc aggttcccta ggatttaaag gttctcgtaa atctactcct   180
ttcgcagcgc aaatggcagc tgaaagtgca gcaaaatcag cacaagaaca tggtttgaaa   240
```
acattagaag taactgttaa aggtcctggt tcaggtcgtg aagcggctat ccgtgcacta    300
caagcagctg gtcttgaagt aacagctatt aaagatgtaa ctccagttcc acataacgga    360
tgtcgtcctc caaaacgtcg tcgcgtataa    390

<210> SEQ ID NO 164
<211> LENGTH: 390
<212> TYPE: DNA
<213> ORGANISM: Listeria monocytogenes

<400> SEQUENCE: 164
atggctcgta aacaaatac tcgtaaacgc cgtgtgaaaa agaatatcga atctggtatt    60
gcacacatcc gttctacatt taataatacg atcgtaatga ttactgacac acatggtaat    120
gctttagctt ggtcaagtgc aggttcccta ggatttaaag gttctcgtaa atctactcct    180
ttcgcagcgc aaatggcagc tgaaagtgca gcaaaatcag cacaagaaca tggtttgaaa    240
acattagaag taactgttaa aggtcctggt tcaggtcgtg aagcggctat ccgtgcacta    300
caagcagctg gtcttgaagt aacagctatt aaagatgtaa ctccagttcc acataacgga    360
tgtcgtcctc caaaacgtcg tcgcgtataa    390

<210> SEQ ID NO 165
<211> LENGTH: 390
<212> TYPE: DNA
<213> ORGANISM: Listeria monocytogenes

<400> SEQUENCE: 165
atggctcgta aacaaatac tcgtaaacgc cgtgtgaaaa agaatatcga atctggtatt    60
gcacacatcc gttctacatt taataatacg atcgtaatga ttactgacac acatggtaat    120
gctttagctt ggtcaagtgc aggttcccta ggatttaaag gttctcgtaa atctactcct    180
ttcgcagcgc aaatggcagc tgaaagtgca gcaaaatcag cacaagaaca tggtttgaaa    240
acattagaag taactgttaa aggtcctggt tcaggtcgtg aagcggctat ccgtgcacta    300
caagcagctg gtcttgaagt aacagctatt aaagatgtaa ctccagttcc acataacgga    360
tgtcgtcctc caaaacgtcg tcgcgtataa    390

<210> SEQ ID NO 166
<211> LENGTH: 390
<212> TYPE: DNA
<213> ORGANISM: Listeria monocytogenes

<400> SEQUENCE: 166
atggctcgta aacaaatac tcgtaaacgc cgtgtgaaaa agaatatcga atccggtatt    60
gcacacattc gttctacatt taataatacg atcgtaatga ttactgacac acatggtaat    120
gctttagctt ggtcaagtgc aggttcccta ggatttaaag gttctcgtaa atctactcct    180
ttcgcagcgc aaatggcagc tgaaagtgca gcaaaatcag cacaagaaca tggtttaaaa    240
acattagaag taactgttaa aggtcctggt tcaggtcgtg aagcggctat ccgtgcacta    300
caagcagctg gtcttgaagt aacagctatt aaagatgtaa ctccagttcc acataacgga    360
tgtcgtcctc caaaacgtcg tcgcgtataa    390

<210> SEQ ID NO 167
<211> LENGTH: 390
<212> TYPE: DNA
<213> ORGANISM: Listeria monocytogenes

<400> SEQUENCE: 167

```
atggctcgta aaacaaatac tcgtaaacgc cgtgtgaaaa agaatatcga atctggtatt      60
gcacacatcc gttctacatt taataatacg atcgtaatga ttactgacac acatggtaat     120
gctttagctt ggtcaagtgc aggttcccta ggatttaaag gttctcgtaa atctactcct     180
ttcgcagcgc aaatggcagc tgaaagtgca gcaaaatcag cacaagaaca tggtttaaaa     240
acattagaag taactgttaa aggtcctggt tcaggtcgtg aagcggctat ccgtgcacta     300
caagcagctg gtcttgaagt aacagctatt aaagatgtaa ctccagttcc acataacgga     360
tgtcgtcctc caaaacgtcg tcgcgtataa                                      390
```

<210> SEQ ID NO 168
<211> LENGTH: 390
<212> TYPE: DNA
<213> ORGANISM: Listeria monocytogenes

<400> SEQUENCE: 168

```
atggctcgta aaacaaatac tcgtaaacgc cgtgtgaaaa agaatatcga atctggtatt      60
gcacacatcc gttctacatt taataatacg atcgtaatga ttactgacac acatggtaat     120
gctttagctt ggtcaagtgc aggttcccta ggatttaaag gttctcgtaa atctactcct     180
ttcgcagcgc aaatggcagc tgaaagtgca gcaaaatcag cacaagaaca tggtttaaaa     240
acattagaag taactgttaa aggtcctggt tcaggtcgtg aagcggctat ccgtgcacta     300
caagcagctg gtcttgaagt aacagctatt aaagatgtaa ctccagttcc acataacgga     360
tgtcgtcctc caaaacgtcg tcgcgtataa                                      390
```

<210> SEQ ID NO 169
<211> LENGTH: 390
<212> TYPE: DNA
<213> ORGANISM: Listeria monocytogenes

<400> SEQUENCE: 169

```
atggctcgta aaacaaatac tcgtaaacgc cgtgtgaaaa agaatatcga atctggtatt      60
gcacacatcc gttctacatt taataatacg atcgtaatga ttactgacac acatggtaat     120
gctttagctt ggtcaagtgc aggttcccta ggatttaaag gttctcgtaa atctactcct     180
ttcgcagcgc aaatggcagc tgaaagtgca gcaaaatcag cacaagaaca tggtttaaaa     240
acattagaag taactgttaa aggtcctggt tcaggtcgtg aagcggctat ccgtgcacta     300
caagcagctg gtcttgaagt aacagctatt aaagatgtaa ctccagttcc acataacgga     360
tgtcgtcctc caaaacgtcg tcgcgtataa                                      390
```

<210> SEQ ID NO 170
<211> LENGTH: 390
<212> TYPE: DNA
<213> ORGANISM: Listeria monocytogenes

<400> SEQUENCE: 170

```
atggctcgta aaacaaatac tcgtaaacgc cgtgtgaaaa agaatatcga atctggtatt      60
gcacacatcc gttctacatt taataatacg atcgtaatga ttactgacac acatggtaat     120
gctttagctt ggtcaagtgc aggttcccta ggatttaaag gttctcgtaa atctactcct     180
ttcgcagcgc aaatggcagc tgaaagtgca gcaaaatcag cacaagaaca tggtttgaaa     240
```

```
acattagaag taactgttaa aggtcctggt tcaggtcgtg aagcggctat ccgtgcacta    300
caagcagctg gtcttgaagt aacagctatt aaagatgtaa ctccagttcc acataacgga    360
tgtcgtcctc caaaacgtcg tcgcgtataa                                     390
```

<210> SEQ ID NO 171
<211> LENGTH: 390
<212> TYPE: DNA
<213> ORGANISM: Listeria monocytogenes

<400> SEQUENCE: 171

```
atggctcgta aaacaaatac tcgtaaacgc cgtgtgaaaa agaatatcga atctggtatt     60
gcacacattc gttctacatt taataatacg atcgtaatga ttactgacac acagggtaat    120
gctttagctt ggtcaagtgc aggttctcta ggatttaaag gttctcgtaa atctactcct    180
ttcgcagcgc aaatggcagc tgaaagtgca gctaagtcag cacaagaaca tggtttgaaa    240
acattagaag taacggttaa aggtcctggt tcaggtcgtg aagcggctat ccgtgcacta    300
caagcagctg gtcttgaagt aacagctatt agagatgtaa ctccagttcc acataacgga    360
tgtcgtcctc caaaacgtcg tcgcgtataa                                     390
```

<210> SEQ ID NO 172
<211> LENGTH: 390
<212> TYPE: DNA
<213> ORGANISM: Listeria monocytogenes

<400> SEQUENCE: 172

```
atggctcgta aaacaaatac tcgtaaacgc cgtgtgaaaa agaatatcga atctggtatt     60
gcacacatcc gttctacatt taataatacg atcgtaatga ttactgacac acatggtaat    120
gctttagctt ggtcaagtgc aggttcccta ggatttaaag gttctcgtaa atctactcct    180
ttcgcagcgc aaatggcagc tgaaagtgca gcaaaatcag cacaagaaca tggtttaaaa    240
acattagaag taactgttaa aggtcctggt tcaggtcgtg aagcggctat ccgtgcacta    300
caagcagctg gtcttgaagt aacagctatt aaagatgtaa ctccagttcc acataacgga    360
tgtcgtcctc caaaacgtcg tcgcgtataa                                     390
```

<210> SEQ ID NO 173
<211> LENGTH: 390
<212> TYPE: DNA
<213> ORGANISM: Listeria monocytogenes

<400> SEQUENCE: 173

```
atggctcgta aaacaaatac tcgtaaacgc cgtgtgaaaa agaatatcga atctggtatt     60
gcacacattc gttctacatt taataatacg atcgtaatga ttactgacac acagggtaat    120
gctttagctt ggtcaagtgc aggttctcta ggatttaaag gttctcgtaa atctactcct    180
ttcgcagcgc aaatggcagc tgaaagtgca gctaagtcag cacaagaaca tggtttgaaa    240
acattagaag taacggttaa aggtcctggt tcaggtcgtg aagcggctat ccgtgcacta    300
caagcagctg gtcttgaagt aacagctatt agagatgtaa ctccagttcc acataacgga    360
tgtcgtcctc caaaacgtcg tcgcgtataa                                     390
```

<210> SEQ ID NO 174
<211> LENGTH: 390
<212> TYPE: DNA
<213> ORGANISM: Listeria monocytogenes

```
<400> SEQUENCE: 174
atggctcgta aaacaaatac tcgtaaacgc cgtgtgaaaa agaatatcga atctggtatt      60
gcacacatcc gttctacatt taataatacg atcgtaatga ttactgacac acatggtaat     120
gctttagctt ggtcaagtgc aggttcccta ggatttaaag gttctcgtaa atctactcct     180
ttcgcagcgc aaatggcagc tgaaagtgca gcaaaatcag cacaagaaca tggtttaaaa     240
acattagaag taactgttaa aggtcctggt tcaggtcgtg aagcggctat ccgtgcacta     300
caagcagctg gtcttgaagt aacagctatt aaagatgtaa ctccagttcc acataacgga     360
tgtcgtcctc caaaacgtcg tcgcgtataa                                      390

<210> SEQ ID NO 175
<211> LENGTH: 390
<212> TYPE: DNA
<213> ORGANISM: Listeria monocytogenes

<400> SEQUENCE: 175
atggctcgta aaacaaatac tcgtaaacgc cgtgtgaaaa agaatatcga atctggtatt      60
gcacacatcc gttctacatt taataatacg atcgtaatga ttactgacac acatggtaat     120
gctttagctt ggtcaagtgc aggttcccta ggatttaaag gttctcgtaa atctactcct     180
ttcgcagcgc aaatggcagc tgaaagtgca gcaaaatcag cacaagaaca tggtttgaaa     240
acattagaag taactgttaa aggtcctggt tcaggtcgtg aagcggctat ccgtgcacta     300
caagcagctg gtcttgaagt aacagctatt aaagatgtaa ctccagttcc acataacgga     360
tgtcgtcctc caaaacgtcg tcgcgtataa                                      390

<210> SEQ ID NO 176
<211> LENGTH: 390
<212> TYPE: DNA
<213> ORGANISM: Listeria monocytogenes

<400> SEQUENCE: 176
atggctcgta aaacaaatac tcgtaaacgc cgtgtgaaaa agaatatcga atctggtatt      60
gcacacatcc gttctacatt taataatacg atcgtaatga ttactgacac acatggtaat     120
gctttagctt ggtcaagtgc aggttcccta ggatttaaag gttctcgtaa atctactcct     180
ttcgcagcgc aaatggcagc tgaaagtgca gcaaaatcag cacaagaaca tggtttaaaa     240
acattagaag taactgttaa aggtcctggt tcaggtcgtg aagcggctat ccgtgcacta     300
caagcagctg gtcttgaagt aacagctatt aaagatgtaa ctccagttcc acataacgga     360
tgtcgtcctc caaaacgtcg tcgcgtataa                                      390

<210> SEQ ID NO 177
<211> LENGTH: 390
<212> TYPE: DNA
<213> ORGANISM: Listeria monocytogenes

<400> SEQUENCE: 177
atggctcgta aaacaaatac tcgtaaacgc cgtgtgaaaa agaatatcga atctggtatt      60
gcacacatcc gttctacatt taataatacg atcgtaatga ttactgacac acatggtaat     120
gctttagctt ggtcaagtgc aggttcccta ggatttaaag gttctcgtaa atctactcct     180
ttcgcagcgc aaatggcagc tgaaagtgca gcaaaatcag cacaagaaca tggtttaaaa     240
acattagaag taactgttaa aggtcctggt tcaggtcgtg aagcggctat ccgtgcacta     300
```

| caagcagctg gtcttgaagt aacagctatt aaagatgtaa ctccagttcc acataacgga | 360 |
| tgtcgtcctc caaaacgtcg tcgcgtataa | 390 |

<210> SEQ ID NO 178
<211> LENGTH: 501
<212> TYPE: DNA
<213> ORGANISM: Listeria monocytogenes

<400> SEQUENCE: 178

| atgagtaaag ttcttgaagc taaacaaagt gcagtagaag aaattaaaac aaaattatca | 60 |
| gctagtgcgt ctacagtaat tgttgattac cgcggcttaa acgttggcga aatcactgaa | 120 |
| ttacgtaaac aattgcgtga tgctggtatt gagtttaaag tttacaaaaa ctcactaact | 180 |
| cgccgtgctg ttgaagctaa cggttatgaa ggtttagaag gagcactaac tggtcctaac | 240 |
| gcaatcgcat tcagtaatga agacgtagtt gcgcctgcga aaattcttaa cgatttcgct | 300 |
| aaagatcatg aagcactaga aatcaaagcc ggtgttattg aaggtaaagt tgcttctctt | 360 |
| gaagaaatta aagcacttgc aacacttcca tcacgcgaag gattgctatc tatgctttgc | 420 |
| aacgtacttc aagctccagt tcgcggtctt gctatcgcta ctaaagctgt tgctgaccaa | 480 |
| aaagaaggac aagaagcata a | 501 |

<210> SEQ ID NO 179
<211> LENGTH: 501
<212> TYPE: DNA
<213> ORGANISM: Listeria monocytogenes

<400> SEQUENCE: 179

| atgagtaaag ttcttgaagc taaacaaagt gcagtagaag aaattaaaac aaaattatca | 60 |
| gctagtgcgt ctacagtaat tgttgattac cgcggcttaa acgttggcga aatcactgac | 120 |
| ttacgtaaac aattgcgtga tgctggtatt gagtttaaag tttacaaaaa ctcactaact | 180 |
| cgccgtgctg ttgaagctaa cggttacgaa ggtttagaag gagctctaac tggtcctaac | 240 |
| gcaatcgcat tcagtaatga agacgtagtt gcgcctgcga aaattcttaa cgatttcgct | 300 |
| aaagatcacg aagcactaga aatcaaagcc ggtgttattg aaggtaaagt tgcttctctt | 360 |
| gaagaaatta aagcacttgc aacacttcca tcacgcgaag gattgctatc tatgctttgc | 420 |
| aacgtacttc aagctccagt tcgcggtctt gctatcgcta ctaaagctgt tgctgaccaa | 480 |
| aaagaaggac aagaagcata a | 501 |

<210> SEQ ID NO 180
<211> LENGTH: 501
<212> TYPE: DNA
<213> ORGANISM: Listeria monocytogenes

<400> SEQUENCE: 180

| atgagtaaag ttcttgaagc taaacaaagt gcagtagaag aaattaaaac aaaattatca | 60 |
| gctagtgcgt ctacagtaat tgttgattac cgcggcttaa acgttggcga aatcactgac | 120 |
| ttacgtaaac aattgcgtga tgctggtatt gagtttaaag tttacaaaaa ctcactaact | 180 |
| cgccgtgctg ttgaagctaa cggttacgaa ggtttagaag gagctctaac tggtcctaac | 240 |
| gcaatcgcat tcagtaatga agacgtagtt gcgcctgcga aaattcttaa cgatttcgct | 300 |
| aaagatcacg aagcactaga aatcaaagcc ggtgttattg aaggtaaagt tgcttctctt | 360 |
| gaagaaatta aagcacttgc aacacttcca tcacgcgaag gattgctatc tatgctttgc | 420 |

| aacgtacttc aagctccagt tcgcggtctt gctatcgcta ctaaagctgt tgctgaccaa | 480 |
|---|---|
| aaagaaggac aagaagcata a | 501 |

<210> SEQ ID NO 181
<211> LENGTH: 501
<212> TYPE: DNA
<213> ORGANISM: Listeria monocytogenes

<400> SEQUENCE: 181

| atgagtaaag ttcttgaagc taaacaaagt gcagtagaag aaattaaaac aaaattatca | 60 |
|---|---|
| gctagtgcgt ctacagtaat tgttgattac cgcggcttaa acgttggcga atcactgac | 120 |
| ttacgtaaac aattgcgtga tgctggtatt gagtttaaag tttacaaaaa ctcactaact | 180 |
| cgccgtgctg ttgaagctaa cggttacgaa ggtttagaag gagctctaac tggtcctaac | 240 |
| gcaatcgcat tcagtaatga agacgtagtt gcgcctgcga aaattcttaa cgatttcgct | 300 |
| aaagatcacg aagcactaga atcaaagcc ggtgttattg aaggtaaagt tgcttctctt | 360 |
| gaagaaatta agcacttgc aacacttcca tcacgcgaag gattgctatc tatgctttgc | 420 |
| aacgtacttc aagctccagt tcgcggtctt gctatcgcta ctaaagctgt tgctgaccaa | 480 |
| aaagaaggac aagaagcata a | 501 |

<210> SEQ ID NO 182
<211> LENGTH: 501
<212> TYPE: DNA
<213> ORGANISM: Listeria monocytogenes

<400> SEQUENCE: 182

| atgagtaaag ttcttgaagc taaacaaagt gcagtagaag aaattaaaac aaaattatca | 60 |
|---|---|
| gctagtgcgt ctacagtaat tgttgattac cgcggcttaa acgttggcga atcactgaa | 120 |
| ttacgtaaac aattgcgtga tgctggtatt gagtttaaag tttacaaaaa ctcactaact | 180 |
| cgccgtgctg ttgaagctaa cggttatgaa ggtttagaag gagctctaac tggtcctaac | 240 |
| gcaatcgcat tcagtaatga agacgtagtt gcgcctgcga aaatccttaa cgatttcgct | 300 |
| aaagatcatg aagcactaga atcaaagcc ggtgttattg aaggtaaagt tgcttctctt | 360 |
| gaagaaatta agcacttgc aacacttcca tcacgcgaag gattgctatc tatgctttgc | 420 |
| aacgtacttc aagctccagt tcgcggtctt gctatcgcta ctaaagctgt tgctgaccaa | 480 |
| aaagaaggac aagaagcata a | 501 |

<210> SEQ ID NO 183
<211> LENGTH: 501
<212> TYPE: DNA
<213> ORGANISM: Listeria monocytogenes

<400> SEQUENCE: 183

| atgagtaaag ttcttgaagc taaacaaagt gcagtagaag aaattaaaac aaaattatca | 60 |
|---|---|
| gctagtgcgt ctacagtaat tgttgattac cgcggcttaa acgttggcga atcactgaa | 120 |
| ttacgtaaac aattgcgtga tgctggtatt gagtttaaag tttacaaaaa ctcactaact | 180 |
| cgccgtgctg ttgaagctaa cggttatgaa ggtttagaag gagcactaac tggtcctaac | 240 |
| gcaatcgcat tcagtaatga agacgtagtt gcgcctgcga aaattcttaa cgatttcgct | 300 |
| aaagatcatg aagcactaga atcaaagcc ggtgttattg aaggtaaagt tgcttctctt | 360 |
| gaagaaatta agcacttgc aacacttcca tcacgcgaag gattgctatc tatgctttgc | 420 |

| aacgtacttc aagctccagt tcgcggtctt gctatcgcta ctaaagctgt tgctgaccaa | 480 |
| aaagaaggac aagaagcata a | 501 |

<210> SEQ ID NO 184
<211> LENGTH: 501
<212> TYPE: DNA
<213> ORGANISM: Listeria monocytogenes

<400> SEQUENCE: 184

| atgagtaaag ttcttgaagc taaacaaagt gcagtagaag aaattaaaac aaaattatca | 60 |
| gctagtgcgt ctacagtaat tgttgattac cgcggcttaa acgttggcga atcactgaa | 120 |
| ttacgtaaac aattgcgtga tgctggtatt gagtttaaag tttacaaaaa ctcactaact | 180 |
| cgccgtgctg ttgaagctaa cggttatgaa ggtttagaag gagcactaac tggtcctaac | 240 |
| gcaatcgcat tcagtaatga agacgtagtt gcgcctgcga aaattcttaa cgatttcgct | 300 |
| aaagatcatg aagcactaga atcaaagcc ggtgttattg aaggtaaagt tgcttctctt | 360 |
| gaagaaatta agcacttgc aacacttcca tcacgcgaag gattgctatc tatgctttgc | 420 |
| aacgtacttc aagctccagt tcgcggtctt gctatcgcta ctaaagctgt tgctgaccaa | 480 |
| aaagaaggac aagaagcata a | 501 |

<210> SEQ ID NO 185
<211> LENGTH: 501
<212> TYPE: DNA
<213> ORGANISM: Listeria monocytogenes

<400> SEQUENCE: 185

| atgagtaaag ttcttgaagc taaacaaagt gcagtagaag aaattaaaac aaaattatca | 60 |
| gctagtgcgt ctacagtaat tgttgattac cgcggcttaa acgttggcga atcactgaa | 120 |
| ttacgtaaac aattgcgtga tgctggtatt gagtttaaag tttacaaaaa ctcactaact | 180 |
| cgccgtgctg ttgaagctaa cggttatgaa ggtttagaag gagcactaac tggtcctaac | 240 |
| gcaatcgcat tcagtaatga agacgtagtt gcgcctgcga aaattcttaa cgatttcgct | 300 |
| aaagatcatg aagcactaga atcaaagcc ggtgttattg aaggtaaagt tgcttctctt | 360 |
| gaagaaatta agcacttgc aacacttcca tcacgcgaag gattgctatc tatgctttgc | 420 |
| aacgtacttc aagctccagt tcgcggtctt gctatcgcta ctaaagctgt tgctgaccaa | 480 |
| aaagaaggac aagaagcata a | 501 |

<210> SEQ ID NO 186
<211> LENGTH: 501
<212> TYPE: DNA
<213> ORGANISM: Listeria monocytogenes

<400> SEQUENCE: 186

| atgagtaaag ttcttgaagc taaacaaagt gcagtagaag aaattaaaac aaaattatca | 60 |
| gctagtgcgt ctacagtaat tgttgattac cgcggcttaa acgttggcga atcactgac | 120 |
| ttacgtaaac aattgcgtga tgctggtatt gagtttaaag tttacaaaaa ctcactaact | 180 |
| cgccgtgctg ttgaagctaa cggttacgaa ggtttagaag gagctctaac tggtcctaac | 240 |
| gcaatcgcat tcagtaatga agacgtagtt gcgcctgcga aaattcttaa cgatttcgct | 300 |
| aaagatcacg aagcactaga atcaaagcc ggtgttattg aaggtaaagt tgcttctctt | 360 |
| gaagaaatta agcacttgc aacacttcca tcacgcgaag gattgctatc tatgctttgc | 420 |

```
aacgtacttc aagctccagt tcgcggtctt gctatcgcta ctaaagctgt tgctgaccaa      480
aaagaaggac aagaagcata a                                                501
```

<210> SEQ ID NO 187
<211> LENGTH: 501
<212> TYPE: DNA
<213> ORGANISM: Listeria monocytogenes

<400> SEQUENCE: 187

```
atgagtaaag ttcttgaagc taaacaaagt gcagtagaag aaattaaagg taaattatca      60
gctagtgcgt ctacagtaat tgttgattac cgcggcttaa acgttggcga atcactgaa      120 ttacgtaaac aattgcgtga cgctggtatt gaatttaaag tctacaaaaa ctcactaact     180
cgccgtgctg ttgaagctaa cggttacgaa ggtttagaag gagctctaac tggtcctaac    240
gcgatcgcat tcagtaatga agacgtagtt gcgcctgcga aaatccttaa cgatttcgct    300
aaagatcatg aagcactaga aatcaaagcg ggtgttattg aaggtaaagt tgcttctctt    360
gaagaaatta agcacttgc aacacttcca tcacgcgaag gattgctatc tatgctttgc     420
aacgtacttc aagctccagt tcgcggtctt gctatcgcta ctaaagctgt tgctgatcaa     480
aaagaagaac aagaagcata a                                                501
```

<210> SEQ ID NO 188
<211> LENGTH: 501
<212> TYPE: DNA
<213> ORGANISM: Listeria monocytogenes

<400> SEQUENCE: 188

```
atgagtaaag ttcttgaagc taaacaaagt gcagtagaag aaattaaaac aaaattatca     60
gctagtgcgt ctacagtaat tgttgattac cgcggcttaa acgttggcga atcactgaa      120 ttacgtaaac aattgcgtga tgctggtatt gagtttaaag tttacaaaaa ctcactaact    180
cgccgtgctg ttgaagctaa cggttatgaa ggtttagaag gagcactaac tggtcctaac    240
gcaatcgcat tcagtaatga agacgtagtt gcgcctgcga aaattcttaa cgatttcgct    300
aaagatcatg aagcactaga aatcaaagcc ggtgttattg aaggtaaagt tgcttctctt    360
gaagaaatta agcacttgc aacacttcca tcacgcgaag gattgctatc tatgctttgc     420
aacgtacttc aagctccagt tcgcggtctt gctatcgcta ctaaagctgt tgctgaccaa     480
aaagaaggac aagaagcata a                                                501
```

<210> SEQ ID NO 189
<211> LENGTH: 501
<212> TYPE: DNA
<213> ORGANISM: Listeria monocytogenes

<400> SEQUENCE: 189

```
atgagtaaag ttcttgaagc taaacaaagt gcagtagaag aaattaaagg taaattatca      60
gctagtgcgt ctacagtaat tgttgattac cgcggcttaa acgttggcga atcactgaa      120 ttacgtaaac aattgcgtga cgctggtatt gaatttaaag tctacaaaaa ctcactaact    180
cgccgtgctg ttgaagctaa cggttacgaa ggtttagaag gagctctaac tggtcctaac    240
gcgatcgcat tcagtaatga agacgtagtt gcgcctgcga aaatccttaa cgatttcgct    300
aaagatcatg aagcactaga aatcaaagcg ggtgttattg aaggtaaagt tgcttctctt    360
gaagaaatta agcacttgc aacacttcca tcacgcgaag gattgctatc tatgctttgc     420
```

```
aacgtacttc aagctccagt tcgcggtctt gctatcgcta ctaaagctgt tgctgatcaa    480
aaagaagaac aagaagcata a                                               501

<210> SEQ ID NO 190
<211> LENGTH: 501
<212> TYPE: DNA
<213> ORGANISM: Listeria monocytogenes

<400> SEQUENCE: 190
atgagtaaag ttcttgaagc taaacaaagt gcagtagaag aaattaaaac aaaattatca     60
gctagtgcgt ctacagtaat tgttgattac cgcggcttaa acgttggcga atcactgaa    120 ttacgtaaac aattgcgtga tgctggtatt gagtttaaag tttacaaaaa ctcactaact    180
cgccgtgctg ttgaagctaa cggttatgaa ggtttagaag gagcactaac tggtcctaac    240
gcaatcgcat tcagtaatga agacgtagtt gcgcctgcga aaattcttaa cgatttcgct    300
aaagatcatg aagcactaga aatcaaagcc ggtgttattg aaggtaaagt tgcttctctt    360
gaagaaatta aagcacttgc aacacttcca tcacgcgaag gattgctatc tatgctttgc    420
aacgtacttc aagctccagt tcgcggtctt gctatcgcta ctaaagctgt tgctgaccaa    480
aaagaaggac aagaagcata a                                               501

<210> SEQ ID NO 191
<211> LENGTH: 501
<212> TYPE: DNA
<213> ORGANISM: Listeria monocytogenes

<400> SEQUENCE: 191
atgagtaaag ttcttgaagc taaacaaagt gcagtagaag aaattaaaac aaaattatca     60
gctagtgcgt ctacagtaat tgttgattac cgcggcttaa acgttggcga atcactgac    120 ttacgtaaac aattgcgtga tgctggtatt gagtttaaag tttacaaaaa ctcactaact    180
cgccgtgctg ttgaagctaa cggttacgaa ggtttagaag gagctctaac tggtcctaac    240
gcaatcgcat tcagtaatga agacgtagtt gcgcctgcga aaattcttaa cgatttcgct    300
aaagatcacg aagcactaga aatcaaagcc ggtgttattg aaggtaaagt tgcttctctt    360
gaagaaatta aagcacttgc aacacttcca tcacgcgaag gattgctatc tatgctttgc    420
aacgtacttc aagctccagt tcgcggtctt gctatcgcta ctaaagctgt tgctgaccaa    480
aaagaaggac aagaagcata a                                               501

<210> SEQ ID NO 192
<211> LENGTH: 501
<212> TYPE: DNA
<213> ORGANISM: Listeria monocytogenes

<400> SEQUENCE: 192
atgagtaaag ttcttgaagc taaacaaagt gcagtagaag aaattaaaac aaaattatca     60
gctagtgcgt ctacagtaat tgttgattac cgcggcttaa acgttggcga atcactgaa    120 ttacgtaaac aattgcgtga tgctggtatt gagtttaaag tttacaaaaa ctcactaact    180
cgccgtgctg ttgaagctaa cggttatgaa ggtttagaag gagcactaac tggtcctaac    240
gcaatcgcat tcagtaatga agacgtagtt gcgcctgcga aaattcttaa cgatttcgct    300
aaagatcatg aagcactaga aatcaaagcc ggtgttattg aaggtaaagt tgcttctctt    360
gaagaaatta aagcacttgc aacacttcca tcacgcgaag gattgctatc tatgctttgc    420
```

| | |
|---|---|
| aacgtacttc aagctccagt tcgcggtctt gctatcgcta ctaaagctgt tgctgaccaa | 480 |
| aaagaaggac aagaagcata a | 501 |

<210> SEQ ID NO 193
<211> LENGTH: 309
<212> TYPE: DNA
<213> ORGANISM: Listeria monocytogenes

<400> SEQUENCE: 193

| | |
|---|---|
| atgtacgcaa ttattgaaac aggtgggaaa caaatcaaag tagaagcagg ccaagagatc | 60 |
| tatgttgaga aattagcagg tgaagttgga gatgttgtta cttttgacaa agttctattc | 120 |
| gtaggtggag attccgctaa agttggcgtt ccattcgtgg aaggcgcaac tgtaacagct | 180 |
| aaagttgaaa acaaggccg tgcgaagaaa ttgacagttt ataaatataa accgaaaaag | 240 |
| aactaccaca aaaaacaagg tcatcgtcaa ccttacacaa aattaactat tgatgcaatc | 300 |
| aatgcttaa | 309 |

<210> SEQ ID NO 194
<211> LENGTH: 309
<212> TYPE: DNA
<213> ORGANISM: Listeria monocytogenes

<400> SEQUENCE: 194

| | |
|---|---|
| atgtacgcaa ttattgaaac aggtgggaaa caaatcaaag tagaagcagg ccaagagatc | 60 |
| tatgttgaga aattagcagg tgaagttggt gatgttgtta cttttgacaa agttctattc | 120 |
| gtaggtggag attccgctaa agttggcgtt ccattcgtgg aaggcgcaac tgtaacagct | 180 |
| aaagttgaaa acaaggccg tgcgaagaaa ttgacagttt ataaatataa accgaaaaag | 240 |
| aactaccaca aaaaacaagg tcatcgtcaa ccttacacaa aattaactat tgatgctatc | 300 |
| aatgcttaa | 309 |

<210> SEQ ID NO 195
<211> LENGTH: 309
<212> TYPE: DNA
<213> ORGANISM: Listeria monocytogenes

<400> SEQUENCE: 195

| | |
|---|---|
| atgtacgcaa ttattgaaac aggtgggaaa caaatcaaag tagaagcagg ccaagagatc | 60 |
| tatgttgaga aattagcagg tgaagttgga gatgttgtta cttttgacaa agttctattc | 120 |
| gtaggtggag attccgctaa agttggcgtt ccattcgtgg aaggcgcaac tgtaacagct | 180 |
| aaagttgaaa acaaggccg tgcgaagaaa ttgacagttt ataaatataa accgaaaaag | 240 |
| aactaccaca aaaaacaagg tcatcgtcaa ccttacacaa aattaactat tgatgcaatc | 300 |
| aatgcttaa | 309 |

<210> SEQ ID NO 196
<211> LENGTH: 309
<212> TYPE: DNA
<213> ORGANISM: Listeria monocytogenes

<400> SEQUENCE: 196

| | |
|---|---|
| atgtacgcaa ttattgaaac aggtgggaaa caaatcaaag tagaagcagg ccaagagatc | 60 |
| tatgttgaga aattagcagg tgaagttgga gatgttgtta cttttgacaa agttctattc | 120 |
| gtaggtggag attccgctaa agttggcgtt ccattcgtgg aaggcgcaac tgtaacagct | 180 |
| aaagttgaaa acaaggccg tgcgaagaaa ttgacagttt ataaatataa accgaaaaag | 240 |

```
aactaccaca aaaaacaagg tcatcgtcaa ccttacacaa aattaactat tgatgcaatc    300
aatgcttaa                                                            309

<210> SEQ ID NO 197
<211> LENGTH: 309
<212> TYPE: DNA
<213> ORGANISM: Listeria monocytogenes

<400> SEQUENCE: 197
atgtacgcaa ttattgaaac aggtgggaaa caaatcaaag tagaagcagg ccaagagatc     60
tatgttgaga aattagcagg tgaagttgga gatgttgtta cttttgacaa agttctattc    120
gtaggtggag attccgctaa agttggcgtt ccattcgtgg aaggcgcaac tgtaacagct    180
aaagttgaaa acaaggccg tgcgaagaaa ttgacagttt ataaatataa accgaaaaag     240
aactaccaca aaaaacaagg tcatcgtcaa ccttacacaa aattaactat tgatgcaatc    300
aatgcttaa                                                            309

<210> SEQ ID NO 198
<211> LENGTH: 309
<212> TYPE: DNA
<213> ORGANISM: Listeria monocytogenes

<400> SEQUENCE: 198
atgtacgcaa ttattgaaac aggtgggaaa caaatcaaag tagaagcagg ccaagagatc     60
tatgttgaga aattagcagg tgaagttggt gatgttgtta cttttgacaa agttctattc    120
gtaggtggag attccgctaa agttggcgtt ccattcgtgg aaggcgcaac tgtaacagct    180
aaagttgaaa acaaggccg tgcgaagaaa ttgacagttt ataaatataa accgaaaaag     240
aactaccaca aaaaacaagg tcatcgtcaa ccttacacaa aattaactat tgatgcaatc    300
aatgcttaa                                                            309

<210> SEQ ID NO 199
<211> LENGTH: 309
<212> TYPE: DNA
<213> ORGANISM: Listeria monocytogenes

<400> SEQUENCE: 199
atgtacgcaa ttattgaaac aggtgggaaa caaatcaaag tagaagcagg ccaagagatc     60
tatgttgaga aattagcagg tgaagttggt gatgttgtta cttttgacaa agttctattc    120
gtaggtggag attccgctaa agttggcgtt ccattcgtgg aaggcgcaac tgtaacagct    180
aaagttgaaa acaaggccg tgcgaagaaa ttgacagttt ataaatataa accgaaaaag     240
aactaccaca aaaaacaagg tcatcgtcaa ccttacacaa aattaactat tgatgctatc    300
aatgcttaa                                                            309

<210> SEQ ID NO 200
<211> LENGTH: 309
<212> TYPE: DNA
<213> ORGANISM: Listeria monocytogenes

<400> SEQUENCE: 200
atgtacgcaa ttattgaaac aggtgggaaa caaatcaaag tagaagcagg ccaagagatc     60
tatgttgaga aattagcagg tgaagttggt gatgttgtta cttttgacaa agttctattc    120
gtaggtggag attccgctaa agttggcgtt ccattcgtgg aaggcgcaac tgtaacagct    180
```
aaagttgaaa aacaaggccg tgcgaagaaa ttgacagttt ataaatataa accgaaaaag    240
aactaccaca aaaaacaagg tcatcgtcaa ccttacacaa aattaactat tgatgctatc    300
aatgcttaa                                                            309

<210> SEQ ID NO 201
<211> LENGTH: 309
<212> TYPE: DNA
<213> ORGANISM: Listeria monocytogenes

<400> SEQUENCE: 201
atgtacgcaa ttattgaaac aggtgggaaa caaatcaaag tagaagcagg ccaagagatc     60
tatgttgaga aattagcagg tgaagttggt gatgttgtta cttttgacaa agttctattc    120
gtaggtggag attccgctaa agttggcgtt ccattcgtgg aaggcgcaac tgtaacagct    180
aaagttgaaa aacaaggccg tgcgaagaaa ttgacagttt ataaatataa accgaaaaag    240
aactaccaca aaaaacaagg tcatcgtcaa ccttacacaa aattaactat tgatgctatc    300
aatgcttaa                                                            309

<210> SEQ ID NO 202
<211> LENGTH: 309
<212> TYPE: DNA
<213> ORGANISM: Listeria monocytogenes

<400> SEQUENCE: 202
atgtacgcaa ttattgaaac aggtgggaaa caaatcaaag tagaagcagg ccaagagatc     60
tatgttgaga aattagcagg tgaagttgga gatgttgtta cttttgacaa agttctattc    120
gtaggtggag attccgctaa agttggcgtt ccattcgtgg aaggcgcaac tgtaacagct    180
aaagttgaaa aacaaggccg tgcgaagaaa ttgacagttt ataaatataa accgaaaaag    240
aactaccaca aaaaacaagg tcatcgtcaa ccttacacaa aattaactat tgatgcaatc    300
aatgcttaa                                                            309

<210> SEQ ID NO 203
<211> LENGTH: 309
<212> TYPE: DNA
<213> ORGANISM: Listeria monocytogenes

<400> SEQUENCE: 203
atgtacgcaa ttattgaaac aggtgggaaa caaatcaaag tagaagcagg ccaagaaatc     60
tatgttgaga aattagcagg tgaagttggt gatgttgtta cttttgacaa agttctattc    120
gtaggcggag attccgctaa agttggcgtt ccattcgtgg acggagcaac tgtaacagct    180
aaagttgaaa aacaaggccg tgcgaagaaa ttgacagttt ataaatataa accgaaaaag    240
aactaccaca aaaaacaagg tcatcgtcaa ccttacacaa aattaactat tgatgcaatc    300
aatgcttaa                                                            309

<210> SEQ ID NO 204
<211> LENGTH: 309
<212> TYPE: DNA
<213> ORGANISM: Listeria monocytogenes

<400> SEQUENCE: 204
atgtacgcaa ttattgaaac aggtgggaaa caaatcaaag tagaagcagg ccaagagatc     60
tatgttgaga aattagcagg tgaagttggt gatgttgtta cttttgacaa agttctattc    120
gtaggtggag attccgctaa agttggcgtt ccattcgtgg aaggcgcaac tgtaacagct    180

```
aaagttgaaa acaaggccg tgcgaagaaa ttgacagttt ataaatataa accgaaaaag    240
aactaccaca aaaaacaagg tcatcgtcaa ccttacacaa aattaactat tgatgctatc    300
aatgcttaa                                                            309

<210> SEQ ID NO 205
<211> LENGTH: 309
<212> TYPE: DNA
<213> ORGANISM: Listeria monocytogenes

<400> SEQUENCE: 205
atgtacgcaa ttattgaaac aggtgggaaa caaatcaaag tagaagcagg ccaagaaatc     60
tatgttgaga aattagcagg tgaagttggt gatgttgtta cttttgacaa agttctattc    120
gtaggcggag attccgctaa agttggcgtt ccattcgtgg acggagcaac tgtaacagct    180
aaagttgaaa acaaggccg tgcgaagaaa ttgacagttt ataaatataa accgaaaaag    240
aactaccaca aaaaacaagg tcatcgtcaa ccttacacaa aattaactat tgatgcaatc    300
aatgcttaa                                                            309

<210> SEQ ID NO 206
<211> LENGTH: 309
<212> TYPE: DNA
<213> ORGANISM: Listeria monocytogenes

<400> SEQUENCE: 206
atgtacgcaa ttattgaaac aggtgggaaa caaatcaaag tagaagcagg ccaagagatc     60
tatgttgaga aattagcagg tgaagttggt gatgttgtta cttttgacaa agttctattc    120
gtaggtggag attccgctaa agttggcgtt ccattcgtgg aaggcgcaac tgtaacagct    180
aaagttgaaa acaaggccg tgcgaagaaa ttgacagttt ataaatataa accgaaaaag    240
aactaccaca aaaaacaagg tcatcgtcaa ccttacacaa aattaactat tgatgctatc    300
aatgcttaa                                                            309

<210> SEQ ID NO 207
<211> LENGTH: 309
<212> TYPE: DNA
<213> ORGANISM: Listeria monocytogenes

<400> SEQUENCE: 207
atgtacgcaa ttattgaaac aggtgggaaa caaatcaaag tagaagcagg ccaagagatc     60
tatgttgaga aattagcagg tgaagttgga gatgttgtta cttttgacaa agttctattc    120
gtaggtggag attccgctaa agttggcgtt ccattcgtgg aaggcgcaac tgtaacagct    180
aaagttgaaa acaaggccg tgcgaagaaa ttgacagttt ataaatataa accgaaaaag    240
aactaccaca aaaaacaagg tcatcgtcaa ccttacacaa aattaactat tgatgcaatc    300
aatgcttaa                                                            309

<210> SEQ ID NO 208
<211> LENGTH: 309
<212> TYPE: DNA
<213> ORGANISM: Listeria monocytogenes

<400> SEQUENCE: 208
atgtacgcaa ttattgaaac aggtgggaaa caaatcaaag tagaagcagg ccaagagatc     60
tatgttgaga aattagcagg tgaagttggt gatgttgtta cttttgacaa agttctattc    120
```

```
gtaggtggag attccgctaa agttggcgtt ccattcgtgg aaggcgcaac tgtaacagct      180
aaagttgaaa acaaggccg tgcgaagaaa ttgacagttt ataaatataa accgaaaaag       240
aactaccaca aaaaacaagg tcatcgtcaa ccttacacaa aattaactat tgatgctatc      300
aatgcttaa                                                              309
```

```
<210> SEQ ID NO 209
<211> LENGTH: 438
<212> TYPE: DNA
<213> ORGANISM: Listeria monocytogenes

<400> SEQUENCE: 209
atgcgtacaa cttatatggc gaaacccggc gaagtagaac gtaaatggta cgttatcgac       60
gctactggtg tttctttagg acgtttatcc agtgaagttg cttcaattct tcgcggaaaa      120
aacaaaccac aatttactcc acatatcgac actggagact ttgtaatcat catcaacgct      180
ggtaagattg gtcttactgg taaaaaagct actgacaaaa tttactaccg tcactctcaa      240
tatccaggcg gtttgaaatc tcgtactgca ggcgaaatgc gtacaaacaa tcctgagaaa      300
ttattagaac tatctatcaa aggtatgctt ccaaaaaatt ctcttggacg tcaattattc      360
aaaaaattac acgtatatgg tggatctgag cacgaacacg cagctcaaca accagaagta      420
tacgaattac gcggttaa                                                    438
```

```
<210> SEQ ID NO 210
<211> LENGTH: 438
<212> TYPE: DNA
<213> ORGANISM: Listeria monocytogenes

<400> SEQUENCE: 210
atgcgtacaa cttatatggc gaaacccggc gaagtagaac gtaaatggta cgttatcgac       60
gctactggtg tttctttagg acgtttatcc agtgaagttg cttcaattct tcgcggaaaa      120
aacaaaccac aatttactcc acatatcgac actggagact ttgtaatcat catcaacgct      180
ggtaagattg gtcttactgg taaaaaagct actgacaaaa tttactaccg tcactctcaa      240
tatccaggcg gtttgaaatc tcgtactgca ggcgaaatgc gtacaaacaa tcctgagaaa      300
ttattagaac tatctatcaa aggtatgctt ccaaaaaatt ctcttggacg tcaattattc      360
aaaaaattac acgtatatgg tggatctgag cacgaacacg cagctcaaca accagaagta      420
tacgaattac gcggttaa                                                    438
```

```
<210> SEQ ID NO 211
<211> LENGTH: 438
<212> TYPE: DNA
<213> ORGANISM: Listeria monocytogenes

<400> SEQUENCE: 211
atgcgtacaa cttatatggc gaaacccggc gaagtagaac gtaaatggta cgttatcgac       60
gctactggtg tttctttagg acgtttatcc agtgaagttg cttcaattct tcgcggaaaa      120
aacaaaccac aatttactcc acatatcgac actggagact ttgtaatcat catcaacgct      180
ggtaagattg gtcttactgg taaaaaagct actgacaaaa tttactaccg tcactctcaa      240
tatccaggcg gtttgaaatc tcgtactgca ggcgaaatgc gtacaaacaa tcctgagaaa      300
ttattagaac tatctatcaa aggtatgctt ccaaaaaatt ctcttggacg tcaattattc      360
aaaaaattac acgtatatgg tggatctgag cacgaacacg cagctcaaca accagaagta      420
tacgaattac gcggttaa                                                    438
```

<210> SEQ ID NO 212
<211> LENGTH: 438
<212> TYPE: DNA
<213> ORGANISM: Listeria monocytogenes

<400> SEQUENCE: 212

```
atgcgtacaa cttatatggc gaaacccggc gaagtagaac gtaaatggta cgttatcgac      60
gctactggtg tttctttagg acgtttatcc agtgaagttg cttcaattct tcgcggaaaa     120
aacaaaccac aatttactcc acatatcgac actggagact ttgtaatcat catcaacgct     180
ggtaagattg gtcttactgg taaaaaagct actgacaaaa tttactaccg tcactctcaa     240
tatccaggcg gtttgaaatc tcgtactgca ggcgaaatgc gtacaaacaa tcctgagaaa     300
ttattagaac tatctatcaa aggtatgctt ccaaaaaatt ctcttgggcg tcaattattc     360
aaaaaattac acgtatatgg tggatctgag cacgaacacg cagctcaaca accagaagta     420
tacgaattac gcggttaa                                                   438
```

<210> SEQ ID NO 213
<211> LENGTH: 438
<212> TYPE: DNA
<213> ORGANISM: Listeria monocytogenes

<400> SEQUENCE: 213

```
atgcgtacaa cttatatggc gaaacccggc gaagtagaac gtaaatggta cgttatcgac      60
gctactggtg tttctttagg acgtttatcc agtgaagttg cttcaattct tcgcggaaaa     120
aacaaaccac aatttactcc acatatcgac actggagact ttgtaatcat catcaacgct     180
ggtaagattg gtcttactgg taaaaaagct actgacaaaa tttactaccg tcactctcaa     240
tatccaggcg gtttgaaatc tcgtactgca ggcgaaatgc gtacaaacaa tcctgagaaa     300
ttattagaac tatctatcaa aggtatgctt ccaaaaaatt ctcttggacg tcaattattc     360
aaaaaattac acgtatatgg tggatctgag cacgaacacg cagctcaaca accagaagta     420
tacgaattac gcggttaa                                                   438
```

<210> SEQ ID NO 214
<211> LENGTH: 438
<212> TYPE: DNA
<213> ORGANISM: Listeria monocytogenes

<400> SEQUENCE: 214

```
atgcgtacaa cttatatggc gaaacccggc gaagtagaac gtaaatggta cgttatcgac      60
gctactggtg tttctttagg acgtttatcc agtgaagttg cttcaattct tcgcggaaaa     120
aacaaaccac aatttactcc acatatcgac actggagact ttgtaatcat catcaacgct     180
ggtaagattg gtcttactgg taaaaaagct actgacaaaa tttactaccg tcactctcaa     240
tatccaggcg gtttgaaatc tcgtactgca ggcgaaatgc gtacaaacaa tcctgagaaa     300
ttattagaac tatctatcaa aggtatgctt ccaaaaaatt ctcttggacg tcaattattc     360
aaaaaattac acgtatatgg tggatctgag cacgaacatg cagctcaaca accagaagta     420
tacgaattac gcggttaa                                                   438
```

<210> SEQ ID NO 215
<211> LENGTH: 438
<212> TYPE: DNA
<213> ORGANISM: Listeria monocytogenes

```
<400> SEQUENCE: 215
atgcgtacaa cttatatggc gaaacccggc gaagtagaac gtaaatggta cgttatcgac      60
gctactggtg tttctttagg acgtttatcc agtgaagttg cttcaattct tcgcggaaaa     120
aacaaaccac aatttactcc acatatcgac actggagact ttgtaatcat catcaacgct     180
ggtaagattg gtcttactgg taaaaaagct actgacaaaa tttactaccg tcactctcaa     240
tatccaggcg gtttgaaatc tcgtactgca ggcgaaatgc gtacaaacaa tcctgagaaa     300
ttattagaac tatctatcaa aggtatgctt ccaaaaaatt ctcttggacg tcaattattc     360
aaaaaattac acgtatatgg tggagctgag cacgaacacg cagctcaaca accagaagta     420
tacgaattac gcggttaa                                                   438

<210> SEQ ID NO 216
<211> LENGTH: 438
<212> TYPE: DNA
<213> ORGANISM: Listeria monocytogenes

<400> SEQUENCE: 216
atgcgtacaa cttatatggc gaaacccggc gaagtagaac gtaaatggta cgttatcgac      60
gctactggtg tttctttagg acgtttatcc agtgaagttg cttcaattct tcgcggaaaa     120
aacaaaccac aatttactcc acatatcgac actggagact ttgtaatcat catcaacgct     180
ggtaagattg gtcttactgg taaaaaagct actgacaaaa tttactaccg tcactctcaa     240
tatccaggcg gtttgaaatc tcgtactgca ggcgaaatgc gtacaaacaa tcctgagaaa     300
ttattagaac tatctatcaa aggtatgctt ccaaaaaatt ctcttggacg tcaattattc     360
aaaaaattac acgtatatgg tggatctgag cacgaacatg cagctcaaca accagaagta     420
tacgaattac gcggttaa                                                   438

<210> SEQ ID NO 217
<211> LENGTH: 438
<212> TYPE: DNA
<213> ORGANISM: Listeria monocytogenes

<400> SEQUENCE: 217
atgcgtacaa cttatatggc gaaacccggc gaagtagaac gtaaatggta cgttatcgac      60
gctactggtg tttctttagg acgtttatcc agtgaagttg cttcaattct tcgcggaaaa     120
aacaaaccac aatttactcc acatatcgac actggagact ttgtaatcat catcaacgct     180
ggtaagattg gtcttactgg taaaaaagct actgacaaaa tttactaccg tcactctcaa     240
tatccaggcg gtttgaaatc tcgtactgca ggcgaaatgc gtacaaacaa tcctgagaaa     300
ttattagaac tatctatcaa aggtatgctt ccaaaaaatt ctcttggacg tcaattattc     360
aaaaaattac acgtatatgg tggatctgag cacgaacacg cagctcaaca accagaagta     420
tacgaattac gcggttaa                                                   438

<210> SEQ ID NO 218
<211> LENGTH: 438
<212> TYPE: DNA
<213> ORGANISM: Listeria monocytogenes

<400> SEQUENCE: 218
atgcgtacaa cttatatggc gaaacccggc gaagtagaac gtaaatggta cgttatcgac      60
gctactggtg tttctttagg acgtttatcc agtgaagttg cttcaattct tcgcggaaaa     120
aacaaaccac aatttactcc acatatcgac actggagact ttgtaatcat catcaacgct     180
```

```
ggtaagattg gtcttactgg taaaaaagct actgacaaaa tttactaccg tcactctcaa    240
tatccaggcg gtttgaaatc tcgtactgca ggcgaaatgc gtacaaacaa tcctgagaaa    300
ttattagaac tatctatcaa aggtatgctt ccaaaaaatt ctcttgggcg tcaattattc    360
aaaaaattac acgtatatgg tggatctgag cacgaacacg cagctcaaca accagaagta    420
tacgaattac gcggttaa                                                  438

<210> SEQ ID NO 219
<211> LENGTH: 438
<212> TYPE: DNA
<213> ORGANISM: Listeria monocytogenes

<400> SEQUENCE: 219
atgcgtacaa cttatatggc gaaacccggc gaagtagaac gtaaatggta cgttatcgac     60
gctactggtg tttctttagg acgtttatcc agtgaagttg cttcaattct tcgcggaaaa    120
actaaaccac aatttactcc acatatcgac actggagact tgtaatcat catcaacgct    180 ggtaagattg gtcttactgg taaaaaagct actgacaaaa tttactaccg tcactctcaa    240
tatccaggcg gtttgaaatc tcgtactgca ggcgaaatgc gtacaaacaa tcctgagaaa    300
ttattagaac tatctatcaa aggtatgctt ccaaaaaatt ctcttggacg tcaattattc    360
aaaaaattac acgtatatgg tggatctgag cacgaacacg cagctcaaca accagaagta    420
tacgaattac gcggttaa                                                  438

<210> SEQ ID NO 220
<211> LENGTH: 438
<212> TYPE: DNA
<213> ORGANISM: Listeria monocytogenes

<400> SEQUENCE: 220
atgcgtacaa cttatatggc gaaacccggc gaagtagaac gtaaatggta cgttatcgac     60
gctactggtg tttctttagg acgtttatcc agtgaagttg cttcaattct tcgcggaaaa    120
aacaaaccac aatttactcc acatatcgac actggagact tgtaatcat catcaacgct    180 ggtaagattg gtcttactgg taaaaaagct actgacaaaa tttactaccg tcactctcaa    240
tatccaggcg gtttgaaatc tcgtactgca ggcgaaatgc gtacaaacaa tcctgagaaa    300
ttattagaac tatctatcaa aggtatgctt ccaaaaaatt ctcttggacg tcaattattc    360
aaaaaattac acgtatatgg tggagctgag cacgaacacg cagctcaaca accagaagta    420
tacgaattac gcggttaa                                                  438

<210> SEQ ID NO 221
<211> LENGTH: 438
<212> TYPE: DNA
<213> ORGANISM: Listeria monocytogenes

<400> SEQUENCE: 221
atgcgtacaa cttatatggc gaaacccggc gaagtagaac gtaaatggta cgttatcgac     60
gctactggtg tttctttagg acgtttatcc agtgaagttg cttcaattct tcgcggaaaa    120
actaaaccac aatttactcc acatatcgac actggagact tgtaatcat catcaacgct    180 ggtaagattg gtcttactgg taaaaaagct actgacaaaa tttactaccg tcactctcaa    240
tatccaggcg gtttgaaatc tcgtactgca ggcgaaatgc gtacaaacaa tcctgagaaa    300
ttattagaac tatctatcaa aggtatgctt ccaaaaaatt ctcttggacg tcaattattc    360
```

```
aaaaaattac acgtatatgg tggatctgag cacgaacacg cagctcaaca accagaagta      420
tacgaattac gcggttaa                                                    438

<210> SEQ ID NO 222
<211> LENGTH: 438
<212> TYPE: DNA
<213> ORGANISM: Listeria monocytogenes

<400> SEQUENCE: 222
atgcgtacaa cttatatggc gaaacccggc gaagtagaac gtaaatggta cgttatcgac       60
gctactggtg tttctttagg acgtttatcc agtgaagttg cttcaattct tcgcggaaaa      120
aacaaaccac aatttactcc acatatcgac actggagact ttgtaatcat catcaacgct      180
ggtaagattg gtcttactgg taaaaaagct actgacaaaa tttactaccg tcactctcaa      240
tatccaggcg gtttgaaatc tcgtactgca ggcgaaatgc gtacaaacaa tcctgagaaa      300
ttattagaac tatctatcaa aggtatgctt ccaaaaaatt ctcttggacg tcaattattc      360
aaaaaattac acgtatatgg tggatctgag cacgaacatg cagctcaaca accagaagta      420
tacgaattac gcggttaa                                                    438

<210> SEQ ID NO 223
<211> LENGTH: 438
<212> TYPE: DNA
<213> ORGANISM: Listeria monocytogenes

<400> SEQUENCE: 223
atgcgtacaa cttatatggc gaaacccggc gaagtagaac gtaaatggta cgttatcgac       60
gctactggtg tttctttagg acgtttatcc agtgaagttg cttcaattct tcgcggaaaa      120
aacaaaccac aatttactcc acatatcgac actggagact ttgtaatcat catcaacgct      180
ggtaagattg gtcttactgg taaaaaagct actgacaaaa tttactaccg tcactctcaa      240
tatccaggcg gtttgaaatc tcgtactgca ggcgaaatgc gtacaaacaa tcctgagaaa      300
ttattagaac tatctatcaa aggtatgctt ccaaaaaatt ctcttgggcg tcaattattc      360
aaaaaattac acgtatatgg tggatctgag cacgaacacg cagctcaaca accagaagta      420
tacgaattac gcggttaa                                                    438

<210> SEQ ID NO 224
<211> LENGTH: 438
<212> TYPE: DNA
<213> ORGANISM: Listeria monocytogenes

<400> SEQUENCE: 224
atgcgtacaa cttatatggc gaaacccggc gaagtagaac gtaaatggta cgttatcgac       60
gctactggtg tttctttagg acgtttatcc agtgaagttg cttcaattct tcgcggaaaa      120
aacaaaccac aatttactcc acatatcgac actggagact ttgtaatcat catcaacgct      180
ggtaagattg gtcttactgg taaaaaagct actgacaaaa tttactaccg tcactctcaa      240
tatccaggcg gtttgaaatc tcgtactgca ggcgaaatgc gtacaaacaa tcctgagaaa      300
ttattagaac tatctatcaa aggtatgctt ccaaaaaatt ctcttggacg tcaattattc      360
aaaaaattac acgtatatgg tggagctgag cacgaacacg cagctcaaca accagaagta      420
tacgaattac gcggttaa                                                    438

<210> SEQ ID NO 225
<211> LENGTH: 393
```

<210> SEQ ID NO 225
<211> LENGTH: 393
<212> TYPE: DNA
<213> ORGANISM: Listeria monocytogenes

<400> SEQUENCE: 225

```
gtggctcaag tacaatatta cggaactggt cgtcgtaaaa gctctgtagc tcgcgtacgt      60
ttagtaccag gcgacggcaa aatcgttatt aacaatagag actgggaaga ttacatccca     120
tttgcagctc ttcgtgaagt tatcaaacaa cctttagtag ctacagaaac tttaggtaac     180
tatgatgtac tagtaaacgt tcacggtggt ggttacactg gtcaagccgg tgctatccgt     240
catggtgtag ctcgtgcact attacaagtg gctcctgagt accgcccagc acttaaatct     300
gctggcctac ttactcgtga ttcacgtatg aaagaacgta aaaaaccagg acttaaaggc     360
gcgcgtcgtg cacctcagtt ctcaaaacgt taa                                  393
```

<210> SEQ ID NO 226
<211> LENGTH: 393
<212> TYPE: DNA
<213> ORGANISM: Listeria monocytogenes

<400> SEQUENCE: 226

```
gtggctcaag tacaatatta cggaactggt cgtcgtaaaa gctctgtagc tcgcgtacgt      60
ttagtaccag gcgacggcaa aatcgttatt aacaatagag actgggaaga ttacatccca     120
ttcgcagctc ttcgtgaagt tatcaaacaa cctttagtag ctacagaaac tttaggtaac     180
tatgatgtac tagtaaacgt tcacggtggt ggttacactg gtcaagccgg tgctatccgt     240
catggtgtag ctcgtgcact attacaagtg gctcctgagt accgcccagc acttaaatct     300
gctggcctac ttactcgtga cccacgtatg aaagaacgta aaaaatacgg acttaaaggc     360
gcgcgtcgtg cacctcagtt ctcaaaacgt taa                                  393
```

<210> SEQ ID NO 227
<211> LENGTH: 393
<212> TYPE: DNA
<213> ORGANISM: Listeria monocytogenes

<400> SEQUENCE: 227

```
gtggctcaag tacaatatta cggaactggt cgtcgtaaaa gctctgtagc tcgcgtacgt      60
ttagtaccag gcgacggcaa aatcgttatt aacaatagag actgggaaga ttacatccca     120
tttgcagctc ttcgtgaagt tatcaaacaa cctttagtag ctacagaaac tttaggtaac     180
tatgatgtac tagtaaacgt tcacggtggt ggttacactg gtcaagccgg tgctatccgt     240
catggtgtag ctcgtgcact attacaagtg gctcctgagt accgcccagc acttaaatct     300
gctggcctac ttactcgtga ttcacgtatg aaagaacgta aaaaaccagg acttaaaggc     360
gcgcgtcgtg cacctcagtt ctcaaaacgt taa                                  393
```

<210> SEQ ID NO 228
<211> LENGTH: 393
<212> TYPE: DNA
<213> ORGANISM: Listeria monocytogenes

<400> SEQUENCE: 228

```
gtggctcaag tacaatatta cggaactggt cgtcgtaaaa gctctgtagc tcgcgtacgt      60
ttagtaccag gcgacggcaa aatcgttatt aacaatagag actgggaaga ttacatccca     120
tttgcagctc ttcgtgaagt tatcaaacaa cctttagtag ctacagaaac tttaggtaac     180
tatgatgtac tagtaaacgt tcacggtggt ggttacactg gtcaagccgg tgctatccgt     240
```

```
catggtgtag ctcgtgcact attacaagtg gctcctgagt accgcccagc acttaaatct    300
gctggcctac ttactcgtga ttcacgtatg aaagaacgta aaaaaccagg acttaaaggc    360
gcgcgtcgtg cacctcagtt ctcaaaacgt taa                                 393
```

<210> SEQ ID NO 229
<211> LENGTH: 393
<212> TYPE: DNA
<213> ORGANISM: Listeria monocytogenes

<400> SEQUENCE: 229

```
gtggctcaag tacaatatta cggaactggt cgtcgtaaaa gctctgtagc tcgcgtacgt     60
ttagtaccag gcgacggcaa atcgttatt aacaatagag actgggaaga ttacatccca    120
tttgcagctc ttcgtgaagt tatcaaacaa cctttagtag ctacagaaac tttaggtaac    180
tatgatgtac tagtaaacgt tcacggtggt ggttacactg gtcaagccgg tgctatccgt    240
catggtgtag ctcgtgcact attacaagtg gctcctgagt accgcccagc acttaaatct    300
gctggcctac ttactcgtga ttcacgtatg aaagaacgta aaaaaccagg acttaaaggc    360
gcgcgtcgtg cacctcagtt ctcaaaacgt taa                                 393
```

<210> SEQ ID NO 230
<211> LENGTH: 393
<212> TYPE: DNA
<213> ORGANISM: Listeria monocytogenes

<400> SEQUENCE: 230

```
gtggctcaag tacaatatta cggaactggt cgtcgtaaaa gctctgtagc tcgcgtacgt     60
ttagtaccag gcgacggcaa atcgttatt aacaatagag actgggaaga ttacatccca    120
tttgcagctc ttcgtgaagt tatcaaacaa cctttagtag ctacagaaac tttaggtaac    180
tatgatgtac tagtaaacgt tcacggtggt ggttacactg gtcaagccgg tgctatccgt    240
catggtgtag ctcgtgcact attacaagtg gctcctgagt accgcccagc acttaaatct    300
gctggcctac ttactcgtga cccacgtatg aaagaacgta aaaaatacgg attgaagggc    360
gcacgtcgtg cacctcagtt ctcaaaacgt taa                                 393
```

<210> SEQ ID NO 231
<211> LENGTH: 393
<212> TYPE: DNA
<213> ORGANISM: Listeria monocytogenes

<400> SEQUENCE: 231

```
gtggctcaag tacaatatta cggaactggt cgtcgtaaaa gctctgtagc tcgcgtacgt     60
ttagtaccag gcgacggcaa atcgttatt aacaatagag actgggaaga ttacatccca    120
tttgcagctc ttcgtgaagt tatcaaacaa cctttagtag ctacagaaac tttaggtaac    180
tatgatgtac tagtaaacgt tcacggtggt ggttacactg gtcaagccgg tgctatccgt    240
catggtgtag ctcgtgcact attacaagtg gctcctgagt accgcccagc acttaaatct    300
gctggcctac ttactcgtga cccacgtatg aaagaacgta aaaaatacgg acttaaaggc    360
gcgcgtcgtg cacctcagtt ctcaaaacgt taa                                 393
```

<210> SEQ ID NO 232
<211> LENGTH: 393
<212> TYPE: DNA
<213> ORGANISM: Listeria monocytogenes

<400> SEQUENCE: 232

| gtggctcaag tacaatatta cggaactggt cgtcgtaaaa gctctgtagc tcgcgtacgt | 60 |
| ttagtaccag gcgacggcaa aatcgttatt aacaatagag actgggaaga ttacatccca | 120 |
| tttgcagctc ttcgtgaagt tatcaaacaa cctttagtag ctacagaaac tttaggtaac | 180 |
| tatgatgtac tagtaaacgt tcacggtggt ggttacactg gtcaagccgg tgctatccgt | 240 |
| catggtgtag ctcgtgcact attacaagtg gctcctgagt accgcccagc acttaaatct | 300 |
| gctggcctac ttactcgtga cccacgtatg aaagaacgta aaaaatacgg acttaaaggc | 360 |
| gcgcgtcgtg cacctcagtt ctcaaaacgt taa | 393 |

<210> SEQ ID NO 233
<211> LENGTH: 393
<212> TYPE: DNA
<213> ORGANISM: Listeria monocytogenes

<400> SEQUENCE: 233

| gtggctcaag tacaatatta cggaactggt cgtcgtaaaa gctctgtagc tcgcgtacgt | 60 |
| ttagtaccag gcgacggcaa aatcgttatt aacaatagag actgggaaga ttacatccca | 120 |
| tttgcagctc ttcgtgaagt tatcaaacaa cctttagtag ctacagaaac tttaggcaac | 180 |
| tatgatgtac tagtaaacgt tcacggtggt ggttacactg gtcaagccgg tgctatccgt | 240 |
| catggtgtag ctcgtgcact attacaagtg gctcctgagt accgcccagc acttaaatct | 300 |
| gctggcctac ttactcgtga cccacgtatg aaagaacgta aaaaatacgg acttaaaggc | 360 |
| gcgcgtcgtg cacctcagtt ctcaaaacgt taa | 393 |

<210> SEQ ID NO 234
<211> LENGTH: 393
<212> TYPE: DNA
<213> ORGANISM: Listeria monocytogenes

<400> SEQUENCE: 234

| gtggctcaag tacaatatta cggaactggt cgtcgtaaaa gctctgtagc tcgcgtacgt | 60 |
| ttagtaccag gcgacggcaa aatcgttatt aacaatagag actgggaaga ttacatccca | 120 |
| tttgcagctc ttcgtgaagt tatcaaacaa cctttagtag ctacagaaac tttaggtaac | 180 |
| tatgatgtac tagtaaacgt tcacggtggt ggttacactg gtcaagccgg tgctatccgt | 240 |
| catggtgtag ctcgtgcact attacaagtg gctcctgagt accgcccagc acttaaatct | 300 |
| gctggcctac ttactcgtga ttcacgtatg aaagaacgta aaaaaccagg acttaaaggc | 360 |
| gcgcgtcgtg cacctcagtt ctcaaaacgt taa | 393 |

<210> SEQ ID NO 235
<211> LENGTH: 393
<212> TYPE: DNA
<213> ORGANISM: Listeria monocytogenes

<400> SEQUENCE: 235

| gtggctcaag tacaatatta cggaactggt cgtcgtaaaa gctctgtagc tcgcgtacgt | 60 |
| ttagtaccag gcgacggcaa aatcgttatt aacaatagag actgggaaga ttacatccca | 120 |
| tttgcagctc ttcgtgaagt tatcaaacaa cctttagtag ctacagaaac tttaggtaac | 180 |
| tatgatgtac tagtaaacgt tcgcggtggt ggttacactg gtcaagccgg tgctatccgt | 240 |
| catggtgtag ctcgtgcact actacaagtg gcacctgagt accgcccagc acttaaatct | 300 |

```
gctggactac ttactcgtga ttcacgtatg aaagaacgta aaaaaccagg acttaaaggc    360
gcgcgtcgtg cacctcagtt ctcaaaacgt taa                                 393
```

<210> SEQ ID NO 236
<211> LENGTH: 393
<212> TYPE: DNA
<213> ORGANISM: Listeria monocytogenes

<400> SEQUENCE: 236

```
gtggctcaag tacaatatta cggaactggt cgtcgtaaaa gctctgtagc tcgcgtacgt    60
ttagtaccag gcgacggcaa aatcgttatt aacaatagag actgggaaga ttacatccca   120
tttgcagctc ttcgtgaagt tatcaaacaa cctttagtag ctacagaaac tttaggtaac   180
tatgatgtac tagtaaacgt tcacggtggt ggttacactg gtcaagccgg tgctatccgt   240
catggtgtag ctcgtgcact attacaagtg gctcctgagt accgcccagc acttaaatct   300
gctggcctac ttactcgtga cccacgtatg aaagaacgta aaaaatacgg acttaaaggc   360
gcgcgtcgtg cacctcagtt ctcaaaacgt taa                                 393
```

<210> SEQ ID NO 237
<211> LENGTH: 393
<212> TYPE: DNA
<213> ORGANISM: Listeria monocytogenes

<400> SEQUENCE: 237

```
gtggctcaag tacaatatta cggaactggt cgtcgtaaaa gctctgtagc tcgcgtacgt    60
ttagtaccag gcgacggcaa aatcgttatt aacaatagag actgggaaga ttacatccca   120
tttgcagctc ttcgtgaagt tatcaaacaa cctttagtag ctacagaaac tttaggtaac   180
tatgatgtac tagtaaacgt tcgcggtggt ggttacactg gtcaagccgg tgctatccgt   240
catggtgtag ctcgtgcact actacaagtg gcacctgagt accgcccagc acttaaatct   300
gctggtctac ttactcgtga ttcacgtatg aaagaacgta aaaaaccagg acttaaaggc   360
gcgcgtcgtg cacctcagtt ctcaaaacgt taa                                 393
```

<210> SEQ ID NO 238
<211> LENGTH: 393
<212> TYPE: DNA
<213> ORGANISM: Listeria monocytogenes

<400> SEQUENCE: 238

```
gtggctcaag tacaatatta cggaactggt cgtcgtaaaa gctctgtagc tcgcgtacgt    60
ttagtaccag gcgacggcaa aatcgttatt aacaatagag actgggaaga ttacatccca   120
tttgcagctc ttcgtgaagt tatcaaacaa cctttagtag ctacagaaac tttaggtaac   180
tatgatgtac tagtaaacgt tcacggtggt ggttacactg gtcaagccgg tgctatccgt   240
catggtgtag ctcgtgcact attacaagtg gctcctgagt accgcccagc acttaaatct   300
gctggcctac ttactcgtga cccacgtatg aaagaacgta aaaaatacgg acttaaaggc   360
gcgcgtcgtg cacctcagtt ctcaaaacgt taa                                 393
```

<210> SEQ ID NO 239
<211> LENGTH: 393
<212> TYPE: DNA
<213> ORGANISM: Listeria monocytogenes

<400> SEQUENCE: 239

```
gtggctcaag tacaatatta cggaactggt cgtcgtaaaa gctctgtagc tcgcgtacgt      60
ttagtaccag gcgacggcaa atcgttatt aacaatagag actgggaaga ttacatccca     120
tttgcagctc ttcgtgaagt tatcaaacaa cctttagtag ctacagaaac tttaggtaac    180
tatgatgtac tagtaaacgt tcacggtggt ggttacactg gtcaagccgg tgctatccgt    240
catggtgtag ctcgtgcact attacaagtg gctcctgagt accgcccagc acttaaatct    300
gctggcctac ttactcgtga ttcacgtatg aagaacgta aaaaaccagg acttaaaggc     360
gcgcgtcgtg cacctcagtt ctcaaaacgt taa                                  393
```

<210> SEQ ID NO 240
<211> LENGTH: 393
<212> TYPE: DNA
<213> ORGANISM: Listeria monocytogenes

<400> SEQUENCE: 240

```
gtggctcaag tacaatatta cggaactggt cgtcgtaaaa gctctgtagc tcgcgtacgt      60
ttagtaccag gcgacggcaa atcgttatt aacaatagag actgggaaga ttacatccca     120
tttgcagctc ttcgtgaagt tatcaaacaa cctttagtag ctacagaaac tttaggtaac    180
tatgatgtac tagtaaacgt tcacggtggt ggttacactg gtcaagccgg tgctatccgt    240
catggtgtag ctcgtgcact attacaagtg gctcctgagt accgcccagc acttaaatct    300
gctggcctac ttactcgtga cccacgtatg aagaacgta aaaaatacgg acttaaaggc     360
gcgcgtcgtg cacctcagtt ctcaaaacgt taa                                  393
```

<210> SEQ ID NO 241
<211> LENGTH: 312
<212> TYPE: DNA
<213> ORGANISM: Listeria innocua

<400> SEQUENCE: 241

```
atgcatgtca aaaaggtga taaagtaaaa gttattactg gtaaagataa aggcaaatcc      60
ggcaaagtgc tcgcagcatt tccgaaaaag gaccgcgtac ttatcgaagg aatcaatatg    120
gttaaaaaac atactaaacc ttccaacatc aacccgcaag gcggaatctt gaatgttgaa    180
gcaccaatcc atgtttcaaa cgtaatgcta attgaccta aaactggcga acctactcgt     240
gtaggctacg aagttaaagg tgataaaaaa gtacgcgtag caaaaaaatc cggtgaagta    300
atagataaat aa                                                         312
```

<210> SEQ ID NO 242
<211> LENGTH: 537
<212> TYPE: DNA
<213> ORGANISM: Listeria innocua

<400> SEQUENCE: 242

```
atgtcccgta taggtaaaaa aactattgtg attcctgcag gtgtaacagt tacacttaat      60
ggatcaacag caacagttaa aggtcctaaa ggtgaacttg taaagagtt caacccagaa     120
attactatta atattgaagg caacgaaatt aacgtttctc gcccgactga taataaaaac    180
caccgtgcac ttcatggtac aactcgtgct attcttaata acatggttgt cggagtttcc    240
gagggttatg aaaagaaatt agaacttatc ggtgttggtt accgtgcgca aaaacaagga    300
gacaaacttg ttcttaacgt agggtactct catccagtag agtttgttgc tcctaaaggc    360
```

```
gtagaaattg aagttcctgc aaacactcaa gtgattgtta aaggatacaa caaagaacac    420
gttggcgagt tagctgcaaa cattcgtgcc gtacgtccac cagagccata taaaggtaaa    480
ggtattcgtt acgaaggcga acatgtacgc cgtaaagaag gtaaaactgg taaataa      537

<210> SEQ ID NO 243
<211> LENGTH: 360
<212> TYPE: DNA
<213> ORGANISM: Listeria innocua

<400> SEQUENCE: 243
gtgattacca aaatcgacaa aaataaagta cgtaaaaaaa gacatgctcg tgttcgttct     60
aagatttctg gaactgaaag tcgtccacgt ttaaacgtat tccgttcaaa caaaaacatt    120
tatgctcaag ttattgatga tgtaaatggt gtgacacttg caagtgcgtc taatttagat    180
aaagatttcg gttctgctga atccaaagtt gatgcagcaa gcaaagttgg cgaactagtt    240
gctaaacgtg cttccgaaaa aggtattact tctgtcactt ttgaccgtgg aggatactta    300
tatcatggcc gcgtaaaagc tcttgctgaa gcagctcgcg aaaatggact agaattttaa    360

<210> SEQ ID NO 244
<211> LENGTH: 441
<212> TYPE: DNA
<213> ORGANISM: Listeria innocua

<400> SEQUENCE: 244
atgaaactac atgaacttaa accttcagaa ggttctcgta agaacgtaa tcgtgttggt      60 cgtggaacag ctctggtaa cggcaaaact tctggacgcg gtcataaagg acaaaaagct    120
cgttccggtg gtggcgtacg cctaggtttt gaaggtggac aacttccact tttccgtcgt    180
attccaaaac gtggattcac aaatatcaac cgtaaagaat ttgctatcgt taacttagat    240
gttttaaacc gctttgaaga tggtacagaa gtaacaccag aacttttaat cgaaactgga    300
attattcgta acgaaaaatc cgggattaaa atttttatctg atggaaatat cgagaaaaaa    360
cttactgtga aagcgaacaa attctctgca gctgccaaag aagctattga agcagccggc    420
ggaaaaactg aggtgatcta a                                              441

<210> SEQ ID NO 245
<211> LENGTH: 390
<212> TYPE: DNA
<213> ORGANISM: Listeria innocua

<400> SEQUENCE: 245
atggctcgta aacaaatac tcgtaaacgt cgtgtgaaaa agaatatcga atctggtatt      60
gcacacattc gttctacatt taataatacg atcgtaatga ttactgacac acatggtaat    120
gctttagctt ggtcaagtgc aggttctcta ggatttaaag gttctcgtaa atctactcct    180
ttcgcagcgc aaatggcagc tgaaagtgca gcaaaatcag cacaagaaca tggtttaaaa    240
acattagaag taactgttaa aggtcctggt tcaggtcgtg aagcggctat ccgtgcacta    300
caagcagctg tcttgaagt aacagctatt aaagatgtaa ctccagttcc acataacgga    360
tgtcgtcctc caaaacgtcg tcgcgtataa                                     390

<210> SEQ ID NO 246
<211> LENGTH: 393
<212> TYPE: DNA
<213> ORGANISM: Listeria innocua
```

<400> SEQUENCE: 246

```
gtggctcaag tacaatatta cggaactggt cgtcgtaaaa gctctgtagc tcgcgtacgt    60
ttagtaccag gcgacggcaa aatcgttatt aacaatagag actgggaaga ttacatccca   120
tttgcagctc ttcgtgaagt tatcaaacaa cctttagtag ctacagaaac tttaggtaac   180
tatgatgtac tagtaaacgt tcacggtggt ggttacactg gtcaagccgg tgctatccgt   240
catggtgtag ctcgtgcact attacaagtg gcccctgagt accgcccagc acttaaatct   300
gctggcctac ttactcgtga cccacgtatg aaagaacgta aaaaatacgg acttaaaggc   360
gcgcgtcgtg cacctcagtt ctcaaaacgt taa                                393
```

<210> SEQ ID NO 247
<211> LENGTH: 246
<212> TYPE: DNA
<213> ORGANISM: Listeria innocua

<400> SEQUENCE: 247

```
atgaaaactg gaattcatcc tgagtaccgt ccagtggtat ttgttgatac tagtactgat    60
ttcaaatttt tgtcaggttc tactaagagc tcaagcgaaa caattaaatg gaagatggc    120
aacgagtatc cattacttcg tgtcgaaatc tcttctgatt cgcacccgtt ctatactggt   180
aaacaaaaac atgcgactgc agacggccgt gtggaccgct tcaacaaaaa atacggtctc   240
aaataa                                                              246
```

<210> SEQ ID NO 248
<211> LENGTH: 273
<212> TYPE: DNA
<213> ORGANISM: Listeria innocua

<400> SEQUENCE: 248

```
atggcagtta aaattcgttt aaaacgtatg ggttctaaaa agaaaccttt ctaccgtatt    60
gtagtcgctg attctcgttt cccacgtgat ggccgttcaa tcgaaactat tggtacttat   120
aatccattac ttgatccggt tgaagtgaaa atcgacgaag aagcaacttt gaaatggatg   180
cataatggtg cgaaaccatc tgatacagtt cgcaatcttc ttagccgcga aggtatcatg   240
gaaaaattcc ataaccaaaa attaggtaaa taa                                273
```

<210> SEQ ID NO 249
<211> LENGTH: 312
<212> TYPE: DNA
<213> ORGANISM: Listeria innocua

<400> SEQUENCE: 249

```
atgcatgtca aaaaggtga taaagtaaaa gttattactg gtaaagataa aggcaaatcc    60
ggcaaagtgc tcgcagcatt tccgaaaaag accgcgtac ttatcgaagg aatcaatatg   120
gttaaaaaac atactaaacc ttccaacatc aacccgcaag gcggaatctt gaatgttgaa   180
gcaccaatcc atgtttcaaa cgtaatgcta attgacccta aaactggcga acctactcgt   240
gtaggatacg aagttaaagg tgataaaaaa gtacgcgtag caaaaaaatc cggtgaagta   300
atagataaat aa                                                       312
```

<210> SEQ ID NO 250
<211> LENGTH: 537
<212> TYPE: DNA
<213> ORGANISM: Listeria innocua

```
<400> SEQUENCE: 250
atgtcccgta taggtaaaaa aactattgtg attcctgcag gtgtaacagt tacacttaat        60
ggatcaacag caacagttaa aggtcctaaa ggtgaacttg taaaagagtt caacccagaa       120
attactatta atattgaagg caacgaaatt aacgtttctc gcccgactga taataaaaac       180
caccgtgcac ttcatggtac aactcgtgct attcttaata acatggttgt cggagtttcc       240
gagggttatg aaaagaaatt agaacttatc ggtgttggtt accgtgcgca aaaacaagga       300
gacaaacttg ttcttaacgt agggtactct catccagtag agtttgttgc tcctaaaggc       360
gtagaaattg aagttcctgc aaacactcaa gtgattgtta aaggatacaa caaagaacac       420
gttggcgagt tagctgcaaa cattcgtgcc gtacgtccac cagagccata taaaggtaaa       480
ggtattcgtt acgaaggcga acatgtacgc cgtaaagaag gtaaaactgg taaataa         537

<210> SEQ ID NO 251
<211> LENGTH: 360
<212> TYPE: DNA
<213> ORGANISM: Listeria innocua

<400> SEQUENCE: 251
gtgattacca aaatcgacaa aaataaagta cgtaaaaaaa gacatgctcg tgttcgttct        60
aagatttctg gaactgaaag tcgtccacgt ttaaacgtat ccgttcaaa caaaaacatt       120 tatgctcaaa ttattgatga tgtaaatggt gtgacacttg caagtgcgtc taatttagat       180
aaagatttcg gttctgctga atccaaagtt gatgcagcaa gcaaagttgg cgaactagtt       240
gctaaacgtg cttccgaaaa aggtattact tctgtcactt ttgaccgtgg aggatactta       300
tatcatggcc gcgtaaaagc tcttgctgaa gcagctcgcg aaaatggact agaattttaa       360

<210> SEQ ID NO 252
<211> LENGTH: 441
<212> TYPE: DNA
<213> ORGANISM: Listeria innocua

<400> SEQUENCE: 252
atgaaactac atgaacttaa accttcagaa ggttctcgta agaacgcaa tcgtgttggt        60 cgtggaacag gctctggtaa cggcaaaact tctggacgcg gtcataaagg acaaaaagct       120
cgttccggtg gtggcgtacg cctaggtttt gaaggtggac aacttccact tttccgtcgt       180
attccaaaac gtggattcac aaatatcaac cgtaaagaat ttgctatcgt aaacttagat       240
gttttaaacc gctttgaaga tggtacagaa gtaacaccag aacttttaat cgaaactgga       300
attattcgta acgaaaaatc cgggattaag attttatctg atggaaatat cgagaaaaaa       360
cttactgtga aagcgaacaa attctctgca gctgcaaaag aagctattga agcagctggc       420
ggaaaaactg aggtgatcta a                                                441

<210> SEQ ID NO 253
<211> LENGTH: 390
<212> TYPE: DNA
<213> ORGANISM: Listeria innocua

<400> SEQUENCE: 253
atggctcgta aacaaatac tcgtaaacgt cgtgtgaaaa agaatatcga atcaggtatt        60
gcacacattc gttctacatt taataatacg atcgtaatga ttactgacac acatggtaat       120
gctttagctt ggtcaagtgc aggttctcta ggatttaaag gttctcgtaa atctactcct       180
ttcgcagcgc aaatggcagc tgaaagtgca gcaaaatcag cacaagaaca tggtttaaaa       240
```

| | |
|---|---|
| acattagaag taactgttaa aggtcctggt tcaggtcgtg aagcggctat ccgtgcacta | 300 |
| caagcagctg gtcttgaagt aacagctatt aaagatgtaa ctccagttcc acataacgga | 360 |
| tgtcgtcctc caaaacgtcg tcgcgtataa | 390 |

<210> SEQ ID NO 254
<211> LENGTH: 393
<212> TYPE: DNA
<213> ORGANISM: Listeria innocua

<400> SEQUENCE: 254

| | |
|---|---|
| gtggctcaag tacaatatta cggaactggt cgtcgtaaaa gctctgtagc tcgcgtacgt | 60 |
| ttagtaccag gcgacggcaa atcgttatt aacaatagag actgggaaga ttacatccca | 120 |
| tttgcagctc ttcgtgaagt tatcaaacaa cctttagtag ctacagaaac tttaggtaac | 180 |
| tatgatgtac tagtaaacgt tcacggtggt ggttacactg gtcaagccgg tgctatccgt | 240 |
| catggtgtag ctcgtgcact attacaagtg gctcctgagt accgcccagc acttaaatct | 300 |
| gctggcctac ttactcgtga cccacgtatg aaagaacgta aaaaatacgg acttaaaggc | 360 |
| gcgcgtcgtg cacctcagtt ctcaaaacgt taa | 393 |

<210> SEQ ID NO 255
<211> LENGTH: 246
<212> TYPE: DNA
<213> ORGANISM: Listeria innocua

<400> SEQUENCE: 255

| | |
|---|---|
| atgaaaactg gaattcatcc tgagtaccgt ccagtggtat ttgttgatac tagtactgat | 60 |
| ttcaaatttt tgtcaggttc tactaagagc tcaagcgaaa caattaaatg ggaagatggc | 120 |
| aacgagtatc cattacttcg tgtcgaaatc tcttctgatt cgcacccgtt ctatactggt | 180 |
| aaacaaaaac atgcgactgc agacggccgt gtggaccgct tcaacaaaaa atatggtctc | 240 |
| aaataa | 246 |

<210> SEQ ID NO 256
<211> LENGTH: 273
<212> TYPE: DNA
<213> ORGANISM: Listeria innocua

<400> SEQUENCE: 256

| | |
|---|---|
| atggcagtta aaattcgttt aaaacgtatg ggttctaaaa agaaaccttt ctaccgtatt | 60 |
| gtagtcgctg attctcgttt cccacgtgat ggccgttcaa tcgaaactat tggtacttat | 120 |
| aatccattac ttgatccggt tgaagtgaaa atcgacgaag aagcaacttt gaaatggatg | 180 |
| cataatggtg cgaaaccatc tgatacagtt cgcaatcttc ttagccgcga aggtatcatg | 240 |
| gaaaaattcc ataaccaaaa attaggtaaa taa | 273 |

<210> SEQ ID NO 257
<211> LENGTH: 312
<212> TYPE: DNA
<213> ORGANISM: Listeria ivanovii

<400> SEQUENCE: 257

| | |
|---|---|
| atgcatgtca aaaaaggtga taaagtaaaa gttattactg gtaaagataa aggcaaatcc | 60 |
| ggcaaagtgc tcgcagcatt tccgaaaaag gaccgcgtac ttattgaagg aattaatatg | 120 |
| gttaaaaaac atacaaaacc ttccaacatc aacccgcaag gcggaatctt gaatgttgaa | 180 |

```
gcaccaatcc atgtttcaaa cgtaatgcta attgaccccta aaacaggcga acctactcgt    240
gtaggctacg aagttaaagg cgataagaaa gtacgcgtag caaaaaaatc cggtgaagta    300
atagataaat aa                                                        312
```

```
<210> SEQ ID NO 258
<211> LENGTH: 537
<212> TYPE: DNA
<213> ORGANISM: Listeria ivanovii

<400> SEQUENCE: 258
atgtcccgta taggtaaaaa aactattgtg attcctgcag gtgtaacagt tacacttaat     60
ggatcaacag caacagttaa aggtcctaaa ggtgaacttg taaaagagtt caacccagaa    120
attactatca atattgaagg caacgaaatt aacgtttctc gcccgactga taataaaaac    180
caccgcgcgc ttcatggtac aacccgtgct atttttaaata acatggttgt cggagttttcc   240 gagggttatg aaaagaaatt agaacttatc ggtgttggtt accgtgcaca aaaacaaggc    300
gacaagcttg ttcttaacgt agggtactct catccagtag aatttgttgc tccgaaaggc    360
gtagaaattg aagttcctgc aaacacacaa gtgattgtta aggatacaa caaagaacac    420 gttggagaat tagctgcaaa cattcgtgcc gtacgtccac cagagccata taaaggtaaa    480
ggtattcgtt acgaaggcga acatgtacgc cgtaaagaag gtaaaactgg taaataa     537
```

```
<210> SEQ ID NO 259
<211> LENGTH: 360
<212> TYPE: DNA
<213> ORGANISM: Listeria ivanovii

<400> SEQUENCE: 259
gtgattacca aaatcgacaa aaataaagta cgtaaaaaaa gacatgctcg tgttcgttct     60
aagatttctg gaactgaaag tcgtccacgt ttaaacgtat tccgttcaaa caaaaacatt    120
tatgctcaaa ttattgatga tgtaaatggt gtgacacttg caagtgcgtc taatttagat    180
aaagatttcg ttctgctga atcaaaagtt gatgcagcaa gcaaagttgg cgaactagtt    240
gctaaacgtg cttccgaaaa aggtattact tctgtcactt ttgaccgtgg aggatactta    300
tatcatggcc gcgtaaaagc tcttgctgaa gcagctcgcg aaaatggact agaattttaa    360
```

```
<210> SEQ ID NO 260
<211> LENGTH: 441
<212> TYPE: DNA
<213> ORGANISM: Listeria ivanovii

<400> SEQUENCE: 260
atgaaactac atgaacttaa gccttcagaa ggttctcgta aagaacgtaa tcgtgttggt     60
cgtggaacag gctctggtaa cggcaaaact tcaggacgcg gtcataaagg acaaaaagct    120
cgttctggtg gtggcgtacg tttaggcttt gaaggtggac aacttccact tttccgtcgt    180
attccaaaac gtggattcac aaatatcaac cgtaaagaat ttgcaatcgt gaacttagat    240
gttttaaacc gctttgaaga tggtacagaa gtaacaccag aacttttaat tgaaactgga    300
ataattcgta acgaaaaatc tggaatcaag attttatcag atggtaaaat cgagaaaaaa    360
cttactgtga aagcgaacaa attctctgca gctgctaaag aagcaattga agcggctggc    420
ggaaaaactg aggtgatcta a                                             441
```

```
<210> SEQ ID NO 261
<211> LENGTH: 390
```

```
<212> TYPE: DNA
<213> ORGANISM: Listeria ivanovii

<400> SEQUENCE: 261
atggctcgta aaacaaatac tcgtaaacgc cgtgtgaaaa agaatatcga atctggtatt 60
gcacacattc gttctacatt taataatacg atcgtaatga ttactgacac acatggtaat 120
gctttagctt ggtcaagtgc aggttctcta gggtttaaag gttctcgtaa atctactcct 180
ttcgcagcgc aaatggcagc tgaaagtgca gctaaatcag cacaagaaca tggtttaaaa 240
acattagaag taactgttaa aggtcctggt tcaggtcgtg aagcggctat ccgtgcacta 300
caagcagctg gtcttgaagt aacagctatt aaagatgtaa ctccagttcc acataacgga 360
tgtcgtcctc caaaacgtcg tcgcgtataa 390

<210> SEQ ID NO 262
<211> LENGTH: 393
<212> TYPE: DNA
<213> ORGANISM: Listeria ivanovii
<400> SEQUENCE: 262
gtggctcaag tacaatatta cggaactggt cgtcgtaaaa gctctgtagc tcgcgtacgt 60
ttagtaccag gcgacggcaa aatcgttatt aacaatagag actgggaaga ttacattcca 120
tttgcagctc ttcgtgaagt tatcaaacaa cctttagtag ctacagaaac tttaggtaat 180
tatgatgtac tagtaaacgt tcacggtggt ggttacactg gtcaagccgg tgctatccgt 240
catggtgtag ctcgtgcact attacaagtg gcacctgagt accgcccagc acttaaatcc 300
gctggtctac ttactcgtga ccctcgtatg aaagaacgta aaaaatacgg acttaaaggc 360
gcgcgtcgtg cacctcagtt ctcaaaacgt taa 393

<210> SEQ ID NO 263
<211> LENGTH: 246
<212> TYPE: DNA
<213> ORGANISM: Listeria ivanovii
<400> SEQUENCE: 263
atgaaaactg gaattcatcc tgagtaccgt caagtggtat ttgttgatac tagtactgat 60
ttcaaatttt tgtcaggttc tactaagagc tcaagcgaaa caattaaatg ggaagatggc 120
aacgagtatc cgttacttcg tgtcgaaatc tcttctgatt cgcatccgtt ctatactggt 180
aaacaaaaac atgctacagc agacggacgt gtggaccgct tcaacaaaaa atacggtctc 240
aaataa 246

<210> SEQ ID NO 264
<211> LENGTH: 273
<212> TYPE: DNA
<213> ORGANISM: Listeria ivanovii
<400> SEQUENCE: 264
atggcagtta aaattcgttt aaaacgtatt ggttctaaaa agaaaccttt ctaccgtatt 60
gtagtagctg attctcgttt cccacgtgac ggccgttcaa tcgaaactat tggtacttat 120
aatccattac ttgatccggt tgaagtgaaa attgacgaag aagcaacttt gaaatggatg 180
cataatggtg cgaaaccatc tgatacagtt cgcaatcttc ttagccgcga aggtatcatg 240
gaaaaattcc ataaccaaaa attaggtaaa taa 273

<210> SEQ ID NO 265
```

```
<211> LENGTH: 312
<212> TYPE: DNA
<213> ORGANISM: Listeria ivanovii

<400> SEQUENCE: 265
atgcatgtca aaaaaggtga taaagtaaaa gttattactg gtaaagataa aggtaaatcc      60
ggcaaagtgc tcgcagcatt tccgaaaaag gaccgcgtac ttattgaagg aattaatatg     120
gttaaaaaac atacaaaacc ttccaacatc aacccgcaag gcggaatctt gaatgttgaa     180
gcacccatcc atgtttcaaa cgtaatgcta attgaccccta aacaggcga acctact

```
gttttaaacc gctttgaaga tggtacagaa gtaacaccag aacttttaat tgaaactggt    300
attattcgta acgaaaaatc cggaatcaag attttatcaa atggtaaaat cgagaaaaaa    360
cttactgtga aagcgaacaa attctctgca gctgctaaag atgcaattga agcggctggc    420
ggaaaaactg aggtgatcta a                                              441
```

<210> SEQ ID NO 269
<211> LENGTH: 390
<212> TYPE: DNA
<213> ORGANISM: Listeria ivanovii

<400> SEQUENCE: 269

```
atggctcgta aaacaaatac tcgtaaacgc cgtgtgaaaa agaatatcga atctggtatt     60
gcacacattc gttctacatt taataatacg atcgtaatga ttactgacac acatggtaat    120
gctttagctt ggtcaagtgc aggttctcta ggatttaaag gttctcgtaa atctactcct    180
ttcgcagcgc aaatggcagc tgaaagtgca gctaaatcag cacaagaaca tggtttgaaa    240
acattagaag taactgttaa aggtcctggt tcaggtcgtg aagcggctat ccgtgcacta    300
caagcagctg gtcttgaagt aacagctatt aaagatgtaa ctccagttcc acataacgga    360
tgtcgtcctc caaaacgtcg tcgcgtataa                                     390
```

<210> SEQ ID NO 270
<211> LENGTH: 393
<212> TYPE: DNA
<213> ORGANISM: Listeria ivanovii

<400> SEQUENCE: 270

```
gtggctcaag tacaatatta cggaactggt cgtcgtaaaa gctctgtagc tcgcgtacgt     60
ttagtaccag cgacggcaa aatcgttatt aacaatagag actgggaaga ttacatccca    120
tttgcagctc ttcgtgaagt tatcaaacaa cctttagtag ctacagaaac tttaggtaac    180
tatgatgtac tagtaaacgt tcacggtggt ggttacactg gtcaagctgg tgctatccgt    240
catggtgtag ctcgtgcact attacaagtg gcacctgagt accgcccagc acttaaatct    300
gctggtctac ttactcgtga ccctcgtatg aaagaacgta agaaatacgg acttaaaggc    360
gcgcgtcgtg cacctcagtt ctcaaaacgt taa                                 393
```

<210> SEQ ID NO 271
<211> LENGTH: 246
<212> TYPE: DNA
<213> ORGANISM: Listeria ivanovii

<400> SEQUENCE: 271

```
atgaaaactg gaattcatcc tgagtaccgt caagtggtat tgttgatac tagtactgat      60 ttcaaatttt tgtcaggttc tactaagagc tcaagcgaaa caattaaatg ggaagatggc    120
aacgagtatc cgttacttcg tgtcgaaatc tcttctgatt cgcatccgtt ctatactggt    180
aaacaaaaac atgctacagc agacggacgt gtggaccgct tcaacaaaaa atacggtctc    240
aaataa                                                               246
```

<210> SEQ ID NO 272
<211> LENGTH: 273
<212> TYPE: DNA
<213> ORGANISM: Listeria ivanovii

<400> SEQUENCE: 272

```
atggcagtta aaattcgttt aaaacgtatt ggttctaaaa agaaaccttt ctaccgtatt      60
gtagtagctg attctcgttt cccacgtgac ggccgttcaa tcgaaactat tggtacttat     120
aatccattac ttgatccggt tgaagtgaaa attgacgaag aagcaacttt gaaatggatg     180
cataatggtg cgaaaccatc tgatacagtt cgcaatcttc ttagccgcga aggtatcatg     240
gaaaaattcc ataaccaaaa attaggtaaa taa                                  273
```

<210> SEQ ID NO 273
<211> LENGTH: 312
<212> TYPE: DNA
<213> ORGANISM: Listeria seeligeri

<400> SEQUENCE: 273

```
atgcatgtca aaaaggtga taaagtaaaa gttattactg gtaaagataa aggcaaatcc       60
ggcaaagtgc tcgcagcatt tccgaagaag atcgcgtac ttattgaagg aattaatatg      120
gtcaaaaaac atacaaaacc ttccaacatc aacccgcaag gcggaatctt gaatgttgaa     180
gcaccaatcc atgtttcaaa cgtgatgcta attgaccta aaacaggcga acctactcgt     240
gtaggctacg aagttaaagg cgataaaaaa gtacgcgtag caaaaaaatc cggtgaagta     300
atagataaat aa                                                         312
```

<210> SEQ ID NO 274
<211> LENGTH: 537
<212> TYPE: DNA
<213> ORGANISM: Listeria seeligeri

<400> SEQUENCE: 274

```
atgtcccgta taggtaaaaa aactattgtg attcctgcag gtgtaacagt tacacttaat      60
ggatcaacag caacagttaa aggtcctaaa ggtgaacttg taaagagtt caacccagaa      120 attactatta atattgaagg caacgaaatt aacgtttctc gcccgactga taataaaaac     180
caccgcgcgc ttcatggtac aactcgtgct attctaaata acatggttgt cggagtttcc     240
gagggttatg aaaagaaatt agaacttatc ggtgttggtt accgtgcgca aaaacaaggc     300
gacaagcttg ttcttaacgt agggtactct catccagtag aatttgttgc tccgaaaggc     360
gtagaaattg aagttcctgc aaacacacaa gtgattgtta aaggatacaa caagaacac     420 gttggagaat tagctgcaaa cattcgtgcc gtacgtccac cagagccgta taaggtaaa     480 ggtattcgtt acgaaggcga acatgtacgc cgtaaagaag gtaaaactgg taaataa      537
```

<210> SEQ ID NO 275
<211> LENGTH: 360
<212> TYPE: DNA
<213> ORGANISM: Listeria seeligeri

<400> SEQUENCE: 275

```
gtgattacca aaatcgacaa aaataaagta cgtaaaaaaa gacatgctcg tgttcgttct      60
aagatttccg gaactgaaag tcgtccacgt ttaaacgtat tccgttcaaa caaaaacatt     120
tatgctcaag taattgatga tgtaaatggt gtgacacttg caagtgcgtc taatttagat     180
aaagatttcg ttctgttga atcaaaagtt gatgcagcaa gcaaagttgg cgaactagtt     240
gctaaacgtg cttccgaaaa aggtattact tctgtcactt ttgaccgtgg aggatactta     300
tatcatggcc gcgtaaaagc tcttgctgaa gcagctcgcg aaaatggact agaattttaa     360
```

<210> SEQ ID NO 276
<211> LENGTH: 441
<212> TYPE: DNA
<213> ORGANISM: Listeria seeligeri

<400> SEQUENCE: 276

| | | |
|---|---|---|
| atgaaactac atgaacttaa gccttcagaa ggttctcgaa agaacgtaa tcgtgttggt | 60 |
| cgtggaacag gctctggtaa cggcaaaact tcaggacgcg gtcataaagg acaaaaagct | 120 |
| cgttccggtg gtggcgtacg tttaggtttt gaaggtggac aacttccact tttccgtcgt | 180 |
| attccaaaac gtggattcac aaatatcaat cgtaaagaat ttgcaatcgt gaacttagat | 240 |
| gttttaaacc gctttgaaga cggtacagaa gtaacaccag aacttttaat tgaatctgga | 300 |
| attattcgta acgaaaaatc cggaatcaag attttatctg atggtaaaat cgagaaaaaa | 360 |
| cttactgtga aagcgaacaa attctctgca gctgcaaaag aagctattga agcggctggc | 420 |
| ggaaaaactg aggtgatcta a | 441 |

<210> SEQ ID NO 277
<211> LENGTH: 390
<212> TYPE: DNA
<213> ORGANISM: Listeria seeligeri

<400> SEQUENCE: 277

| | | |
|---|---|---|
| atggctcgta aaacaaatac tcgtaaacgc cgtgtgaaaa agaatatcga atctggtatt | 60 |
| gcacacattc gttctacatt taataatacg atcgtaatga ttactgacac acagggtaat | 120 |
| gctttagctt ggtcaagtgc aggttctcta ggatttaaag gttctcgtaa atctactcct | 180 |
| ttcgcagcgc aaatggcagc tgaaagtgca gctaagtcag cacaagaaca tggtttgaaa | 240 |
| acattagaag taacggttaa aggtcctggt tcaggtcgtg aagcggctat ccgtgcacta | 300 |
| caagcagctg gtcttgaagt aacagctatt agagatgtaa ctccagttcc acataacgga | 360 |
| tgtcgtcctc caaaacgtcg tcgcgtataa | 390 |

<210> SEQ ID NO 278
<211> LENGTH: 393
<212> TYPE: DNA
<213> ORGANISM: Listeria seeligeri

<400> SEQUENCE: 278

| | | |
|---|---|---|
| gtggctcaag tacaatatta cggaactggt cgtcgtaaaa gctctgtagc tcgcgtacgt | 60 |
| ttagtaccag gcgacggcaa aatcgttatt aacaatagag actgggaaga ttacatccca | 120 |
| tttgcagctc ttcgtgaagt tatcaaacaa ccttagtag ctacagaaac tttaggtaac | 180 |
| tatgatgtac tagtaaacgt tcacggtggt ggttacactg gtcaagccgg tgctatccgt | 240 |
| catggtgtag ctcgtgcact attacaagtg gctcctgagt accgcccagc acttaaatct | 300 |
| gctggcctac ttactcgtga ttcacgtatg aaagaacgta aaaaaccagg acttaaaggc | 360 |
| gcgcgtcgtg cacctcagtt ctcaaaacgt taa | 393 |

<210> SEQ ID NO 279
<211> LENGTH: 246
<212> TYPE: DNA
<213> ORGANISM: Listeria seeligeri

<400> SEQUENCE: 279

| | | |
|---|---|---|
| atgaaaactg gaattcatcc tgagtaccgt caagtggtat tgttgatac tagtactgat | 60 |
| ttcaaatttt tgtcaggttc tactaagagc tcaagcgaaa caattaaatg ggaagatggc | 120 |

```
aacgagtatc cgttacttcg tgtcgaaatc tcttctgatt cgcatccgtt ctatactggt    180
aaacaaaaac atgctacagc agacggacgt gtggaccgct tcaacaaaaa atatggtctc    240
aaataa                                                                246

<210> SEQ ID NO 280
<211> LENGTH: 273
<212> TYPE: DNA
<213> ORGANISM: Listeria seeligeri

<400> SEQUENCE: 280
atggcagtta aaattcgttt aaaacgtatt ggttctaaaa agaaaccttt ctaccgtatt     60
gtagtagctg attctcgttt cccacgtgac ggccgttcaa tcgaaactat tggtacttat    120
aatccattgc ttgatccggt tgaagtgaaa attgacgaag aagcaacttt gaaatggatg    180
cataatggtg cgaaaccatc tgatacagtt cgcaatcttc ttagccgcga aggtatcatg    240
gaaaaattcc ataaccaaaa attaggtaaa taa                                 273

<210> SEQ ID NO 281
<211> LENGTH: 312
<212> TYPE: DNA
<213> ORGANISM: Listeria welshimeri

<400> SEQUENCE: 281
atgcatgtca aaaaggtga taaagtaaaa gttattactg gtaaagataa aggcaaatcc      60
ggcaaagtgc tcgcagcatt tccgaaaaag gatcgcgtac ttattgaagg aattaatatg    120
gtcaaaaaac atacaaaacc ttccaacatc aatccgcaag gcggaatctt gaatgttgaa    180
gcaccaatcc atgtttcaaa cgtaatgcta attgacccta aaacaggcga acctactcgt    240
gtaggctacg aagttaaagg cgataaaaaa gtacgcgtag caaaaaaatc cggtgaagta    300
atagataaat aa                                                        312

<210> SEQ ID NO 282
<211> LENGTH: 537
<212> TYPE: DNA
<213> ORGANISM: Listeria welshimeri

<400> SEQUENCE: 282
atgtcccgta taggtaaaaa aactattgtg att

<400> SEQUENCE: 283

| gtgattacca aaatcgacaa aaataaagta cgtaaaaaaa gacatgctcg tgttcgttct | 60 |
| aaaatttccg gaactgaaag tcgtccacgt ttaaacgtat tccgttcaaa caaaaacatt | 120 |
| tatgctcaag taattgatga tgtaaatggt gtgacacttg caagtgcgtc taatttagat | 180 |
| aaagatttcg gttctgctga atcaaaagtt gatgcagcaa gcaaagttgg cgaactagtt | 240 |
| gctaaacgtg cttccgaaaa aggtattact tctgtcactt ttgaccgtgg aggatactta | 300 |
| tatcatggcc gcgtaaaagc tcttgctgaa gcagctcgcg aaaatggact agaattttaa | 360 |

<210> SEQ ID NO 284
<211> LENGTH: 441
<212> TYPE: DNA
<213> ORGANISM: Listeria welshimeri

<400> SEQUENCE: 284

| atgaaactac atgaacttaa gccttcagaa ggttctcgta agaacgtaa tcgtgttggt | 60 |
| cgtggaacag gctctggtaa cggcaaaact tcaggacgcg gtcataaagg acaaaaagct | 120 |
| cgttccggtg gtggcgtacg tttaggcttt gaaggtggac aacttccact tttccgtcgt | 180 |
| attccaaaac gtggattcac aaatatcaac cgtaaagaat ttgcaatcgt gaacttagat | 240 |
| gttttaaacc gctttgaaga cggtacagaa gtaacaccag aacttttaat tgaatctgga | 300 |
| attattcgta acgaaaaatc cggaatcaag atttttatctg atggtaaaat cgagaaaaaa | 360 |
| cttactgtga aagcgaacaa attctctgca gctgcaaaag aagctattga agcggctggc | 420 |
| ggaaaaactg aggtgatcta a | 441 |

<210> SEQ ID NO 285
<211> LENGTH: 390
<212> TYPE: DNA
<213> ORGANISM: Listeria welshimeri

<400> SEQUENCE: 285

| atggctcgta aaacaaatac tcgta

```
gctggcctac ttactcgtga ttcacgtatg aaagaacgta aaaaaccagg acttaaaggc    360
gcgcgtcgtg cacctcagtt ctcaaaacgt taa                                393

<210> SEQ ID NO 287
<211> LENGTH: 246
<212> TYPE: DNA
<213> ORGANISM: Listeria welshimeri

<400> SEQUENCE: 287
atgaaaactg gaattcatcc tgagtaccgt caagtggtat ttgttgatac tagtactgat    60
ttcaaatttt tgtcaggttc tactaagagc tcaagcgaaa caattaaatg ggaagatggc    120
aacgagtatc cgttacttcg tgtcgaaatc tcttctgatt cgcatccgtt ctatactggt    180
aaacaaaaac atgctacagc agacggacgt gtggaccgct tcaacaaaaa atacggtctc    240
aaataa                                                              246

<210> SEQ ID NO 288
<211> LENGTH: 273
<212> TYPE: DNA
<213> ORGANISM: Listeria welshimeri

<400> SEQUENCE: 288
atggcagtta aaattcgttt a

```
gttgaagtgg aagtaccagc aaacacgaaa gttatcgttc gcggtattaa caaagaacac    420
gttggcgaat tggctgcaaa tatccgttcc gtacgtccgc cagagcctta taaggtaaa     480 ggtatccgtt acgaaggcga atttgtacgt cgtaaagaag gtaagactgg taaataa       537
```

<210> SEQ ID NO 291
<211> LENGTH: 360
<212> TYPE: DNA
<213> ORGANISM: Listeria rocourtiae

<400> SEQUENCE: 291

```
gtgattacca aaatcgacaa aaataaagtg cgtaaaaaaa gacatggtcg tgttcgttct     60
aagatttctg gaactgcagc tcgtccacgc ttgaacgtat tccgttcaaa caaaaacatt    120
tatgctcaac ttatcgatga tgttaacggt gtaacaatcg ctagcgcatc taacgtagat    180
aaagatttcc ctaaagcgga gtccaaagtt gacgctgcta caaaagtagg cgaaatcgtt    240
gcaaaacgcg ctgcagaaaa aggtgttaaa gctgttgtat ttgatcgcgg aggttactta    300
taccacggtc gtgtgcaagc tttggctgaa gctgctcgtg aaaatggatt ggaattttaa    360
```

<210> SEQ ID NO 292
<211> LENGTH: 441
<212> TYPE: DNA
<213> ORGANISM: Listeria rocourtiae

<400> SEQUENCE: 292

```
atgaaacttc acgaacttaa acctgcagaa ggttctcgta agagcgtaa tcgtgttggt      60 cgtggtatga gttctggtaa cggtaaaaca tcaggacgcg gtcacaaagg tcaaaaagca    120
cgttcaggtg gcggtgtacg cctaggtttc gaaggtggac aactaccatt gttccgtcgt    180
attccaaaac gtggttttac aaatattaac cgtaaagaat acgctgttgt gaacattgat    240 gtttttaaatc gctttgaaga tggtacagaa gtaacacctg aattattaat tgaaacaggt    300
atcgtccgta atgcaaaatc tggaattaag attttgtcta acggcgcaat cgagaaaaaa    360
cttacggtga agctaacaa attctcatca gctgctaaag aggctatcga ggctgctggt    420
ggacaaactg aggtgatcta a                                              441
```

<210> SEQ ID NO 293
<211> LENGTH: 390
<212> TYPE: DNA
<213> ORGANISM: Listeria rocourtiae

<400> SEQUENCE: 293

```
atggctcgta aaactaatac tcgtaaacgt cgtgtgaaaa agaatatcga agctggtatt     60
gcacacattc gttctacatt caataataca atcgtaacga ttactgacat gcatggtaac    120
gcagtagcat ggtcaagtgc aggagcttta ggattcaaag gagctcgtaa atcgacacct    180
ttcgcagcgc aattagcggc agaaacgtgt gcaaaagctg cacaagagca tggtttaaaa    240
actttggaag taacagttaa aggaccaggt tcaggacgtg aagcagcaat tcgtgcgctt    300
caagcggcag tcttgatgt aactgctatt aaagatgtga ctccagttcc tcataacgga    360
tgtcgtcctc caaaacgtcg tcgtgtctaa                                     390
```

<210> SEQ ID NO 294
<211> LENGTH: 393
<212> TYPE: DNA
<213> ORGANISM: Listeria rocourtiae

```
<400> SEQUENCE: 294
gtggctcaag tacaatatta tggaacaggt cgtcgtaaaa gctcagtagc tcgtgtacgt      60
ttagtaccag gcgatggcaa agtagttatc aacggtagag attgggaaga ttacattcca     120
ttcgcggctc ttcgcgaagt tattaaacaa ccattagttg caactgaaac tctaggaaac     180
tatgatgttt tagtaaacgt aaacggtggt ggttatactg gtcaagctgg agcaatccgt     240
cacggaattt cacgtgcatt gctacaagtt gcaccggatt atcgttctcc attaaaacgt     300
gcaggtctat taactcgtga cccacgtatg aaagaacgta agaaaccagg acttaaaggc     360
gcgcgtcgtg cacctcagtt ctcaaaacgt taa                                   393

<210> SEQ ID NO 295
<211> LENGTH: 246
<212> TYPE: DNA
<213> ORGANISM: Listeria rocourtiae

<400> SEQUENCE: 295
atgaaagctg gaattcaccc ggaataccgt caagtggtat ttcttgatac tagtacagat      60
ttcaaatttc tttctggttc tactaagggc tcgaacgaaa ctattcaatg ggaagatggc     120
aacgagtatc cattactacg tgtcgaaatc agttctgatt ctcacccatt ctatactggt     180
aaacaaaaac atgcgacagc cgatggacgt gtcgatcgtt caacaagaa atacggcatc      240 aaataa                                                                 246

<210> SEQ ID NO 296
<211> LENGTH: 273
<212> TYPE: DNA
<213> ORGANISM: Listeria rocourtiae

<400> SEQUENCE: 296
atggcagtta aaattcgttt aaaacgtatg ggttctaaca agaaaccttt ctaccgtatt      60
caagttgcag attctcgttc tccacgtgat ggtcgttcaa tcgcaacagt gggtacatac     120
aatccactgt tgaacccagc agaagtgaaa atcgacgaag aagcagtttt aaaatggttg     180
cataatggcg cgaaaccatc tgacacagtt cgtaacttgt tgtcaaatga aggcattatg     240
gaaaaattcc acaattcaaa actaggtaag taa                                   273

<210> SEQ ID NO 297
<211> LENGTH: 312
<212> TYPE: DNA
<213> ORGANISM: Listeria grayi

<400> SEQUENCE: 297
atgcatatta aaaaaggtga taaagttcaa gttattactg gtaaagataa aggcaaatcc      60
ggtgcagtac tcgctgcatt tccaaagaaa gaccgtgtaa ttgttgaagg aatcaacatg     120
atcaaaaaac atgcgaaacc ttccaacgtg aatccacaag gtggaatctt aaacgttgaa     180
gcaccaattc acgtttctaa cgtaatgctt atcgatccta aatctggaga acccacacgc     240
gtgagttacc aagtgaagga tgacaagaaa gtgcgagttg ctaaaaaatc cggtgaagtt     300
ttagataaat aa                                                          312

<210> SEQ ID NO 298
<211> LENGTH: 537
<212> TYPE: DNA
<213> ORGANISM: Listeria grayi
```

<400> SEQUENCE: 298

```
atgtcccgta ttggtaaaaa gacaattgtc attcctgaag gtgtaacagt tacacttgat        60
ggttcaactg ctacagtaaa aggccctaaa ggtcaacttg taaaagaatt taaccctgac       120
attaaaattg atatcgaagg caatgaaatc aacgtttctc gcccaagtga tcataaaaca       180
catcgttctc ttcacggaac gactcgtgcg atcttaaata acatggtcgt aggtgtttcc       240
gaaggttacg aaaaaacatt agaattgatc ggtgttggtt accgtgctca aaacaaggaa       300
acaaacttg ttcttaacgt aggttactct catccagtag aatttgaagc tccagaaggc       360
gttgaaattg atgttcctgc aaatacgaaa gtaattgtta aggatacaa caaagaacac       420
gttggagaac tagctgctaa tattcgtgct actcgtcctc ctgaacctta taaggtaaa       480
gggatccgtt acgaaggcga atatgtacgc cgcaaagaag gtaaaactgg taaataa         537
```

<210> SEQ ID NO 299
<211> LENGTH: 360
<212> TYPE: DNA
<213> ORGANISM: Listeria grayi

<400> SEQUENCE: 299

```
gtgattacca aaatcgacaa aaataaagtc cgtaaaagaa gacatgcacg tgtccgttct        60
aagattactg gaacagaatc tcgtccacgc ttgaacgtat ccgttctaa caaaaacatt       120
tacgcgcaag ttatcgacga cgtaaatggc gtgacacttg caagtgcatc taatctagat       180
aaagaatttg gctctagcga atcgaaagtt gacgcagcta gcaaagttgg cgcattagtt       240
gcgaaacgtg ctgctgataa aggcattact tctgttactt ttgaccgtgg aggctattta       300
tatcatggcc gagtgaaagc tttggctgaa gctgctcgtg aaaatggttt agaattttaa       360
```

<210> SEQ ID NO 300
<211> LENGTH: 441
<212> TYPE: DNA
<213> ORGANISM: Listeria grayi

<400> SEQUENCE: 300

```
atgaaactac acgaacttaa accttctgag ggatctcgta aggaacgcaa tcgtgttggt        60
cgtggtacag gctctggtaa cggtaaaact tccggtcgcg gacataaagg gcaaaaagct       120
cgttccggcg gtggtgtacg tttaggcttt gaaggtggac aacttccact tttccgtcgt       180
cttccaaaac gtgggttcac aaatatcaac cgcaaagaat atgcagttgt taatgttggg       240
actttaaaacc gttttgaaga tggtacagaa gtaacaccag aattgttaat tgaaactggt       300
gtgatcagca atgcaaaatc tggtatcaaa gtattatcag aaggaaaaat tgagaagaaa       360
ttaactgtta aggctaacaa attctcagca gcggctaaag aagcaatcga agctgctggt       420
ggacaaactg aggtgatcta a                                                 441
```

<210> SEQ ID NO 301
<211> LENGTH: 390
<212> TYPE: DNA
<213> ORGANISM: Listeria grayi

<400> SEQUENCE: 301

```
atggctcgta aaacgaatac tcgtaaacgt cgtgtgaaaa agaatatcga agcaggtatt        60
gctcacatcc gttctacatt taacaatacg atcgtaatga tcactgatgt acatggtaat       120
gctttggcat ggtctagtgc aggtgcttta ggatttaaag gttctaaaaa atctactcct       180
```

```
ttcgcagctc aaatggcagc tgaaagtgca gctaaatcag ctcaagaaca tggcattaaa    240
actcttgaag taacagtaaa aggtcctggt gcaggtcgcg aggctgctat ccgtgcgctt    300
caagctgcag gtatcgaagt tactgctatt aaagatgtaa ctcctgttcc tcacaatggt    360
tgtcgccctc aaaacgtcg tcgtgtataa                                      390

<210> SEQ ID NO 302
<211> LENGTH: 393
<212> TYPE: DNA
<213> ORGANISM: Listeria grayi

<400> SEQUENCE: 302
gtggctcaag tacaatatta cggaacaggt cgtcgtaaaa gctcagtagc tcgtgtacgt     60
ctagtaccag cgacggcaa agttgttatc aataatagag actgggaaga ttacatccca    120
ttcgcagcac tacgcgaagt aatcaaacaa cctttagtag caacagatgc tttaggaaaa    180
tatgacgtat tagtaaacgt tcatggtgga ggctacactg gtcaagccgg tgctatccgt    240
cacggcgtgg cacgtgcact attacttgta tcacctgagt accgcccagc acttaaatct    300
gctggattgc taactcgtga ccctcgtatg aaagaacgta aaaaatacgg tcttaaagcg    360
gctcgtcgcg cacctcagtt ctcaaaacgt taa                                 393

<210> SEQ ID NO 303
<211> LENGTH: 246
<212> TYPE: DNA
<213> ORGANISM: Listeria grayi

<400> SEQUENCE: 303
atgaaaaaag aaattcatcc gaattatcga ccagttgtat ttgtagatac tactacagat     60
tttaaattct tgtctggttc tacaaaaaac tccagtgaaa caattacatg ggaagacgga    120
aacgaatatc cacttcttcg tgtggaaatt tcttctgact ctcatccatt ctacactggt    180
aaacaaaaac atgctgccgc tgatggacgt gttgaccgct tcaacaaaaa atacggcatc    240
aaataa                                                               246

<210> SEQ ID NO 304
<211> LENGTH: 273
<212> TYPE: DNA
<213> ORGANISM: Listeria grayi

<400> SEQUENCE: 304
atggcagtta aaattcgttt aaaacgtatg ggttctaaaa agaaaccttt ttatcgtatc     60
gttgtagctg actctcgcta tccacgtgat ggccgttcga tcgaaactgt tggaacatac    120
aacccgttgt taaatccagc agaagtgaaa atcaatgaag agtctgtttt gaaatggatg    180
cataatggtg cgaaaccatc tgatacagtt cgtaacttat tcagtaacga aggtatcatg    240
gaaaaattcc acaaccaaaa attaggtaaa taa                                 273

<210> SEQ ID NO 305
<211> LENGTH: 20
<212> TYPE: DNA
<213> ORGANISM: Artificial Sequence
<220> FEATURE:
<223> OTHER INFORMATION: PCR primer
```

```
<400> SEQUENCE: 305
catggcggat gttcaggtaa                                              20

<210> SEQ ID NO 306
<211> LENGTH: 20
<212> TYPE: DNA
<213> ORGANISM: Artificial Sequence
<220> FEATURE:
<223> OTHER INFORMATION: PCR prime

<400> SEQUENCE: 306
ctccttccag aataacgggt                                              20

<210> SEQ ID NO 307
<211> LENGTH: 20
<212> TYPE: DNA
<213> ORGANISM: Artificial Sequence
<220> FEATURE:
<223> OTHER INFORMATION: PCR primer

<400> SEQUENCE: 307
agcagcacaa aacgtggtac                                              20

<210> SEQ ID NO 308
<211> LENGTH: 20
<212> TYPE: DNA
<213> ORGANISM: Artificial Sequence
<220> FEATURE:
<223> OTHER INFORMATION: PCR primer

<400> SEQUENCE: 308
aaggaggact aacgaatgcc                                              20

<210> SEQ ID NO 309
<211> LENGTH: 20
<212> TYPE: DNA
<213> ORGANISM: Artificial Sequence
<220> FEATURE:
<223> OTHER INFORMATION: PCR primer

<400> SEQUENCE: 309
tgcacgcaac ttacaaggca                                              20

<210> SEQ ID NO 310
<211> LENGTH: 20
<212> TYPE: DNA
<213> ORGANISM: Artificial Sequence
<220> FEATURE:
<223> OTHER INFORMATION: PCR primer

<400> SEQUENCE: 310
cggacgcaat aaccaaggta                                              20

<210> SEQ ID NO 311
<211> LENGTH: 20
<212> TYPE: DNA
<213> ORGANISM: Artificial Sequence
<220> FEATURE:
<223> OTHER INFORMATION: PCR primer

<400> SEQUENCE: 311
aatgaacccg aacgatcacc                                              20

<210> SEQ ID NO 312
```

```
<211> LENGTH: 20
<212> TYPE: DNA
<213> ORGANISM: Artificial Sequence
<220> FEATURE:
<223> OTHER INFORMATION: PCR primer

<400> SEQUENCE: 312
tacaagcgca aaagccgttg                                               20

<210> SEQ ID NO 313
<211> LENGTH: 20
<212> TYPE: DNA
<213> ORGANISM: Artificial Sequence
<220> FEATURE:
<223> OTHER INFORMATION: PCR primer

<400> SEQUENCE: 313
gtgcagctaa ccgtgtgaat                                               20

<210> SEQ ID NO 314
<211> LENGTH: 20
<212> TYPE: DNA
<213> ORGANISM: Artificial Sequence
<220> FEATURE:
<223> OTHER INFORMATION: PCR primer

<400> SEQUENCE: 314
aggcggaact gaagttgcat                                               20

<210> SEQ ID NO 315
<211> LENGTH: 20
<212> TYPE: DNA
<213> ORGANISM: Artificial Sequence
<220> FEATURE:
<223> OTHER INFORMATION: PCR primer

<400> SEQUENCE: 315
acccgttatt ctggaaggag                                               20

<210> SEQ ID NO 316
<211> LENGTH: 20
<212> TYPE: DNA
<213> ORGANISM: Artificial Sequence
<220> FEATURE:
<223> OTHER INFORMATION: PCR primer

<400> SEQUENCE: 316
aaggcattac acccatggca                                               20

<210> SEQ ID NO 317
<211> LENGTH: 20
<212> TYPE: DNA
<213> ORGANISM: Artificial Sequence
<220> FEATURE:
<223> OTHER INFORMATION: PCR primer

<400> SEQUENCE: 317
ctcgtccatt gtctgcaact                                               20

<210> SEQ ID NO 318
<211> LENGTH: 22
<212> TYPE: DNA
<213> ORGANISM: Artificial Sequence
<220> FEATURE:
<223> OTHER INFORMATION: PCR primer
```

<400> SEQUENCE: 318
caaacgtaat gctamttgac cc                                       22

<210> SEQ ID NO 319
<211> LENGTH: 21
<212> TYPE: DNA
<213> ORGANISM: Artificial Sequence
<220> FEATURE:
<223> OTHER INFORMATION: PCR primer

<400> SEQUENCE: 319
cgtggtaact atacgttggg t                                        21

<210> SEQ ID NO 320
<211> LENGTH: 20
<212> TYPE: DNA
<213> ORGANISM: Artificial Sequence
<220> FEATURE:
<223> OTHER INFORMATION: PCR primer

<400> SEQUENCE: 320
gactggcgaa cgtgtaatca                                          20

<210> SEQ ID NO 321
<211> LENGTH: 22
<212> TYPE: DNA
<213> ORGANISM: Artificial Sequence
<220> FEATURE:
<223> OTHER INFORMATION: PCR primer

<400> SEQUENCE: 321
tcctgcaaac acwcaagtga tt                                       22

<210> SEQ ID NO 322
<211> LENGTH: 22
<212> TYPE: DNA
<213> ORGANISM: Artificial Sequence
<220> FEATURE:
<223> OTHER INFORMATION: PCR primer

<400> SEQUENCE: 322
ggagggacat attacatgcc tg                                       22

<210> SEQ ID NO 323
<211> LENGTH: 18
<212> TYPE: DNA
<213> ORGANISM: Artificial Sequence
<220> FEATURE:
<223> OTHER INFORMATION: PCR primer

<400> SEQUENCE: 323
ttaatcggac gccctcaa                                            18

<210> SEQ ID NO 324
<211> LENGTH: 20
<212> TYPE: DNA
<213> ORGANISM: Artificial Sequence
<220> FEATURE:
<223> OTHER INFORMATION: PCR primer

<400> SEQUENCE: 324
ctctaccaaa cgcgatgttc                                          20

<210> SEQ ID NO 325

```
<211> LENGTH: 22
<212> TYPE: DNA
<213> ORGANISM: Artificial Sequence
<220> FEATURE:
<223> OTHER INFORMATION: PCR primer

<400> SEQUENCE: 325
ggaaacacag agctagacaa gg                                          22

<210> SEQ ID NO 326
<211> LENGTH: 20
<212> TYPE: DNA
<213> ORGANISM: Artificial Sequence
<220> FEATURE:
<223> OTHER INFORMATION: PCR primer

<400> SEQUENCE: 326
cctgacacgc ggaagaatta                                             20

<210> SEQ ID NO 327
<211> LENGTH: 20
<212> TYPE: DNA
<213> ORGANISM: Artificial Sequence
<220> FEATURE:
<223> OTHER INFORMATION: PCR primer

<400> SEQUENCE: 327
aaggcccgtc caaaacagta                                             20

<210> SEQ ID NO 328
<211> LENGTH: 20
<212> TYPE: DNA
<213> ORGANISM: Artificial Sequence
<220> FEATURE:
<223> OTHER INFORMATION: PCR primer

<400> SEQUENCE: 328
cagcgatgat gccaagtatg                                             20

<210> SEQ ID NO 329
<211> LENGTH: 20
<212> TYPE: DNA
<213> ORGANISM: Artificial Sequence
<220> FEATURE:
<223> OTHER INFORMATION: PCR primer

<400> SEQUENCE: 329
gaagcagttt cacttggagc                                             20

<210> SEQ ID NO 330
<211> LENGTH: 20
<212> TYPE: DNA
<213> ORGANISM: Artificial Sequence
<220> FEATURE:
<223> OTHER INFORMATION: PCR primer

<400> SEQUENCE: 330
aactggctga ccttggctta                                             20

<210> SEQ ID NO 331
<211> LENGTH: 20
<212> TYPE: DNA
<213> ORGANISM: Artificial Sequence
<220> FEATURE:
<223> OTHER INFORMATION: PCR primer
```

<400> SEQUENCE: 331
cccctgtgat ggcgagtctt                                               20

<210> SEQ ID NO 332
<211> LENGTH: 25
<212> TYPE: DNA
<213> ORGANISM: Artificial Sequence
<220> FEATURE:
<223> OTHER INFORMATION: PCR primer

<400> SEQUENCE: 332
tcttctcgca taacatcgac ttgaa                                         25

<210> SEQ ID NO 333
<211> LENGTH: 24
<212> TYPE: DNA
<213> ORGANISM: Artificial Sequence
<220> FEATURE:
<223> OTHER INFORMATION: PCR primer

<400> SEQUENCE: 333
tgaaggattt aagtgagtgc atgt                                          24

<210> SEQ ID NO 334
<211> LENGTH: 21
<212> TYPE: DNA
<213> ORGANISM: Artificial Sequence
<220> FEATURE:
<223> OTHER INFORMATION: PCR primer

<400> SEQUENCE: 334
cgcatcgctt gtttcatatc t                                             21

<210> SEQ ID NO 335
<211> LENGTH: 22
<212> TYPE: DNA
<213> ORGANISM: Artificial Sequence
<220> FEATURE:
<223> OTHER INFORMATION: PCR primer

<400> SEQUENCE: 335
ttcgggagct aatttgtttc aa                                            22

<210> SEQ ID NO 336
<211> LENGTH: 22
<212> TYPE: DNA
<213> ORGANISM: Artificial Sequence
<220> FEATURE:
<223> OTHER INFORMATION: PCR primer

<400> SEQUENCE: 336
aacgttttca gaactgaggt gc                                            22

<210> SEQ ID NO 337
<211> LENGTH: 24
<212> TYPE: DNA
<213> ORGANISM: Artificial Sequence
<220> FEATURE:
<223> OTHER INFORMATION: PCR primer

<400> SEQUENCE: 337
cacatatcga cactggagac tttg                                          24

<210> SEQ ID NO 338

```
<211> LENGTH: 20
<212> TYPE: DNA
<213> ORGANISM: Artificial Sequence
<220> FEATURE:
<223> OTHER INFORMATION: PCR primer

<400> SEQUENCE: 338
ctggaatcaa agtcgaccca                                               20

<210> SEQ ID NO 339
<211> LENGTH: 22
<212> TYPE: DNA
<213> ORGANISM: Artificial Sequence
<220> FEATURE:
<223> OTHER INFORMATION: PCR primer

<400> SEQUENCE: 339
gcagcagtta cgccaaattc tt                                            22

<210> SEQ ID NO 340
<211> LENGTH: 30
<212> TYPE: DNA
<213> ORGANISM: Artificial Sequence
<220> FEATURE:
<223> OTHER INFORMATION: PCR primer

<400> SEQUENCE: 340
tgttataata tytatactgt gtgtaaaagc                                    30

<210> SEQ ID NO 341
<211> LENGTH: 24
<212> TYPE: DNA
<213> ORGANISM: Artificial Sequence
<220> FEATURE:
<223> OTHER INFORMATION: PCR primer

<400> SEQUENCE: 341
tgagaccgta yttttttgttg aagc                                         24
```